United States Patent
Koepke

(10) Patent No.: US 11,459,589 B2
(45) Date of Patent: *Oct. 4, 2022

(54) MICROBIAL FERMENTATION FOR THE PRODUCTION OF TERPENES

(71) Applicant: LanzaTech NZ, Inc., Skokie, IL (US)

(72) Inventor: Michael Koepke, Chicago, IL (US)

(73) Assignee: LanzaTech NZ, Inc., Skokie, IL (US)

( * ) Notice: Subject to any disclaimer, the term of this patent is extended or adjusted under 35 U.S.C. 154(b) by 134 days.

This patent is subject to a terminal disclaimer.

(21) Appl. No.: 17/095,064

(22) Filed: Nov. 11, 2020

(65) Prior Publication Data

US 2021/0062229 A1 Mar. 4, 2021

Related U.S. Application Data

(63) Continuation of application No. 15/867,306, filed on Jan. 10, 2018, now Pat. No. 10,913,958, which is a continuation of application No. 14/656,827, filed on Mar. 13, 2015, now abandoned, which is a continuation of application No. 13/909,012, filed on Jun. 3, 2013, now abandoned.

(60) Provisional application No. 61/654,412, filed on Jun. 1, 2012.

(51) Int. Cl.

| C12P 5/00 | (2006.01) |
|---|---|
| C12N 15/74 | (2006.01) |
| C12N 9/88 | (2006.01) |
| C12N 9/10 | (2006.01) |
| C12N 9/12 | (2006.01) |
| C12N 9/04 | (2006.01) |
| C12N 15/52 | (2006.01) |
| C12P 7/42 | (2006.01) |
| C12P 9/00 | (2006.01) |

(52) U.S. Cl.
CPC ........... *C12P 5/007* (2013.01); *C12N 9/0006* (2013.01); *C12N 9/1022* (2013.01); *C12N 9/1025* (2013.01); *C12N 9/1029* (2013.01); *C12N 9/1085* (2013.01); *C12N 9/1205* (2013.01); *C12N 9/1229* (2013.01); *C12N 9/88* (2013.01); *C12N 15/52* (2013.01); *C12N 15/74* (2013.01); *C12P 7/42* (2013.01); *C12P 9/00* (2013.01); *C12Y 101/01088* (2013.01); *C12Y 101/01267* (2013.01); *C12Y 117/07001* (2013.01); *C12Y 202/01007* (2013.01); *C12Y 203/01009* (2013.01); *C12Y 203/0301* (2013.01); *C12Y 205/0101* (2013.01); *C12Y 205/0109* (2013.01); *C12Y 207/01036* (2013.01); *C12Y 207/01148* (2013.01); *C12Y 207/04002* (2013.01); *C12Y 207/0706* (2013.01); *C12Y 401/01033* (2013.01); *C12Y 402/03027* (2013.01); *C12Y 402/03046* (2013.01); *C12Y 406/01012* (2013.01); *C12Y 503/03002* (2013.01); *Y02E 50/30* (2013.01)

(58) Field of Classification Search
None
See application file for complete search history.

(56) References Cited

U.S. PATENT DOCUMENTS

| 2012/0157725 A1* | 6/2012 | McAuliffe | B01J 31/10 585/254 |
| 2014/0234926 A1* | 8/2014 | Beck | C12P 7/065 435/146 |

* cited by examiner

*Primary Examiner* — Robert B Mondesi
*Assistant Examiner* — Todd M Epstein
(74) *Attorney, Agent, or Firm* — Stephen M. Chong

(57) ABSTRACT

The invention provides a method for producing a terpene or a precursor thereof by microbial fermentation. Typically, the method involves culturing a recombinant bacterium in the presence of a gaseous substrate whereby the bacterium produces a terpene or a precursor thereof, such as mevalonic acid, isopentenyl pyrophosphate, dimethylallyl pyrophosphate, isoprene, geranyl pyrophosphate, farnesyl pyrophosphate, and/or farnesene. The bacterium may comprise one or more exogenous enzymes, such as enzymes in mevalonate, DXS, or terpene biosynthesis pathways.

30 Claims, 20 Drawing Sheets

Specification includes a Sequence Listing.

SEQUENCE LISTING

```
<160> NUMBER OF SEQ ID NOS: 111

<210> SEQ ID NO 1
<211> LENGTH: 1875
<212> TYPE: DNA
<213> ORGANISM: Clostridium autoethanogenum

<400> SEQUENCE: 1
atgagtaatt tattagataa ttataaagat ataaatgacg taaagaagat gtcgttaaat      60
gataaaaaaa agctagctag agaaattaga aaattttttaa tagacaaagt atctaagaca     120
ggaggtcatt tggcgtctaa cttaggggtt gtggagctca ctttgagttt atttagtgta     180
tttgatctaa attatgataa acttatatgg gatgtgggac atcaggctta tgtgcataaa     240
atcctcacgg gaagaaagga taaatttgat actttaaggc aatttggagg attaagtgga     300
tttcctaaaa ggtgcgaaag tatatatgat tttttcgaaa cagggcatag tagtacttca     360
atatctgcag cacttggaat ggctagggct agagatttaa agcatgagaa atataatgtt     420
gttgcagtta taggagatgg agcacttact ggaggtatgg cactagaggc cctaaatgat     480
gtaggttata gaaaaactaa gcttataata atattaaatg ataatcaaat gtctatagga     540
aaaaatgtag gtggagtatc taaatattta aataaactta gagtggaccc taagtataat     600
aaatttaaag cggatgtaga agctaaatta aaaaagatac ctaatatagg aaaaggaatg     660
gcaaaatatc ttgaaaaggt aaaaaatgga ataaaacaaa tggtagttcc tggaatgttt     720
tttgaagata tgggaattaa atatttagga ccaatagatg gtcataatat aaaagaactt     780
acagacgtac tcgcttctgc aaaagacata caaggtccag ttattataca tataataact     840
aagaaaggaa aaggatatga atttgcagaa aaaaatccag gtaaattcca tggaataggg     900
ccttttaatt gcgccaatgg tgaactggat gctggatctt caaatactta ttccaaggcc     960
tttggaaatg aaatggtaaa gctagcagaa aaagacgata gaatagtggc tataactgca    1020
gccatgaggg atggaacagg tcttaaaagt tttctcaaa agtttcctga aaggtttttt    1080 gatgtggaa tagcagaaca gcatgctgta accctggcag ctggaatggc acaggcaaat    1140
ttaaaacctg tatttgcagt ttactctact tttcttcaaa gagcttatga tcaacttatt    1200
catgatgtat gtatgcaaaa acttccagta gtttttgctg tagatagggc cggcattgta    1260
```

```
ggagaagatg gtgaaacaca tcagggaata tttgatttat cttacttaac ggaaatgcca   1320
catatgacgc ttatgtctcc taaatgtata gatgaacttc catatatgtt aaatgggca    1380 ttaggccaga gttttcctgt agctataagg tatccaaggg gaggagatag tgtatgtctc   1440
aatcccgtag aaaattttaa acttggaaag tgggactgta tttcaaatga aggcagtgta   1500
gcaataattg ctcagggtaa aatggtacaa aatgcagtgt tagcaggaaa aaaacttaaa   1560
gaaaagggta tagatgtaag gattataagt gcatgtttta ttaagccgct ggacaaggaa   1620
atgttaaaca ggttagttga agaaagtgta actatcgtta ctgttgaaga caatgtaata   1680
agaggaggat taggatccta tatattagaa tatgtaaata aattaaataa aaaagtaaaa   1740
ataataaact tagggtttga tgataagttt gtacagcatg gaaaatccga tatttttgtat  1800 aagctgtatg gtttggatcc taaaggtatc gtaaatagtg tacttgaagc agcagaggta   1860
agtcatatat tttaa                                                    1875

<210> SEQ ID NO 2
<211> LENGTH: 627
<212> TYPE: PRT
<213> ORGANISM: Clostridium autoethanogenum

<400> SEQUENCE: 2

Met Ser Asn Leu Leu Asp Asn Tyr Lys Asp Ile Asn Asp Val Lys Lys
1               5                   10                  15

Met Ser Leu Asn Asp Lys Lys Leu Ala Arg Glu Ile Arg Lys Phe
            20                  25                  30

Leu Ile Asp Lys Val Ser Lys Thr Gly Gly His Leu Ala Ser Asn Leu
        35                  40                  45

Gly Val Val Glu Leu Thr Leu Ser Leu Phe Ser Val Phe Asp Leu Asn
    50                  55                  60

Tyr Asp Lys Leu Ile Trp Asp Val Gly His Gln Ala Tyr Val His Lys
65                  70                  75                  80

Ile Leu Thr Gly Arg Lys Asp Lys Phe Asp Thr Leu Arg Gln Phe Gly
                85                  90                  95

Gly Leu Ser Gly Phe Pro Lys Arg Cys Glu Ser Ile Tyr Asp Phe Phe
            100                 105                 110

Glu Thr Gly His Ser Ser Thr Ser Ile Ser Ala Ala Leu Gly Met Ala
        115                 120                 125

Arg Ala Arg Asp Leu Lys His Glu Lys Tyr Asn Val Val Ala Val Ile
    130                 135                 140

Gly Asp Gly Ala Leu Thr Gly Gly Met Ala Leu Glu Ala Leu Asn Asp
145                 150                 155                 160

Val Gly Tyr Arg Lys Thr Lys Leu Ile Ile Ile Leu Asn Asp Asn Gln
                165                 170                 175

Met Ser Ile Gly Lys Asn Val Gly Val Ser Lys Tyr Leu Asn Lys
            180                 185                 190

Leu Arg Val Asp Pro Lys Tyr Asn Lys Phe Lys Ala Asp Val Glu Ala
        195                 200                 205

Lys Leu Lys Lys Ile Pro Asn Ile Gly Lys Gly Met Ala Lys Tyr Leu
    210                 215                 220

Glu Lys Val Lys Asn Gly Ile Lys Gln Met Val Val Pro Gly Met Phe
225                 230                 235                 240

Phe Glu Asp Met Gly Ile Lys Tyr Leu Gly Pro Ile Asp Gly His Asn
                245                 250                 255
```

Ile Lys Glu Leu Thr Asp Val Leu Ala Ser Ala Lys Asp Ile Gln Gly
            260                 265                 270

Pro Val Ile Ile His Ile Ile Thr Lys Lys Gly Lys Gly Tyr Glu Phe
        275                 280                 285

Ala Glu Lys Asn Pro Gly Lys Phe His Gly Ile Gly Pro Phe Asn Cys
    290                 295                 300

Ala Asn Gly Glu Leu Asp Ala Gly Ser Ser Asn Thr Tyr Ser Lys Ala
305                 310                 315                 320

Phe Gly Asn Glu Met Val Lys Leu Ala Glu Lys Asp Asp Arg Ile Val
                325                 330                 335

Ala Ile Thr Ala Ala Met Arg Asp Gly Thr Gly Leu Lys Ser Phe Ser
            340                 345                 350

Gln Lys Phe Pro Glu Arg Phe Phe Asp Val Gly Ile Ala Glu Gln His
        355                 360                 365

Ala Val Thr Leu Ala Ala Gly Met Ala Gln Ala Asn Leu Lys Pro Val
    370                 375                 380

Phe Ala Val Tyr Ser Thr Phe Leu Gln Arg Ala Tyr Asp Gln Leu Ile
385                 390                 395                 400

His Asp Val Cys Met Gln Lys Leu Pro Val Val Phe Ala Val Asp Arg
                405                 410                 415

Ala Gly Ile Val Gly Glu Asp Gly Glu Thr His Gln Gly Ile Phe Asp
            420                 425                 430

Leu Ser Tyr Leu Thr Glu Met Pro His Met Thr Leu Met Ser Pro Lys
        435                 440                 445

Cys Ile Asp Glu Leu Pro Tyr Met Leu Lys Trp Ala Leu Gly Gln Ser
450                 455                 460

Phe Pro Val Ala Ile Arg Tyr Pro Arg Gly Gly Asp Ser Val Cys Leu
465                 470                 475                 480

Asn Pro Val Glu Asn Phe Lys Leu Gly Lys Trp Asp Cys Ile Ser Asn
                485                 490                 495

Glu Gly Ser Val Ala Ile Ile Ala Gln Gly Lys Met Val Gln Asn Ala
            500                 505                 510

Val Leu Ala Gly Lys Lys Leu Lys Glu Lys Gly Ile Asp Val Arg Ile
        515                 520                 525

Ile Ser Ala Cys Phe Ile Lys Pro Leu Asp Lys Glu Met Leu Asn Arg
    530                 535                 540

Leu Val Glu Glu Ser Val Thr Ile Val Thr Val Glu Asp Asn Val Ile
545                 550                 555                 560

Arg Gly Gly Leu Gly Ser Tyr Ile Leu Glu Tyr Val Asn Lys Leu Asn
                565                 570                 575

Lys Lys Val Lys Ile Ile Asn Leu Gly Phe Asp Asp Lys Phe Val Gln
            580                 585                 590

His Gly Lys Ser Asp Ile Leu Tyr Lys Leu Tyr Gly Leu Asp Pro Lys
        595                 600                 605

Gly Ile Val Asn Ser Val Leu Glu Ala Ala Glu Val Ser His Ile Phe
    610                 615                 620

Arg Glu Phe
625

<210> SEQ ID NO 3
<211> LENGTH: 1158
<212> TYPE: DNA
<213> ORGANISM: Clostridium autoethanogenum

<400> SEQUENCE: 3

-continued

```
atgaagagaa tttcaataat tggagccaca ggttctatag gaacccaaac tcttgatgta      60
cttagaaaac aaaaaggaga ttttcagctt ataggtgtat ctgcaaatag tagtgtagat     120
aaacttttac atataataga tgaatttaac cccaaatatg cggtgctaac cgaaaaagaa     180
tcttatttaa agataaaaga tattttagt aataaaaaat caaatacaaa aatattattt     240
ggagtagatg gattaaatac tatagctagt cttcctgaag ttgatatggt tgtaacatct     300
gtagttggaa tgatagggct tgtaccaact ataaaagcaa ttaaagcgaa gaaagacata     360
gctttagcta ataaggagac attagttgta ggaggagaac tggttacaaa attatcgaaa     420
gaaaataata taaaaatatt tcctgtagat tcagagcata gtgctgtttt tcaatgcctt     480
cagggaaata attttgacga agttgctaat ttgattttaa ccgcttcagg tggaccttt      540 aggggaaaaa caaaagatca actctcaaaa gtaactgtaa agaggcgtt gaatcatcca     600 aattggagta tgggaaaaaa gctcacaata gattctgcta ctcttatgaa taagggactt     660
gaagttatag aagctcactt cttatttaac ttaccttatg aaaatataaa ggttgtagtt     720
catccacaaa gtatagtaca ttctatggtg aatatagggg atggaagtgt tatggcacag     780
cttgccactg cagatatgag attacctata caatatgcac tgaattatcc gaaaagaaag     840
gaagctgtaa tagataaatt ggacttctat agcgtaggaa atttaagttt tgaaaagcct     900
gatacagata cattcagacc acttaaatta gcttatgaag cagggaggat aggaggcaca     960
atgccagcta tactaaattg tgcaaatgag gaagcagtaa gtttattcct tgctaataaa    1020
ataaattttt tggatatagg caacatatta gaagagtgta tgaataaatt tacttcacaa    1080
agtacgtata ctctggatga tttacttgac ctagaaataa aagttaagaa atatgtaaaa    1140
gataaattta tcaaataa                                                  1158
```

<210> SEQ ID NO 4
<211> LENGTH: 385
<212> TYPE: PRT
<213> ORGANISM: Clostridium autoethanogenum

<400> SEQUENCE: 4

```
Met Lys Arg Ile Ser Ile Ile Gly Ala Thr Gly Ser Ile Gly Thr Gln
1               5                   10                  15

Thr Leu Asp Val Leu Arg Lys Gln Lys Gly Asp Phe Gln Leu Ile Gly
            20                  25                  30

Val Ser Ala Asn Ser Ser Val Asp Lys Leu Leu His Ile Ile Asp Glu
        35                  40                  45

Phe Asn Pro Lys Tyr Ala Val Leu Thr Glu Lys Glu Ser Tyr Leu Lys
    50                  55                  60

Ile Lys Asp Ile Phe Ser Asn Lys Lys Ser Asn Thr Lys Ile Leu Phe
65                  70                  75                  80

Gly Val Asp Gly Leu Asn Thr Ile Ala Ser Leu Pro Glu Val Asp Met
                85                  90                  95

Val Val Thr Ser Val Val Gly Met Ile Gly Leu Val Pro Thr Ile Lys
            100                 105                 110

Ala Ile Lys Ala Lys Lys Asp Ile Ala Leu Ala Asn Lys Glu Thr Leu
        115                 120                 125

Val Val Gly Gly Glu Leu Val Thr Lys Leu Ser Lys Glu Asn Asn Ile
    130                 135                 140

Lys Ile Phe Pro Val Asp Ser Glu His Ser Ala Val Phe Gln Cys Leu
145                 150                 155                 160
```

Gln Gly Asn Asn Phe Asp Glu Val Ala Asn Leu Ile Leu Thr Ala Ser
            165                 170                 175

Gly Gly Pro Phe Arg Gly Lys Thr Lys Asp Gln Leu Ser Lys Val Thr
        180                 185                 190

Val Lys Glu Ala Leu Asn His Pro Asn Trp Ser Met Gly Lys Lys Leu
    195                 200                 205

Thr Ile Asp Ser Ala Thr Leu Met Asn Lys Gly Leu Glu Val Ile Glu
210                 215                 220

Ala His Phe Leu Phe Asn Leu Pro Tyr Glu Asn Ile Lys Val Val Val
225                 230                 235                 240

His Pro Gln Ser Ile Val His Ser Met Val Glu Tyr Arg Asp Gly Ser
            245                 250                 255

Val Met Ala Gln Leu Ala Thr Ala Asp Met Arg Leu Pro Ile Gln Tyr
        260                 265                 270

Ala Leu Asn Tyr Pro Lys Arg Lys Glu Ala Val Ile Asp Lys Leu Asp
    275                 280                 285

Phe Tyr Ser Val Gly Asn Leu Ser Phe Glu Lys Pro Asp Thr Asp Thr
290                 295                 300

Phe Arg Pro Leu Lys Leu Ala Tyr Glu Ala Gly Arg Ile Gly Gly Thr
305                 310                 315                 320

Met Pro Ala Ile Leu Asn Cys Ala Asn Glu Glu Ala Val Ser Leu Phe
            325                 330                 335

Leu Ala Asn Lys Ile Asn Phe Leu Asp Ile Gly Asn Ile Leu Glu Glu
        340                 345                 350

Cys Met Asn Lys Phe Thr Ser Gln Ser Thr Tyr Thr Leu Asp Asp Leu
    355                 360                 365

Leu Asp Leu Glu Ile Lys Val Lys Lys Tyr Val Lys Asp Lys Phe Ile
370                 375                 380

Lys
385

<210> SEQ ID NO 5
<211> LENGTH: 693
<212> TYPE: DNA
<213> ORGANISM: Clostridium autoethanogenum

<400> SEQUENCE: 5
atgaatggta attatgctat tattgtagct gccggcaagg gaaaaagaat gggaactact      60
attaataagc aatttattaa aattaagggt aagcctatat tatattattc cataagggca    120
ttttccataa atcctcttat agatggaatt atactggtat gtgcagaaac tgagatagaa    180
tattgtaaaa gagaagtagt agataaatat gggcttcaga aggtaattaa attagttgct    240
gggggtaaag aacgtcagga ttcggtattt aatggactag gagttttaga aaagaaaac     300 tgtagtgttg ttctaattca cgatggggct agaccttttg tcactagtaa aattattgat    360
gatggaataa atattctaa taggtatggg gcttgtgctt gtggagttag gcctaaggat    420
acactaaaag ttagggaaga agtggatttt tcttcttcta cattagagag aaaaagttta    480
tttgcagttc aaactccgca gtgttttaaa tatgatttaa tttatgactg tcataaaaaa    540
ttaatgaatg aaaaaatgtg tgttactgat gatactatgg tagtagagcg ttatggaaat    600
aaggtttatt tgtatgaagg taactatgaa aacataaaag tgaccacacc agaagattta    660
aatatagctg aaagtatagt tgaaaaatat taa                                 693

<210> SEQ ID NO 6

```
<211> LENGTH: 230
<212> TYPE: PRT
<213> ORGANISM: Clostridium autoethanogenum

<400> SEQUENCE: 6
```

| | | | | | | | | | | | | | | |
|---|---|---|---|---|---|---|---|---|---|---|---|---|---|---|
| Met | Asn | Gly | Asn | Tyr | Ala | Ile | Ile | Val | Ala | Ala | Gly | Lys | Gly | Arg |
| 1 | | | | 5 | | | | | 10 | | | | | 15 |
| Met | Gly | Thr | Thr | Ile | Asn | Lys | Gln | Phe | Ile | Lys | Ile | Lys | Gly | Lys | Pro |
| | | | | 20 | | | | | 25 | | | | | 30 |
| Ile | Leu | Tyr | Tyr | Ser | Ile | Arg | Ala | Phe | Ser | Ile | Asn | Pro | Leu | Ile | Asp |
| | | | 35 | | | | | 40 | | | | | 45 | | |
| Gly | Ile | Ile | Leu | Val | Cys | Ala | Glu | Thr | Glu | Ile | Glu | Tyr | Cys | Lys | Arg |
| 50 | | | | | 55 | | | | | 60 | | | | | |
| Glu | Val | Val | Asp | Lys | Tyr | Gly | Leu | Gln | Lys | Val | Ile | Lys | Leu | Val | Ala |
| 65 | | | | | 70 | | | | | 75 | | | | | 80 |
| Gly | Gly | Lys | Glu | Arg | Gln | Asp | Ser | Val | Phe | Asn | Gly | Leu | Gly | Val | Leu |
| | | | | 85 | | | | | 90 | | | | | 95 | |
| Glu | Lys | Glu | Asn | Cys | Ser | Val | Val | Leu | Ile | His | Asp | Gly | Ala | Arg | Pro |
| | | | 100 | | | | | 105 | | | | | 110 | | |
| Phe | Val | Thr | Ser | Lys | Ile | Ile | Asp | Asp | Gly | Ile | Lys | Tyr | Ser | Asn | Arg |
| | | | 115 | | | | | 120 | | | | | 125 | | |
| Tyr | Gly | Ala | Cys | Ala | Cys | Gly | Val | Arg | Pro | Lys | Asp | Thr | Leu | Lys | Val |
| | 130 | | | | | 135 | | | | | 140 | | | | |
| Arg | Glu | Glu | Ser | Gly | Phe | Ser | Ser | Ser | Thr | Leu | Glu | Arg | Lys | Ser | Leu |
| 145 | | | | | 150 | | | | | 155 | | | | | 160 |
| Phe | Ala | Val | Gln | Thr | Pro | Gln | Cys | Phe | Lys | Tyr | Asp | Leu | Ile | Tyr | Asp |
| | | | | 165 | | | | | 170 | | | | | 175 | |
| Cys | His | Lys | Lys | Leu | Met | Asn | Glu | Lys | Met | Cys | Val | Thr | Asp | Asp | Thr |
| | | | 180 | | | | | 185 | | | | | 190 | | |
| Met | Val | Val | Glu | Arg | Tyr | Gly | Asn | Lys | Val | Tyr | Leu | Tyr | Glu | Gly | Asn |
| | | 195 | | | | | 200 | | | | | 205 | | | |
| Tyr | Glu | Asn | Ile | Lys | Val | Thr | Thr | Pro | Glu | Asp | Leu | Asn | Ile | Ala | Glu |
| | 210 | | | | | 215 | | | | | 220 | | | | |
| Ser | Ile | Val | Glu | Lys | Tyr | | | | | | | | | | |
| 225 | | | | | 230 | | | | | | | | | | |

```
<210> SEQ ID NO 7
<211> LENGTH: 798
<212> TYPE: DNA
<213> ORGANISM: Clostridium autoethanogenum
<400> SEQUENCE: 7
gtgggaaaaa gaaagatgg gtatcatctt ttgaaaatga taatgcagaa tatagactta      60
tatgatgttt taaaaataga tgagatcaaa actggaatac agatatgctc taataataga     120
tatattccct gtgacaggag aaatttggtt tacagagcag caaaattatt tattgataaa     180
tataatataa agaatggaat tagtatataac ataggtaaaa atatacctgt atcagctgga    240
cttgctggtg aagtgcgga tgctgcagct atactaaaga ctatgagaaa tatttatact     300
cctgaagtaa gtgataaaga attgagcgaa ttaggcttaa atatagggc agatgttcct      360
tattgtataa taggaggtac agccttgtgc gaggggatag agagaaggt tacaccactc      420
atgccgttta gaaaccatat actcatatta attaaccac cttttggagt gagcacagca      480
gaggtatata agagtttaga cataagtaaa ataaaaggc atcctaatac agaaatttta     540
atagatgcgg ttaatgaatc aaaattggag atgctgagta aaacatgaa aaatgttttg     600
```

```
gaaaatgtaa ctttaaaaaa atatcccgtg cttagaaaaa taaaaactga tttgatagat    660
tttggagcag ttggttcact tatgagtgga agcggtccaa gcattttgc ttttttttgat    720 gatatgctaa aagcacagaa atgttatgat aatatgaaaa ctaggtatag agaggtgttt    780
attacaagaa ccatttaa                                                 798
```

<210> SEQ ID NO 8
<211> LENGTH: 265
<212> TYPE: PRT
<213> ORGANISM: Clostridium autoethanogenum

<400> SEQUENCE: 8

```
Met Gly Lys Arg Lys Asp Gly Tyr His Leu Leu Lys Met Ile Met Gln
1               5                   10                  15

Asn Ile Asp Leu Tyr Asp Val Leu Lys Ile Asp Glu Ile Lys Thr Gly
            20                  25                  30

Ile Gln Ile Cys Ser Asn Asn Arg Tyr Ile Pro Cys Asp Arg Arg Asn
        35                  40                  45

Leu Val Tyr Arg Ala Ala Lys Leu Phe Ile Asp Lys Tyr Asn Ile Lys
    50                  55                  60

Asn Gly Ile Ser Ile Asn Ile Gly Lys Asn Ile Pro Val Ser Ala Gly
65                  70                  75                  80

Leu Ala Gly Gly Ser Ala Asp Ala Ala Ala Ile Leu Lys Thr Met Arg
                85                  90                  95

Asn Ile Tyr Thr Pro Glu Val Ser Asp Lys Glu Leu Ser Glu Leu Gly
            100                 105                 110

Leu Asn Ile Gly Ala Asp Val Pro Tyr Cys Ile Ile Gly Gly Thr Ala
        115                 120                 125

Leu Cys Glu Gly Ile Gly Glu Lys Val Thr Pro Leu Met Pro Phe Arg
    130                 135                 140

Asn His Ile Leu Ile Leu Ile Lys Pro Pro Phe Gly Val Ser Thr Ala
145                 150                 155                 160

Glu Val Tyr Lys Ser Leu Asp Ile Ser Lys Ile Lys Arg His Pro Asn
                165                 170                 175

Thr Glu Ile Leu Ile Asp Ala Val Asn Glu Ser Lys Leu Glu Met Leu
            180                 185                 190

Ser Lys Asn Met Lys Asn Val Leu Glu Asn Val Thr Leu Lys Lys Tyr
        195                 200                 205

Pro Val Leu Arg Lys Ile Lys Thr Asp Leu Ile Asp Phe Gly Ala Val
    210                 215                 220

Gly Ser Leu Met Ser Gly Ser Gly Pro Ser Ile Phe Ala Phe Phe Asp
225                 230                 235                 240

Asp Met Leu Lys Ala Gln Lys Cys Tyr Asp Asn Met Lys Thr Arg Tyr
                245                 250                 255

Arg Glu Val Phe Ile Thr Arg Thr Ile
            260                 265
```

<210> SEQ ID NO 9
<211> LENGTH: 480
<212> TYPE: DNA
<213> ORGANISM: Clostridium autoethanogenum

<400> SEQUENCE: 9

```
gtgaaaatcg ggcttggtta tgatgtccat aaattagttt ataatagacc tcttattta     60 ggaggcgtaa atatcccttt tgaaaaggt cttatgggac attcagatgc agatgtactt   120
```

```
cttcatgcaa taatggatag tctccttgga gccttgtgtc taggtgatat cggcaagcat    180
ttccctgata atgataataa atataagaac atatgtagtc ttaaattgct gtcacatgta    240
tcagctttga ttaatgaaaa aggatatact atagggaaca tagattctat tataatagcc    300
gaaaagccta aactttcttc atacatacaa gatatgaggg taaatatagc taaaactcta    360
aatgtaacta cagccgtaat aagtgtaaaa gccactacag aggaaggtct tggctttacc    420
ggcaaaggag aaggcatagc cgctcaaagc atctgtttgt taacagctaa ttcaaaataa    480
```

<210> SEQ ID NO 10
<211> LENGTH: 159
<212> TYPE: PRT
<213> ORGANISM: Clostridium autoethanogenum

<400> SEQUENCE: 10

```
Met Lys Ile Gly Leu Gly Tyr Asp Val His Lys Leu Val Tyr Asn Arg
1               5                   10                  15

Pro Leu Ile Leu Gly Gly Val Asn Ile Pro Phe Glu Lys Gly Leu Met
            20                  25                  30

Gly His Ser Asp Ala Asp Val Leu Leu His Ala Ile Met Asp Ser Leu
        35                  40                  45

Leu Gly Ala Leu Cys Leu Gly Asp Ile Gly Lys His Phe Pro Asp Asn
    50                  55                  60

Asp Asn Lys Tyr Lys Asn Ile Cys Ser Leu Lys Leu Leu Ser His Val
65                  70                  75                  80

Ser Ala Leu Ile Asn Glu Lys Gly Tyr Thr Ile Gly Asn Ile Asp Ser
                85                  90                  95

Ile Ile Ile Ala Glu Lys Pro Lys Leu Ser Ser Tyr Ile Gln Asp Met
            100                 105                 110

Arg Val Asn Ile Ala Lys Thr Leu Asn Val Thr Thr Ala Val Ile Ser
        115                 120                 125

Val Lys Ala Thr Thr Glu Glu Gly Leu Gly Phe Thr Gly Lys Gly Glu
    130                 135                 140

Gly Ile Ala Ala Gln Ser Ile Cys Leu Leu Thr Ala Asn Ser Lys
145                 150                 155
```

<210> SEQ ID NO 11
<211> LENGTH: 1051
<212> TYPE: DNA
<213> ORGANISM: Clostridium autoethanogenum

<400> SEQUENCE: 11

```
ttgaatagag taaaaagaa acagtaaag gtaggcaata tatttttagg tggagatttt       60
ccagtagccg tacaatctat gacaaatacg gatactaggg atgtagaagc cactacagct    120
cagatatttc agctaaaaga agcaggttgt gatatcgtca gatgtgcggt gcctgatgat    180
atagcttgca attccatgaa aaaaatcata gaaagagtag atattccact tgtagcagat    240
atacattttg attataagtt ggcgcttaaa tctatagaaa atgggatatc tgcacttaga    300
ataaatcctg gaatattgg aagcatagaa agagtacgag aagtggcaag agcagcaaaa    360
gaagctaata ttccaattag aataggggta aactctggat cattaaaaaa agatatttta    420
aataaatatg gtagagtttg ttcggatgca ctagtagaga gtgctctaga acatgtaaaa    480
attttggaaa acgtaggatt ttatgatata gttatatcca taaaatcttc aaatgtaaat    540
cagatgatag aaagttatag aaaaatatct gaaattgtag attatccact tcaccttgga    600
gtaacagaag caggaactat ttggcgagga actataaaat caagcatagg cataggtact    660
```

```
cttttgatgg aaggtatagg agacactata agagtatctc ttacaggaaa tccagtggaa    720
gaagtaagag tgggaaaaga atattaaaa tcctgtggaa ttataaaaga aggtgtggaa    780
tttatatcat gtcccacctg tggtagaact gaaattgatt taattaaaat agctgagcaa    840
gtggaaaaaa gacttttaaa tatgcataaa aacataaagg ttgctgttat gggatgtgta    900
gtaaatggac caggtgaggc tcgggaagca gatattggta tagcaggcgg caaaggtgaa    960
ggcattatat ttaaaaaagg aaaaatagta aaaaaggtaa gtgaagaaag tttagtagaa   1020
tcacttatag aagaaataga aaacatttga r                                 1051
```

<210> SEQ ID NO 12
<211> LENGTH: 349
<212> TYPE: PRT
<213> ORGANISM: Clostridium autoethanogenum

<400> SEQUENCE: 12

```
Met Asn Arg Val Lys Lys Thr Val Lys Val Gly Asn Ile Phe Leu
1               5                   10                  15

Gly Gly Asp Phe Pro Val Ala Val Gln Ser Met Thr Asn Thr Asp Thr
                20                  25                  30

Arg Asp Val Glu Ala Thr Thr Ala Gln Ile Phe Gln Leu Lys Glu Ala
            35                  40                  45

Gly Cys Asp Ile Val Arg Cys Ala Val Pro Asp Ile Ala Cys Asn
        50                  55                  60

Ser Met Lys Lys Ile Ile Glu Arg Val Asp Ile Pro Leu Val Ala Asp
65              70                  75                  80

Ile His Phe Asp Tyr Lys Leu Ala Leu Lys Ser Ile Glu Asn Gly Ile
                85                  90                  95

Ser Ala Leu Arg Ile Asn Pro Gly Asn Ile Gly Ser Ile Glu Arg Val
            100                 105                 110

Arg Glu Val Ala Arg Ala Ala Lys Glu Ala Asn Ile Pro Ile Arg Ile
        115                 120                 125

Gly Val Asn Ser Gly Ser Leu Lys Lys Asp Ile Leu Asn Lys Tyr Gly
    130                 135                 140

Arg Val Cys Ser Asp Ala Leu Val Glu Ser Ala Leu Glu His Val Lys
145                 150                 155                 160

Ile Leu Glu Asn Val Gly Phe Tyr Asp Ile Val Ile Ser Ile Lys Ser
                165                 170                 175

Ser Asn Val Asn Gln Met Ile Glu Ser Tyr Arg Lys Ile Ser Glu Ile
            180                 185                 190

Val Asp Tyr Pro Leu His Leu Gly Val Thr Glu Ala Gly Thr Ile Trp
        195                 200                 205

Arg Gly Thr Ile Lys Ser Ser Ile Gly Ile Gly Thr Leu Leu Met Glu
    210                 215                 220

Gly Ile Gly Asp Thr Ile Arg Val Ser Leu Thr Gly Asn Pro Val Glu
225                 230                 235                 240

Glu Val Arg Val Gly Lys Glu Ile Leu Lys Ser Cys Gly Ile Ile Lys
                245                 250                 255

Glu Gly Val Glu Phe Ile Ser Cys Pro Thr Cys Gly Arg Thr Glu Ile
            260                 265                 270

Asp Leu Ile Lys Ile Ala Glu Gln Val Glu Lys Arg Leu Leu Asn Met
        275                 280                 285

His Lys Asn Ile Lys Val Ala Val Met Gly Cys Val Val Asn Gly Pro
    290                 295                 300
```

```
Gly Glu Ala Arg Glu Ala Asp Ile Gly Ile Ala Gly Gly Lys Gly Glu
305                 310                 315                 320

Gly Ile Ile Phe Lys Lys Gly Lys Ile Val Lys Val Ser Glu Glu
                325                 330                 335

Ser Leu Val Glu Ser Leu Ile Glu Glu Ile Glu Asn Ile
            340                 345

<210> SEQ ID NO 13
<211> LENGTH: 1923
<212> TYPE: DNA
<213> ORGANISM: Clostridium autoethanogenum

<400> SEQUENCE: 13
```

| | | | | | |
|---|---|---|---|---|---|
| gtgataaaat | tgaacattat | tttagcagac | aaatccggat | tttgctttgg | agtaaaaaga |    60 |
| gctgtagacg | aatctttaaa | ggttcaaaaa | aaatttaata | aaaaaatata | tactttaggt |   120 |
| cctttgattc | ataatagtga | tgtagtaaat | aaattaaagg | aaaaaggtat | atatcctata |   180 |
| gaaatagata | atatagataa | tctaagggaa | gatgatgtgg | ttataatacg | ttctcatggt |   240 |
| gttcccgaaa | aaatattttt | tactttaaaa | aataaaaaaa | taaacatagt | aaatgcaact |   300 |
| tgcccatatg | ttttaaatat | acaaagaaaa | gtacaagaat | attataaatt | agggtattct |   360 |
| atattaatag | taggagataa | aaatcatcct | gaagtaattg | aataaatgg | atggtgtgaa |   420 |
| aataaagctt | taatatctaa | agatggcacc | aatttagaaa | agttaccatc | aaaactgtgt |   480 |
| atagtttctc | aaactacaga | aaacaatct | aactgggaaa | agtgcttag | tatagtggct |   540 |
| aaaaattgta | agaatttat | tgcttttaat | actatatgca | gtgccacaga | atttcgtcag |   600 |
| aaggcagcag | cagatatttc | taaagaagta | gatatgatgg | tagtaatagg | tggtaaaaac |   660 |
| agctctaata | ctactaaact | ttatgaaata | tgtaaagata | actgcaataa | tactattat |   720 |
| gttgaaaatt | caggagaaat | acctgatgat | ataagtaatt | gtaataaaat | taaaactata |   780 |
| ggtgttacag | caggagcttc | aacaccagat | tggataataa | aggaggcaat | tttaaaaatg |   840 |
| agtgatgaca | aaaatttaga | actaaatgag | caactatctt | atatggacaa | aaatgatacc |   900 |
| caaataatat | taggtgaaaa | aattaagggt | acagtaatat | ctgtaaatcc | aaaagaggtt |   960 |
| tttttaaata | taggatataa | atcagaaggt | gtacttccaa | aacgtgaaat | aacaaaaaat |  1020 |
| gaaagtgaca | acttagaaga | attaattcat | tgtggagatg | aattatatgt | taaagtaata |  1080 |
| agaagacaaa | atgaagatgg | atatgtggta | ttatctaaga | tagaattaga | aagagaaaat |  1140 |
| gcttataaag | aattaaagga | agctaatgga | aatagtcagg | tattaaaggt | tattgtaaaa |  1200 |
| gaagctgtaa | atggaggtct | tgttgccaat | tacaaaggtg | ctagggtatt | tatacctgct |  1260 |
| tctcatgtag | aattatatca | tgtagatgat | ctttcacaat | atgtagataa | agagcttgat |  1320 |
| gtaactataa | ttgaatttaa | agaagaaaag | aaaggtacca | gaatagtagc | ttcaagaaga |  1380 |
| gaccttttga | aatggaaag | agaaaaaatg | gaagaacaga | cttggaatgt | gcttgaaaaa |  1440 |
| gatactgtag | tagatggtga | agttagaaga | ttgactgatt | ttggcgcatt | tgttgatgta |  1500 |
| caaggagttg | acgggcttct | acatgtatct | gaactttcct | ggggaagagt | tggaaaacca |  1560 |
| agtgatgttt | taaaaatcgg | agatacgatt | aaggtttata | tcttagacat | tgataaagaa |  1620 |
| aaaaagaagt | tatctttatc | tttaaaaaag | ctcatggaag | atccatggat | caacgtagac |  1680 |
| ataaaatatc | ctgttggcaa | tgtagttctt | ggtaaagtag | ttaggtttgc | aaattttggt |  1740 |
| gcatttgttg | aattagagcc | aggtgtagat | gcattagttc | atatatcaca | aataagccat |  1800 |
| aagagaatag | ataaaccaga | agatgtactt | aaaataggtc | aggaaataaa | ggctaagatc |  1860 |

```
cttgaagtaa acaaagatag cgaaaaaata gctttaagta taaagaagt agatgaaatc    1920 taa                                                                1923
```

<210> SEQ ID NO 14
<211> LENGTH: 640
<212> TYPE: PRT
<213> ORGANISM: Clostridium autoethanogenum

<400> SEQUENCE: 14

```
Met Ile Lys Leu Asn Ile Ile Leu Ala Asp Lys Ser Gly Phe Cys Phe
1               5                  10                  15

Gly Val Lys Arg Ala Val Asp Glu Ser Leu Lys Val Gln Lys Lys Phe
            20                  25                  30

Asn Lys Lys Ile Tyr Thr Leu Gly Pro Leu Ile His Asn Ser Asp Val
        35                  40                  45

Val Asn Lys Leu Lys Glu Lys Gly Ile Tyr Pro Ile Glu Ile Asp Asn
    50                  55                  60

Ile Asp Asn Leu Arg Glu Asp Val Val Ile Ile Arg Ser His Gly
65                  70                  75                  80

Val Pro Glu Lys Ile Phe Phe Thr Leu Lys Asn Lys Lys Ile Asn Ile
                85                  90                  95

Val Asn Ala Thr Cys Pro Tyr Val Leu Asn Ile Gln Arg Lys Val Gln
            100                 105                 110

Glu Tyr Tyr Lys Leu Gly Tyr Ser Ile Leu Ile Val Gly Asp Lys Asn
        115                 120                 125

His Pro Glu Val Ile Gly Ile Asn Gly Trp Cys Glu Asn Lys Ala Leu
    130                 135                 140

Ile Ser Lys Asp Gly Thr Asn Leu Glu Lys Leu Pro Ser Lys Leu Cys
145                 150                 155                 160

Ile Val Ser Gln Thr Thr Glu Lys Gln Ser Asn Trp Glu Lys Val Leu
                165                 170                 175

Ser Ile Val Ala Lys Asn Cys Lys Glu Phe Ile Ala Phe Asn Thr Ile
            180                 185                 190

Cys Ser Ala Thr Glu Phe Arg Gln Lys Ala Ala Ala Asp Ile Ser Lys
        195                 200                 205

Glu Val Asp Met Met Val Val Ile Gly Gly Lys Asn Ser Ser Asn Thr
    210                 215                 220

Thr Lys Leu Tyr Glu Ile Cys Lys Asp Asn Cys Asn Asn Thr Ile Tyr
225                 230                 235                 240

Val Glu Asn Ser Gly Glu Ile Pro Asp Asp Ile Ser Asn Cys Asn Lys
                245                 250                 255

Ile Lys Thr Ile Gly Val Thr Ala Gly Ala Ser Thr Pro Asp Trp Ile
            260                 265                 270

Ile Lys Glu Ala Ile Leu Lys Met Ser Asp Asp Lys Asn Leu Glu Leu
        275                 280                 285

Asn Glu Gln Leu Ser Tyr Met Asp Lys Asn Asp Thr Gln Ile Ile Leu
    290                 295                 300

Gly Glu Lys Ile Lys Gly Thr Val Ile Ser Val Asn Pro Lys Glu Val
305                 310                 315                 320

Phe Leu Asn Ile Gly Tyr Lys Ser Glu Gly Val Leu Pro Lys Arg Glu
                325                 330                 335

Ile Thr Lys Asn Glu Ser Asp Asn Leu Glu Glu Leu Ile His Cys Gly
            340                 345                 350
```

Asp Glu Leu Tyr Val Lys Val Ile Arg Arg Gln Asn Glu Asp Gly Tyr
        355                 360                 365

Val Val Leu Ser Lys Ile Glu Leu Glu Arg Glu Asn Ala Tyr Lys Glu
    370                 375                 380

Leu Lys Glu Ala Asn Gly Asn Ser Gln Val Leu Lys Val Ile Val Lys
385                 390                 395                 400

Glu Ala Val Asn Gly Leu Val Ala Asn Tyr Lys Gly Ala Arg Val
                405                 410                 415

Phe Ile Pro Ala Ser His Val Glu Leu Tyr His Val Asp Asp Leu Ser
            420                 425                 430

Gln Tyr Val Asp Lys Glu Leu Asp Val Thr Ile Glu Phe Lys Glu
        435                 440                 445

Glu Lys Lys Gly Thr Arg Ile Val Ala Ser Arg Arg Asp Leu Leu Arg
    450                 455                 460

Met Glu Arg Glu Lys Met Glu Glu Gln Thr Trp Asn Val Leu Glu Lys
465                 470                 475                 480

Asp Thr Val Val Asp Gly Glu Val Arg Arg Leu Thr Asp Phe Gly Ala
                485                 490                 495

Phe Val Asp Val Gln Gly Val Asp Gly Leu Leu His Val Ser Glu Leu
            500                 505                 510

Ser Trp Gly Arg Val Gly Lys Pro Ser Asp Val Leu Lys Ile Gly Asp
        515                 520                 525

Thr Ile Lys Val Tyr Ile Leu Asp Ile Asp Lys Glu Lys Lys Lys Leu
    530                 535                 540

Ser Leu Ser Leu Lys Lys Leu Met Glu Asp Pro Trp Ile Asn Val Asp
545                 550                 555                 560

Ile Lys Tyr Pro Val Gly Asn Val Val Leu Gly Lys Val Val Arg Phe
                565                 570                 575

Ala Asn Phe Gly Ala Phe Val Glu Leu Glu Pro Gly Val Asp Ala Leu
            580                 585                 590

Val His Ile Ser Gln Ile Ser His Lys Arg Ile Asp Lys Pro Glu Asp
        595                 600                 605

Val Leu Lys Ile Gly Gln Glu Ile Lys Ala Lys Ile Leu Glu Val Asn
    610                 615                 620

Lys Asp Ser Glu Lys Ile Ala Leu Ser Ile Lys Glu Val Asp Glu Ile
625                 630                 635                 640

<210> SEQ ID NO 15
<211> LENGTH: 882
<212> TYPE: DNA
<213> ORGANISM: Clostridium autoethanogenum

<400> SEQUENCE: 15
atggaaatta aaggtgtaat tgaaacatta agagaggaat tgaataaata cctctatgac      60
tatatggagg gaaaaggatc ttataataag agagtatatg aagctatgca gtatagctta    120
gatgcaggag gaaagagaat aagacctcta ctatttcttt tgacatataa actttataag    180
acagattgca atgaggttat ggatatagca gcagctatag aaatgataca cacttattcc    240
ttaattcatg atgatttacc tgctatggac aatgatgatt taagaagggg caaacctaca    300
aatcataagg tatttggaga agctattgct gtacttgcgg gagatggact tttaaatgaa    360
gcaatgagtc tgatgtttag acactgtatt gggaaaaagg ataacgctat aagggcttgt    420
agcattattt ctgaaagtgc aggagctgat gggatggttg cggacagac agtggatatt    480 ttaagtgaaa acactaagat acctatagat cagctctatt acatgcacag taaaaaaacg    540

```
ggagcgctca taaaaggatc tataatatct gcagcagtat atgcgggagc aagtaaagct    600
gaaatagata aattaagcta ttatggagaa aagttaggat tggcatttca aataaaggat    660
gatatattgg atttaacagg agatactgct cttttaggta aaaagataaa aagtgatcta    720
aataataaca aaactacatt tataagtact tatggaataa ataaatgcaa agaaatgtgc    780
aattcaatta caagtgaatg tataggagta ctgaatggga tgagtgtaga tacttcttat    840
ctaaaagatt taacatcatt ttttattaaat agagaaaagt ga                     882
```

<210> SEQ ID NO 16
<211> LENGTH: 293
<212> TYPE: PRT
<213> ORGANISM: Clostridium autoethanogenum
<400> SEQUENCE: 16

```
Met Glu Ile Lys Gly Val Ile Glu Thr Leu Arg Glu Leu Asn Lys
1               5                   10                  15

Tyr Leu Tyr Asp Tyr Met Glu Gly Lys Gly Ser Tyr Asn Lys Arg Val
            20                  25                  30

Tyr Glu Ala Met Gln Tyr Ser Leu Asp Ala Gly Gly Lys Arg Ile Arg
        35                  40                  45

Pro Leu Leu Phe Leu Leu Thr Tyr Lys Leu Tyr Lys Thr Asp Cys Asn
    50                  55                  60

Glu Val Met Asp Ile Ala Ala Ala Ile Glu Met Ile His Thr Tyr Ser
65                  70                  75                  80

Leu Ile His Asp Asp Leu Pro Ala Met Asp Asn Asp Leu Arg Arg
                85                  90                  95

Gly Lys Pro Thr Asn His Lys Val Phe Gly Glu Ala Ile Ala Val Leu
            100                 105                 110

Ala Gly Asp Gly Leu Leu Asn Glu Ala Met Ser Leu Met Phe Arg His
        115                 120                 125

Cys Ile Gly Lys Lys Asp Asn Ala Ile Arg Ala Cys Ser Ile Ile Ser
    130                 135                 140

Glu Ser Ala Gly Ala Asp Gly Met Val Gly Gly Gln Thr Val Asp Ile
145                 150                 155                 160

Leu Ser Glu Asn Thr Lys Ile Pro Ile Asp Gln Leu Tyr Tyr Met His
                165                 170                 175

Ser Lys Lys Thr Gly Ala Leu Ile Lys Gly Ser Ile Ile Ser Ala Ala
            180                 185                 190

Val Tyr Ala Gly Ala Ser Lys Ala Glu Ile Asp Lys Leu Ser Tyr Tyr
        195                 200                 205

Gly Glu Lys Leu Gly Leu Ala Phe Gln Ile Lys Asp Asp Ile Leu Asp
    210                 215                 220

Leu Thr Gly Asp Thr Ala Leu Leu Gly Lys Lys Ile Lys Ser Asp Leu
225                 230                 235                 240

Asn Asn Asn Lys Thr Thr Phe Ile Ser Thr Tyr Gly Ile Asn Lys Cys
                245                 250                 255

Lys Glu Met Cys Asn Ser Ile Thr Ser Glu Cys Ile Gly Val Leu Asn
            260                 265                 270

Gly Met Ser Val Asp Thr Ser Tyr Leu Lys Asp Leu Thr Ser Phe Leu
        275                 280                 285

Leu Asn Arg Glu Lys
    290
```

-continued

<210> SEQ ID NO 17
<211> LENGTH: 519
<212> TYPE: DNA
<213> ORGANISM: Clostridium autoethanogenum

<400> SEQUENCE: 17

```
atgaataaaa caaggaaaat ggttttttta agctttctaa caagtatggc tttagtcata      60
tacataatag aaactcaagt tccggtttta tttcccggaa taaaattagg acttgcaaat     120
acaatttccc tagctgcact tatacttata ggatggaaag aagccttact aattatgttt     180
ttaaggacgc ttctaggatc tatgtttggt gggacaatgt ctacctttat gttcagcata     240
gccggaggaa ttttaagtaa cattgttatg atccttctat acaaatattt taaaaattcc     300
ttaagtctat ggactataag catatgcggg gcaatatttc acaacatagg ccaacttttta    360
gtagcttcta tagtaattca agattttagg atatacatat atctaccggt gcttttaatc     420
tctgctataa tcacaggata ctttataggt tggtgcgtga attcctaac taataactta      480
tataaaattc ctatgtttaa agaattaaaa ataagtaa                             519
```

<210> SEQ ID NO 18
<211> LENGTH: 172
<212> TYPE: PRT
<213> ORGANISM: Clostridium autoethanogenum

<400> SEQUENCE: 18

```
Met Asn Lys Thr Arg Lys Met Val Phe Leu Ser Phe Leu Thr Ser Met
1               5                   10                  15

Ala Leu Val Ile Tyr Ile Ile Glu Thr Gln Val Pro Val Leu Phe Pro
            20                  25                  30

Gly Ile Lys Leu Gly Leu Ala Asn Thr Ile Ser Leu Ala Ala Leu Ile
        35                  40                  45

Leu Ile Gly Trp Lys Glu Ala Leu Leu Ile Met Phe Leu Arg Thr Leu
    50                  55                  60

Leu Gly Ser Met Phe Gly Gly Thr Met Ser Thr Phe Met Phe Ser Ile
65                  70                  75                  80

Ala Gly Gly Ile Leu Ser Asn Ile Val Met Ile Leu Leu Tyr Lys Tyr
                85                  90                  95

Phe Lys Asn Ser Leu Ser Leu Trp Thr Ile Ser Ile Cys Gly Ala Ile
            100                 105                 110

Phe His Asn Ile Gly Gln Leu Val Ala Ser Ile Val Ile Gln Asp
        115                 120                 125

Phe Arg Ile Tyr Ile Tyr Leu Pro Val Leu Leu Ile Ser Ala Ile Ile
    130                 135                 140

Thr Gly Tyr Phe Ile Gly Trp Cys Val Lys Phe Leu Thr Asn Asn Leu
145                 150                 155                 160

Tyr Lys Ile Pro Met Phe Lys Glu Leu Lys Asn Lys
                165                 170
```

<210> SEQ ID NO 19
<211> LENGTH: 825
<212> TYPE: DNA
<213> ORGANISM: Clostridium autoethanogenum

<400> SEQUENCE: 19

```
atgaacttcg atggaatttc aattccaata ataaaagaac ttaatcaact tgagttagag      60
ttaaaaaata ttgcatcaaa attagattct actgttacac aagatatttt tacctacttt     120
ttttcaattc caggtaaaag actaagacct acattaacat ttttatctgc aggtgctatt     180
```

-continued

```
agtagcgagc ttacttcatc tgcaaaacac aacttaattc agttgtcaat aagcttagag     240
cttattcaca gcgctagtct aattcatgat gatatcatag atggtgactt actaagacgt     300
ggtcagaaaa ccttaaataa gacctttgga aataaaatag cagtacttgc cggtgatgct     360
ttgtactcaa gggcctttac tattttctca gatactctgc aagagaatt tgcgcaggta      420
atgggcagag ttactgaatc aatgtctgta gctgaaatat aaatgctaa caatccctct      480
cccgatcgtg aaacctattt taaaatcatc ttaggaaaaa cagcatcttt catgagcgct     540
tgttgtaggc ttggtggcag catagcttat gccccttacg aagagtctaa tatgctttct     600
aaatacggtg aaaaccttgg tatggcatat caaatactgg atgattatat cgatgaggat     660
cccgttgcaa tgaaaaatgt aactattgaa gagggatttg aatttgcata taatgccaaa     720
gcttctattg aaaatttaaa agactcagca tacaaacaaa gcttaataat gttagtagac     780
tatgttttag attttatag tcctaaggta gagaatacat tatag                      825
```

<210> SEQ ID NO 20
<211> LENGTH: 274
<212> TYPE: PRT
<213> ORGANISM: Clostridium autoethanogenum

<400> SEQUENCE: 20

```
Met Asn Phe Asp Gly Ile Ser Ile Pro Ile Ile Lys Glu Leu Asn Gln
1               5                   10                  15

Leu Glu Leu Glu Leu Lys Asn Ile Ala Ser Lys Leu Asp Ser Thr Val
            20                  25                  30

Thr Gln Asp Ile Phe Thr Tyr Phe Phe Ser Ile Pro Gly Lys Arg Leu
        35                  40                  45

Arg Pro Thr Leu Thr Phe Leu Ser Ala Gly Ala Ile Ser Ser Glu Leu
    50                  55                  60

Thr Ser Ser Ala Lys His Asn Leu Ile Gln Leu Ser Ile Ser Leu Glu
65                  70                  75                  80

Leu Ile His Ser Ala Ser Leu Ile His Asp Asp Ile Ile Asp Gly Asp
                85                  90                  95

Leu Leu Arg Arg Gly Gln Lys Thr Leu Asn Lys Thr Phe Gly Asn Lys
            100                 105                 110

Ile Ala Val Leu Ala Gly Asp Ala Leu Tyr Ser Arg Ala Phe Thr Ile
        115                 120                 125

Phe Ser Asp Thr Leu Pro Arg Glu Phe Ala Gln Val Met Gly Arg Val
    130                 135                 140

Thr Glu Ser Met Ser Val Ala Glu Ile Leu Asn Ala Asn Asn Pro Ser
145                 150                 155                 160

Pro Asp Arg Glu Thr Tyr Phe Lys Ile Ile Leu Gly Lys Thr Ala Ser
                165                 170                 175

Phe Met Ser Ala Cys Cys Arg Leu Gly Gly Ser Ile Ala Tyr Ala Pro
            180                 185                 190

Tyr Glu Glu Ser Asn Met Leu Ser Lys Tyr Gly Glu Asn Leu Gly Met
        195                 200                 205

Ala Tyr Gln Ile Leu Asp Asp Tyr Ile Asp Glu Asp Pro Val Ala Met
    210                 215                 220

Lys Asn Val Thr Ile Glu Glu Gly Phe Glu Phe Ala Tyr Asn Ala Lys
225                 230                 235                 240

Ala Ser Ile Glu Asn Leu Lys Asp Ser Ala Tyr Lys Gln Ser Leu Ile
                245                 250                 255
```

```
Met Leu Val Asp Tyr Val Leu Asp Phe Tyr Ser Pro Lys Val Glu Asn
        260                 265                 270

Thr Leu
```

<210> SEQ ID NO 21
<211> LENGTH: 1797
<212> TYPE: DNA
<213> ORGANISM: Populus tremuloides

<400> SEQUENCE: 21

```
catatggcaa cagaattatt atgtttacac agacctatat cacttactca caaactttt      60
aggaatccat tacctaaagt tattcaagct acacctttaa cattaaaact taggtgtagt    120
gtttctacag aaaatgtatc atttagtgag acagaaactg aaacaagaag atcagcaaat    180
tatgaaccaa attcttggga ttatgattat cttctttctt ctgatactga tgagtcaata    240
gaagtacata agataaggc taagaaatta gaagctgaag ttaggagaga aataaataat     300
gagaaggctg aatttcttac acttcttgaa cttattgata tgtacaaag acttggatta     360
ggatatagat ttgagtctga tataagaaga gcattagata gatttgtaag tagtggagga    420
tttgatggag ttactaaaac ttcattacat ggaacagcat tatcatttag gttattaagg    480
caacatggtt ttgaagtatc tcaagaagct tttagtggat ttaaagatca gaatggaaac    540
tttcttgaga atttaaagga agacataaaa gcaattcttt ctctttatga agcatcattt    600
ttagcattag aaggtgagaa tatattagat gaggctaaag tatttgcaat atctcatctt    660
aaagaactta gtgaagaaaa gattggtaaa gaattagctg aacaagtttc acatgcttta    720
gaattaccat tacatagaag aacacaaaga ttagaagcag tttggtcaat agaagcatat    780
agaaagaaag aagacgcaaa tcaagtactt ttagaacttg caatacttga ctacaatatg    840
attcaaagtg tatatcagag ggatttaaga gaaacatcaa gatggtggag aagagtagga    900
ttagcaacta aattacattt tgctagagat aggcttattg aaagtttta ttgggctgtt     960
ggagttgctt ttgaaccaca atattctgat gcagaaata gtgtagcaaa gatgttttca   1020
tttgttacta taattgacga tatttacgat gtatatggaa ctttagatga acttgaactt   1080
tttactgatg cagttgaaag atgggatgta aatgctatta atgatcttcc tgattatatg   1140
aagttatgtt ttcttgcact ttacaatact attaacgaga tagcttacga taacttaaaa   1200
gataaaggtg agaacatact tccttatta acaaaagcat gggcagattt atgtaatgca   1260
tttcttcaag aagctaagtg gctttataat aaatcaacac ctacatttga tgattatttt   1320
ggaaatgcat ggaaaagttc tagtggacct ttacagctta ttttgcctta ttttgctgta   1380
gtacagaaca ttaaaaagga agagattgag aatcttcaga aatatcatga cataatatca   1440
agacctagtc acatttttag gctttgtaat gatttagcat ctgcttcagc agaaatagca   1500
agaggtgaaa ctgctaattc tgtaagttgt tatatgagaa caaaaggtat atctgaagaa   1560
ttagctactg aaagtgttat gaatcttata gacgaaactt ggaagaaaat gaacaaagaa   1620
aaacttggtg gatctttatt tgcaaaacct tttgttgaga ctgctataaa tttagctaga   1680
cagtctcatt gcacatatca taatggtgat gcacatacta gtccagatga attaactagg   1740
aaaagagtac ttagtgtaat aactgaacca atattaccat ttgaaagata agaattc      1797
```

<210> SEQ ID NO 22
<211> LENGTH: 617
<212> TYPE: DNA
<213> ORGANISM: Clostridium autoethanogenum

<400> SEQUENCE: 22

```
ggttaatgtt aaaaatttat agtataactt taaaaaactg tcttaaaaag ttgttatata    60
aaaaatgttg acaattaaac agctatttag tgcaaaacaa ccataaaaat ttaaaaaata   120
ccataaatta cttgaaaaat agttgataat aatgtagagt tataaacaaa ggtgaaaagc   180
attacttgta ttctttttta tatattatta taaattaaaa tgaagctgta ttagaaaaaa   240
tacacacctg taatataaaa ttttaaatta attttttaatt ttttcaaaat gtattttaca   300
tgtttagaat tttgatgtat attaaaatag tagaatacat aagatactta atttaattaa   360
agatagttaa gtacttttca atgtgctttt ttagatgttt aatacaaatc tttaattgta   420
aaagaaatgc tgtactattt actgtactag tgacgggatt aaactgtatt aattataaat   480
aaaaaataag tacagttgtt taaaattata ttttgtatta aatctaatag tacgatgtaa   540
gttattttat actattgcta gtttaataaa aagatttaat tatatacttg aaaaggagag   600
gaattttat gcgtaaa                                                   617
```

```
<210> SEQ ID NO 23
<211> LENGTH: 30
<212> TYPE: DNA
<213> ORGANISM: Artificial Sequence
<220> FEATURE:
<223> OTHER INFORMATION: oligonucleotide Ppfor-NotI-F
```

<400> SEQUENCE: 23

```
aagcggccgc aaaatagttg ataataatgc                                     30
```

```
<210> SEQ ID NO 24
<211> LENGTH: 30
<212> TYPE: DNA
<213> ORGANISM: Artificial Sequence
<220> FEATURE:
<223> OTHER INFORMATION: oligonucleotide Ppfor-NdeI-R
```

<400> SEQUENCE: 24

```
tacgcatatg aattcctctc cttttcaagc                                     30
```

```
<210> SEQ ID NO 25
<211> LENGTH: 5345
<212> TYPE: DNA
<213> ORGANISM: Artificial Sequence
<220> FEATURE:
<223> OTHER INFORMATION: plasmid pMTL 85146-ispS
```

<400> SEQUENCE: 25

```
aattcgagct cggtacccgg ggatcctcta gagtcgacgt cacgcgtcca tggagatctc    60
gaggcctgca gacatgcaag cttggcactg gccgtcgttt tacaacgtcg tgactgggaa   120
aaccctggcg ttacccaact taatcgcctt gcagcacatc cccctttcgc cagctggcgt   180
aatagcgaag aggcccgcac cgatcgccct tcccaacagt tgcgcagcct gaatggcgaa   240
tggcgctagc ataaaaataa gaagcctgca tttgcaggct tcttattttt atggcgcgcc   300
gcattcactt cttttctata taaatatgag cgaagcgaat aagcgtcgga aaagcagcaa   360
aaagtttcct tttgctgtt ggagcatggg ggttcagggg gtgcagtatc tgacgtcaat   420
gccgagcgaa agcgagccga agggtagcat ttacgttaga taacccctg atatgctccg   480
acgctttata tagaaaagaa gattcaacta ggtaaaatct taatataggt tgagatgata   540
aggtttataa ggaatttgtt tgttctaatt tttcactcat tttgttctaa tttcttttaa   600
caaatgttct ttttttttta gaacagttat gatatagtta gaatagttta aaataaggag   660
```

```
tgagaaaaag atgaaagaaa gatatggaac agtctataaa ggctctcaga ggctcataga      720
cgaagaaagt ggagaagtca tagaggtaga caagttatac cgtaaacaaa cgtctggtaa      780
cttcgtaaag gcatatatag tgcaattaat aagtatgtta gatatgattg gcggaaaaaa      840
acttaaaatc gttaactata tcctagataa tgtccactta agtaacaata caatgatagc      900
tacaacaaga gaaatagcaa aagctacagg aacaagtcta caaacagtaa taacaacact      960
taaaatctta gaagaaggaa atattataaa aagaaaaact ggagtattaa tgttaaaccc     1020
tgaactacta atgagaggcg acgaccaaaa acaaaaatac ctcttactcg aatttgggaa     1080
ctttgagcaa gaggcaaatg aaatagattg acctcccaat aacaccacgt agttattggg     1140
aggtcaatct atgaaatgcg attaagggcc ggccagtggg caagttgaaa aattcacaaa     1200
aatgtggtat aatatctttg ttcattagag cgataaactt gaatttgaga gggaacttag     1260
atggtatttg aaaaaattga taaaaatagt tggaacagaa aagagtattt tgaccactac     1320
tttgcaagtg taccttgtac ctacagcatg accgttaaag tggatatcac acaaataaag     1380
gaaaagggaa tgaaactata tcctgcaatg ctttattata ttgcaatgat tgtaaaccgc     1440
cattcagagt ttaggacggc aatcaatcaa gatggtgaat tggggatata tgatgagatg     1500
ataccaagct atacaatatt tcacaatgat actgaaacat tttccagcct ttggactgag     1560
tgtaagtctg actttaaatc attttttagca gattatgaaa gtgatacgca acggtatgga     1620
aacaatcata gaatggaagg aaagccaaat gctccggaaa acatttttaa tgtatctatg     1680
ataccgtggt caaccttcga tggctttaat ctgaatttgc agaaaggata tgattatttg     1740
attcctattt ttactatggg gaaatattat aaagaagata caaaattat acttcctttg     1800 gcaattcaag ttcatcacgc agtatgtgac ggatttcaca tttgccgttt tgtaaacgaa     1860
ttgcaggaat tgataaatag ttaacttcag gtttgtctgt aactaaaaac aagtatttaa     1920
gcaaaaacat cgtagaaata cggtgttttt tgttaccctca agtttaaact ccttttgat     1980 aatctcatga ccaaaatccc ttaacgtgag ttttcgttcc actgagcgtc agacccgta     2040 gaaaagatca aaggatcttc ttgagatcct ttttttctgc gcgtaatctg ctgcttgcaa     2100
acaaaaaaac caccgctacc agcggtggtt tgtttgccgg atcaagagct accaactctt     2160
tttccgaagg taactggctt cagcagagcg cagataccaa atactgttct tctagtgtag     2220
ccgtagttag gccaccactt caagaactct gtagcaccgc ctacatacct cgctctgcta     2280
atcctgttac cagtggctgc tgccagtggc gataagtcgt gtcttaccgg gttggactca     2340
agacgatagt taccggataa ggcgcagcgg tcgggctgaa cggggggttc gtgcacacag     2400
cccagcttgg agcgaacgac ctacaccgaa ctgagatacc tacagcgtga gctatgagaa     2460
agcgccacgc ttcccgaagg gagaaaggcg gacaggtatc cggtaagcgg cagggtcgga     2520
acaggagagc gcacgaggga gcttccaggg ggaaacgcct ggtatcttta tagtcctgtc     2580
gggtttcgcc acctctgact tgagcgtcga tttttgtgat gctcgtcagg ggggcggagc     2640
ctatggaaaa acgccagcaa cgcggccttt ttacggttcc tggccttttg ctggccttt     2700 gctcacatgt tctttcctgc gttatcccct gattctgtgg ataaccgtat taccgccttt     2760
gagtgagctg ataccgctcg ccgcagccga acgaccgagc gcagcgagtc agtgagcgag     2820
gaagcggaag agcgcccaat acgcagggcc ccctgcagga taaaaaaatt gtagataaat     2880
tttataaaat agttttatct acaattttt tatcaggaaa cagctatgac cgcggccgcg     2940
gttaatgtta aaaattata gtataacttt aaaaaactgt cttaaaagt tgttatataa     3000
```

```
aaaatgttga caattaaaca gctatttagt gcaaacaac cataaaaatt taaaaaatac    3060 cataaaattac ttgaaaaata gttgataata atgtagagtt ataaacaaag gtgaaaagca   3120
ttacttgtat tctttttat atattattat aaattaaaat gaagctgtat tagaaaaaat    3180
acacacctgt aatataaaat tttaaattaa tttttaattt tttcaaaatg tattttacat   3240
gtttagaatt ttgatgtata ttaaaatagt agaatacata agatacttaa tttaattaaa   3300
gatagttaag tacttttcaa tgtgcttttt tagatgttta atacaaatct ttaattgtaa   3360
aagaaatgct gtactatta ctgtactagt gacgggatta aactgtatta attataaata    3420
aaaaataagt acagttgttt aaaattatat tttgtattaa atctaatagt acgatgtaag   3480
ttattttata ctattgctag tttaataaaa agatttaatt atatacttga aaggagagg    3540 aattttatg cgtcatatgg caacagaatt attatgttta cacagaccta tatcacttac   3600
tcacaaactt tttaggaatc cattacctaa agttattcaa gctacacctt taacattaaa   3660
acttaggtgt agtgtttcta cagaaaatgt atcatttagt gagacagaaa ctgaaacaag   3720
aagatcagca aattatgaac caaattcttg ggattatgat tatcttcttt cttctgatac   3780
tgatgagtca atagaagtac ataaagataa ggctaagaaa ttagaagctg aagttaggag   3840
agaaataaat aatgagaagg ctgaatttct tacacttctt gaacttattg ataatgtaca   3900
aagacttgga ttaggatata gatttgagtc tgatataaga agagcattag atagatttgt   3960
aagtagtgga ggatttgatg gagttactaa aacttcatta catggaacag cattatcatt   4020
taggttatta aggcaacatg gttttgaagt atctcaagaa gcttttagtg gatttaaaga   4080
tcagaatgga aactttcttg agaatttaaa ggaagacata aaagcaattc tttctcttta   4140
tgaagcatca tttttagcat tagaaggtga gaatatatta gatgaggcta aagtatttgc   4200
aatatctcat cttaaagaac ttagtgaaga aaagattggt aaagaattag ctgaacaagt   4260
ttcacatgct ttagaattac cattacatag aagaacacaa agattagaag cagtttggtc   4320
aatagaagca tatagaaaga aagaagacgc aaatcaagta cttttagaac ttgcaatact   4380
tgactacaat atgattcaaa gtgtatatca gagggattta agagaaacat caagatggtg   4440
gagaagagta ggattagcaa ctaaattaca ttttgctaga gataggctta ttgaaagttt   4500
ttattgggct gttggagttg cttttgaacc acaatattct gattgcagaa atagtgtagc   4560
aaagatgttt tcatttgtta ctataattga cgatatttac gatgtatatg aactttaga   4620 tgaacttgaa ctttttactg atgcagttga aagatgggat gtaaatgcta ttaatgatct   4680
tcctgattat atgaagttat gttttcttgc actttacaat actattaacg agatagctta   4740
cgataactta aaagataaag gtgagaacat acttccttat ttaacaaaag catgggcaga   4800
tttatgtaat gcatttcttc aagaagctaa gtggctttat aataaatcaa cacctacatt   4860
tgatgattat tttggaaatg catggaaaag ttctagtgga cctttacagc ttattttttgc   4920 ttattttgct gtagtacaga acattaaaaa ggaagagatt gagaatcttc agaaatatca   4980
tgacataata tcaagaccta gtcacatttt taggctttgt aatgatttag catctgcttc   5040
agcagaaata gcaagaggtg aaactgctaa ttctgtaagt tgttatatga gaacaaaagg   5100
tatatctgaa gaattagcta ctgaaagtgt tatgaatctt atagacgaaa cttggaagaa   5160
aatgaacaaa gaaaaacttg gtggatcttt atttgcaaaa ccttttgttg agactgctat   5220
aaatttagct agacagtctc attgcacata tcataatggt gatgcacata ctagtccaga   5280
tgaattaact aggaaaagag tacttagtgt aataactgaa ccaatattac catttgaaag   5340
ataag                                                              5345
```

<210> SEQ ID NO 26
<211> LENGTH: 26
<212> TYPE: DNA
<213> ORGANISM: Artificial Sequence
<220> FEATURE:
<223> OTHER INFORMATION: Oligonucleotide Idi-Cbei-SacI-F

<400> SEQUENCE: 26
gtgagctcga aagggaaat taaatg                                    26

<210> SEQ ID NO 27
<211> LENGTH: 27
<212> TYPE: DNA
<213> ORGANISM: Artificial Sequence
<220> FEATURE:
<223> OTHER INFORMATION: Oligonucleotide Idi-Cbei-KpnI-R

<400> SEQUENCE: 27
atggtacccc aaatctttat ttagacg                                  27

<210> SEQ ID NO 28
<211> LENGTH: 5905
<212> TYPE: DNA
<213> ORGANISM: Artificial Sequence
<220> FEATURE:
<223> OTHER INFORMATION: plasmid pMTL85246-ispS-idi

<400> SEQUENCE: 28

```
ccggggatcc tctagagtcg acgtcacgcg tccatggaga tctcgaggcc tgcagacatg     60
caagcttggc actggccgtc gttttacaac gtcgtgactg ggaaaaccct ggcgttaccc    120
aacttaatcg ccttgcagca catccccctt tcgccagctg gcgtaatagc gaagaggccc    180
gcaccgatcg cccttcccaa cagttgcgca gcctgaatgg cgaatggcgc tagcataaaa    240
ataagaagcc tgcatttgca ggcttcttat ttttatggcg cgccgcattc acttcttttc    300
tatataaata tgagcgaagc gaataagcgt cggaaaagca gcaaaagtt tcctttttgc     360 tgttggagca tgggggttca ggggtgcag tatctgacgt caatgccgag cgaaagcgag    420
ccgaagggta gcatttacgt tagataaccc cctgatatgc tccgacgctt tatatagaaa    480
agaagattca actaggtaaa atcttaatat aggttgagat gataaggttt taaggaatt     540 tgtttgttct aatttttcac tcattttgtt ctaatttctt ttaacaaatg ttcttttttt    600
tttagaacag ttatgatata gttagaatag tttaaaataa ggagtgagaa aaagatgaaa    660
gaaagatatg aacagtctca taaggctct cagaggctca tagacgaaga agtggagaa      720 gtcatagagg tagacaagtt ataccgtaaa caaacgtctg gtaacttcgt aaaggcatat    780
atagtgcaat aataagtat gttagatatg attggcggaa aaaaacttaa aatcgttaac    840
tatatcctag ataatgtcca cttaagtaac aatacaatga tagctacaac aagagaaata   900
gcaaaagcta caggaacaag tctacaaaca gtaataacaa cacttaaaat cttagaagaa    960
ggaaatatta taaaagaaa aactggagta ttaatgttaa accctgaact actaatgaga   1020
ggcgacgacc aaaacaaaa atacctctta ctcgaatttg gaactttga gcaagaggca    1080 aatgaaatag attgacctcc caataacacc acgtagttat gggaggtca atctatgaaa    1140 tgcgattaag ggccggccag tgggcaagtt gaaaaattca caaaatgtg gtataatatc    1200 tttgttcatt agagcgataa acttgaattt gagagggaac ttagatggta tttgaaaaaa    1260
ttgataaaaa tagttggaac agaaaagagt attttgacca ctactttgca agtgtacctt    1320
```

```
gtacctacag catgaccgtt aaagtggata tcacacaaat aaaggaaaag ggaatgaaac    1380
tatatcctgc aatgctttat tatattgcaa tgattgtaaa ccgccattca gagtttagga    1440
cggcaatcaa tcaagatggt gaattgggga tatatgatga gatgatacca agctatacaa    1500
tatttcacaa tgatactgaa acattttcca gcctttggac tgagtgtaag tctgacttta    1560
aatcattttt agcagattat gaaagtgata cgcaacggta tggaaacaat catagaatgg    1620
aaggaaagcc aaatgctccg gaaaacattt ttaatgtatc tatgataccg tggtcaacct    1680
tcgatggctt taatctgaat ttgcagaaag gatatgatta tttgattcct attttttacta   1740 tggggaaata ttataaagaa gataacaaaa ttatacttcc tttggcaatt caagttcatc    1800
acgcagtatg tgacggattt cacatttgcc gttttgtaaa cgaattgcag gaattgataa    1860
atagttaact tcaggtttgt ctgtaactaa aaacaagtat ttaagcaaaa acatcgtaga    1920
aatacggtgt tttttgttac cctaagttta aactcctttt tgataatctc atgaccaaaa    1980
tcccttaacg tgagttttcg ttccactgag cgtcagaccc cgtagaaaag atcaaaggat    2040
cttcttgaga tccttttttt ctgcgcgtaa tctgctgctt gcaaacaaaa aaaccaccgc    2100
taccagcggt ggtttgtttg ccggatcaag agctaccaac tcttttccg aaggtaactg     2160 gcttcagcag agcgcagata ccaaatactg ttcttctagt gtagccgtag ttaggccacc    2220
acttcaagaa ctctgtagca ccgcctacat acctcgctct gctaatcctg ttaccagtgg    2280
ctgctgccag tggcgataag tcgtgtctta ccgggttgga ctcaagacga tagttaccgg    2340
ataaggcgca gcggtcgggc tgaacggggg gttcgtgcac acagcccagc ttggagcgaa    2400
cgacctacac cgaactgaga tacctacagc gtgagctatg agaaagcgcc acgcttcccg    2460
aagggagaaa ggcggacagg tatccggtaa gcggcagggt cggaacagga gagcgcacga    2520
gggagcttcc agggggaaac gcctggtatc tttatagtcc tgtcgggttt cgccacctct    2580
gacttgagcg tcgatttttg tgatgctcgt caggggggcg gagcctatgg aaaaacgcca    2640
gcaacgcggc cttttacgg ttcctggcct tttgctggcc ttttgctcac atgttctttc     2700
ctgcgttatc ccctgattct gtggataacc gtattaccgc ctttgagtga gctgataccg    2760
ctcgccgcag ccgaacgacc gagcgcagcg agtcagtgag cgaggaagcg gaagagcgcc    2820
caatacgcag ggcccctgc aggataaaaa aattgtagat aaatttata aatagtttt      2880 atctacaatt tttttatcag gaaacagcta tgaccgcggc cgcggttaat gttaaaaatt    2940
tatagtataa ctttaaaaaa ctgtcttaaa aagttgttat ataaaaatg ttgacaatta    3000 aacagctatt tagtgcaaaa caaccataaa aatttaaaaa ataccataaa ttacttgaaa    3060
aatagttgat aataatgtag agttataaac aaaggtgaaa agcattactt gtattctttt    3120
ttatatatta ttataaatta aaatgaagct gtattagaaa aaatacacac ctgtaatata    3180
aaattttaaa ttaattttta atttttttcaa aatgtatttt acatgtttag aatttttgatg   3240 tatattaaaa tagtagaata cataagatac ttaatttaat taaagatagt taagtacttt    3300
tcaatgtgct tttttagatg tttaatacaa atctttaatt gtaaagaaaa tgctgtacta    3360
tttactgtac tagtgacggg attaaactgt attaattata aataaaaaat aagtacagtt    3420
gtttaaaatt atattttgta ttaaatctaa tagtacgatg taagttattt tatactattg    3480
ctagtttaat aaaaagattt aattatatac ttgaaaagga gaggaatttt tatgcgtcat    3540
atggcaacag aattattatg tttacacaga cctatatcac ttactcacaa acttttagg    3600 aatccattac ctaaagttat tcaagctaca ccttttaacat taaaacttag gtgtagtgtt    3660
tctacagaaa atgtatcatt tagtgagaca gaaactgaaa caagaagatc agcaaattat    3720
```

```
gaaccaaatt cttgggatta tgattatctt ctttcttctg atactgatga gtcaatagaa    3780
gtacataaag ataaggctaa gaaattagaa gctgaagtta ggagagaaat aaataatgag    3840
aaggctgaat ttcttacact tcttgaactt attgataatg tacaaagact tggattagga    3900
tatagatttg agtctgatat aagaagagca ttagatagat ttgtaagtag tggaggattt    3960
gatggagtta ctaaaacttc attacatgga acagcattat catttaggtt attaaggcaa    4020
catggttttg aagtatctca agaagctttt agtggattta agatcagaa tggaaacttt     4080
cttgagaatt taaaggaaga cataaaagca attctttctc tttatgaagc atcatttta    4140
gcattagaag gtgagaatat attagatgag gctaaagtat ttgcaatatc tcatcttaaa    4200
gaacttagtg aagaaaagat tggtaaagaa ttagctgaac aagtttcaca tgctttagaa    4260
ttaccattac atagaagaac acaaagatta gaagcagttt ggtcaataga agcatataga    4320
aagaaagaag acgcaaatca agtactttta gaacttgcaa tacttgacta caatatgatt    4380
caaagtgtat atcagaggga tttaagaaaa acatcaagat ggtggagaag agtaggatta    4440
gcaactaaat tacattttgc tagagatagg cttattgaaa gtttttattg ggctgttgga    4500
gttgcttttg aaccacaata ttctgattgc agaaatagtg tagcaaagat gtttcattt    4560
gttactataa ttgacgatat ttacgatgta tatggaactt tagatgaact tgaactttt    4620
actgatgcag ttgaaagatg ggatgtaaat gctattaatg atcttcctga ttatatgaag    4680
ttatgttttc ttgcacttta caatactatt aacgagatag cttacgataa cttaaaagat    4740
aaaggtgaga acatacttcc ttatttaaca aaagcatggg cagatttatg taatgcattt    4800
cttcaagaag ctaagtggct ttataataaa tcaacaccta catttgatga ttattttgga    4860
aatgcatgga aaagttctag tggaccttta cagcttattt ttgcttattt tgctgtagta    4920
cagaacatta aaaaggaaga gattgagaat cttcagaaat atcatgacat aatatcaaga    4980
cctagtcaca tttttaggct ttgtaatgat ttagcatctg cttcagcaga aatagcaaga    5040
ggtgaaactg ctaattctgt aagttgttat atgagaacaa aaggtatatc tgaagaatta    5100
gctactgaaa gtgttatgaa tcttatagac gaaacttgga agaaaatgaa caaagaaaaa    5160
cttggtggat ctttatttgc aaaacctttt gttgagactg ctataaattt agctagacag    5220
tctcattgca catatcataa tggtgatgca catactagtc cagatgaatt aactaggaaa    5280
agagtactta gtgtaataac tgaaccaata ttaccatttg aaagataaga attcgagctc    5340
gaaagggaa attaaatggc agaatatata atagctgtag atgaatttga taacgaaata    5400
ggttcaattg aaaaaatgga ggctcaccgt aaaggaacat tacatagagc ttttctata    5460
ttagtattta attctaaaaa tcaattgtta ttacagaaaa gaaatgtaaa aaaatatcat    5520
tcgcctggtc tctggacaaa tacgtgctgt agtcatccaa gatacggtga agtttacat    5580
gatgcgattt atagaaggct taaggaagaa atgggtttta catgtgaact tgaagaagta    5640
tttagtttta tttataaagt aaaacttgaa gataatcttt ttgaaaatga atatgatcat    5700
gtattcattg ggaaatatga tggagaaata attgtaaaca aagatgaagt agatgatttt    5760
aagtgggttg atattaatga ggttaagaag gatattatag aaaggccaga agcatacact    5820
tattggttca agtatttagt taataaggca gaaaacaaaa tatttaaata agtaagaatt    5880
tcgtctaaat aaagatttgg ggtac                                         5905
```

<210> SEQ ID NO 29
<211> LENGTH: 29
<212> TYPE: DNA

```
<213> ORGANISM: Artificial Sequence
<220> FEATURE:
<223> OTHER INFORMATION: Oligonucleotide Dxs-SalI-F

<400> SEQUENCE: 29
gcagtcgact ttattaaagg gatagataa                                        29

<210> SEQ ID NO 30
<211> LENGTH: 31
<212> TYPE: DNA
<213> ORGANISM: Artificial Sequence
<220> FEATURE:
<223> OTHER INFORMATION: Oligonucleotide Dxs-XhoI-R

<400> SEQUENCE: 30
tgctcgagtt aaaatatatg acttacctct g                                     31

<210> SEQ ID NO 31
<211> LENGTH: 7784
<212> TYPE: DNA
<213> ORGANISM: Artificial Sequence
<220> FEATURE:
<223> OTHER INFORMATION: plasmid pMTL85246-ispS-idi-dxs

<400> SEQUENCE: 31
```

| | | | | | |
|---|---|---|---|---|---|
| tcgaggcctg | cagacatgca | agcttggcac | tggccgtcgt | tttacaacgt | cgtgactggg | 60 |
| aaaaccctgg | cgttacccaa | cttaatcgcc | ttgcagcaca | tccccctttc | gccagctggc | 120 |
| gtaatagcga | agaggcccgc | accgatcgcc | cttcccaaca | gttgcgcagc | ctgaatggcg | 180 |
| aatggcgcta | gcataaaaat | aagaagcctg | catttgcagg | cttcttattt | ttatggcgcg | 240 |
| ccgcattcac | ttcttttcta | tataaatatg | agcgaagcga | ataagcgtcg | gaaaagcagc | 300 |
| aaaaagtttc | cttttgctg | ttggagcatg | ggggttcagg | gggtgcagta | tctgacgtca | 360 |
| atgccgagcg | aaagcgagcc | gaagggtagc | atttacgtta | gataaccccc | tgatatgctc | 420 |
| cgacgcttta | tatagaaaag | aagattcaac | taggtaaaat | cttaatatag | gttgagatga | 480 |
| taaggtttat | aaggaatttg | tttgttctaa | ttttcactc | attttgttct | aatttctttt | 540 |
| aacaaatgtt | cttttttttt | tagaacagtt | atgatatagt | tagaatagtt | taaaataagg | 600 |
| agtgagaaaa | agatgaaaga | aagatatgga | acagtctata | aaggctctca | gaggctcata | 660 |
| gacgaagaaa | gtggagaagt | catagaggta | gacaagttat | accgtaaaca | aacgtctggt | 720 |
| aacttcgtaa | aggcatatat | agtgcaatta | ataagtatgt | tagatatgat | tggcggaaaa | 780 |
| aaacttaaaa | tcgttaacta | tatcctagat | aatgtccact | taagtaacaa | tacaatgata | 840 |
| gctacaacaa | gagaaatagc | aaaagctaca | ggaacaagtc | tacaaacagt | aataacaaca | 900 |
| cttaaaatct | tagaagaagg | aaatattata | aaagaaaaa | ctggagtatt | aatgttaaac | 960 |
| cctgaactac | taatgagagg | cgacgaccaa | aaacaaaaat | acctcttact | cgaatttggg | 1020 |
| aactttgagc | aagaggcaaa | tgaaatagat | tgacctccca | ataacaccac | gtagttattg | 1080 |
| ggaggtcaat | ctatgaaatg | cgattaaggg | ccggccagtg | ggcaagttga | aaaattcaca | 1140 |
| aaaatgtggt | ataatatctt | tgttcattag | agcgataaac | ttgaatttga | gagggaactt | 1200 |
| agatggtatt | tgaaaaaatt | gataaaaata | gttggaacag | aaaagagtat | tttgaccact | 1260 |
| actttgcaag | tgtaccttgt | acctacagca | tgaccgttaa | agtggatatc | acacaaataa | 1320 |
| aggaaaaggg | aatgaaacta | tatcctgcaa | tgctttatta | tattgcaatg | attgtaaacc | 1380 |
| gccattcaga | gtttaggacg | gcaatcaatc | aagatggtga | attggggata | tatgatgaga | 1440 |
| tgataccaag | ctatacaata | tttcacaatg | atactgaaac | attttccagc | ctttggactg | 1500 |

```
agtgtaagtc tgactttaaa tcattttttag cagattatga aagtgatacg caacggtatg    1560
gaaacaatca tagaatggaa ggaaagccaa atgctccgga aaacattttt aatgtatcta    1620
tgataccgtg gtcaaccttc gatggcttta atctgaattt gcagaaagga tatgattatt    1680
tgattcctat ttttactatg gggaaatatt ataaagaaga taacaaaatt atacttcctt    1740
tggcaattca agttcatcac gcagtatgtg acggatttca catttgccgt tttgtaaacg    1800
aattgcagga attgataaat agttaacttc aggtttgtct gtaactaaaa acaagtattt    1860
aagcaaaaac atcgtagaaa tacggtgttt tttgttaccc taagtttaaa ctccttttg    1920 ataatctcat gaccaaaatc ccttaacgtg agttttcgtt ccactgagcg tcagaccccg    1980
tagaaaagat caaaggatct tcttgagatc ctttttttct gcgcgtaatc tgctgcttgc    2040
aaacaaaaaa accaccgcta ccagcggtgg tttgtttgcc ggatcaagag ctaccaactc    2100
tttttccgaa ggtaactggc ttcagcagag cgcagatacc aaatactgtt cttctagtgt    2160
agccgtagtt aggccaccac ttcaagaact ctgtagcacc gcctacatac ctcgctctgc    2220
taatcctgtt accagtggct gctgccagtg gcgataagtc gtgtcttacc gggttggact    2280
caagacgata gttaccggat aaggcgcagc ggtcgggctg aacggggggt tcgtgcacac    2340
agcccagctt ggagcgaacg acctacaccg aactgagata cctacagcgt gagctatgag    2400
aaagcgccac gcttcccgaa gggagaaagg cggacaggta tccggtaagc ggcagggtcg    2460
gaacaggaga gcgcacgagg gagcttccag ggggaaacgc ctggtatctt tatagtcctg    2520
tcgggtttcg ccacctctga cttgagcgtc gatttttgtg atgctcgtca ggggggcgga    2580
gcctatggaa aaacgccagc aacgcggcct ttttacggtt cctggccttt tgctggcctt    2640
ttgctcacat gttctttcct gcgttatccc ctgattctgt ggataaccgt attaccgcct    2700
ttgagtgagc tgataccgct cgccgcagcc gaacgaccga gcgcagcgag tcagtgagcg    2760
aggaagcgga agagcgccca atacgcaggg ccccctgcag gataaaaaaa ttgtagataa    2820
attttataaa atagttttat ctacaatttt tttatcagga aacagctatg accgcggccg    2880
cggttaatgt taaaaattta tagtataact ttaaaaaact gtcttaaaaa gttgttatat    2940
aaaaaatgtt gacaattaaa cagctatta gtgcaaaaca accataaaaa tttaaaaaat    3000
accataaatt acttgaaaaa tagttgataa taatgtagag ttataaacaa aggtgaaaag    3060
cattacttgt attcttttt atatattatt ataaattaaa atgaagctgt attagaaaaa    3120
atacacacct gtaatataaa attttaaatt aattttttaat tttttcaaaa tgtattttac    3180
atgtttagaa ttttgatgta tattaaaata gtagaataca taagtacttt aatttaatta    3240
aagatagtta agtactttc aatgtgcttt tttagatgtt taatacaaat ctttaattgt    3300
aaaagaaatg ctgtactatt tactgtacta gtgacgggat taaactgtat taattataaa    3360
taaaaaataa gtacagttgt ttaaaattat attttgtatt aaatctaata gtacgatgta    3420
agttatttta tactattgct agtttaataa aaagatttaa ttatatactt gaaaaggaga    3480 ggaatttta tgcgtcatat ggcaacagaa ttattatgtt tacacagacc tatatcactt    3540
actcacaaac ttttttaggaa tccattacct aaagttattc aagctacacc tttaacatta    3600
aaacttaggt gtagtgtttc tacagaaaat gtatcattta gtgagacaga aactgaaaca    3660
agaagatcag caaattatga accaaattct tgggattatg attatcttct ttcttctgat    3720
actgatgagt caatagaagt acataaagat aaggctaaga aattgagaagc tgaagttagg    3780 agagaaataa ataatgagaa ggctgaattt cttcacacttc ttgaacttat tgataatgta    3840
```

```
caaagacttg gattaggata tagatttgag tctgatataa gaagagcatt agatagattt    3900
gtaagtagtg gaggatttga tggagttact aaaacttcat tacatggaac agcattatca    3960
tttaggttat taaggcaaca tggttttgaa gtatctcaag aagcttttag tggatttaaa    4020
gatcagaatg gaaactttct tgagaattta aggaagaca taaaagcaat tctttctctt     4080
tatgaagcat cattttagc attagaaggt gagaatatat tagatgaggc taaagtattt     4140
gcaatatctc atcttaaaga acttagtgaa gaaaagattg gtaaagaatt agctgaacaa    4200
gtttcacatg ctttagaatt accattacat agaagaacac aaagattaga agcagtttgg    4260
tcaatagaag catatagaaa gaaagaagac gcaaatcaag tacttttaga acttgcaata    4320
cttgactaca atatgattca aagtgtatat cagagggatt taagagaaac atcaagatgg    4380
tggagaagag taggattagc aactaaatta cattttgcta gagataggct tattgaaagt    4440
ttttattggg ctgttggagt tgcttttgaa ccacaatatt ctgattgcag aaatagtgta    4500
gcaaagatgt tttcatttgt tactataatt gacgatattt acgatgtata tggaaccttta   4560 gatgaacttg aacttttac tgatgcagtt gaaagatggg atgtaaatgc tattaatgat     4620
cttcctgatt atatgaagtt atgttttctt gcactttaca atactattaa cgagatagct    4680
tacgataact taaaagataa aggtgagaac atacttcctt atttaacaaa agcatgggca    4740
gatttatgta atgcatttct tcaagaagct aagtggcttt ataataaatc aacacctaca    4800
tttgatgatt attttggaaa tgcatggaaa agttctagtg gacctttaca gcttattttt    4860
gcttattttg ctgtagtaca gaacattaaa aaggaagaga ttgagaatct tcagaaatat    4920
catgacataa tatcaagacc tagtcacatt tttaggcttt gtaatgattt agcatctgct    4980
tcagcagaaa tagcaagagg tgaaactgct aattctgtaa gttgttatat gagaacaaaa    5040
ggtatatctg aagaattagc tactgaaagt gttatgaatc ttatagacga aacttggaag    5100
aaaatgaaca aagaaaaact tggtggatct ttatttgcaa aaccttttgt tgagactgct    5160
ataaatttag ctagacagtc tcattgcaca tatcataatg gtgatgcaca tactagtcca    5220
gatgaattaa ctaggaaaag agtacttagt gtaataactg aaccaatatt accatttgaa    5280
agataagaat tcgagctcga aaggggaaat taaatggcag aatatataat agctgtagat    5340
gaatttgata acgaaatagg ttcaattgaa aaaatggagg ctcaccgtaa aggaacatta    5400
catagagctt tttctatatt agtatttaat tctaaaaatc aattgttatt acagaaaaga    5460
aatgtaaaaa aatatcattc gcctggtctc tggacaaata cgtgctgtag tcatccaaga    5520
tacggtgaaa gttacatga tgcgatttat agaaggctta aggaagaaat gggttttaca     5580
tgtgaacttg aagaagtatt tagttttatt tataaagtaa aacttgaaga taatcttttt    5640
gaaaatgaat atgatcatgt attcattggg aaatatgatg gagaaataat tgtaaacaaa    5700
gatgaagtag atgattttaa gtgggttgat attaatgagg ttaagaagga tattatagaa    5760
aggccagaag catacactta ttggttcaag tatttagtta ataaggcaga aaacaaaata    5820
tttaaataag taagaatttc gtctaaataa agatttgggg tacccgggga tcctctagag    5880
tcgactttat taagggata gataaggatg agtaatttat tagataatta taaagatata    5940
aatgacgtaa agaagatgtc gttaaatgat aaaaaaagc tagctagaga aattagaaaa    6000 ttttaatag acaaagtatc taagacagga ggtcatttgg cgtctaactt aggggttgtg    6060
gagctcactt tgagtttatt tagtgtattt gatctaaatt atgataaact tatatgggat    6120
gtgggacatc aggcttatgt gcataaaatc ctcacgggaa gaaaggataa atttgatact    6180
ttaaggcaat ttggaggatt aagtggatt cctaaaaggt gcgaaagtat atatgatttt    6240
```

```
ttcgaaacag ggcatagtag tacttcaata tctgcagcac ttggaatggc tagggctaga    6300
gatttaaagc atgagaaata taatgttgtt gcagttatag gagatggagc acttactgga    6360
ggtatggcac tagaggccct aaatgatgta ggttatagaa aaactaagct tataataata    6420
ttaaatgata atcaaatgtc tataggaaaa aatgtaggtg gagtatctaa atatttaaat    6480
aaacttagag tggaccctaa gtataataaa tttaaagcgg atgtagaagc taaattaaaa    6540
aagataccta atataggaaa aggaatggca aaatatcttg aaaaggtaaa aaatggaata    6600
aaacaaatgg tagttcctgg aatgtttttt gaagatatgg gaattaaata tttaggacca    6660
atagatggtc ataatataaa agaacttaca gacgtactcg cttctgcaaa agacatacaa    6720
ggtccagtta ttatacatat aataactaag aaaggaaaag gatatgaatt tgcaagaaaa    6780
aaatccaggt aaattccatg gaatagggcc ttttaattgc gccaatggtg aactggatgc    6840
tggatcttca aatacttatt ccaaggcctt tggaaatgaa atggtaaagc tagcagaaaa    6900
agacgataga atagtggcta taactgcagc catgagggat ggaacaggtc ttaaaagttt    6960
ttctcaaaag tttcctgaaa ggttttttga tgtgggaata gcagaacagc atgctgtaac    7020
cctggcagct ggaatggcac aggcaaattt aaaacctgta tttgcagttt actctacttt    7080
tcttcaaaga gcttatgatc aacttattca tgatgtatgt atgcaaaaac ttccagtagt    7140
ttttgctgta gatagggccg gcattgtagg agaagatggt gaaacacatc agggaatatt    7200
tgatttatct tacttaacgg aaatgccaca tatgacgctt atgtctccta aatgtataga    7260
tgaacttcca tatatgttaa aatgggcatt aggccagagt tttcctgtag ctataaggta    7320
tccaagggga ggagatagtg tatgtctcaa tcccgtagaa aattttaaac ttggaaagtg    7380
ggactgtatt tcaaatgaag gcagtgtagc aataattgct cagggtaaaa tggtacaaaa    7440
tgcagtgtta gcaggaaaaa aacttaaaga aaagggtata gatgtaagga ttataagtgc    7500
atgttttatt aagccgctgg acaaggaaat gttaaacagg ttagttgaag aaagtgtaac    7560
tatcgttact gttgaagaca atgtaataag aggaggatta ggatcctata tattagaata    7620
tgtaaataaa ttaaataaaa aagtaaaaat aataaactta gggtttgatg ataagtttgt    7680
acagcatgga aaatccgata ttttgtataa gctgtatggt ttggatccta aaggtatcgt    7740
aaatagtgta cttgaagcag cagaggtaag tcatatattt taac                    7784
```

<210> SEQ ID NO 32
<211> LENGTH: 17
<212> TYPE: DNA
<213> ORGANISM: Artificial Sequence
<220> FEATURE:
<223> OTHER INFORMATION: Oligonucleotide M13R

<400> SEQUENCE: 32
caggaaacag ctatgac                                                   17

<210> SEQ ID NO 33
<211> LENGTH: 20
<212> TYPE: DNA
<213> ORGANISM: Artificial Sequence
<220> FEATURE:
<223> OTHER INFORMATION: Oligonucleotides Isoprene-seq1

<400> SEQUENCE: 33
gttattcaag ctacaccttt                                                20

<210> SEQ ID NO 34

```
<211> LENGTH: 20
<212> TYPE: DNA
<213> ORGANISM: Artificial Sequence
<220> FEATURE:
<223> OTHER INFORMATION: Oligonucleotide Isoprene-seq2

<400> SEQUENCE: 34
gattggtaaa gaattagctg                                               20

<210> SEQ ID NO 35
<211> LENGTH: 18
<212> TYPE: DNA
<213> ORGANISM: Artificial Sequence
<220> FEATURE:
<223> OTHER INFORMATION: Oligonucleotide Isoprene-seq3

<400> SEQUENCE: 35
tcaagaagct aagtggct                                                 18

<210> SEQ ID NO 36
<211> LENGTH: 17
<212> TYPE: DNA
<213> ORGANISM: Artificial Sequence
<220> FEATURE:
<223> OTHER INFORMATION: Oligonucleotide Isoprene-seq4

<400> SEQUENCE: 36
ctcaccgtaa aggaaca                                                  17

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide Isoprene-seq5

<400> SEQUENCE: 37
gctagctaga gaaattagaa                                               20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide Isoprene-seq6

<400> SEQUENCE: 38
ggaatggcaa aatatcttga                                               20

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide Isoprene-seq7

<400> SEQUENCE: 39
gaaacacatc agggaatatt                                               20

<210> SEQ ID NO 40
<211> LENGTH: 1179
<212> TYPE: DNA
<213> ORGANISM: Clostridium acetobutylicum

<400> SEQUENCE: 40
atgaaagagg ttgttattgc atcagctgtt agaactgcaa taggatctta tggaaaaagt    60
```

-continued

| | |
|---|---|
| cttaaagatg taccagcagt agacttaggt gcaactgcaa taaaggaagc agtaaagaaa | 120 |
| gcaggtataa aacctgaaga tgttaatgaa gttattttag gaaacgtatt acaagctgga | 180 |
| cttggacaga atccagctag acaggcatca ttcaaagcag gattaccagt agagatacct | 240 |
| gctatgacta ttaataaagt ttgtggttca ggattaagaa cagtttcttt agctgctcaa | 300 |
| attataaaag ctggtgacgc agatgtaata atagcaggtg gtatggaaaa tatgtcaaga | 360 |
| gcaccatacc ttgctaataa tgctagatgg ggttatagaa tgggaaacgc taaatttgta | 420 |
| gacgaaatga taactgatgg actttgggat gcatttaacg attatcacat gggaattact | 480 |
| gctgaaaata tagctgagag atggaatata agtagagaag aacaagatga gtttgcactt | 540 |
| gcatctcaga aaaaggcaga agaagctatt aaatcaggac aatttaaaga tgaaattgtt | 600 |
| ccagtagtaa ttaaaggtag aaaaggtgaa acagttgtag acactgatga acatcctaga | 660 |
| tttggatcta caatagaagg tttagctaaa ttaaagcctg cttttaagaa agacggaaca | 720 |
| gtaactgctg gaaacgcatc aggttttaaat gattgtgcag ctgttttagt tattatgtct | 780 |
| gctgaaaagg caaaggaatt aggtgttaaa ccacttgcta agatagttag ttatggttca | 840 |
| gcaggtgtag atcctgctat tatgggatat ggaccttttt atgctacaaa ggcagctatt | 900 |
| gaaaaggctg gttggacagt tgatgaactt gatcttatag agtcaaatga ggcatttgca | 960 |
| gcacaaagtc ttgctgttgc taaggatctt aaattcgata tgaataaagt aaatgtaaac | 1020 |
| ggtggtgcta tagcacttgg tcatccaata ggtgctagtg gtgctagaat tttagttaca | 1080 |
| ttagttcatg caatgcaaaa gagagacgct aaaaagggac ttgcaacttt atgcataggt | 1140 |
| ggtggtcaag gaacagcaat acttcttgaa aaatgttaa | 1179 |

<210> SEQ ID NO 41
<211> LENGTH: 1140
<212> TYPE: DNA
<213> ORGANISM: Staphylococcus aureus subsp. aureus

<400> SEQUENCE: 41

| | |
|---|---|
| atgaatcagg ctgttatagt tgctgcaaag agaactgcat ttggaaaata tggtggtact | 60 |
| ttaaaacacc ttgaaccaga acaattactt aagccattat ttcagcactt taaagaaaaa | 120 |
| tatcctgaag ttatatctaa aatagatgat gtagttttag gaaacgtagt tggaaatggt | 180 |
| ggtaatattg ctagaaaagc acttcttgaa gcaggattaa aagatagtat accaggtgta | 240 |
| actatagaca gacaatgcgg atctggatta gaatcagtac aatacgcatg tagaatgata | 300 |
| caagcaggtg ctgaaaaagt ttatattgca ggtggtgttg aatctacatc aagagccacct | 360 |
| tggaaaataa agagaccaca ttctgtttat gaaactgcat taccagagtt ctatgaaaga | 420 |
| gcatcattcg cacctgaaat gtcagatcca agtatgatac aaggtgctga gaatgtagct | 480 |
| aaaatgtatg atgttagtag agaacttcaa gatgagtttg catacagatc acatcaactt | 540 |
| acagctgaaa atgtaaagaa tggaaatatt tcacaagaaa ttcttccaat aacagtaaag | 600 |
| ggtgaaatat tcaatactga tgaaagttta aaatctcata ttccaaaaga taattttcggt | 660 |
| agatttaaac ctgtaataaa aggtggtact gtaacagctg ctaatagttg tatgaagaac | 720 |
| gatggtgcag tattattact tattatggaa aaggatatgg cttatgaact tggatttgag | 780 |
| catggattat tatttaaaga cggtgtaact gtaggtgtag atagtaactt tccaggaata | 840 |
| ggacctgttc ctgctatatc aaatctttta aagagaaacc aacttacaat agaaaatatt | 900 |
| gaagtaattg agataaatga agcatttttct gctcaggtag ttgcttgtca gcaagctctt | 960 |

```
aatataagta atactcagtt aaacatttgg ggtggtgcat tagcaagtgg tcatccttat    1020
ggtgcatcag gtgcacagtt agttacaaga ttattttata tgttcgataa agagacaatg    1080
attgcttcta tgggaatagg tggtggttta ggaaatgcag ctcttttac tagattttaa     1140
```

<210> SEQ ID NO 42
<211> LENGTH: 1167
<212> TYPE: DNA
<213> ORGANISM: Staphylococcus aureus subsp. aureus

<400> SEQUENCE: 42

```
atgactatag gaattgacaa aataaacttt tacgtaccaa atattatgt agatatggca       60 aaattagcag aagcaagaca agtagaccca aataaatttc ttattggaat aggacagact    120
gaaatggcag ttagtccagt aaaccaagat atagtatcaa tgggtgctaa tgctgctaaa    180
gatataataa ctgatgaaga caaaagaaa ataggaatgg taatagtagc aactgagtca     240
gcagtagatg cagcaaaggc agcagcagta cagattcata atttattagg tattcaacca    300
tttgcaagat gtttcgaaat gaagaagca tgttatgctg ctactcctgc aattcagtta     360
gctaaggatt atttagctac aagaccaaat gagaaagttt tagttatagc tacagataca    420
gctagatatg gacttaattc aggtggtgaa cctactcaag gtgctggtgc tgttgctatg    480
gttatagctc ataatcctag tatacttgca ttaaatgaag acgctgttgc ttatacagaa    540
gatgtttatg atttctggag accaacagga cataagtatc cattagtaga tggtgcttta    600
tcaaaagacg catatattag atcttttcaa caatcttgga tgaatatgc taagagacaa     660 ggaaagagtt tagctgattt tgctagtctt tgctttcatg ttcctttac taaaatgggt     720 aaaaaggctt tagaatctat aatagataac gcagatgaaa caactcaaga gagattaaga    780
tctggatatg aagatgcagt tgattacaat agatatgttg gaaatatata cacaggaagt    840
ctttatcttt ctcttataag tcttcttgaa aatagagatt tacaggctgg tgaaactatt    900
ggattatttt catacggatc aggttctgtt ggtgaatttt attcagctac acttgtagaa    960
ggatataaag atcaccttga tcaggcagca cacaaagcac ttttaaacaa tagaactgaa    1020
gtatcagtag atgcatacga aacattttc aagagatttg atgatgtaga atttgatgaa    1080
gagcaggatg cagttcatga agatagacat atattctatc tttcaaacat agagaataat    1140
gtaagagaat atcatagacc tgaataa                                         1167
```

<210> SEQ ID NO 43
<211> LENGTH: 1278
<212> TYPE: DNA
<213> ORGANISM: Staphylococcus aureus subsp. aureus

<400> SEQUENCE: 43

```
atgcaatcat tagacaaaaa tttcagacat ttatcaagac aacaaaagtt acaacaatta      60
gttgataaac agtggctttc agaagatcag tttgatattt tacttaatca tcctcttata    120
gatgaagaag ttgctaatag tcttatagaa aatgtaattg cacagggtgc attaccagtt    180
ggacttcttc ctaatataat agttgatgat aaggcttatg ttgtaccaat gatggttgaa    240
gaacctagtt tgttgcagc tgcatcttat ggtgctaaat tagtaaatca gacaggtgga     300
tttaaaactg tatcatcaga aagaataatg attggacaga tagtatttga tggtgtagat    360
gacactgaaa aattaagtgc agatattaaa gcattagaaa aacaaataca taagattgca    420
gatgaagcat atcctagtat aaaagcaaga ggtggtggtt atcaaagaat agcaatagat    480
acatttccag agcaacaact tttaagtctt aaggtatttg tagatacaaa agatgctatg    540
```

```
ggtgctaata tgcttaatac tatacttgag gcaataactg cattccttaa aaatgaatct      600
cctcaatcag atatattaat gtctatactt tcaaaccatg caactgctag tgtagtaaaa      660
gtacaaggtg agatagatgt aaaagatctt gctagaggtg aaagaacagg tgaagaagta      720
gctaagagaa tggaaagagc ttctgtatta gctcaggttg atattcatag agctgcaaca      780
cataacaaag gtgttatgaa tggaatacat gctgttgttt agctacagg aaatgatact       840 agaggtgctg aagcatctgc acatgcatac gcatcaagag acggacaata tagaggtata      900
gcaacttgga gatatgatca gaagagacaa agacttattg gaactattga agttccaatg      960
acacttgcta tagtaggtgg tggtactaaa gtattaccaa tagctaaggc atcattagag     1020
ttattaaatg ttgattctgc acaagaactt ggacacgtag ttgctgctgt tggattagca     1080
caaaactttg ctgcttgtag agcacttgtt tctgaaggta ttcaacaagg acacatgtca     1140
ttacaatata aaagtttagc aatagtagta ggtgcaaaag gtgacgagat agcacaagta     1200
gcagaagctc ttaaacagga accaagagct aatacacagg ttgctgaaag aattttacag     1260
gaaattagac agcaataa                                                   1278

<210> SEQ ID NO 44
<211> LENGTH: 552
<212> TYPE: DNA
<213> ORGANISM: Clostridium autoethanogenum

<400> SEQUENCE: 44
agatagtcat aatagttcca gaatagttca atttagaaat tagactaaac ttcaaaatgt       60
ttgttaaata tataccaatc tagtatagat attttttaaa tactggactt aaacagtagt      120
aatttgccta aaaatttttt tcaattttt ttaaaaaatc cttttcaagt tgtacattgt       180
tatggtaata tgtaattgaa gaagttatgt agtaatattg taaacgtttc ttgattttt       240 tacatccatg tagtgcttaa aaaaccaaaa tatgtcacat gcacttgtat atttcaaata      300
acaatattta ttttctcgtt aaattcacaa ataatttatt aataatatca ataaccaaga      360
ttatacttaa atggatgttt attttttaac acttttatag taaatatatt tattttatgt      420
agtaaaaagg ttataattat aattgtattt attacaatta ttaaaataa aaaatagggt      480 tttaggtaaa attaagttat tttaagaagt aattacaata aaaattgaag ttatttcttt      540
aaggaggaaa tt                                                         552

<210> SEQ ID NO 45
<211> LENGTH: 386
<212> TYPE: DNA
<213> ORGANISM: Clostridium autoethanogenum

<400> SEQUENCE: 45
gttataattt tcaattttca ttcttttta aggagattag catacatttt atcataatta        60
tacagacaat atagtaatat atgatgttaa aatatcaata tatggttaaa aatctgtata      120
ttttttccca ttttaattat ttgtactata atattacact gagtgtattg catatttaaa     180
aaatatttgg tacaattagt tagttaaata aattctaaat tgtaaattat cagaatcctt     240
attaaggaaa tacatagatt taaggagaaa tcataaaag gtgtaatata aactggctaa      300
aattgagcaa aaattgagca attaagactt tttgattgta tcttttata tatttaaggt      360 atataatctt atttatattg gggggaa                                          386

<210> SEQ ID NO 46
```

<211> LENGTH: 21
<212> TYPE: DNA
<213> ORGANISM: Artificial Sequence
<220> FEATURE:
<223> OTHER INFORMATION: oligonucleotide pUC57-F

<400> SEQUENCE: 46
agcagattgt actgagagtg c                                            21

<210> SEQ ID NO 47
<211> LENGTH: 21
<212> TYPE: DNA
<213> ORGANISM: Artificial Sequence
<220> FEATURE:
<223> OTHER INFORMATION: oligonucleotide pUC57-R

<400> SEQUENCE: 47
acagctatga ccatgattac g                                            21

<210> SEQ ID NO 48
<211> LENGTH: 3552
<212> TYPE: DNA
<213> ORGANISM: Artificial Sequence
<220> FEATURE:
<223> OTHER INFORMATION: plasmid pMTL 85245

<400> SEQUENCE: 48
aaactccttt tgataatct catgaccaaa atcccttaac gtgagttttc gttccactga     60
gcgtcagacc ccgtagaaaa gatcaaagga tcttcttgag atcctttttt tctgcgcgta    120
atctgctgct tgcaaacaaa aaaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat    600 ctttatagtc ctgtcgggtt tcgccacctc tgacttgagc gtcgattttt gtgatgctcg    660 tcagggggc ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggcccctg caggataaaa    900 aaattgtaga taaattttat aaaatagttt tatctacaat ttttttatca ggaaacagct    960
atgaccgcgg ccgcaatatg atattatgt ccattgtgaa agggattata ttcaactatt   1020
attccagtta cgttcataga aattttcctt tctaaaatat tttattccat gtcaagaact   1080
ctgtttattt cattaaagaa ctataagtac aaagtataag gcatttgaaa aaataggcta   1140
gtatattgat tgattattta ttttaaaatg cctaagtgaa atatatacat attataacaa   1200
taaaataagt attagtgtag gattttttaaa tagagtatct attttcagat taaattttg    1260 attatttgat ttacattata taatattgag taaagtattg actagcaaaa ttttttgata   1320
ctttaatttg tgaaatttct tatcaaaagt tatattttg aataattttt attgaaaaat   1380
acaactaaaa aggattatag tataagtgtg tgtaattttg tgttaaattt aagggagga   1440

```
aatgaacatg aaacatatgg tgaccatgat tacgaattcg agctcggtac ccggggatcc    1500
tctagagtcg acgtcacgcg tccatggaga tctcgaggcc tgcagacatg caagcttggc    1560
actggccgtc gttttacaac gtcgtgactg ggaaaaccct ggcgttaccc aacttaatcg    1620
ccttgcagca catccccctt tcgccagctg gcgtaatagc gaagaggccc gcaccgatcg    1680
cccttcccaa cagttgcgca gcctgaatgg cgaatggcgc tagcataaaa ataagaagcc    1740
tgcatttgca ggcttcttat ttttatggcg cgccgcattc acttcttttc tatataaata    1800
tgagcgaagc gaataagcgt cggaaaagca gcaaaagtt tccttttttgc tgttggagca    1860 tgggggttca gggggtgcag tatctgacgt caatgccgag cgaaagcgag ccgaagggta    1920
gcatttacgt tagataaccc cctgatatgc tccgacgctt tatatagaaa agaagattca    1980
actaggtaaa atcttaatat aggttgagat gataaggttt ataaggaatt tgtttgttct    2040 aattttttcac tcattttgtt ctaatttctt ttaacaaatg ttctttttt tttagaacag    2100 ttatgatata gttagaatag tttaaaataa ggagtgagaa aaagatgaaa gaaagatatg    2160
gaacagtcta taaaggctct cagaggctca tagacgaaga aagtggagaa gtcatagagg    2220
tagacaagtt ataccgtaaa caacgtctg gtaacttcgt aaaggcatat atagtgcaat    2280
taataagtat gttagatatg attggcggaa aaaaacttaa aatcgttaac tatatcctag    2340
ataatgtcca cttaagtaac aatacaatga tagctacaac aagagaaata gcaaaagcta    2400
caggaacaag tctacaaaca gtaataacaa cacttaaaat cttagaagaa ggaaatatta    2460
taaaaagaaa aactggagta ttaatgttaa accctgaact actaatgaga ggcgacgacc    2520
aaaaacaaaa atacctctta ctcgaatttg gaactttga gcaagaggca aatgaaatag    2580 attgaccctcc caataacacc acgtagttat tgggaggtca atctatgaaa tgcgattaag    2640
ggccggccga agcaaactta agagtgtgtt gatagtgcag tatcttaaaa tttttgtataa    2700 taggaattga agttaaatta gatgctaaaa atttgtaatt aagaaggagt gattacatga    2760
acaaaaatat aaaatattct caaaactttt taacgagtga aaaagtactc aaccaaataa    2820
taaaacaatt gaatttaaaa gaaaccgata ccgtttacga aattggaaca ggtaaagggc    2880
atttaacgac gaaactggct aaaataagta aacaggtaac gtctattgaa ttagacagtc    2940
atctattcaa cttatcgtca gaaaaattaa aactgaatac tcgtgtcact ttaattcacc    3000
aagatattct acagtttcaa ttccctaaca acagaggta taaaattgtt gggagtattc    3060
cttaccattt aagcacacaa attattaaaa aagtggtttt tgaaagccat gcgtctgaca    3120
tctatctgat tgttgaagaa ggattctaca agcgtacctt ggatattcac cgaacactag    3180
ggttgctctt gcacactcaa gtctcgattc agcaattgct taagctgcca gcggaatgct    3240
ttcatcctaa accaaaagta aacagtgtct taataaaact tacccgccat accacagatg    3300
ttccagataa atattggaag ctatatacgt actttgtttc aaaatgggtc aatcgagaat    3360
atcgtcaact gttactaaaa aatcagtttc atcaagcaat gaaacacgcc aaagtaaaca    3420
atttaagtac cgttacttat gagcaagtat tgtctatttt taatagttat ctattattta    3480 acggaggaa ataattctat gagtcgcttt tgtaaatttg gaaagttaca cgttactaaa    3540
gggaatgtgt tt                                                       3552
```

<210> SEQ ID NO 49
<211> LENGTH: 4186
<212> TYPE: DNA
<213> ORGANISM: Artificial Sequence
<220> FEATURE:

<223> OTHER INFORMATION: plasmid pMTL 83145

<400> SEQUENCE: 49

```
aaactccttt tgataatct catgaccaaa atcccttaac gtgagttttc gttccactga      60
gcgtcagacc ccgtagaaaa gatcaaagga tcttcttgag atccttttt tctgcgcgta     120
atctgctgct tgcaaacaaa aaaccaccg ctaccagcgg tggtttgttt gccggatcaa     180
gagctaccaa ctcttttcc gaaggtaact ggcttcagca gagcgcagat accaaatact     240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat    600
ctttatagtc ctgtcgggtt tcgccacctc tgacttgagc gtcgattttt gtgatgctcg    660
tcagggggc ggagcctatg gaaaaacgcc agcaacgcgg ccttttacg gttcctggcc     720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggccccctg caggataaaa    900
aaattgtaga taaatttat aaaatagttt tatctacaat ttttttatca ggaaacagct     960
atgaccgcgg ccgcaatatg atattatgt ccattgtgaa agggattata ttcaactatt    1020
attccagtta cgttcataga aattttcctt tctaaaatat tttattccat gtcaagaact   1080
ctgtttattt cattaaagaa ctataagtac aaagtataag gcatttgaaa aaataggcta   1140
gtatattgat tgattatta ttttaaaatg cctaagtgaa atatatacat attataacaa    1200
taaaataagt attagtgtag gatttttaaa tagagtatct attttcagat taaatttttg    1260
attatttgat ttacattata taatattgag taaagtattg actagcaaaa ttttttgata    1320
ctttaatttg tgaaatttct tatcaaaagt tatattttg aataattttt attgaaaaat    1380
acaactaaaa aggattatag tataagtgtg tgtaattttg tgttaaattt aagggagga    1440
aatgaacatg aaacatatgg tgaccatgat tacgaattcg agctcggtac ccggggatcc   1500
tctagagtcg acgtcacgcg tccatggaga tctcgaggcc tgcagacatg caagcttggc   1560
actggccgtc gttttacaac gtcgtgactg ggaaaaccct ggcgttaccc aacttaatcg   1620
ccttgcagca catcccccctt tcgccagctg gcgtaatagc gaagaggccc gcaccgatcg   1680
cccttcccaa cagttgcgca gcctgaatgg cgaatggcgc tagcataaaa ataagaagcc   1740
tgcatttgca ggcttcttat ttttatggcg cgccgccatt attttttga acaattgaca    1800
attcattct tattttta taagtgatag tcaaaaggca taacagtgct gaatagaaag      1860
aaatttacag aaaagaaaat tatagaattt agtatgatta ttatactca tttatgaatg    1920
tttaattgaa tacaaaaaaa aatacttgtt atgtattcaa ttacgggtta aaatatagac    1980
aagttgaaaa atttaataaa aaaataagtc ctcagctctt atatattaag ctaccaactt   2040
agtatataag ccaaaactta aatgtgctac caacacatca agccgttaga gaactctatc   2100
tatagcaata tttcaaatgt accgacatac aagagaaaca ttaactatat atattcaatt   2160
tatgagatta tcttaacaga tataaatgta aattgcaata agtaagattt agaagtttat   2220
agcctttgtg tattggaagc agtacgcaaa ggcttttta tttgataaaa attagaagta    2280
```

```
tatttattt  ttcataatta  atttatgaaa  atgaaagggg  gtgagcaaag  tgacagagga    2340
aagcagtatc  ttatcaaata  acaaggtatt  agcaatatca  ttattgactt  tagcagtaaa    2400
cattatgact  tttatagtgc  ttgtagctaa  gtagtacgaa  aggggagct   ttaaaaagct    2460 ccttggaata  catagaattc  ataaattaat  ttatgaaaag  aagggcgtat  atgaaaactt    2520
gtaaaaattg  caaagagttt  attaaagata  ctgaaatatg  caaaatacat  tcgttgatga    2580
ttcatgataa  aacagtagca  acctattgca  gtaaatacaa  tgagtcaaga  tgtttacata    2640
aagggaaagt  ccaatgtatt  aattgttcaa  agatgaaccg  atatggatgg  tgtgccataa    2700
aaatgagatg  ttttacagag  gaagaacaga  aaaagaacg   tacatgcatt  aaatattatg    2760
caaggagctt  taaaaagct   catgtaaaga  agagtaaaaa  gaaaaaataa  tttatttatt    2820
aatttaatat  tgagagtgcc  gacacagtat  gcactaaaaa  atatatctgt  ggtgtagtga    2880
gccgatacaa  aaggatagtc  actcgcattt  tcataataca  tcttatgtta  tgattatgtg    2940
tcggtgggac  ttcacgacga  aaacccacaa  taaaaaaaga  gttcgggta   gggttaagca    3000 tagttgaggc  aactaaacaa  tcaagctagg  atatgcagta  gcagaccgta  aggtcgttgt    3060
ttaggtgtgt  tgtaatacat  acgctattaa  gatgtaaaaa  tacggatacc  aatgaaggga    3120
aaagtataat  ttttggatgt  agtttgtttg  ttcatctatg  ggcaaactac  gtccaaagcc    3180
gtttccaaat  ctgctaaaaa  gtatatcctt  tctaaaatca  agtcaagta   tgaaatcata    3240 aataaagttt  aattttgaag  ttattatgat  attatgtttt  tctattaaaa  taaattaagt    3300
atatagaata  gtttaataat  agtatatact  taatgtgata  agtgtctgac  agtgtcacag    3360
aaaggatgat  tgttatggat  tataagcggc  cggccagtgg  gcaagttgaa  aaattcacaa    3420
aaatgtggta  taatatcttt  gttcattaga  gcgataaact  tgaatttgag  agggaactta    3480
gatggtattt  gaaaaaattg  ataaaaatag  ttggaacaga  aaagagtatt  ttgaccacta    3540
ctttgcaagt  gtaccttgta  cctacagcat  gaccgttaaa  gtggatatca  cacaaataaa    3600
ggaaaaggga  atgaaactat  atcctgcaat  gctttattat  attgcaatga  ttgtaaaccg    3660
ccattcagag  tttaggacgg  caatcaatca  agatggtgaa  ttggggatat  atgatgagat    3720
gataccaagc  tatacaatat  ttcacaatga  tactgaaaca  ttttccagcc  tttggactga    3780
gtgtaagtct  gactttaaat  cattttttagc  agattatgaa  agtgatacgc  aacggtatgg    3840
aaacaatcat  agaatggaag  gaaagccaaa  tgctccggaa  acattttta   atgtatctat    3900 gataccgtgg  tcaaccttcg  atggctttaa  tctgaatttg  cagaaaggat  atgattattt    3960
gattcctatt  tttactatgg  ggaaatatta  taaagaagat  aacaaaatta  tacttccttt    4020
ggcaattcaa  gttcatcacg  cagtatgtga  cggatttcac  atttgccgtt  ttgtaaacga    4080
attgcaggaa  ttgataaata  gttaacttca  ggtttgtctg  taactaaaaa  caagtattta    4140
agcaaaaaca  tcgtagaaat  acggtgtttt  ttgttaccct  aagttt                   4186
```

<210> SEQ ID NO 50
<211> LENGTH: 9827
<212> TYPE: DNA
<213> ORGANISM: Artificial Sequence
<220> FEATURE:
<223> OTHER INFORMATION: plasmid pMTL8215-Pptaack-thlA-HMGS-Patp-HMGR

<400> SEQUENCE: 50

```
cctgcaggat  aaaaaaattg  tagataaatt  ttataaaata  gttttatcta  caatttttttt    60 atcaggaaac  agctatgacc  gcggccgcag  atagtcataa  tagttccaga  atagttcaat   120
```

```
ttagaaatta gactaaactt caaaatgttt gttaaatata taccaatcta gtatagatat      180
tttttaaata ctggacttaa acagtagtaa tttgcctaaa aaatttttc aattttttt       240 aaaaaatcct tttcaagttg tacattgtta tggtaatatg taattgaaga agttatgtag      300
taatattgta aacgtttctt gattttttta catccatgta gtgcttaaaa aaccaaaata     360
tgtcacatgc acttgtatat ttcaaataac aatatttatt ttctcgttaa attcacaaat     420
aatttattaa taatatcaat aaccaagatt atacttaaat ggatgtttat tttttaacac     480
ttttatagta aatatattta ttttatgtag taaaaaggtt ataattataa ttgtatttat     540
tacaattaat taaaataaaa aatagggttt taggtaaaat taagttattt taagaagtaa     600
ttacaataaa aattgaagtt atttctttaa ggaggaaatt catatgaaag aggttgttat     660
tgcatcagct gttagaactg caataggatc ttatggaaaa agtcttaaag atgtaccagc     720
agtagactta ggtgcaactg caataaagga agcagtaaag aaagcaggta taaaacctga     780
agatgttaat gaagttattt taggaaacgt attacaagct ggacttggac agaatccagc     840
tagacaggca tcattcaaag caggattacc agtagagata cctgctatga ctattaataa     900
agtttgtggt tcaggattaa gaacagtttc tttagctgct caaattataa agctggtga     960 cgcagatgta ataatagcag gtggtatgga aaatatgtca agagcaccat accttgctaa    1020
taatgctaga tggggttata gaatgggaaa cgctaaattt gtagacgaaa tgataactga    1080
tggactttgg gatgcattta acgattatca catgggaatt actgctgaaa atatagctga    1140
gagatggaat ataagtagag aagaacaaga tgagtttgca cttgcatctc agaaaaaggc    1200
agaagaagct attaaatcag gacaatttaa agatgaaatt gttccagtag taattaaagg    1260
tagaaaaggt gaaacagttg tagacactga tgaacatcct agatttggat ctacaataga    1320
aggtttagct aaattaaagc ctgcttttaa gaaagacgga acagtaactg ctggaaacgc    1380
atcaggttta aatgattgtg cagctgtttt agttattatg tctgctgaaa aggcaaagga    1440
attaggtgtt aaaccacttg ctaagatagt tagttatggt tcagcaggtg tagatcctgc    1500
tattatggga tatggacctt tttatgctac aaaggcagct attgaaaagg ctggttggac    1560
agttgatgaa cttgatctta tagagtcaaa tgaggcattt gcagcacaaa gtcttgctgt    1620
tgctaaggat cttaaattcg atatgaataa agtaaatgta aacggtggtg ctatagcact    1680
tggtcatcca ataggtgcta gtggtgctag aattttagtt acattagttc atgcaatgca    1740
aaagagagac gctaaaaagg gacttgcaac tttatgcata ggtggtggtc aaggaacagc    1800
aatacttctt gaaaaatgtt aagaattcga ggcttttact aaaaacaata aaaacaggag    1860
gaaataatat gactatagga attgacaaaa taaactttta cgtaccaaaa tattatgtag    1920
atatggcaaa attagcagaa gcaagacaag tagacccaaa taaatttctt attggaatag    1980
gacagactga aatggcagtt agtccagtaa accaagatat agtatcaatg ggtgctaatg    2040
ctgctaaaga tataataact gatgaagaca aaaagaaaat aggaatggta atagtagcaa    2100
ctgagtcagc agtagatgca gcaaaggcag cagcagtaca gattcataat ttattaggta    2160
ttcaaccatt tgcaagatgt ttcgaaatga agaagcatg ttatgctgct actcctgcaa    2220
ttcagttagc taaggattat ttagctacaa gaccaaatga gaaagttta gttatagcta    2280 cagatacagc tagatatgga cttaattcag gtggtgaacc tactcaaggt gctggtgctg    2340
ttgctatggt tatagctcat aatcctagta tacttgcatt aaatgaagac gctgttgctt    2400
atacagaaga tgtttatgat ttctggagac caacaggaca taagtatcca ttagtagatg    2460
gtgctttatc aaaagacgca tatattagat ctttttcaaca atcttggaat gaatatgcta    2520
```

```
agagacaagg aaagagttta gctgattttg ctagtctttg ctttcatgtt cctttcacta    2580
aaatgggtaa aaaggcttta gaatctataa tagataacgc agatgaaaca actcaagaga    2640
gattaagatc tggatatgaa gatgcagttg attacaatag atatgttgga aatatataca    2700
caggaagtct ttatctttct cttataagtc ttcttgaaaa tagagattta caggctggtg    2760
aaactattgg attattttca tacggatcag gttctgttgg tgaattttat tcagctacac    2820
ttgtagaagg atataaagat caccttgatc aggcagcaca caaagcactt ttaaacaata    2880
gaactgaagt atcagtagat gcatacgaaa cattttccaa gagatttgat gatgtagaat    2940
ttgatgaaga gcaggatgca gttcatgaag atagacatat attctatctt tcaaacatag    3000
agaataatgt aagagaatat catagacctg aataagagct cgttataatt ttcaattttc    3060
attcttttta aaggagatta gcatacattt tatcataatt atacagacaa tatagtaata    3120
tatgatgtta aaatatcaat atatggttaa aaatctgtat attttttccc attttaatta    3180
tttgtactat aatattacac tgagtgtatt gcatatttaa aaaatatttg gtacaattag    3240
ttagttaaat aaattctaaa ttgtaaatta tcagaatcct tattaaggaa atacatagat    3300
ttaaggagaa atcataaaaa ggtgtaatat aaactggcta aaattgagca aaaattgagc    3360
aattaagact ttttgattgt atctttttat atatttaagg tatataatct tatttatatt    3420 ggggggaaggt accatgcaat cattagacaa aaatttcaga catttatcaa gacaacaaaa    3480
gttacaacaa ttagttgata aacagtggct ttcagaagat cagtttgata ttttacttaa    3540
tcatcctctt atagatgaag aagttgctaa tagtcttata gaaaatgtaa ttgcacaggg    3600
tgcattacca gttggacttc ttcctaatat aatagttgat gataaggctt atgttgtacc    3660
aatgatggtt gaagaaccta gtgttgttgc agctgcatct tatggtgcta aattagtaaa    3720
tcagacaggt ggattttaaaa ctgtatcatc agaaagaata atgattggac agatagtatt    3780
tgatggtgta gatgacactg aaaaattaag tgcagatatt aaagcattag aaaaacaaat    3840
acataagatt gcagatgaag catatcctag tataaaagca agaggtggtg gttatcaaag    3900
aatagcaata gatacatttc cagagcaaca actttttaagt cttaaggtat ttgtagatac    3960
aaaagatgct atgggtgcta atatgcttaa tactatactt gaggcaataa ctgcattcct    4020
taaaaatgaa tctcctcaat cagatatatt aatgtctata ctttcaaacc atgcaactgc    4080
tagtgtagta aaagtacaag gtgagataga tgtaaaagat cttgctagag gtgaaagaac    4140
aggtgaagaa gtagctaaga gaatggaaag agcttctgta ttagctcagg ttgatattca    4200
tagagctgca acacataaca aaggtgttat gaatggaata catgctgttg ttttagctac    4260
aggaaatgat actagaggtg ctgaagcatc tgcacatgca tacgcatcaa gagacggaca    4320
atatagaggt atagcaactt ggagatatga tcagaagaga caaagactta ttggaactat    4380
tgaagttcca atgacacttg ctatagtagg tggtggtact aaagtattac caatagctaa    4440
ggcatcatta gagttattaa atgttgattc tgcacaagaa cttggacacg tagttgctgc    4500
tgttggatta gcacaaaact ttgctgcttg tagagcactt gtttctgaag gtattcaaca    4560
aggacacatg tcattacaat ataaaagttt agcaatagta gtaggtgcaa aaggtgacga    4620
gatagcacaa gtagcagaag ctcttaaaca ggaaccaaga gctaatacac aggttgctga    4680
aagaatttta caggaaatta gacagcaata atctagagtc gacgtcacgc gtccatggag    4740
atctcgaggc ctgcagacat gcaagcttgg cactggccgt cgttttacaa cgtcgtgact    4800
gggaaaaccc tggcgttacc caacttaatc gccttgcagc acatccccct ttcgccagct    4860
```

```
ggcgtaatag cgaagaggcc cgcaccgatc gcccttccca acagttgcgc agcctgaatg    4920
gcgaatggcg ctagcataaa aataagaagc ctgcatttgc aggcttctta tttttatggc    4980
gcgccgttct gaatccttag ctaatggttc aacaggtaac tatgacgaag atagcaccct    5040
ggataagtct gtaatggatt ctaaggcatt taatgaagac gtgtatataa aatgtgctaa    5100 tgaaaagaa aatgcgttaa aagagcctaa aatgagttca aatggttttg aaattgattg    5160
gtagtttaat ttaatatatt ttttctattg gctatctcga tacctataga atcttctgtt    5220
cacttttgtt tttgaaatat aaaaaggggc tttttagccc cttttttta aaactccgga    5280 ggagtttctt cattcttgat actatacgta actattttcg atttgacttc attgtcaatt    5340
aagctagtaa aatcaatggt taaaaaacaa aaaacttgca ttttctacc tagtaattta     5400 taattttaag tgtcgagttt aaaagtataa tttaccagga aaggagcaag ttttttaata    5460
aggaaaaatt tttccttta aaattctatt tcgttatatg actaattata atcaaaaaaa     5520 tgaaatataaa caagaggtaa aaactgcttt agagaaatgt actgataaaa aagaaaaaa    5580 tcctagattt acgtcataca tagcaccttt aactactaag aaaaatattg aaaggacttc    5640
cacttgtgga gattatttgt ttatgttgag tgatgcagac ttagaacatt ttaaattaca    5700
taaaggtaat ttttgcggta atagattttg tccaatgtgt agttggcgac ttgcttgtaa    5760
ggatagttta gaaatatcta ttcttatgga gcatttaaga aagaagaaa ataaagagtt     5820 tatattttta actcttacaa ctccaaatgt aaaaagttat gatcttaatt attctattaa    5880
acaatataat aaatctttta aaaaattaat ggagcgtaag gaagttaagg ataaactaa     5940 aggttatata agaaaattag aagtaactta ccaaaaggaa aaatacataa caaaggattt    6000
atggaaaata aaaaaagatt attatcaaaa aaaaggactt gaaattggtg atttagaacc    6060
taattttgat acttataatc ctcattttca tgtagttatt gcagtaaata aaagttattt    6120
tacagataaa aattattata taaatcgaga agatggttg gaattatgga agtttgctac     6180
taaggatgat tctataactc aagttgatgt tagaaaagca aaaattaatg attataaaga    6240
ggtttacgaa cttgcgaaat attcagctaa agacactgat tatttaatat cgaggccagt    6300
atttgaaatt ttttataaag cattaaaagg caagcaggta ttagttttta gtggattttt    6360
taaagatgca cacaaattgt acaagcaagg aaaacttgat gtttataaaa agaaagatga    6420 aattaaaatat gtctatatag tttattataa ttggtgcaaa aaacaatatg aaaaactag     6480 aataagggaa cttacggaag atgaaaaga agaattaaat caagatttaa tagatgaaat     6540
agaaatagat taaagtgtaa ctatactta tatatatatg attaaaaaaa taaaaacaa      6600 cagcctatta ggttgttgtt ttttatttc tttattaatt ttttaatttt ttagttttta     6660
gttctttttt aaaataagtt tcagcctctt tttcaatatt ttttaaagaa ggagtatttg    6720
catgaattgc cttttttcta acagacttag gaaatatttt aacagtatct tcttgcgccg    6780
gtgattttgg aacttcataa cttactaatt tataattatt atttttcttt ttaattgtaa    6840
cagttgcaaa agaagctgaa cctgttcctt caactagttt atcatcttca atataatatt    6900
cttgacctat atagtataaa tatattttta ttatattttt acttttttct gaatctatta    6960
ttttataatc ataaaaagtt ttaccaccaa aagaaggttg tactccttct ggtccaacat    7020
atttttttac tatattatct aaataatttt tgggaactgg tgttgtaatt tgattaatcg    7080
aacaaccagt tatacttaaa ggaattataa ctataaaaat ataggatt atcttttaa       7140 atttcattat tggcctcctt tttattaaat ttatgttacc ataaaaagga cataacggga    7200
atatgtagaa tatttttaat gtagacaaaa ttttacataa atataaagaa aggaagtgtt    7260
```

```
tgtttaaatt ttatagcaaa ctatcaaaaa ttaggggat aaaaatttat gaaaaaaagg    7320
ttttcgatgt tatttttatg tttaacttta atagtttgtg gtttatttac aaattcggcc    7380
ggccagtggg caagttgaaa aattcacaaa aatgtggtat aatatctttg ttcattagag    7440
cgataaactt gaatttgaga gggaacttag atggtatttg aaaaaattga taaaaatagt    7500
tggaacagaa aagagtattt tgaccactac tttgcaagtg taccttgtac ctacagcatg    7560
accgttaaag tggatatcac acaaataaag gaaaagggaa tgaaactata tcctgcaatg    7620
ctttattata ttgcaatgat tgtaaaccgc cattcagagt ttaggacggc aatcaatcaa    7680
gatggtgaat tggggatata tgatgagatg ataccaagct atacaatatt tcacaatgat    7740
actgaaacat tttccagcct ttggactgag tgtaagtctg actttaaatc attttttagca   7800 gattatgaaa gtgatacgca acggtatgga aacaatcata gaatggaagg aaagccaaat    7860
gctccggaaa acattttaa tgtatctatg ataccgtggt caaccttcga tggctttaat    7920
ctgaatttgc agaaaggata tgattatttg attcctattt ttactatggg gaaatattat    7980
aaagaagata acaaaattat acttcctttg gcaattcaag ttcatcacgc agtatgtgac    8040
ggatttcaca tttgccgttt tgtaaacgaa ttgcaggaat tgataaatag ttaacttcag    8100
gtttgtctgt aactaaaaac aagtatttaa gcaaaaacat cgtagaaata cggtgttttt    8160 tgttaccta agtttaaact ccttttttgat aatctcatga ccaaaatccc ttaacgtgag    8220
ttttcgttcc actgagcgtc agacccgta gaaaagatca aggatcttc ttgagatcct      8280 tttttctgc gcgtaatctg ctgcttgcaa acaaaaaac caccgctacc agcggtggtt      8340
tgtttgccgg atcaagagct accaactctt tttccgaagg taactggctt cagcagagcg    8400
cagataccaa atactgttct tctagtgtag ccgtagttag gccaccactt caagaactct    8460
gtagcaccgc ctacatacct cgctctgcta atcctgttac cagtggctgc tgccagtggc    8520
gataagtcgt gtcttaccgg gttggactca agacgatagt taccggataa ggcgcagcgg    8580
tcgggctgaa cggggggttc gtgcacacag cccagcttgg agcgaacgac ctacaccgaa    8640
ctgagatacc tacagcgtga gctatgagaa agcgccacgc ttcccgaagg gagaaaggcg    8700
gacaggtatc cggtaagcgg cagggtcgga acaggagagc gcacgaggga gcttccaggg    8760
ggaaacgcct ggtatcttta tagtcctgtc gggtttcgcc acctctgact tgagcgtcga    8820
tttttgtgat gctcgtcagg gggcggagc ctatggaaaa acgccagcaa cgcggccttt     8880
ttacggttcc tggccttttg ctggcctttt gctcacatgt tctttcctgc gttatcccct    8940
gattctgtgg ataaccgtat taccgccttt gagtgagctg ataccgctcg ccgcagccga    9000
acgaccgagc gcagcgagtc agtgagcgag gaagcggaag agcgcccaat acgcagggcc    9060
ccctgcttcg gggtcattat agcgattttt tcggtatatc catccttttt cgcacgatat    9120
acaggatttt gccaagggt tcgtgtagac tttccttggt gtatccaacg gcgtcagccg     9180
ggcaggatag gtgaagtagg cccacccgcg agcgggtgtt ccttcttcac tgtcccttat    9240
tcgcacctgg cggtgctcaa cgggaatcct gctctgcgag gctggccggc taccgccggc    9300
gtaacagatg agggcaagcg gatggctgat gaaaccaagc caaccaggaa gggcagccca    9360
cctatcaagg tgtactgcct tccagacgaa cgaagagcga ttgaggaaaa ggcggcggcg    9420
gccggcatga gcctgtcggc ctacctgctg gccgtcggcc agggctacaa aatcacgggc    9480
gtcgtggact atgagcacgt ccgcgagctg gcccgcatca atggcgacct gggccgcctg    9540
ggcggcctgc tgaaactctg gctcaccgac gacccgcgca cggcgcggtt cggtgatgcc    9600
```

| | |
|---|---:|
| acgatcctcg ccctgctggc gaagatcgaa gagaagcagg acgagcttgg caaggtcatg | 9660 |
| atgggcgtgg tccgcccgag ggcagagcca tgactttttt agccgctaaa acggccgggg | 9720 |
| ggtgcgcgtg attgccaagc acgtccccat gcgctccatc aagaagagcg acttcgcgga | 9780 |
| gctggtgaag tacatcaccg acgagcaagg caagaccgat cgggccc | 9827 |

<210> SEQ ID NO 51
<211> LENGTH: 843
<212> TYPE: DNA
<213> ORGANISM: Staphylococcus aureus subsp. aureus

<400> SEQUENCE: 51

| | |
|---|---:|
| atgatagctg ttccatttaa cgctggaaaa ataaaagttt taattgaggc attagaatct | 60 |
| ggaaattatt catcaataaa atcagatgta tatgacggaa tgttatatga tgcaccagat | 120 |
| caccttaaat cattagtaaa cagatttgta gaacttaata atataactga gccattagca | 180 |
| gtaactatac agacaaatct tcctccttca agaggtcttg gatctagtgc agctgttgct | 240 |
| gttgcttttg taagagcaag ttatgatttc ttaggaaaaa gtttaactaa agaagagctt | 300 |
| atagaaaagg ctaattgggc tgaacaaata gctcatggaa agccatctgg aatagataca | 360 |
| caaacaatag tatctggaaa gcctgttggg tttcaaaagg gacatgcaga aacacttaaa | 420 |
| actctttcac ttgatggata catggtagta attgatacag gtgttaaagg aagtacaaga | 480 |
| caggctgtag aagatgttca taaactttgc gaagatcctc aatatatgag tcacgtaaaa | 540 |
| cacataggaa aacttgtact tagagcatct gatgttattg aacatcataa ctttgaagca | 600 |
| cttgctgata tattcaatga atgtcatgct gatttaaagg ctcttacagt aagtcatgac | 660 |
| aaaatagaac agttaatgaa gataggaaaa gaaaatggtg ctatagctgg taaattaact | 720 |
| ggtgctggta gaggtggttc aatgttatta cttgcaaaag acttaccaac tgcaaagaat | 780 |
| atagttaaag cagtagagaa agctggtgca gcacatactt ggattgaaaa tttaggtggt | 840 |
| taa | 843 |

<210> SEQ ID NO 52
<211> LENGTH: 1077
<212> TYPE: DNA
<213> ORGANISM: Staphylococcus aureus subsp. aureus

<400> SEQUENCE: 52

| | |
|---|---:|
| atgatacaag taaaggcacc aggaaaatta tatatagcag gtgaatacgc tgttacagaa | 60 |
| ccaggatata aatctgttct tatagctctt gatagatttg ttacagctac tattgaggaa | 120 |
| gctgatcaat acaaaggaac aatacattca aaggcattac atcacaatcc agtaactttt | 180 |
| agtagagatg aagattctat tgttatatca gacccacacg cagcaaaaca acttaattat | 240 |
| gtagtaactg ctatagaaat atttgagcaa tatgcaaaat catgtgacat agcaatgaag | 300 |
| cattttcatt taactataga ttctaactta gatgatagta atggacataa gtatggactt | 360 |
| ggatcttctg ctgctgtttt agtttcagta attaaagtac ttaacgaatt ttatgatatg | 420 |
| aaactttcaa acctttatat atataagtta gcagtaattg ctaatatgaa attacagagt | 480 |
| ttatcttcat gcggtgatat agcagtaagt gtttattcag gttggttagc ttattctaca | 540 |
| tttgaccatg aatgggtaaa acaccagata gaagatacaa cagttgaaga agtacttatt | 600 |
| aaaaattggc ctggattaca catagagcca cttcaagctc ctgaaaatat ggaagttctt | 660 |
| ataggttgga caggtagtcc agctagtagt cctcatttttg tttctgaagt taaaagactt | 720 |
| aagtcagatc cttcattttta cggtgatttc ttagaagatt cacatagatg tgtagaaaaa | 780 |

| | |
|---|---:|
| ttaattcatg cattcaaaac taataatatt aagggtgttc agaaaatggt aagacagaat | 840 |
| agaactatta tacaaagaat ggataaggaa gcaacagttg atatagagac tgagaagtta | 900 |
| aaatatttat gtgatattgc tgaaaaatat catggtgcaa gtaaaacttc aggtgctggt | 960 |
| ggtggtgatt gcggaataac tataataaat aaggatgtag acaaagagaa atatatgat | 1020 |
| gaatggacta acatggaat aaagcctctt aagtttaata tttatcatgg acaataa | 1077 |

<210> SEQ ID NO 53
<211> LENGTH: 984
<212> TYPE: DNA
<213> ORGANISM: Staphylococcus aureus subsp. aureus

<400> SEQUENCE: 53

| | |
|---|---:|
| atgataaaat ctggaaaagc aagagcacac actaatatag cacttataaa atattggggt | 60 |
| aagaaagatg aggcattaat aataccaatg aataactcaa tatcagtaac tttagaaaag | 120 |
| tttttatactg aaacaaaagt tacatttaac gatcagctta ctcaagatca attttggctt | 180 |
| aatggtgaaa aagtttctgg aaaagaatta gaaaagattt caaagtatat ggatattgtt | 240 |
| agaaatagag ctggaataga ttggtatgct gagataaat ctgataattt tgttcctaca | 300 |
| gctgctggtc ttgctagttc tgctagtgct tatgcagcat tagctgctgc atgtaaccaa | 360 |
| gcacttgatt tacagttaag tgataaagac ttaagtagat tagctagaat tggatcagga | 420 |
| tcagcatcaa gatcaatata cggtggtttt gcagaatggg aaaaaggata taatgacgaa | 480 |
| acttcttatg ctgttccatt agaaagtaat cactttgaag atgatcttgc tatgattttt | 540 |
| gtagtaataa accaacattc taaaaaggtt ccttcaagat atggaatgtc tcttacaaga | 600 |
| aatacaagta gattctatca atattggtta gaccatattg atgaagatct tgcagaagca | 660 |
| aaggcagcaa tacaagataa ggattttaag agattaggtg aagttattga agagaatgga | 720 |
| cttagaatgc atgctacaaa tcttggatca actccacctt ttacttactt agtacaagag | 780 |
| tcatacgatg taatggcatt agtacatgag tgtagagaag caggatatcc atgctatttc | 840 |
| actatggatg ctggacctaa tgtaaaaata cttgtagaga agaaaaacaa acaacagata | 900 |
| atagataaac ttttaactca gttcgataat aatcagataa tagatagtga tattatagct | 960 |
| acaggtattg aaattataga ataa | 984 |

<210> SEQ ID NO 54
<211> LENGTH: 516
<212> TYPE: DNA
<213> ORGANISM: Clostridium beijerinckii

<400> SEQUENCE: 54

| | |
|---|---:|
| atggcagagt atataatagc agtagatgag ttcgataacg aaataggatc aatagaaaag | 60 |
| atggaagctc atagaaaagg aacacttcat agagcattca gtattttagt ttttaactca | 120 |
| aagaatcaac ttttattaca gaaaagaaat gtaaagaaat atcactctcc aggattatgg | 180 |
| acaaacactt gttgtagtca cccaagatat ggtgaatctc ttcatgatgc tatatacaga | 240 |
| agattaaaag aagagatggg atttacttgc gaacttgaag aagtattctc attcatatat | 300 |
| aaggtaaaac ttgaagataa tttatttgag atgaatatg accatgtatt tattggtaaa | 360 |
| tatgatggtg agataattgt taataaagat gaagttgatg attttaaatg ggtagacatt | 420 |
| aatgaagtta aaaggacat aatagaaaga cctgaggcat atacttactg gtttaagtat | 480 |
| cttgtaaaata aagctgaaaa taagatatttt aaataa | 516 |

<210> SEQ ID NO 55
<211> LENGTH: 120
<212> TYPE: DNA
<213> ORGANISM: Clostridium autoethanogenum

<400> SEQUENCE: 55

| | | |
|---|---|---|
| atatcgatac agataaaaaa atatataata cagaagaaaa aattataaat ttgtggtata | 60 |
| atataaagta tagtaattta agtttaaacc tcgtgaaaac gctaacaaat aataggaggt | 120 |

<210> SEQ ID NO 56
<211> LENGTH: 900
<212> TYPE: DNA
<213> ORGANISM: Escherichia coli

<400> SEQUENCE: 56

| | |
|---|---|
| atggatttcc cacaacaatt agaagcatgt gtaaaacagg ctaatcaggc acttagtaga | 60 |
| tttattgctc ctcttccttt tcaaaataca ccagtagtag aaactatgca atacggtgca | 120 |
| cttttaggtg gtaaaagatt aagaccattc ttagtatatg ctacaggaca tatgtttggt | 180 |
| gtatcaacta atactttaga cgctccagct gctgctgttg aatgtattca tgcatattct | 240 |
| ttaatacatg atgacttacc agcaatggat gacgatgatt taagaagagg tttacctaca | 300 |
| tgtcatgtta aatttggtga agctaatgca attttagcag gtgacgcttt acaaaactta | 360 |
| gctttttcta tactttcaga tgcagacatg cctgaagttt cagatagaga tagaatttct | 420 |
| atgatatcag agcttgcatc tgcatcagga atagctggaa tgtgcggtgg tcaagcactt | 480 |
| gatttagatg cagaaggtaa acacgtacca cttgatgcat tagagagaat tcatagacat | 540 |
| aaaacaggtg ctcttataag agcagcagta agattaggtg ctttaagtgc tggtgacaag | 600 |
| ggtagaagag cacttccagt acttgataag tatgcagaaa gtataggatt agcttttcaa | 660 |
| gttcaagatg acatacttga cgttgttggt gatactgcta ctttaggaaa agacagggt | 720 |
| gcagatcagc aattaggaaa atctacatac cctgctttac ttggattaga acaggctaga | 780 |
| aagaaagcaa gagacttaat agatgacgca agacaaagtc ttaaacagtt agctgaacaa | 840 |
| tcacttgaca caagtgcact tgaagcactt gcagattata ttatacagag aaacaagtaa | 900 |

<210> SEQ ID NO 57
<211> LENGTH: 975
<212> TYPE: DNA
<213> ORGANISM: Malus x domestica

<400> SEQUENCE: 57

| | |
|---|---|
| atggaattta gagtacattt acaggcagac aacgaacaga aaatatttca aaatcaaatg | 60 |
| aaaccagagc cagaagcatc atatcttata aatcaaagaa gaagtgctaa ttataaaacca | 120 |
| aacatttgga aaaacgattt tcttgatcag tctttaatat caaaatatga tggtgatgaa | 180 |
| tatagaaaac tttcagaaaa gttaatagaa gaagtaaaga tatacatatc agcagagact | 240 |
| atggatttag ttgctaaatt agaacttata gattctgtta gaaaacttgg acttgctaat | 300 |
| cttttttgaga aagaaataaa ggaagcatta gacagtatag cagcaataga atcagataat | 360 |
| ttaggaacta gagacgatct ttatggaaca gctcttcatt ttaagattct tagacagcat | 420 |
| ggatataagg taagtcaaga tatatttggt agatttatgg atgagaaagg aacattagaa | 480 |
| aatcatcact ttgcacactt aaaaggaatg ttagaattat ttgaggcaag taatcttgga | 540 |
| tttgaaggtg aagacatatt agatgaagct aaagcatctc ttacacttgc tcttagagat | 600 |
| tcaggacata tttgttatcc agactcaaac ttaagtagag atgtagttca tagtttagaa | 660 |

```
ttacctagtc atagaagagt tcaatggttc gatgtaaaat ggcagattaa tgcatacgaa    720
aaagatattt gtagagtaaa tgcaacttta ttagagttag caaagttaaa ttttaatgtt    780
gttcaagctc agcttcagaa gaatcttaga gaagctagta gatggtgggc taatcttggt    840
ttcgcagata atttaaagtt tgctagagat agacttgtag agtgttttc atgcgcagta     900 ggtgtagcat ttgaaccaga gcattcatct tttagaatat gtttaactaa ggtaattaat    960
cttgttctta ttata                                                     975
```

<210> SEQ ID NO 58
<211> LENGTH: 13817
<212> TYPE: DNA
<213> ORGANISM: Artificial Sequence
<220> FEATURE:
<223> OTHER INFORMATION: pMTL8314-Pptaack-thlA-HMGS-Patp-HMGR-Prnf-MK-
    PMK-PMD-Pfor-idi-ispS

<400> SEQUENCE: 58

```
aaactccttt ttgataatct catgaccaaa atcccttaac gtgagttttc gttccactga     60
gcgtcagacc ccgtagaaaa gatcaaagga tcttcttgag atcctttttt tctgcgcgta    120
atctgctgct tgcaaacaaa aaaaccaccg ctaccagcgg tggtttgttt gccggatcaa    180
gagctaccaa ctcttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccgta    540 agcggcaggg tcggaacagg agagcgcacg agggagcttc caggggggaaa cgcctggtat    600 ctttatagtc ctgtcgggtt tcgccacctc tgacttgagc gtcgattttt gtgatgctcg    660
tcaggggggc ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggccccctg caggataaaa    900
aaattgtaga taaattttat aaaatagttt tatctacaat ttttttatca ggaaacagct    960
atgaccgcgg ccgcagatag tcataatagt tccagaatag ttcaatttag aaattagact    1020
aaacttcaaa atgtttgtta aatatatacc aatctagtat agatattttt taaatactgg    1080
acttaaacag tagtaatttg cctaaaaat tttttcaatt ttttttaaaa aatccttttc    1140
aagttgtaca ttgttatggt aatatgtaat tgaagaagtt atgtagtaat attgtaaacg    1200
tttcttgatt tttttacatc catgtagtgc ttaaaaaacc aaaatatgtc acatgcactt    1260
gtatatttca ataacaata tttatttct cgttaaattc acaataatt tattaataat    1320 atcaataacc aagattatac ttaaatggat gtttattttt taacactttt atagtaaata    1380
tatttatttt atgtagtaaa aaggttataa ttataattgt atttattaca attaattaaa    1440
ataaaaaata gggttttagg taaaattaag ttattttaag aagtaattac aataaaaatt    1500
gaagttattt ctttaaggag gaaattcata tgaaagaggt tgttattgca tcagctgtta    1560
gaactgcaat aggatcttat ggaaaaagtc ttaaagatgt accagcagta gacttaggtg    1620
caactgcaat aaaggaagca gtaaagaaag caggtatcaaa acctgaagat gttaatgaag    1680
```

```
ttattttagg aaacgtatta caagctggac ttggacagaa tccagctaga caggcatcat    1740
tcaaagcagg attaccagta gagatacctg ctatgactat taataaagtt tgtggttcag    1800
gattaagaac agtttcttta gctgctcaaa ttataaaagc tggtgacgca gatgtaataa    1860
tagcaggtgg tatggaaaat atgtcaagag caccatacct tgctaataat gctagatggg    1920
gttatagaat gggaaacgct aaatttgtag acgaaatgat aactgatgga ctttgggatg    1980
catttaacga ttatcacatg ggaattactg ctgaaaatat agctgagaga tggaatataa    2040
gtagagaaga acaagatgag tttgcacttg catctcagaa aaaggcagaa gaagctatta    2100
aatcaggaca atttaaagat gaaattgttc cagtagtaat taaaggtaga aaaggtgaaa    2160
cagttgtaga cactgatgaa catcctagat ttggatctac aatagaaggt ttagctaaat    2220
taaagcctgc ttttaagaaa gacggaacag taactgctgg aaacgcatca ggtttaaatg    2280
attgtgcagc tgttttagtt attatgtctg ctgaaaaggc aaaggaatta ggtgttaaac    2340
cacttgctaa gatagttagt tatggttcag caggtgtaga tcctgctatt atgggatatg    2400
gaccttttta tgctacaaag gcagctattg aaaaggctgg ttggacagtt gatgaacttg    2460
atcttataga gtcaaatgag gcatttgcag cacaaagtct tgctgttgct aaggatctta    2520
aattcgatat gaataaagta aatgtaaacg gtggtgctat agcacttggt catccaatag    2580
gtgctagtgg tgctagaatt ttagttacat tagttcatgc aatgcaaaag agagacgcta    2640
aaaagggact tgcaactttt tgcataggtg gtggtcaagg aacagcaata cttcttgaaa    2700
aatgttaaga attcgaggct tttactaaaa acaataaaaa caggaggaaa taatatgact    2760
ataggaattg acaaaataaa ctttacgta ccaaaatatt atgtagatat ggcaaaatta    2820
gcagaagcaa gacaagtaga cccaaataaa tttcttattg gaataggaca gactgaaatg    2880
gcagttagtc cagtaaacca agatatagta tcaatgggtg ctaatgctgc taaagatata    2940
ataactgatg aagacaaaaa gaaaatagga atggtaatag tagcaactga gtcagcagta    3000
gatgcagcaa aggcagcagc agtacagatt cataatttat taggtattca accatttgca    3060
agatgtttcg aaatgaaaga agcatgttat gctgctactc ctgcaattca gttagctaag    3120
gattatttag ctacaagacc aaatgagaaa gttttagtta tagctacaga tacagctaga    3180
tatggactta attcaggtgg tgaacctact caaggtgctg gtgctgttgc tatggttata    3240
gctcataatc ctagtatact tgcattaaat gaagacgctc ttgcttatac agaagatgtt    3300
tatgatttct ggagaccaac aggacataag tatccattag tagatggtgc tttatcaaaa    3360
gacgcatata ttagatcttt tcaacaatct tggaatgaat atgctaagag acaaggaaag    3420
agtttagctg attttgctag tctttgcttt catgttcctt ttactaaaat gggtaaaaag    3480
gctttagaat ctataataga taacgcagat gaaacaactc aagagagatt aagatctgga    3540
tatgaagatg cagttgatta caatagatat gttggaaata tatacacagg aagtctttat    3600
ctttctctta taagtcttct tgaaaataga gatttacagg ctggtgaaac tattggatta    3660
ttttcatacg gatcaggttc tgttggtgaa ttttattcag ctacacttgt agaaggatat    3720
aaagatcacc ttgatcaggc agcacacaaa gcactttttaa acaatagaac tgaagtatca    3780
gtagatgcat acgaaacatt tttcaagaga tttgatgatg tagaatttga tgaagagcag    3840
gatgcagttc atgaagatag acatatattc tatctttcaa acatagagaa taatgtaaga    3900
gaatatcata gacctgaata agagctcgtt ataattttca attttcattc ttttttaaagg    3960 agattagcat acattttatc ataattatac agacaatata gtaatatatg atgttaaaat    4020
```

```
atcaatatat ggttaaaaat ctgtatattt tttcccattt taattatttg tactataata    4080
ttacactgag tgtattgcat atttaaaaaa tatttggtac aattagttag ttaaataaat    4140
tctaaattgt aaattatcag aatccttatt aaggaaatac atagatttaa ggagaaatca    4200
taaaaaggtg taatataaac tggctaaaat tgagcaaaaa ttgagcaatt aagacttttt    4260
gattgtatct ttttatatat ttaaggtata taatcttatt tatattgggg gaaggtacca    4320
tgcaatcatt agacaaaaat ttcagacatt tatcaagaca acaaaagtta caacaattag    4380
ttgataaaca gtggctttca gaagatcagt ttgatatttt acttaatcat cctcttatag    4440
atgaagaagt tgctaatagt cttatagaaa atgtaattgc acagggtgca ttaccagttg    4500
gacttcttcc taatataata gttgatgata aggcttatgt tgtaccaatg atggttgaag    4560
aacctagtgt tgttgcagct gcatcttatg gtgctaaatt agtaaatcag acaggtggat    4620
ttaaaactgt atcatcagaa agaataatga ttggacagat agtatttgat ggtgtagatg    4680
acactgaaaa attaagtgca gatattaaag cattagaaaa acaaatacat aagattgcag    4740
atgaagcata tcctagtata aaagcaagag gtggtggtta tcaaagaata gcaatagata    4800
catttccaga gcaacaactt ttaagtctta aggtatttgt agatacaaaa gatgctatgg    4860
gtgctaatat gcttaatact atacttgagg caataactgc attccttaaa aatgaatctc    4920
ctcaatcaga tatattaatg tctatacttt caaaccatgc aactgctagt gtagtaaaag    4980
tacaaggtga gatagatgta aaagatcttg ctagaggtaa agaacaggt gaagaagtag    5040
ctaagagaat ggaaagagct tctgtattag ctcaggttga tattcataga gctgcaacac    5100
ataacaaagg tgttatgaat ggaatacatg ctgttgtttt agctacagga aatgatacta    5160
gaggtgctga agcatctgca catgcatacg catcaagaga cggacaatat agaggtatag    5220
caacttggag atatgatcag aagagacaaa gacttattgg aactattgaa gttccaatga    5280
cacttgctat agtaggtggt ggtactaaag tattaccaat agctaaggca tcattagagt    5340
tattaaatgt tgattctgca caagaacttg gacacgtagt tgctgctgtt ggattagcac    5400
aaaactttgc tgcttgtaga gcacttgttt ctgaaggtat tcaacaagga cacatgtcat    5460
tacaatataa aagtttagca atagtagtag gtgcaaaagg tgacgagata gcacaagtag    5520
cagaagctct taaacaggaa ccaagagcta atacacaggt tgctgaaaga attttacagg    5580
aaattagaca gcaataatct agaatatcga tacagataaa aaatatata atacagaaga    5640
aaaaattata aatttgtggt ataatataaa gtatagtaat ttaagtttaa acctcgtgaa    5700
aacgctaaca aataatagga ggtcaattga tgatagctgt tccatttaac gctggaaaaa    5760
taaaagttt aattgaggca ttagaatctg gaaattattc atcaataaaa tcagatgtat    5820
atgacggaat gttatatgat gcaccagatc accttaaatc attagtaaac agatttgtag    5880
aacttaataa tataactgag ccattagcag taactataca gacaaatctt cctccttcaa    5940
gaggtcttgg atctagtgca gctgttgctg ttgcttttgt aagagcaagt tatgatttct    6000
taggaaaaag tttaactaaa gaagagctta tagaaaaggc taattgggct gaacaaatag    6060
ctcatggaaa gccatctgga atagatacac aaacaatagt atctggaaag cctgtttggt    6120
ttcaaaaggg acatgcagaa acacttaaaa ctctttcact tgatggatac atggtagtaa    6180
ttgatacagg tgttaaagga agtacaagac aggctgtaga agatgttcat aaactttgcg    6240
aagatcctca atatatgagt cacgtaaaac acataggaaa acttgtactt agagcatctg    6300
atgttattga acatcataac tttgaagcac ttgctgatat attcaatgaa tgtcatgctg    6360
atttaaaggc tcttacagta agtcatgaca aaatagaaca gttaatgaag ataggaaaag    6420
```

-continued

| | |
|---|---|
| aaaatggtgc tatagctggt aaattaactg gtgctggtag aggtggttca atgttattac | 6480 |
| ttgcaaaaga cttaccaact gcaaagaata tagttaaagc agtagagaaa gctggtgcag | 6540 |
| cacatacttg gattgaaaat ttaggtggtt aagtcgacaa agacactaaa aaattataaa | 6600 |
| agtaaaggag gacattaaat gatacaagta aaggcaccag gaaaattata tatagcaggt | 6660 |
| gaatacgctg ttacagaacc aggatataaa tctgttctta tagctcttga tagatttgtt | 6720 |
| acagctacta ttgaggaagc tgatcaatac aaaggaacaa tacattcaaa ggcattacat | 6780 |
| cacaatccag taacttttag tagagatgaa gattctattg ttatatcaga cccacacgca | 6840 |
| gcaaaacaac ttaattatgt agtaactgct atagaaatat ttgagcaata tgcaaaatca | 6900 |
| tgtgacatag caatgaagca tttttcattta actatagatt ctaacttaga tgatagtaat | 6960 |
| ggacataagt atggacttgg atcttctgct gctgttttag tttcagtaat taagtactt | 7020 |
| aacgaatttt atgatatgaa actttcaaac ctttatatat ataagttagc agtaattgct | 7080 |
| aatatgaaat tacagagttt atcttcatgc ggtgatatag cagtaagtgt ttattcaggt | 7140 |
| tggttagctt attctacatt tgaccatgaa tgggtaaaac accagataga agatacaaca | 7200 |
| gttgaagaag tacttattaa aaattggcct ggattacaca tagagccact tcaagctcct | 7260 |
| gaaaatatgg aagttcttat aggttggaca ggtagtccag ctagtagtcc tcattttgtt | 7320 |
| tctgaagtta aaagacttaa gtcagatcct tcattttacg gtgatttctt agaagattca | 7380 |
| catagatgtg tagaaaaatt aattcatgca ttcaaaacta ataatattaa gggtgttcag | 7440 |
| aaaatggtaa gacagaatag aactattata caaagaatgg ataaggaagc aacagttgat | 7500 |
| atagagactg agaagttaaa atatttatgt gatattgctg aaaaatatca tggtgcaagt | 7560 |
| aaaacttcag gtgctggtgg tggtgattgc ggaataacta taataaataa ggatgtagac | 7620 |
| aaagagaaaa tatatgatga atggactaaa catggaataa agcctcttaa gtttaatatt | 7680 |
| tatcatggac aataaccatg gtcaataatc ttacaataaa taaagaaag gaggcaaaaa | 7740 |
| tatgataaaa tctggaaaag caagagcaca cactaatata gcacttataa atattgggg | 7800 |
| taagaaagat gaggcattaa taataccaat gaataactca atatcagtaa ctttagaaaa | 7860 |
| gtttatact gaaacaaaag ttacatttaa cgatcagctt actcaagatc aattttggct | 7920 |
| taatggtgaa aaagtttctg gaaaagaatt agaaaagatt tcaaagtata tggatattgt | 7980 |
| tagaaatgaa gctggaatag attggtatgc tgagataaga tctgataatt ttgttcctac | 8040 |
| agctgctggt cttgctagtt ctgctagtgc ttatgcagca ttagctgctg catgtaacca | 8100 |
| agcacttgat ttacagttaa gtgataaaga cttaagtaga ttagctagaa ttggatcagg | 8160 |
| atcagcatca agatcaatat acggtggttt tgcagaatgg gaaaaaggat ataatgacga | 8220 |
| aacttcttat gctgttccat tagaaagtaa tcactttgaa gatgatcttg ctatgatttt | 8280 |
| tgtagtaata aaccaacatt ctaaaaaggt tccttcaaga tatggaatgt ctcttacaag | 8340 |
| aaatacaagt agattctatc aatattggtt agaccatatt gatgaagatc ttgcagaagc | 8400 |
| aaaggcagca atacaagata aggattttaa gagattaggt gaagttattg aagagaatgg | 8460 |
| acttagaatg catgctacaa atcttggatc aactccacct tttacttact tagtacaaga | 8520 |
| gtcatacgat gtaatggcat tagtacatga gtgtagagaa gcaggatatc catgctatttt | 8580 |
| cactatggat gctggaccta atgtaaaaat acttgtagag aagaaaaaca aacaacagat | 8640 |
| aatagataaa cttttaactc agttcgataa taatcagata atagatagtg atattatagc | 8700 |
| tacaggtatt gaaattatag aataaactag ttgtatatta aaatagtaga atacataaga | 8760 |

```
tacttaattt aattaaagat agttaagtac ttttcaatgt gctttttag atgtttaata      8820
caaatcttta attgtaaaag aaatgctgta ctatttactg ttctagtgac gggattaaac      8880
tgtattaatt ataaataaaa aataagtaca gttgtttaaa attatatttt gtattaaatc      8940
taatagtacg atgtaagtta ttttatacta ttgctagttt aataaaaaga tttaattata      9000
tacttgaaaa ggagaggaac tcgagatggc agagtatata atagcagtag atgagttcga      9060
taacgaaata ggatcaatag aaaagatgga agctcataga aaaggaacac ttcatagagc      9120
attcagtatt ttagttttta actcaaagaa tcaacttttta ttacagaaaa gaaatgtaaa     9180
gaaatatcac tctccaggat tatggacaaa cacttgttgt agtcacccaa gatatggtga      9240
atctcttcat gatgctatat acagaagatt aaaagaagag atgggattta cttgcgaact      9300
tgaagaagta ttctcattca tatataaggt aaaacttgaa gataatttat ttgagaatga      9360
atatgaccat gtatttattg gtaaatatga tggtgagata attgttaata aagatgaagt      9420
tgatgatttt aaatgggtag acattaatga agttaaaaag gacataatag aaagacctga      9480
ggcatatact tactggttta agtatcttgt aaataaagct gaaataaaga tatttaaata      9540
aaccggtggg aggaaatgaa catggcaaca gaattattat gtttacacag acctatatca      9600
cttactcaca aactttttag gaatccatta cctaaagtta ttcaagctac acctttaaca      9660
ttaaaactta ggtgtagtgt ttctacagaa aatgtatcat ttagtgagac agaaactgaa      9720
acaagaagat cagcaaatta tgaaccaaat tcttgggatt atgattatct tctttcttct      9780
gatactgatg agtcaataga agtacataaa gataaggcta agaaattaga agctgaagtt      9840
aggagagaaa taaataatga gaaggctgaa tttcttacac ttcttgaact tattgataat      9900
gtacaaagac ttggattagg atatagattt gagtctgata taagaagagc attagataga      9960
tttgtaagta gtgaggatt tgatggagtt actaaaactt cattacatgg aacagcatta     10020
tcatttaggt tattaaggca acatggtttt gaagtatctc aagaagcttt tagtggattt     10080
aaagatcaga atggaaactt tcttgagaat ttaaaggaag acataaaagc aattctttct     10140
ctttatgaag catcattttt agcattagaa ggtgagaata tattagatga ggctaaagta     10200
tttgcaatat ctcatcttaa agaacttagt gaagaaaaga ttggtaaaga attagctgaa     10260
caagtttcac atgctttaga attaccatta catagaagaa cacaaagatt agaagcagtt     10320
tggtcaatag aagcatatag aaagaaagaa gacgcaaatc aagtactttt agaacttgca     10380
atacttgact acaatatgat tcaaagtgta tatcagaggg atttaagaga aacatcaaga     10440
tggtggagaa gagtaggatt agcaactaaa ttacattttg ctagagatag gcttattgaa     10500
agttttatt gggctgttgg agttgctttt gaaccacaat attctgattg cagaaatagt      10560
gtagcaaaga tgttttcatt tgttactata attgacgata tttacgatgt atatggaact     10620
ttagatgaac ttgaactttt tactgatgca gttgaaagat gggatgtaaa tgctattaat     10680
gatcttcctg attatatgaa gttatgtttt cttgcacttt acaatactat taacgagata     10740
gcttacgata acttaaaaga taaggtgag aacatacttc cttatttaac aaaagcatgg      10800
gcagatttat gtaatgcatt tcttcaagaa gctaagtggc tttataataa atcaacacct     10860
acatttgatg attattttgg aaatgcatgg aaaagttcta gtggacctt acagcttatt      10920
tttgcttatt ttgctgtagt acagaacatt aaaaaggaag agattgagaa tcttcagaaa     10980
tatcatgaca taatatcaag acctagtcac attttttaggc tttgtaatga tttagcatct     11040
gcttcagcag aaatagcaag aggtgaaact gctaattctg taagttgtta tatgagaaca     11100
aaaggtatat ctgaagaatt agctactgaa agtgttatga atcttataga cgaaacttgg     11160
```

```
aagaaaatga acaaagaaaa acttggtgga tctttatttg caaaacctttt tgttgagact    11220
gctataaatt tagctagaca gtctcattgc acatatcata atggtgatgc acatactagt    11280
ccagatgaat taactaggaa aagagtactt agtgtaataa ctgaaccaat attaccattt    11340
gaaagataag ctagcataaa aataagaagc ctgcatttgc aggcttctta tttttatggc    11400
gcgccgccat tattttttg aacaattgac aattcatttc ttatttttta ttaagtgata    11460
gtcaaaaggc ataacagtgc tgaatagaaa gaaatttaca gaaaagaaaa ttatagaatt    11520
tagtatgatt aattatactc atttatgaat gtttaattga atacaaaaaa aaatacttgt    11580
tatgtattca attacgggtt aaaatataga caagttgaaa aatttaataa aaaaataagt    11640
cctcagctct tatatattaa gctaccaact tagtatataa gccaaaactt aaatgtgcta    11700
ccaacacatc aagccgttag agaactctat ctatagcaat atttcaaatg taccgacata    11760
caagagaaac attaactata tatattcaat ttatgagatt atcttaacag atataaatgt    11820
aaattgcaat aagtaagatt tagaagttta tagcctttgt gtattggaag cagtacgcaa    11880
aggcttttt atttgataaa aattagaagt atatttattt tttcataatt aatttatgaa    11940
aatgaaaggg ggtgagcaaa gtgacagagg aaagcagtat cttatcaaat aacaaggtat    12000
tagcaatatc attattgact ttagcagtaa acattatgac ttttatagtg cttgtagcta    12060
agtagtacga aagggggagc tttaaaaagc tccttggaat acatagaatt cataaattaa    12120
tttatgaaaa gaagggcgta tatgaaaact tgtaaaaatt gcaagagtt tattaaagat    12180
actgaaatat gcaaaataca ttcgttgatg attcatgata aaacagtagc aacctattgc    12240
agtaaataca atgagtcaag atgtttacat aaagggaaag tccaatgtat taattgttca    12300
aagatgaacc gatatggatg gtgtgccata aaaatgagat gttttacaga ggaagaacag    12360
aaaaagaac gtacatgcat taaatattat gcaaggagct ttaaaaagc tcatgtaaag    12420
aagagtaaaa agaaaaaata atttatttat taatttaata ttgagagtgc cgacacagta    12480
tgcactaaaa aatatatctg tggtgtagtg agccgataca aaaggatagt cactcgcatt    12540
ttcataatac atcttatgtt atgattatgt gtcggtggga cttcacgacg aaaacccaca    12600
ataaaaaaag agttcggggt agggttaagc atagttgagg caactaaaca atcaagctag    12660
gatatgcagt agcagaccgt aaggtcgttg tttaggtgtg ttgtaataca tacgctatta    12720
agatgtaaaa atacgatac caatgaaggg aaaagtataa ttttttggatg tagtttgttt    12780
gttcatctat gggcaaacta cgtccaaagc cgtttccaaa tctgctaaaa agtatatcct    12840
ttctaaaatc aaagtcaagt atgaaatcat aaataaagtt taattttgaa gttattatga    12900
tattatgttt ttctattaaa ataaattaag tatatagaat agtttaataa tagtatatac    12960
ttaatgtgat aagtgtctga cagtgtcaca gaaaggatga ttgttatgga ttataagcgg    13020
ccggccagtg ggcaagttga aaaattcaca aaaatgtggt ataatatctt tgttcattag    13080
agcgataaac ttgaatttga gagggaactt agatggtatt tgaaaaaatt gataaaaata    13140
gttggaacag aaaagagtat tttgaccact actttgcaag tgtaccttgt acctacagca    13200
tgaccgttaa agtggatatc acacaaataa aggaaaaggg aatgaaacta tatcctgcaa    13260
tgctttatta tattgcaatg attgtaaacc gccattcaga gttaggacg gcaatcaatc    13320
aagatggtga attggggata tatgatgaga tgataccaag ctatacaata tttcacaatg    13380
atactgaaac attttccagc ctttggactg agtgtaagtc tgactttaaa tcattttag    13440
cagattatga aagtgatacg caacggtatg gaaacaatca tagaatggaa ggaaagccaa    13500
```

| | |
|---|---:|
| atgctccgga aaacattttt aatgtatcta tgataccgtg gtcaaccttc gatggcttta | 13560 |
| atctgaattt gcagaaagga tatgattatt tgattcctat ttttactatg gggaaatatt | 13620 |
| ataaagaaga taacaaaatt atacttcctt tggcaattca agttcatcac gcagtatgtg | 13680 |
| acggatttca catttgccgt tttgtaaacg aattgcagga attgataaat agttaacttc | 13740 |
| aggtttgtct gtaactaaaa acaagtattt aagcaaaaac atcgtagaaa tacggtgttt | 13800 |
| tttgttaccc taagttt | 13817 |

<210> SEQ ID NO 59
<211> LENGTH: 14709
<212> TYPE: DNA
<213> ORGANISM: Artificial Sequence
<220> FEATURE:
<223> OTHER INFORMATION: plasmid
    pMTL8314-Pptaack-thlA-HMGS-Patp-HMGR-Prnf-MK-PMK-PMD-Pfor-idi-isp
    A-FS

<400> SEQUENCE: 59

| | |
|---|---:|
| aaactccttt ttgataatct catgaccaaa atcccttaac gtgagttttc gttccactga | 60 |
| gcgtcagacc ccgtagaaaa gatcaaagga tcttcttgag atcctttttt tctgcgcgta | 120 |
| atctgctgct tgcaaacaaa aaaaccaccg ctaccagcgg tggtttgttt gccggatcaa | 180 |
| gagctaccaa ctcttttttcc gaaggtaact ggcttcagca gagcgcagat accaaatact | 240 |
| gttcttctag tgtagccgta gttaggccac cacttcaaga actctgtagc accgcctaca | 300 |
| tacctcgctc tgctaatcct gttaccagtg gctgctgcca gtggcgataa gtcgtgtctt | 360 |
| accgggttgg actcaagacg atagttaccg gataaggcgc agcggtcggg ctgaacgggg | 420 |
| ggttcgtgca cacagcccag cttggagcga acgacctaca ccgaactgag atacctacag | 480 |
| cgtgagctat gagaaagcgc cacgcttccc gaagggagaa aggcggacag gtatccggta | 540 |
| agcggcaggg tcggaacagg agagcgcacg agggagcttc caggggggaaa cgcctggtat | 600 |
| ctttatagtc ctgtcgggtt tcgccacctc tgacttgagc gtcgattttt gtgatgctcg | 660 |
| tcagggggggc ggagcctatg gaaaaacgcc agcaacgcgg cctttttacg gttcctggcc | 720 |
| ttttgctggc cttttgctca catgttcttt cctgcgttat cccctgattc tgtggataac | 780 |
| cgtattaccg cctttgagtg agctgatacc gctcgccgca gccgaacgac cgagcgcagc | 840 |
| gagtcagtga gcgaggaagc ggaagagcgc ccaatacgca gggcccctg caggataaaa | 900 |
| aaattgtaga taaattttat aaaatagttt tatctacaat ttttttatca ggaaacagct | 960 |
| atgaccgcgg ccgcagatag tcataatagt tccagaatag ttcaatttag aaattagact | 1020 |
| aaacttcaaa atgtttgtta aatatatacc aatctagtat agatattttt taaatactgg | 1080 |
| acttaaacag tagtaatttg cctaaaaaat tttttcaatt tttttttaaaa aatccttttc | 1140 |
| aagttgtaca ttgttatggt aatatgtaat tgaagaagtt atgtagtaat attgtaaacg | 1200 |
| tttcttgatt tttttacatc catgtagtgc ttaaaaaacc aaaatatgtc acatgcactt | 1260 |
| gtatatttca ataacaata tttatttct cgttaaattc acaataatt tattaataat | 1320 |
| atcaataacc aagattatac ttaaatggat gtttattttt taacacttttt atagtaaata | 1380 |
| tatttatttt atgtagtaaa aaggttataa ttataattgt atttattaca attaattaaa | 1440 |
| ataaaaaata gggtttttagg taaattaag ttattttaag aagtaattac aataaaaatt | 1500 |
| gaagttattt ctttaaggag gaaattcata tgaaagaggt tgttattgca tcagctgtta | 1560 |
| gaactgcaat aggatcttat ggaaaaagtc ttaaagatgt accagcagta gacttaggtg | 1620 |
| caactgcaat aaaggaagca gtaaagaaag caggtataaa acctgaagat gttaatgaag | 1680 |

```
ttattttagg aaacgtatta caagctggac ttggacagaa tccagctaga caggcatcat      1740
tcaaagcagg attaccagta gagatacctg ctatgactat taataaagtt tgtggttcag      1800
gattaagaac agtttcttta gctgctcaaa ttataaaagc tggtgacgca gatgtaataa      1860
tagcaggtgg tatggaaaat atgtcaagag caccatacct tgctaataat gctagatggg      1920
gttatagaat gggaaacgct aaatttgtag acgaaatgat aactgatgga ctttgggatg      1980
catttaacga ttatcacatg gaattactg ctgaaaatat agctgagaga tggaatataa        2040
gtagagaaga acaagatgag tttgcacttg catctcagaa aaaggcagaa gaagctatta      2100
aatcaggaca atttaaagat gaaattgttc cagtagtaat taaaggtaga aaaggtgaaa      2160
cagttgtaga cactgatgaa catcctagat ttggatctac aatagaaggt ttagctaaat      2220
taaagcctgc ttttaagaaa gacggaacag taactgctgg aaacgcatca ggtttaaatg      2280
attgtgcagc tgttttagtt attatgtctg ctgaaaaggc aaaggaatta ggtgttaaac      2340
cacttgctaa gatagttagt tatggttcag caggtgtaga tcctgctatt atgggatatg      2400
gaccttttta tgctacaaag gcagctattg aaaaggctgg ttggacagtt gatgaacttg      2460
atcttataga gtcaaatgag gcatttgcag cacaaagtct tgctgttgct aaggatctta      2520
aattcgatat gaataaagta aatgtaaacg gtggtgctat agcacttggt catccaatag      2580
gtgctagtgg tgctagaatt ttagttacat tagttcatgc aatgcaaaag agagacgcta      2640
aaaagggact tgcaacttta tgcataggtg gtggtcaagg aacagcaata cttcttgaaa      2700
aatgttaaga attcgaggct tttactaaaa acaataaaaa caggaggaaa taatatgact      2760
ataggaattg acaaaataaa cttttacgta ccaaaatatt atgtagatat ggcaaaatta      2820
gcagaagcaa gacaagtaga cccaaataaa tttcttattg gaataggaca gactgaaatg      2880
gcagttagtc cagtaaacca agatatagta tcaatgggtg ctaatgctgc taaagatata      2940
ataactgatg aagacaaaaa gaaaatagga atggtaatag tagcaactga gtcagcagta      3000
gatgcagcaa aggcagcagc agtacagatt cataatttat taggtattca accatttgca      3060
agatgtttcg aaatgaaaga agcatgttat gctgctactc ctgcaattca gttagctaag      3120
gattatttag ctacaagacc aaatgagaaa gttttagtta tagctacaga tacagctaga      3180
tatggactta attcaggtgg tgaacctact caaggtgctg gtgctgttgc tatggttata      3240
gctcataatc ctagtatact tgcattaaat gaagacgctc ttgcttatac agaagatgtt      3300
tatgatttct ggagaccaac aggacataag tatccattag tagatggtgc tttatcaaaa      3360
gacgcatata ttagatcttt tcaacaatct tggaatgaat atgctaagag acaaggaaag      3420
agtttagctg attttgctag tctttgcttt catgttcctt ttactaaaat gggtaaaaag      3480
gctttagaat ctataataga taacgcagat gaaacaactc aagagagatt aagatctgga      3540
tatgaagatg cagttgatta caatagatat gttggaaata tatacacagg aagtctttat      3600
ctttctctta taagtcttct tgaaaataga gatttacagg ctggtgaaac tattggatta      3660
ttttcatacg gatcaggttc tgttggtgaa ttttattcag ctacacttgt agaaggatat      3720
aaagatcacc ttgatcaggc agcacacaaa gcacttttaa acaatagaac tgaagtatca      3780
gtagatgcat acgaaacatt tttcaagaga tttgatgatg tagaatttga tgaagagcag      3840
gatgcagttc atgaagatag acatatattc tatctttcaa acatagagaa taatgtaaga      3900
gaatatcata gacctgaata agagctcgtt ataattttca attttcattc tttttaaagg      3960
agattagcat acatttttatc ataattatac agacaatata gtaatatatg atgttaaaat      4020
```

```
atcaatatat ggttaaaaat ctgtatattt tttcccattt taattatttg tactataata    4080
ttacactgag tgtattgcat atttaaaaaa tatttggtac aattagttag ttaaataaat    4140
tctaaattgt aaattatcag aatccttatt aaggaaatac atagatttaa ggagaaatca    4200
taaaaaggtg taatataaac tggctaaaat tgagcaaaaa ttgagcaatt aagacttttt    4260
gattgtatct ttttatatat ttaaggtata taatcttatt tatattgggg gaaggtacca    4320
tgcaatcatt agacaaaaat ttcagacatt tatcaagaca acaaaagtta caacaattag    4380
ttgataaaca gtggctttca gaagatcagt ttgatatttt acttaatcat cctcttatag    4440
atgaagaagt tgctaatagt cttatagaaa atgtaattgc acagggtgca ttaccagttg    4500
gacttcttcc taatataata gttgatgata aggcttatgt tgtaccaatg atggttgaag    4560
aacctagtgt tgttgcagct gcatcttatg gtgctaaatt agtaaatcag acaggtggat    4620
ttaaaactgt atcatcagaa agaataatga ttggacagat agtatttgat ggtgtagatg    4680
acactgaaaa attaagtgca gatattaaag cattagaaaa acaaatacat aagattgcag    4740
atgaagcata tcctagtata aaagcaagag gtggtggtta tcaaagaata gcaatagata    4800
catttccaga gcaacaactt ttaagtctta aggtatttgt agatacaaaa gatgctatgg    4860
gtgctaatat gcttaatact atacttgagg caataactgc attccttaaa aatgaatctc    4920
ctcaatcaga tatattaatg tctatacttt caaaccatgc aactgctagt gtagtaaaag    4980
tacaaggtga gatagatgta aaagatcttg ctagaggtaa agaacaggt gaagaagtag    5040
ctaagagaat ggaaagagct tctgtattag ctcaggttga tattcataga gctgcaacac    5100
ataacaaagg tgttatgaat ggaatacatg ctgttgtttt agctacagga aatgatacta    5160
gaggtgctga agcatctgca catgcatacg catcaagaga cggacaatat agaggtatag    5220
caacttggag atatgatcag aagagacaaa gacttattgg aactattgaa gttccaatga    5280
cacttgctat agtaggtggt ggtactaaag tattaccaat agctaaggca tcattagagt    5340
tattaaatgt tgattctgca caagaacttg gacacgtagt tgctgctgtt ggattagcac    5400
aaaactttgc tgcttgtaga gcacttgttt ctgaaggtat tcaacaagga cacatgtcat    5460
tacaatataa aagtttagca atagtagtag gtgcaaaagg tgacgagata gcacaagtag    5520
cagaagctct taaacaggaa ccaagagcta atacacaggt tgctgaaaga attttacagg    5580
aaattagaca gcaataatct agaatatcga tacagataaa aaatatata atacagaaga    5640
aaaaattata aatttgtggt ataatataaa gtatagtaat ttaagtttaa acctcgtgaa    5700
aacgctaaca aataatagga ggtcaattga tgatagctgt tccatttaac gctggaaaaa    5760
taaaagtttt aattgaggca ttagaatctg gaaattattc atcaataaaa tcagatgtat    5820
atgacggaat gttatatgat gcaccagatc accttaaatc attagtaaac agatttgtag    5880
aacttaataa tataactgag ccattagcag taactataca gacaaatctt cctccttcaa    5940
gaggtcttgg atctagtgca gctgttgctg ttgcttttgt aagagcaagt tatgatttct    6000
taggaaaaag tttaactaaa gaagagctta tagaaaaggc taattgggct gaacaaatag    6060
ctcatggaaa gccatctgga atagatacac aaacaatagt atctggaaag cctgtttggt    6120
ttcaaaaggg acatgcagaa acacttaaaa ctctttcact tgatggatac atggtagtaa    6180
ttgatacagg tgttaaagga agtacaagac aggctgtaga agatgttcat aaactttgcg    6240
aagatcctca atatatgagt cacgtaaaac acataggaaa acttgtactt agagcatctg    6300
atgttattga acatcataac tttgaagcac ttgctgatat attcaatgaa tgtcatgctg    6360
atttaaaggc tcttacagta agtcatgaca aaatagaaca gttaatgaag ataggaaaag    6420
```

```
aaaatggtgc tatagctggt aaattaactg gtgctggtag aggtggttca atgttattac    6480
ttgcaaaaga cttaccaact gcaaagaata tagttaaagc agtagagaaa gctggtgcag    6540
cacatacttg gattgaaaat ttaggtggtt aagtcgacaa agacactaaa aaattataaa    6600
agtaaaggag gacattaaat gatacaagta aaggcaccag gaaaattata tatagcaggt    6660
gaatacgctg ttacagaacc aggatataaa tctgttctta tagctcttga tagatttgtt    6720
acagctacta ttgaggaagc tgatcaatac aaaggaacaa tacattcaaa ggcattacat    6780
cacaatccag taacttttag tagagatgaa gattctattg ttatatcaga cccacacgca    6840
gcaaaacaac ttaattatgt agtaactgct atagaaatat ttgagcaata tgcaaaatca    6900
tgtgacatag caatgaagca ttttcattta actatagatt ctaacttaga tgatagtaat    6960
ggacataagt atggacttgg atcttctgct gctgttttag tttcagtaat taagtactt     7020
aacgaatttt atgatatgaa actttcaaac ctttatatat ataagttagc agtaattgct    7080
aatatgaaat tacagagttt atcttcatgc ggtgatatag cagtaagtgt ttattccaggt   7140
tggttagctt attctacatt tgaccatgaa tgggtaaaac accagataga agatacaaca    7200
gttgaagaag tacttattaa aaattggcct ggattacaca tagagccact tcaagctcct    7260
gaaaatatgg aagttcttat aggttggaca ggtagtccag ctagtagtcc tcattttgtt    7320
tctgaagtta aaagacttaa gtcagatcct tcattttacg gtgatttctt agaagattca    7380
catagatgtg tagaaaaatt aattcatgca ttcaaaacta ataatattaa gggtgttcag    7440
aaaatggtaa gacagaatag aactattata caaagaatgg ataaggaagc aacagttgat    7500
atagagactg agaagttaaa atatttatgt gatattgctg aaaaatatca tggtgcaagt    7560
aaaacttcag gtgctggtgg tggtgattgc ggaataacta taataaataa ggatgtagac    7620
aaagagaaaa tatatgatga atggactaaa catggaataa agcctcttaa gtttaatatt    7680
tatcatggac aataaccatg gtcaataatc ttacaataaa taaagaaag gaggcaaaaa     7740
tatgataaaa tctggaaaag caagagcaca cactaatata gcacttataa atattgggg     7800
taagaaagat gaggcattaa taataccaat gaataactca atatcagtaa ctttagaaaa    7860
gttttatact gaaacaaaag ttacatttaa cgatcagctt actcaagatc aattttggct    7920
taatggtgaa aaagtttctg gaaaagaatt agaaaagatt tcaaagtata tggatattgt    7980
tagaaatataga gctggaatag attggtatgc tgagatagaa tctgataatt tgttcctac    8040
agctgctggt cttgctagtt ctgctagtgc ttatgcagca ttagctgctg catgtaacca    8100
agcacttgat ttacagttaa gtgataaaga cttaagtaga ttagctagaa ttggatcagg    8160
atcagcatca agatcaatat acggtggttt tgcagaatgg gaaaaaggat ataatgacga    8220
aacttcttat gctgttccat tagaaagtaa tcactttgaa gatgatcttg ctatgatttt    8280
tgtagtaata aaccaacatt ctaaaaaggt tccttcaaga tatggaatgt ctcttacaag    8340
aaatacaagt agattctatc aatattggtt agaccatatt gatgaagatc ttgcagaagc    8400
aaaggcagca atacaagata aggattttaa gagattaggt gaagttattg aagagaatgg    8460
acttagaatg catgctacaa atcttggatc aactccacct tttacttact tagtacaaga    8520
gtcatacgat gtaatggcat tagtacatga gtgtagagaa gcaggatatc catgctatt     8580
cactatggat gctggaccta atgtaaaaat acttgtagag aagaaaaaca aacaacagat    8640
aatagataaa cttttaactc agttcgataa taatcagata atagatagtg atattatagc    8700
tacaggtatt gaaattatag aataaactag ttgtatatta aaatagtaga atacataaga    8760
```

```
tacttaatttt aattaaagat agttaagtac ttttcaatgt gctttttttag atgtttaata    8820
caaatcttta attgtaaaag aaatgctgta ctatttactg ttctagtgac gggattaaac    8880
tgtattaatt ataaataaaa aataagtaca gttgtttaaa attatatttt gtattaaatc    8940
taatagtacg atgtaagtta ttttatacta ttgctagttt aataaaaaga tttaattata    9000
tacttgaaaa ggagaggaac tcgagatggc agagtatata atagcagtag atgagttcga    9060
taacgaaata ggatcaatag aaaagatgga agctcataga aaaggaacac ttcatagagc    9120
attcagtatt ttagttttta actcaaagaa tcaactttta ttacagaaaa gaaatgtaaa    9180
gaaatatcac tctccaggat tatggacaaa cacttgttgt agtcacccaa gatatggtga    9240
atctcttcat gatgctatat acagaagatt aaaagaagag atgggattta cttgcgaact    9300
tgaagaagta ttctcattca tatataaggt aaaacttgaa gataatttat ttgagaatga    9360
atatgaccat gtatttattg gtaaatatga tggtgagata attgttaata aagatgaagt    9420
tgatgatttt aaatgggtag acattaatga agttaaaaag gacataatag aaagacctga    9480
ggcatatact tactggttta agtatcttgt aaataaagct gaaaataaga tatttaaata    9540
aaccggtcag taacgaatag aattagaaaa acaaaggagg caagacaatg gatttcccac    9600
aacaattaga agcatgtgta aaacaggcta atcaggcact tagtagattt attgctcctc    9660
ttcctttttca aaatacacca gtagtagaaa ctatgcaata cggtgcactt ttaggtggta    9720
aaagattaag accattctta gtatatgcta caggacacat gtttggtgta tcaactaata    9780
ctttagacgc tccagctgct gctgttgaat gtattcatgc ttattcttta atacatgatg    9840
acttaccagc aatggatgac gatgatttaa gaagaggttt acctacatgt catgttaaat    9900
ttggtgaagc taatgcaatt ttagcaggtg acgctttaca aactttagct ttttctatac    9960
tttcagatgc agacatgcct gaagtttcag atagagatag aatttctatg atatcagagc   10020
ttgcatctgc atcaggaata gctggaatgt gcggtggtca agcacttgat ttagatgcag   10080
aaggtaaaca cgtaccactt gatgctttag agagaataca tagacataaa acaggtgctc   10140
ttataagagc agcagtaaga ttaggtgctt taagtgctgg tgacaagggt agaagagcac   10200
ttccagtact tgataagtat gcagaaagta taggattagc ttttcaagtt caagatgaca   10260
tacttgacgt tgttggtgat actgctactt taggaaaaag acagggtgca gatcagcaat   10320
taggaaaatc tacataccct gctttacttg gattagaaca ggctagaaag aaagcaagag   10380
acttaataga tgacgcaaga caaagtctta aacagttagc tgaacaatca cttgacacaa   10440
gtgcacttga agcacttgca gattatatta tacagagaaa caagtaaaag ctttttaaagg   10500
agggaaaaa atggaattta gagtacattt acaggcagac aacgaacaga aaatatttca   10560
aaatcaaatg aaaccagagc cagaagcatc atatcttata aatcaaagaa gaagtgctaa   10620
ttataaacca aacatttgga aaaacgattt tcttgatcag tctttaatat caaaatatga   10680
tggtgatgaa tatagaaaac tttcagaaaa gttaatagaa gaagtaaaga tatacatatc   10740
agcagagact atggatttag ttgctaaatt agaacttata gattctgtta gaaaacttgg   10800
acttgctaat cttttttgaga aagaaataaa ggaagcatta gacagtatag cagcaataga   10860
atcagataat ttaggaacta gagacgatct ttatggaaca gctcttcatt ttaagattct   10920
tagacagcat ggatataagg taagtcaaga tatatttggt agatttatgg atgagaaagg   10980
aacattagaa aatcatcact ttgcacactt aaaaggaatg ttagaattat ttgaggcaag   11040
taatcttgga tttgaaggtg aagacatatt agatgaagct aaagcatctc ttacacttgc   11100
tcttagagat tcaggacata tttgttatcc agactcaaac ttaagtagag atgtagttca   11160
```

```
tagtttagaa ttacctagtc atagaagagt tcaatggttc gatgtaaaat ggcagattaa    11220
tgcatacgaa aaagatattt gtagagtaaa tgcaacttta ttagagttag caaagttaaa    11280 tttaatgtt gttcaagctc agcttcagaa gaatcttaga gaagctagta gatggtgggc    11340
taatcttggt ttcgcagata atttaaagtt tgctagagat agacttgtag agtgttttc    11400 atgcgcagta ggtgtagcat ttgaaccaga gcattcatct tttagaatat gtttaactaa    11460
ggtaattaat cttgttctta ttatagatga tgtatacgat atatatggat ctgaagaaga    11520
gttaaaacat tttacaaatg ctgttgatag atgggacagt agagaaacag aacagcttcc    11580
tgaatgcatg aaaatgtgtt ttcaagtatt atataacact acttgcgaaa tagcaagaga    11640
gatagaagaa gaaaacggtt ggaatcaagt attacctcaa cttactaagg tttgggctga    11700
tttttgtaag gctctttag ttgaagcaga gtggtacaat aaatcacata ttccaacatt    11760
agaagaatat cttagaaacg gatgtatatc aagtagtgta tctgtacttt tagttcactc    11820
tttcttttca ataactcatg aaggtacaaa agaaatggct gatttcttac ataaaaatga    11880
agatctttta tacaacataa gtcttatagt aagattaaac aatgatttag gtacatcagc    11940
tgctgaacag gaaagaggtg attctccttc ttctatagtt tgctatatga gagaagttaa    12000
tgcttctgaa gagactgcaa gaaagaatat aaagggaatg attgataatg cttggaaaaa    12060
ggttaatgga aaatgtttca caactaacca agttccattt ctttcatcat tcatgaataa    12120
tgcaactaac atggcaagag tagcacactc attatataaa gacggtgatg gttttggtga    12180
tcaagaaaaa ggacctagaa cacatattct tagtttatta ttccaacctt tagtaaatta    12240
agctagcata aaaataagaa gcctgcattt gcaggcttct tattttatg gcgcgccgcc    12300 attattttt tgaacaattg acaattcatt tcttattttt tattaagtga tagtcaaaag    12360
gcataacagt gctgaataga aagaaatta cagaaaagaa aattatagaa tttagtatga    12420
ttaattatac tcatttatga atgtttaatt gaatacaaaa aaaaatactt gttatgtatt    12480
caattacggg ttaaaatata gacaagttga aaaatttaat aaaaaaataa gtcctcagct    12540
cttatatatt aagctaccaa cttagtatat aagccaaaac ttaaatgtgc taccaacaca    12600
tcaagccgtt agagaactct atctatagca atatttcaaa tgtaccgaca tacaagagaa    12660
acattaacta tatatattca atttatgaga ttatcttaac agatataaat gtaaattgca    12720
ataagtaaga tttagaagtt tatagccttt gtgtattgga agcagtacgc aaaggctttt    12780
ttatttgata aaattagaa gtatatttat ttttcataa ttaatttatg aaaatgaaag    12840
ggggtgagca aagtgacaga ggaaagcagt atcttatcaa ataacaaggt attagcaata    12900
tcattattga ctttagcagt aaacattatg actttatag tgcttgtagc taagtagtac    12960 gaaagggga gctttaaaaa gctccttgga atacataaa ttcataaatt aatttatgaa    13020
aagaagggcg tatatgaaaa cttgtaaaaa ttgcaaagag tttattaaag atactgaaat    13080
atgcaaaata cattcgttga tgattcatga taaaacagta gcaacctatt gcagtaaata    13140
caatgagtca agatgtttac ataaagggaa agtccaatgt attaattgtt caaagatgaa    13200
ccgatatgga tggtgtgcca taaaaatgag atgttttaca gaggaagaac agaaaaaaga    13260
acgtacatgc attaaatatt atgcaaggag ctttaaaaaa gctcatgtaa agaagagtaa    13320
aaagaaaaaa taatttattt attaatttaa tattgagagt gccgacacag tatgcactaa    13380
aaaatatatc tgtggtgtag tgagccgata caaaaggata gtcactcgca ttttcataat    13440
acatcttatg ttatgattat gtgtcggtgg gacttcacga cgaaaaccca caataaaaaa    13500
```

```
agagttcggg gtagggttaa gcatagttga ggcaactaaa caatcaagct aggatatgca    13560
gtagcagacc gtaaggtcgt tgtttaggtg tgttgtaata catacgctat taagatgtaa    13620
aaatacggat accaatgaag ggaaaagtat aattttttgga tgtagtttgt ttgttcatct    13680
atgggcaaac tacgtccaaa gccgtttcca aatctgctaa aaagtatatc ctttctaaaa    13740
tcaaagtcaa gtatgaaatc ataaataaag tttaattttg aagttattat gatattatgt    13800
ttttctatta aaataaatta agtatataga atagtttaat aatagtatat acttaatgtg    13860
ataagtgtct gacagtgtca cagaaaggat gattgttatg gattataagc ggccggccag    13920
tgggcaagtt gaaaaattca caaaaatgtg gtataatatc tttgttcatt agagcgataa    13980
acttgaattt gagagggaac ttagatggta tttgaaaaaa ttgataaaaa tagttggaac    14040
agaaaagagt attttgacca ctactttgca agtgtacctt gtacctacag catgaccgtt    14100
aaagtggata tcacacaaat aaaggaaaag ggaatgaaac tatatcctgc aatgctttat    14160
tatattgcaa tgattgtaaa ccgccattca gagtttagga cggcaatcaa tcaagatggt    14220
gaattgggga tatatgatga gatgatacca agctatacaa tatttcacaa tgatactgaa    14280
acatttttca gcctttggac tgagtgtaag tctgacttta aatcattttt agcagattat    14340
gaaagtgata cgcaacggta tggaaacaat catagaatgg aaggaaagcc aaatgctccg    14400
gaaaacattt ttaatgtatc tatgataccg tggtcaacct tcgatggctt taatctgaat    14460
ttgcagaaag gatatgatta tttgattcct attttttacta tggggaaata ttataaagaa    14520
gataacaaaa ttatacttcc tttggcaatt caagttcatc acgcagtatg tgacggattt    14580
cacatttgcc gttttgtaaa cgaattgcag gaattgataa atagttaact tcaggtttgt    14640
ctgtaactaa aaacaagtat ttaagcaaaa acatcgtaga aatacggtgt tttttgttac    14700
cctaagttt                                                            14709
```

<210> SEQ ID NO 60
<211> LENGTH: 601
<212> TYPE: PRT
<213> ORGANISM: Artificial Sequence
<220> FEATURE:
<223> OTHER INFORMATION: hybrid Type II methyltransferase

<400> SEQUENCE: 60

```
Met Phe Pro Cys Asn Ala Tyr Ile Glu Tyr Gly Asp Lys Asn Met Asn
1               5                   10                  15

Ser Phe Ile Glu Asp Val Glu Gln Ile Tyr Asn Phe Ile Lys Lys Asn
            20                  25                  30

Ile Asp Val Glu Glu Lys Met His Phe Ile Glu Thr Lys Gln Lys
        35                  40                  45

Ser Asn Met Lys Lys Glu Ile Ser Phe Ser Glu Tyr Tyr Lys Gln
    50                  55                  60

Lys Ile Met Asn Gly Lys Asn Gly Val Val Tyr Thr Pro Pro Glu Met
65                  70                  75                  80

Ala Ala Phe Met Val Lys Asn Leu Ile Asn Val Asn Asp Val Ile Gly
                85                  90                  95

Asn Pro Phe Ile Lys Ile Ile Asp Pro Ser Cys Gly Ser Gly Asn Leu
            100                 105                 110

Ile Cys Lys Cys Phe Leu Tyr Leu Asn Arg Ile Phe Ile Lys Asn Ile
        115                 120                 125

Glu Val Ile Asn Ser Lys Asn Asn Leu Asn Leu Lys Leu Glu Asp Ile
    130                 135                 140
```

```
Ser Tyr His Ile Val Arg Asn Asn Leu Phe Gly Phe Asp Ile Asp Glu
145                 150                 155                 160

Thr Ala Ile Lys Val Leu Lys Ile Asp Leu Phe Leu Ile Ser Asn Gln
                165                 170                 175

Phe Ser Glu Lys Asn Phe Gln Val Lys Asp Phe Leu Val Glu Asn Ile
                180                 185                 190

Asp Arg Lys Tyr Asp Val Phe Ile Gly Asn Pro Pro Tyr Ile Gly His
            195                 200                 205

Lys Ser Val Asp Ser Ser Tyr Ser Tyr Val Leu Arg Lys Ile Tyr Gly
        210                 215                 220

Ser Ile Tyr Arg Asp Lys Gly Asp Ile Ser Tyr Cys Phe Phe Gln Lys
225                 230                 235                 240

Ser Leu Lys Cys Leu Lys Glu Gly Gly Lys Leu Val Phe Val Thr Ser
                245                 250                 255

Arg Tyr Phe Cys Glu Ser Cys Ser Gly Lys Glu Leu Arg Lys Phe Leu
                260                 265                 270

Ile Glu Asn Thr Ser Ile Tyr Lys Ile Ile Asp Phe Tyr Gly Ile Arg
            275                 280                 285

Pro Phe Lys Arg Val Gly Ile Asp Pro Met Ile Ile Phe Leu Val Arg
        290                 295                 300

Thr Lys Asn Trp Asn Asn Asn Ile Glu Ile Ile Arg Pro Asn Lys Ile
305                 310                 315                 320

Glu Lys Asn Glu Lys Asn Lys Phe Leu Asp Ser Leu Phe Leu Asp Lys
                325                 330                 335

Ser Glu Lys Cys Lys Lys Phe Ser Ile Ser Gln Lys Ser Ile Asn Asn
                340                 345                 350

Asp Gly Trp Val Phe Val Asp Glu Val Glu Lys Asn Ile Ile Asp Lys
            355                 360                 365

Ile Lys Glu Lys Ser Lys Phe Ile Leu Lys Asp Ile Cys His Ser Cys
        370                 375                 380

Gln Gly Ile Ile Thr Gly Cys Asp Arg Ala Phe Ile Val Asp Arg Asp
385                 390                 395                 400

Ile Ile Asn Ser Arg Lys Ile Glu Leu Arg Leu Ile Lys Pro Trp Ile
                405                 410                 415

Lys Ser Ser His Ile Arg Lys Asn Glu Val Ile Lys Gly Glu Lys Phe
                420                 425                 430

Ile Ile Tyr Ser Asn Leu Ile Glu Asn Glu Thr Glu Cys Pro Asn Ala
            435                 440                 445

Ile Lys Tyr Ile Glu Gln Tyr Lys Lys Arg Leu Met Glu Arg Arg Glu
        450                 455                 460

Cys Lys Lys Gly Thr Arg Lys Trp Tyr Glu Leu Gln Trp Gly Arg Lys
465                 470                 475                 480

Pro Glu Ile Phe Glu Glu Lys Lys Ile Val Phe Pro Tyr Lys Ser Cys
                485                 490                 495

Asp Asn Arg Phe Ala Leu Asp Lys Gly Ser Tyr Phe Ser Ala Asp Ile
            500                 505                 510

Tyr Ser Leu Val Leu Lys Lys Asn Val Pro Phe Thr Tyr Glu Ile Leu
        515                 520                 525

Leu Asn Ile Leu Asn Ser Pro Leu Tyr Glu Phe Tyr Phe Lys Thr Phe
            530                 535                 540

Ala Lys Lys Leu Gly Glu Asn Leu Tyr Glu Tyr Tyr Pro Asn Asn Leu
545                 550                 555                 560

Met Lys Leu Cys Ile Pro Ser Ile Asp Phe Gly Gly Glu Asn Asn Ile
```

```
            565                 570                 575
Glu Lys Lys Leu Tyr Asp Phe Phe Gly Leu Thr Asp Lys Glu Ile Glu
        580                 585                 590

Ile Val Glu Lys Ile Lys Asp Asn Cys
        595                 600

<210> SEQ ID NO 61
<211> LENGTH: 419
<212> TYPE: DNA
<213> ORGANISM: Clostridium autoethanogenum

<400> SEQUENCE: 61
agaaattttc ctttctaaaa tattttattc catgtcaaga actctgttta tttcattaaa      60
gaactataag tacaaagtat aaggcatttg aaaaaatagg ctagtatatt gattgattat     120
ttattttaaa atgcctaagt gaaatatata catattataa caataaaata agtattagtg     180
taggattttt aaatagagta tctatttttca gattaaattt ttgattattt gatttacatt     240
atataatatt gagtaaagta ttgactagca aaattttttg atactttaat ttgtgaaatt     300
tcttatcaaa agttatattt ttgaataatt tttattgaaa aatacaacta aaaaggatta     360
tagtataagt gtgtgtaatt ttgtgttaaa tttaagggga ggaaatgaac atgaaattg      419

<210> SEQ ID NO 62
<211> LENGTH: 567
<212> TYPE: DNA
<213> ORGANISM: Clostridium autoethanogenum

<400> SEQUENCE: 62
ctcctaattt tgaaatctaa tatatctatt aaatcatatt ttcatatgta aataaataag      60
tttttatgca attttgaaaa aggtatttgc ataaaacggc ttgaaatcaa tagttaacgc     120
aatagttatt cttttagcat acattaagtc aacaaaatta gcatgtaata attatgaata     180
attattacat atattcaata ttatattaaa aaaaatactt tgttttaagt ataaagtaaa     240
aaaataggca taaatgtaac aaaaactgtt aatttttttgt gtcaataatt tttgttatat     300
tattttaatt aaatttttca catgtataat taaaagtaag atagatattc taatgtactt     360
acttaggtag aaaaacatgt atacaaaatt aaaaaactat tataacacat agtatcaata     420
ttgaaggtaa tactgttcaa tatcgataca gataaaaaaa atatataata cagaagaaaa     480
aattataaat ttgtggtata atataaagta tagtaattta agtttaaacc tcgtgaaaac     540
gctaacaaat aataggaggt gtattat                                          567

<210> SEQ ID NO 63
<211> LENGTH: 1806
<212> TYPE: DNA
<213> ORGANISM: Artificial Sequence
<220> FEATURE:
<223> OTHER INFORMATION: hybrid Type II methyltransferase

<400> SEQUENCE: 63
atgtttccgt gcaatgccta tatcgaatat ggtgataaaa atatgaacag ctttatcgaa      60
gatgtggaac agatctacaa cttcattaaa agaacattg atgtggaaga aaagatgcat     120
ttcattgaaa cctataaaca gaaaagcaac atgaagaaag agattagctt tagcgaagaa     180
tactataaac agaagattat gaacggcaaa atggcgttg tgtacacccc gccggaaatg     240
gcggccttta tggttaaaaa tctgatcaac gttaacgatg ttattggcaa tccgtttatt     300
aaaatcattg acccgagctg cggtagcggc aatctgattt gcaaatgttt tctgtatctg     360
```

```
aatcgcatct ttattaagaa cattgaggtg attaacagca aaaataacct gaatctgaaa      420
ctggaagaca tcagctacca catcgttcgc aacaatctgt ttggcttcga tattgacgaa      480
accgcgatca aagtgctgaa aattgatctg tttctgatca gcaaccaatt tagcgagaaa      540
aatttccagg ttaaagactt tctggtggaa aatattgatc gcaaatatga cgtgttcatt      600
ggtaatccgc cgtatatcgg tcacaaaagc gtggacagca gctacagcta cgtgctgcgc      660
aaaatctacg gcagcatcta ccgcgacaaa ggcgatatcg ctattgtttc ttttcagaag      720
agcctgaaat gtctgaagga aggtggcaaa ctggtgtttg tgaccagccg ctacttctgc      780
gagagctgca gcgtaaagaa actgcgtaaa ttcctgatcg aaaacacgag catttacaag      840
atcattgatt tttacggcat ccgcccgttc aaacgcgtgg gtatcgatcc gatgattatt      900
tttctggttc gtacgaagaa ctggaacaat aacattgaaa ttattcgccc gaacaagatt      960
gaaaagaacg aaaagaacaa attcctggat agcctgttcc tggacaaaag cgaaaagtgt     1020
aaaaagttta gcattagcca gaaaagcatt aataacgatg gctgggtttt cgtggacgaa     1080
gtggagaaaa acattatcga caaaatcaaa gagaaaagca gttcattct gaaagatatt     1140 tgccatagct gtcaaggcat tatcaccggt gtgatcgcg cctttattgt ggaccgtgat     1200
atcatcaata gccgtaagat cgaactgcgt ctgattaaac cgtggattaa aagcagccat     1260
atccgtaaga tgaagttat taagggcgaa aaattcatca tctatagcaa cctgattgag     1320
aatgaaaccg agtgtccgaa tgcgattaaa tatatcgaac agtacaagaa acgtctgatg     1380
gagcgccgcg aatgcaaaaa gggcacgcgt aagtggtatg aactgcaatg gggccgtaaa     1440
ccggaaatct tcgaagaaaa gaaaattgtt ttcccgtata aaagctgtga caatcgtttt     1500
gcactggata agggtagcta ttttagcgca gacatttata gcctggttct gaagaaaaat     1560
gtgccgttca cctatgagat cctgctgaat atcctgaata gcccgctgta cgagttttac     1620
tttaagacct tcgcgaaaaa gctgggcgag aatctgtacg agtactatcc gaacaacctg     1680
atgaagctgt gcatcccgag catcgatttc ggcggtgaga caatattga gaaaaagctg     1740 tatgatttct ttggtctgac ggataaagaa attgagattg tggagaagat caaagataac     1800
tgctaa                                                                1806
```

<210> SEQ ID NO 64
<211> LENGTH: 4709
<212> TYPE: DNA
<213> ORGANISM: Artificial Sequence
<220> FEATURE:
<223> OTHER INFORMATION: designed methylation plasmid

<400> SEQUENCE: 64

```
gtttgccacc tgacgtctaa gaaaggaat attcagcaat tgcccgtgc cgaagaaagg       60 cccacccgtg aaggtgagcc agtgagttga ttgctacgta attagttagt tagcccttag     120
tgactcgtaa tacgactcac tatagggctc gaggcggccg cgcaacgcaa ttaatgtgag     180
ttagctcact cattaggcac cccaggcttt acactttatg cttccggctc gtatgttgtg     240
tggaattgtg agcggataac aatttcacac aggaaacaca tatgtttccg tgcaatgcct     300
atatcgaata tggtgataaa aatatgaaca gctttatcga agatgtggaa cagatctaca     360
acttcattaa aaagaacatt gatgtggaag aaaagatgca tttcattgaa acctataaac     420
agaaaagcaa catgaagaaa gagattagct ttagcgaaga atactataaa cagaagatta     480
tgaacggcaa aaatggcgtt gtgtacaccc cgccggaaat ggcggccttt atggttaaaa     540
```

```
atctgatcaa cgttaacgat gttattggca atccgtttat taaaatcatt gacccgagct    600
gcggtagcgg caatctgatt tgcaaatgtt ttctgtatct gaatcgcatc tttattaaga    660
acattgaggt gattaacagc aaaaataacc tgaatctgaa actggaagac atcagctacc    720
acatcgttcg caacaatctg tttggcttcg atattgacga aaccgcgatc aaagtgctga    780
aaattgatct gtttctgatc agcaaccaat ttagcgagaa aaatttccag gttaaagact    840
ttctggtgga aaatattgat cgcaaatatg acgtgttcat tggtaatccg ccgtatatcg    900
gtcacaaaag cgtggacagc agctacagct acgtgctgcg caaaatctac ggcagcatct    960
accgcgacaa aggcgatatc agctattgtt tctttcagaa gagcctgaaa tgtctgaagg   1020
aaggtggcaa actggtgttt gtgaccagcc gctacttctg cgagagctgc agcggtaaag   1080
aactgcgtaa attcctgatc gaaaacacga gcatttacaa gatcattgat ttttacggca   1140
tccgcccgtt caaacgcgtg ggtatcgatc cgatgattat ttttctggtt cgtacgaaga   1200
actggaacaa taacattgaa attattcgcc cgaacaagat tgaaaagaac gaaaagaaca   1260
aattcctgga tagcctgttc ctggacaaaa gcgaaaagtg taaaaagttt agcattagcc   1320
agaaaagcat taataacgat ggctgggttt cgtggacga agtggagaaa aacattatcg   1380
acaaaatcaa agagaaaagc aagttcattc tgaaagatat ttgccatagc tgtcaaggca   1440
ttatcaccgg ttgtgatcgc gcctttattg tggaccgtga tatcatcaat agccgtaaga   1500
tcgaactgcg tctgattaaa ccgtggatta aaagcagcca tatccgtaag aatgaagtta   1560
ttaagggcga aaaattcatc atctatagca acctgattga gaatgaaacc gagtgtccga   1620
atgcgattaa atatatcgaa cagtacaaga aacgtctgat ggagcgccgc gaatgcaaaa   1680
agggcacgcg taagtggtat gaactgcaat ggggccgtaa accggaaatc ttcgaagaaa   1740
agaaaattgt tttcccgtat aaaagctgtg acaatcgttt tgcactggat aagggtagct   1800
attttagcgc agacatttat agcctggttc tgaagaaaaa tgtgccgttc acctatgaga   1860
tcctgctgaa tatcctgaat agcccgctgt acgagtttta ctttaagacc ttcgcgaaaa   1920
agctgggcga gaatctgtac gagtactatc gaacaacct gatgaagctg tgcatcccga   1980
gcatcgattt cggcggtgag aacaatattg agaaaaagct gtatgatttc tttggtctga   2040
cggataaaga aattgagatt gtggagaaga tcaaagataa ctgctaagaa ttcgatatca   2100
cccgggaact agtctgcagc cctttagtga gggttaattg gagtcactaa gggtagtta   2160
gttagattag cagaaagtca aaagcctccg accggaggct tttgactaaa acttcccttg   2220
gggttatcat tggggctcac tcaaaggcgg taatcagata aaaaaaatcc ttagctttcg   2280
ctaaggatga tttctgctag agatggaata gactggatgg aggcggataa agttgcagga   2340
ccacttctgc gctcggccct tccggctggc tggtttattg ctgataaatc tggagccggt   2400
gagcgtgggt ctcgcggtat cattgcagca ctggggccag atggtaagcc ctcccgtatc   2460
gtagttatct acacgacggg gagtcaggca actatggatg aacgaaatag acagatcgct   2520
gagataggtg cctcactgat taagcattgg taactgtcag accaagttta ctcatatata   2580
ctttagattg atttaaaact tcattttaa tttaaaagga tctaggtgaa gatcctttt    2640
gataatctca tgaccaaaat cccttaacgt gagttttcgt tccactgagc gtcagacccc   2700
ttaataagat gatcttcttg agatcgtttt ggtctgcgcg taatctcttg ctctgaaaac   2760
gaaaaaaccg ccttgcaggg cggttttttcg aaggttctct gagctaccaa ctctttgaac   2820
cgaggtaact ggcttggagg agcgcagtca ccaaaacttg tcctttcagt ttagccttaa   2880
ccggcgcatg acttcaagac taactcctct aaatcaatta ccagtggctg ctgccagtgg   2940
```

```
tgcttttgca tgtctttccg ggttggactc aagacgatag ttaccggata aggcgcagcg    3000
gtcggactga acgggggtt cgtgcataca gtccagcttg gagcgaactg cctacccgga     3060
actgagtgtc aggcgtggaa tgagacaaac gcggccataa cagcggaatg acaccggtaa    3120
accgaaaggc aggaacagga gagcgcacga gggagccgcc aggggaaacg cctggtatct    3180
ttatagtcct gtcgggtttc gccaccactg atttgagcgt cagatttcgt gatgcttgtc    3240
aggggggcgg agcctatgga aaaacggctt tgccgcggcc ctctcacttc ctgttaagt     3300 atcttcctgg catcttccag gaaatctccg ccccgttcgt aagccatttc cgctcgccgc    3360
agtcgaacga ccgagcgtag cgagtcagtg agcgaggaag cggaatatat cctgtatcac    3420
atattctgct gacgcaccgg tgcagccttt ttctcctgc cacatgaagc acttcactga     3480
caccctcatc agtgccaaca tagtaagcca gtatacactc cgctagcgct gaggtctgcc    3540
tcgtgaagaa ggtgttgctg actcatacca ggcctgaatc gccccatcat ccagccagaa    3600
agtgagggag ccacggttga tgagagcttt gttgtaggtg gaccagttgg tgattttgaa    3660
cttttgcttt gccacggaac ggtctgcgtt gtcgggaaga tgcgtgatct gatccttcaa    3720
ctcagcaaaa gttcgattta ttcaacaaag ccacgttgtg tctcaaaatc tctgatgtta    3780
cattgcacaa gataaaaata tatcatcatg aacaataaaa ctgtctgctt acataaacag    3840
taatacaagg ggtgtttact agaggttgat cgggcacgta agaggttcca actttcacca    3900
taatgaaata agatcactac cgggcgtatt ttttgagtta tcgagatttt caggagctaa    3960
ggaagctaaa atggagaaaa aaatcacggg atataccacc gttgatatat cccaatggca    4020
tcgtaaagaa cattttgagg catttcagtc agttgctcaa tgtacctata accagaccgt    4080
tcagctggat attacggcct ttttaaagac cgtaaagaaa aataagcaca gttttatcc     4140 ggcctttatt cacattcttg cccgcctgat gaacgctcac ccggagtttc gtatggccat    4200
gaaagacggt gagctggtga tctgggatag tgttcaccct tgttacaccg ttttccatga    4260
gcaaactgaa acgttttcgt ccctctggag tgaataccac gacgatttcc ggcagtttct    4320
ccacatatat tcgcaagatg tggcgtgtta cggtgaaaac ctggcctatt tccctaaagg    4380
gtttattgag aatatgtttt ttgtctcagc caatccctgg gtgagtttca ccagttttga    4440
tttaaacgtg gccaatatgg acaacttctt cgccccgtt ttcacgatgg gcaaatatta     4500
tacgcaaggc gacaaggtgc tgatgccgct ggcgatccag gttcatcatg ccgtttgtga    4560
tggcttccat gtcggccgca tgcttaatga attacaacag tactgtgatg agtggcaggg    4620 cgggcgtaa taatactagc tccggcaaaa aaacgggcaa ggtgtcacca ccctgccctt    4680
tttctttaaa accgaaaaga ttacttcgc                                     4709
```

<210> SEQ ID NO 65
<211> LENGTH: 18
<212> TYPE: DNA
<213> ORGANISM: Artificial Sequence
<220> FEATURE:
<223> OTHER INFORMATION: Oligonucleotide colE1-F

<400> SEQUENCE: 65
cgtcagaccc cgtagaaa                                                 18

<210> SEQ ID NO 66
<211> LENGTH: 18
<212> TYPE: DNA
<213> ORGANISM: Artificial Sequence
<220> FEATURE:

<223> OTHER INFORMATION: Oligonucleotide colE1-R

<400> SEQUENCE: 66
ctctcctgtt ccgaccct                                                  18

<210> SEQ ID NO 67
<211> LENGTH: 37
<212> TYPE: DNA
<213> ORGANISM: Artificial Sequence
<220> FEATURE:
<223> OTHER INFORMATION: Oligonucleotide fD1

<400> SEQUENCE: 67
ccgaattcgt cgacaacaga gtttgatcct ggctcag                             37

<210> SEQ ID NO 68
<211> LENGTH: 37
<212> TYPE: DNA
<213> ORGANISM: Artificial Sequence
<220> FEATURE:
<223> OTHER INFORMATION: Oligonucleotide Rp2

<400> SEQUENCE: 68
cccgggatcc aagcttacgg ctaccttgtt acgactt                             37

<210> SEQ ID NO 69
<211> LENGTH: 25
<212> TYPE: DNA
<213> ORGANISM: Artificial Sequence
<220> FEATURE:
<223> OTHER INFORMATION: Oligonucleotide ispS-F

<400> SEQUENCE: 69
aggctgaatt tcttacactt cttga                                          25

<210> SEQ ID NO 70
<211> LENGTH: 25
<212> TYPE: DNA
<213> ORGANISM: Artificial Sequence
<220> FEATURE:
<223> OTHER INFORMATION: Oligonucleotide ispS-R

<400> SEQUENCE: 70
gtaactccat caaatcctcc actac                                          25

<210> SEQ ID NO 71
<211> LENGTH: 25
<212> TYPE: DNA
<213> ORGANISM: Artificial Sequence
<220> FEATURE:
<223> OTHER INFORMATION: Oligonucleotide idi-F

<400> SEQUENCE: 71
atacgtgctg tagtcatcca agata                                          25

<210> SEQ ID NO 72
<211> LENGTH: 25
<212> TYPE: DNA
<213> ORGANISM: Artificial Sequence
<220> FEATURE:
<223> OTHER INFORMATION: Oligonucleotide idiR

<400> SEQUENCE: 72
tcttcaagtt cacatgtaaa accca                                          25

<210> SEQ ID NO 73
<211> LENGTH: 25
<212> TYPE: DNA
<213> ORGANISM: Artificial Sequence
<220> FEATURE:
<223> OTHER INFORMATION: oligonucleotide dxs-F

<400> SEQUENCE: 73

```
acaaagtatc taagacagga ggtca                                           25
```

<210> SEQ ID NO 74
<211> LENGTH: 25
<212> TYPE: DNA
<213> ORGANISM: Artificial Sequence
<220> FEATURE:
<223> OTHER INFORMATION: oligonucleotide dxs-R

<400> SEQUENCE: 74

```
gatgtcccac atcccatata agttt                                           25
```

<210> SEQ ID NO 75
<211> LENGTH: 6018
<212> TYPE: DNA
<213> ORGANISM: Artificial Sequence
<220> FEATURE:
<223> OTHER INFORMATION: plasmid pMTL85246-IspS-Idi

<400> SEQUENCE: 75

```
ccggggatcc tctagagtcg acgtcacgcg tccatggaga tctcgaggcc tgcagacatg     60
caagcttggc actggccgtc gttttacaac gtcgtgactg ggaaaaccct ggcgttaccc    120
aacttaatcg ccttgcagca catccccctt tcgccagctg gcgtaatagc gaagaggccc    180
gcaccgatcg cccttcccaa cagttgcgca gcctgaatgg cgaatggcgc tagcataaaa    240
ataagaagcc tgcatttgca ggcttcttat ttttatggcg cgccgcattc acttcttttc    300
tatataaata tgagcgaagc gaataagcgt cggaaaagca gcaaaagtt tccttttgc     360 tgttggagca tgggggttca gggggtgcag tatctgacgt caatgccgag cgaaagcgag    420
ccgaagggta gcatttacgt tagataaccc cctgatatgc tccgacgctt tatatagaaa    480
agaagattca actaggtaaa atcttaatat aggttgagat gataaggttt ataaggaatt    540
tgtttgttct aatttttcac tcatttttgtt ctaatttctt ttaacaaatg ttcttttttt    600
tttagaacag ttatgatata gttagaatag tttaaaataa ggagtgagaa aaagatgaaa    660
gaaagatatg gaacagtcta taaaggctct cagaggctca tagacgaaga agtggagaa     720 gtcatagagg tagacaagtt ataccgtaaa caaacgtctg gtaacttcgt aaaggcatat    780
atagtgcaat aataagtat gttagatatg attggcggaa aaaaacttaa aatcgttaac    840
tatatcctag ataatgtcca cttaagtaac aatacaatga tagctacaac aagagaaata    900
gcaaaagcta caggaacaag tctacaaaca gtaataacaa cacttaaaat cttagaagaa    960
ggaaatatta taaaagaaa aactggagta ttaatgttaa accctgaact actaatgaga   1020
ggcgacgacc aaaaacaaaa atacctctta ctcgaatttg gaactttga gcaagaggca   1080 aatgaaatag attgacctcc caataacacc acgtagttat tgggaggtca atctatgaaa   1140
tgcgattaag ggccggccga agcaaactta agagtgtgtt gatagtgcag tatcttaaaa   1200
ttttgtataa taggaattga agttaaatta gatgctaaaa atttgtaatt aagaaggagt   1260
gattacatga acaaaaatat aaaatattct caaaactttt taacgagtga aaagtactc    1320 aaccaaataa taaaacaatt gaatttaaaa gaaaccgata ccgtttacga aattggaaca   1380
```

```
ggtaaagggc atttaacgac gaaactggct aaaataagta aacaggtaac gtctattgaa    1440
ttagacagtc atctattcaa cttatcgtca gaaaaattaa aactgaatac tcgtgtcact    1500
ttaattcacc aagatattct acagtttcaa ttccctaaca aacagaggta taaaattgtt    1560
gggagtattc cttaccattt aagcacacaa attattaaaa aagtggtttt tgaaagccat    1620
gcgtctgaca tctatctgat tgttgaagaa ggattctaca agcgtacctt ggatattcac    1680
cgaacactag ggttgctctt gcacactcaa gtctcgattc agcaattgct taagctgcca    1740
gcggaatgct ttcatcctaa accaaaagta aacagtgtct taataaaact tacccgccat    1800
accacagatg ttccagataa atattggaag ctatatacgt actttgtttc aaaatgggtc    1860
aatcgagaat atcgtcaact gtttactaaa aatcagtttc atcaagcaat gaaacacgcc    1920
aaagtaaaca atttaagtac cgttacttat gagcaagtat tgtctatttt taatagttat    1980
ctattattta acgggaggaa ataattctat gagtcgcttt tgtaaatttg gaaagttaca    2040
cgttactaaa gggaatgtgt ttaaactcct ttttgataat ctcatgacca aaatcccctta   2100 acgtgagttt tcgttccact gagcgtcaga ccccgtagaa aagatcaaag gatcttcttg    2160
agatcctttt tttctgcgcg taatctgctg cttgcaaaca aaaaaaccac cgctaccagc    2220
ggtggtttgt ttgccggatc aagagctacc aactcttttt ccgaaggtaa ctggcttcag    2280
cagagcgcag ataccaaata ctgttcttct agtgtagccg tagttaggcc accacttcaa    2340
gaactctgta gcaccgccta catacctcgc tctgctaatc ctgttaccag tggctgctgc    2400
cagtggcgat aagtcgtgtc ttaccgggtt ggactcaaga cgatagttac cggataaggc    2460
gcagcggtcg ggctgaacgg ggggttcgtg cacacagccc agcttggagc gaacgaccta    2520
caccgaactg agatacctac agcgtgagct atgagaaagc gccacgcttc ccgaagggag    2580
aaaggcggac aggtatccgg taagcggcag ggtcggaaca ggagagcgca cgagggagct    2640
tccaggggga aacgcctggt atctttatag tcctgtcggg tttcgccacc tctgacttga    2700
gcgtcgattt ttgtgatgct cgtcaggggg gcggagccta tggaaaaacg ccagcaacgc    2760
ggccttttta cggttcctgg ccttttgctg gccttttgct cacatgttct ttcctgcgtt    2820
atcccctgat tctgtggata accgtattac cgcctttgag tgagctgata ccgctcgccg    2880
cagccgaacg accgagcgca gcgagtcagt gagcgaggaa gcggaagagc gcccaatacg    2940
cagggccccc tgcaggataa aaaaattgta gataaatttt ataaaatagt tttatctaca    3000
atttttttat caggaaacag ctatgaccgc ggccgcggtt aatgttaaaa atttatagta    3060
taactttaaa aaactgtctt aaaaagttgt tatataaaaa atgttgacaa ttaaacagct    3120
atttagtgca aaacaaccat aaaaatttaa aaaataccat aaattacttg aaaaatagtt    3180
gataataatg tagagttata aacaaaggtg aaaagcatta cttgtattct ttttttatata   3240 ttattataaa ttaaaatgaa gctgtattag aaaaaataca cacctgtaat ataaaatttt    3300
aaattaattt ttaatttttt caaaatgtat tttacatgtt tagaattttg atgtatatta    3360
aaatagtaga atacataaga tacttaattt aattaaagat agttaagtac ttttcaatgt    3420
gcttttttag atgtttaata caaatcttta attgtaaaag aaatgctgta ctatttactg    3480
tactagtgac gggattaaac tgtattaatt ataaataaaa aataagtaca gttgtttaaa    3540
attatatttt gtattaaatc taatagtacg atgtaagtta ttttatacta ttgctagttt    3600
aataaaaaga tttaattata tacttgaaaa ggagaggaat ttttatgcgt catatggcaa    3660
cagaattatt atgtttacac agacctatat cacttactca caaacttttt aggaatccat    3720
tacctaaagt tattcaagct acacctttaa cattaaaact taggtgtagt gtttctacag    3780
```

```
aaaatgtatc atttagtgag acagaaactg aaacaagaag atcagcaaat tatgaaccaa    3840
attcttggga ttatgattat cttctttctt ctgatactga tgagtcaata gaagtacata    3900
aagataaggc taagaaatta gaagctgaag ttaggagaga aataaataat gagaaggctg    3960
aatttcttac acttcttgaa cttattgata atgtacaaag acttggatta ggatatagat    4020
ttgagtctga tataagaaga gcattagata gatttgtaag tagtggagga tttgatggag    4080
ttactaaaac ttcattacat ggaacagcat tatcatttag gttattaagg caacatggtt    4140
ttgaagtatc tcaagaagct tttagtggat ttaaagatca gaatggaaac tttcttgaga    4200
atttaaagga agacataaaa gcaattcttt ctctttatga agcatcattt ttagcattag    4260
aaggtgagaa tatattagat gaggctaaag tatttgcaat atctcatctt aaagaactta    4320
gtgaagaaaa gattggtaaa gaattagctg aacaagtttc acatgcttta gaattaccat    4380
tacatagaag aacacaaaga ttagaagcag tttggtcaat agaagcatat agaaagaaag    4440
aagacgcaaa tcaagtactt ttagaacttg caatacttga ctacaatatg attcaaagtg    4500
tatatcagag ggatttaaga gaaacatcaa gatggtggag aagagtagga ttagcaacta    4560
aattacattt tgctagagat aggcttattg aaagttttta ttgggctgtt ggagttgctt    4620
ttgaaccaca atattctgat tgcagaaata gtgtagcaaa gatgttttca tttgttacta    4680
taattgacga tatttacgat gtatatggaa ctttagatga acttgaactt tttactgatg    4740
cagttgaaag atgggatgta aatgctatta atgatcttcc tgattatatg aagttatgtt    4800
ttcttgcact ttacaatact attaacgaga tagcttacga taacttaaaa gataaaggtg    4860
agaacatact tccttattta acaaaagcat gggcagattt atgtaatgca tttcttcaag    4920
aagctaagtg gctttataat aaatcaacac ctacatttga tgattatttt ggaaatgcat    4980
ggaaaagttc tagtggacct ttacagctta ttttttgctta ttttgctgta gtacagaaca    5040
ttaaaaagga agagattgag aatcttcaga aatatcatga cataatatca agacctagtc    5100
acatttttag gctttgtaat gatttagcat ctgcttcagc agaaatagca agaggtgaaa    5160
ctgctaattc tgtaagttgt tatatgagaa caaaaggtat atctgaagaa ttagctactg    5220
aaagtgttat gaatcttata gacgaaactt ggaagaaaat gaacaaagaa aaacttggtg    5280
gatctttatt tgcaaaacct tttgttgaga ctgctataaa tttagctaga cagtctcatt    5340
gcacatatca taatggtgat gcacatacta gtccagatga attaactagg aaaagagtac    5400
ttagtgtaat aactgaacca atattaccat ttgaaagata agaattcgag ctcgaaaggg    5460
gaaattaaat ggcagaatat ataatagctg tagatgaatt tgataacgaa ataggttcaa    5520
ttgaaaaaat ggaggctcac cgtaaaggaa cattacatag agcttttttct atattagtat    5580 ttaattctaa aaatcaattg ttattacaga aagaaatgt aaaaaaatat cattcgcctg    5640
gtctctggac aaatacgtgc tgtagtcatc caagatacgg tgaaagttta catgatgcga    5700
tttatagaag gcttaaggaa gaaatggggtt ttacatgtga acttgaagaa gtatttagtt    5760
ttatttataa agtaaaactt gaagataatc ttttttgaaaa tgaatatgat catgtattca    5820
ttgggaaata tgatggagaa ataattgtaa acaaagatga agtagatgat tttaagtggg    5880
ttgatattaa tgaggttaag aaggatatta tagaaaggcc agaagcatac acttattggt    5940
tcaagtattt agttaataag gcagaaaaca aaatatttaa ataagtaaga atttcgtcta    6000
aataaagatt tggggtac                                                 6018
```

<210> SEQ ID NO 76

<211> LENGTH: 6909
<212> TYPE: DNA
<213> ORGANISM: Artificial Sequence
<220> FEATURE:
<223> OTHER INFORMATION: plasmid pMTL 82151-Patp-HMGR

<400> SEQUENCE: 76

| | |
|---|---|
| cctgcaggat aaaaaaattg tagataaatt ttataaaata gttttatcta caattttttt | 60 |
| atcaggaaac agctatgacc gcggccgctg tatccatatg accatgatta cgaattcgag | 120 |
| ctcgttataa ttttcaattt tcattctttt taaaggagat tagcatacat tttatcataa | 180 |
| ttatacagac aatatagtaa tatatgatgt taaaatatca atatatggtt aaaaatctgt | 240 |
| atatttttc ccatttaat tatttgtact ataatattac actgagtgta ttgcatattt | 300 |
| aaaaaatatt tggtacaatt agttagttaa ataaattcta aattgtaaat tatcagaatc | 360 |
| cttattaagg aaatacatag atttaaggag aaatcataaa aaggtgtaat ataaactggc | 420 |
| taaaattgag caaaaattga gcaattaaga cttttgatt gtatctttt atatatttaa | 480 |
| ggtatataat cttatttata ttggggaag gtaccatgca atcattagac aaaaatttca | 540 |
| gacatttatc aagacaacaa agttacaac aattagttga taaacagtgg ctttcagaag | 600 |
| atcagtttga tattttactt aatcatcctc ttatagtga agaagttgct aatagtctta | 660 |
| tagaaaatgt aattgcacag ggtgcattac cagttggact tcttcctaat ataatagttg | 720 |
| atgataaggc ttatgttgta ccaatgatgg ttgaagaacc tagtgttgtt gcagctgcat | 780 |
| cttatggtgc taaattagta aatcagacag gtggatttaa aactgtatca tcagaaagaa | 840 |
| taatgattgg acagatagta tttgatggtg tagatgcaca tgaaaaatta agtgcagata | 900 |
| ttaaagcatt agaaaacaa atacataaga ttgcagatga agcatatcct agtataaaag | 960 |
| caagaggtgg tggttatcaa agaatagcaa tagatacatt tccagagcaa caactttta | 1020 |
| gtcttaaggt atttgtagat acaaaagatg ctatgggtgc taatatgctt aatactatac | 1080 |
| ttgaggcaat aactgcattc cttaaaaatg aatctcctca atcagatata ttaatgtcta | 1140 |
| tactttcaaa ccatgcaact gctagtgtag taaaagtaca aggtgagata gatgtaaaag | 1200 |
| atcttgctag aggtgaaaga acaggtgaag aagtagctaa gagaatggaa agagcttctg | 1260 |
| tattagctca ggttgatatt catagagctg caacacataa caaggtgtt atgaatggaa | 1320 |
| tacatgctgt tgttttagct acaggaaatg atactagagg tgctgaagca tctgcacatg | 1380 |
| catacgcatc aagagacgga caatatagag gtatagcaac ttggagatat gatcagaaga | 1440 |
| gacaaagact tattgaaact attgaagttc caatgacact tgctatagta ggtggtggta | 1500 |
| ctaaagtatt accaatagct aaggcatcat tagagttatt aaatgttgat tctgcacaag | 1560 |
| aacttggaca cgtagttgct gctgttggat tagcacaaaa ctttgctgct tgtagagcac | 1620 |
| ttgtttctga aggtattcaa caaggacaca tgtcattaca atataaaagt ttagcaatag | 1680 |
| tagtaggtgc aaaaggtgac gagatagcac aagtagcaga agctcttaaa caggaaccaa | 1740 |
| gagctaatac acaggttgct gaaagaattt tacaggaaat tagacagcaa taatctagag | 1800 |
| tcgacgtcac gcgtccatgg agatctcgag gcctgcagac atgcaagctt ggcactggcc | 1860 |
| gtcgttttac aacgtcgtga ctgggaaaac cctggcgtta cccaacttaa tcgccttgca | 1920 |
| gcacatcccc ctttcgccag ctggcgtaat agcgaagagg cccgcaccga tcgcccttcc | 1980 |
| caacagttgc gcagcctgaa tggcgaatgg cgctagcata aaaataagaa gcctgcattt | 2040 |
| gcaggcttct tatttttatg gcgcgccgtt ctgaatcctt agctaatggt tcaacaggta | 2100 |
| actatgacga agatagcacc ctggataagt ctgtaatgga ttctaaggca tttaatgaag | 2160 |

```
acgtgtatat aaaatgtgct aatgaaaaag aaaatgcgtt aaaagagcct aaaatgagtt    2220
caaatggttt tgaaattgat tggtagttta atttaatata ttttttctat tggctatctc    2280
gatacctata gaatcttctg ttcactttg tttttgaaat ataaaaaggg gcttttagc      2340 cccttttttt taaaactccg gaggagtttc ttcattcttg atactatacg taactatttt    2400
cgatttgact tcattgtcaa ttaagctagt aaaatcaatg gttaaaaaac aaaaaacttg    2460
catttttcta cctagtaatt tataatttta agtgtcgagt ttaaaagtat aatttaccag    2520
gaaaggagca agttttttaa taaggaaaaa ttttccttt taaaattcta tttcgttata     2580
tgactaatta taatcaaaaa aatgaaaata aacaagaggt aaaaactgct ttagagaaat    2640
gtactgataa aaaagaaaa aatcctagat ttacgtcata catagcacct ttaactacta     2700
agaaaaatat tgaaaggact tccacttgtg gagattattt gtttatgttg agtgatgcag    2760
acttagaaca ttttaaatta cataaaggta attttttgcgg taatagattt tgtccaatgt   2820
gtagttggcg acttgcttgt aaggatagtt tagaaatatc tattcttatg gagcatttaa    2880
gaaaagaaga aaataaagag tttatatttt taactcttac aactccaaat gtaaaaagtt    2940
atgatcttaa ttattctatt aaacaatata ataaatcttt taaaaaatta atggagcgta    3000
aggaagttaa ggatataact aaaggttata taagaaaatt agaagtaact taccaaaagg    3060
aaaaatacat aacaaaggat ttatggaaaa taaaaaaaga ttattatcaa aaaaaaggac    3120
ttgaaattgg tgatttagaa cctaattttg atacttataa tcctcatttt catgtagtta    3180
ttgcagttaa taaaagttat tttacagata aaaattatta tataaatcga gaaagatggt    3240
tggaattatg gaagtttgct actaaggatg attctataac tcaagttgat gttagaaaag    3300
caaaaattaa tgattataaa gaggtttacg aacttgcgaa atattcagct aaagacactg    3360
attatttaat atcgaggcca gtatttgaaa ttttttataa agcattaaaa ggcaagcagg    3420
tattagtttt tagtggattt tttaaagatg cacacaaatt gtacaagcaa ggaaaacttg    3480
atgtttataa aaagaaagat gaaattaaat atgtctatat agtttattat aattggtgca    3540
aaaaacaata tgaaaaaact agaataaggg aacttacgga agatgaaaaa gaagaattaa    3600
atcaagattt aatagatgaa atagaaatag attaaagtgt aactatactt tatatatata    3660
tgattaaaaa aataaaaaac aacagcctat taggttgttg ttttttattt tctttattaa    3720
tttttttaat ttttagtttt tagttctttt ttaaaataag tttcagcctc ttttttcaata   3780 tttttaaag aaggagtatt tgcatgaatt gccttttttc taacagactt aggaaatatt     3840
ttaacagtat cttcttgcgc cggtgatttt ggaacttcat aacttactaa tttataatta    3900
ttattttctt ttttaattgt aacagttgca aaagaagctg aacctgttcc ttcaactagt    3960
ttatcatctt caatataata ttcttgacct atatagtata aatatatttt tattatattt    4020
ttactttttt ctgaatctat tattttataa tcataaaaag ttttaccacc aaaagaaggt    4080
tgtactcctt ctggtccaac atatttttt actatattat ctaaataatt tttgggaact     4140
ggtgttgtaa tttgattaat cgaacaacca gttatactta aaggaattat aactataaaa    4200
atatatagga ttatcttttt aaatttcatt attggcctcc tttttattaa atttatgtta    4260
ccataaaaag gacataacgg gaatatgtag aatattttta atgtagacaa aattttacat    4320
aaatataaag aaaggaagtg tttgtttaaa tttttatagca aactatcaaa aattagggg    4380 ataaaaattt atgaaaaaaa ggttttcgat gttattttta tgtttaactt taatagtttg    4440
tggtttattt acaaattcgg ccggccagtg ggcaagttga aaaattcaca aaaatgtggt    4500
```

```
ataatatctt tgttcattag agcgataaac ttgaatttga gagggaactt agatggtatt    4560
tgaaaaaatt gataaaaata gttggaacag aaaagagtat tttgaccact actttgcaag    4620
tgtaccttgt acctacagca tgaccgttaa agtggatatc acacaaataa aggaaaaggg    4680
aatgaaacta tatcctgcaa tgctttatta tattgcaatg attgtaaacc gccattcaga    4740
gtttaggacg gcaatcaatc aagatggtga attggggata tatgatgaga tgataccaag    4800
ctatacaata tttcacaatg atactgaaac attttccagc ctttggactg agtgtaagtc    4860
tgactttaaa tcatttttag cagattatga aagtgatacg caacggtatg gaaacaatca    4920
tagaatggaa ggaaagccaa atgctccgga aaacattttt aatgtatcta tgataccgtg    4980
gtcaaccttc gatggcttta atctgaattt gcagaaagga tatgattatt tgattcctat    5040
ttttactatg gggaaatatt ataaagaaga taacaaaatt atacttcctt tggcaattca    5100
agttcatcac gcagtatgtg acggatttca catttgccgt tttgtaaacg aattgcagga    5160
attgataaat agttaacttc aggtttgtct gtaactaaaa acaagtattt aagcaaaaac    5220
atcgtagaaa tacggtgttt tttgttaccc taagtttaaa ctccttttg ataatctcat    5280 gaccaaaatc ccttaacgtg agttttcgtt ccactgagcg tcagacccg tagaaaagat    5340 caaaggatct tcttgagatc cttttttttct gcgcgtaatc tgctgcttgc aaacaaaaaa    5400
accaccgcta ccagcggtgg tttgtttgcc ggatcaagag ctaccaactc ttttccgaa    5460 ggtaactggc ttcagcagag cgcagatacc aaatactgtt cttctagtgt agccgtagtt    5520
aggccaccac ttcaagaact ctgtagcacc gcctacatac ctcgctctgc taatcctgtt    5580
accagtggct gctgccagtg cgataagtc gtgtcttacc gggttggact caagacgata    5640
gttaccggat aaggcgcagc ggtcgggctg aacggggggt tcgtgcacac agcccagctt    5700
ggagcgaacg acctacaccg aactgagata cctacagcgt gagctatgag aaagcgccac    5760 gcttccgaa gggagaaagg cggacaggta tccggtaagc ggcagggtcg aacaggaga    5820 gcgcacgagg gagcttccag ggggaaacgc ctggtatctt tatagtcctg tcgggtttcg    5880
ccacctctga cttgagcgtc gatttttgtg atgctcgtca ggggggcgga gcctatggaa    5940
aaacgccagc aacgcggcct ttttacggtt cctggccttt tgctggcctt ttgctcacat    6000
gttctttcct gcgttatccc ctgattctgt ggataaccgt attaccgcct ttgagtgagc    6060
tgataccgct cgccgcagcc gaacgaccga gcgcagcgag tcagtgagcg aggaagcgga    6120
agagcgccca atacgcaggg ccccctgctt cggggtcatt atagcgattt tttcggtata    6180
tccatccttt ttcgcacgat atacaggatt ttgccaaagg gttcgtgtag actttccttg    6240
gtgtatccaa cggcgtcagc cgggcaggat aggtgaagta ggcccacccg cgagcgggtg    6300
ttccttcttc actgtccctt attcgcacct ggcggtgctc aacgggaatc ctgctctgcg    6360
aggctggccg gctaccgccg cgtaacaga tgagggcaag cggatggctg atgaaaccaa    6420
gccaaccagg aagggcagcc cacctatcaa ggtgtactgc cttccagacg aacgaagagc    6480
gattgaggaa aaggcggcgg cggccggcat gagcctgtcg gcctacctgc tggccgtcgg    6540
ccagggctac aaaatcacgg gcgtcgtgga ctatgagcac gtccgcgagc tggcccgcat    6600
caatggcgac ctgggccgcc tgggcggcct gctgaaactc tggctcaccg acgaccgcg    6660 cacggcgcgg ttcggtgatg ccacgatcct cgccctgctg gcgaagatcg aagagaagca    6720
ggacgagctt ggcaaggtca tgatgggcgt ggtccgcccg agggcagagc catgactttt    6780
ttagccgcta aaacgccgg ggggtgcgcg tgattgccaa gcacgtcccc atgcgctcca    6840
tcaagaagag cgacttcgcg gagctggtga agtacatcac cgacgagcaa ggcaagaccg    6900
```

```
<210> SEQ ID NO 77
<211> LENGTH: 31
<212> TYPE: DNA
<213> ORGANISM: Artificial Sequence
<220> FEATURE:
<223> OTHER INFORMATION: oligonucleotide EcoRI-HMGS_F

<400> SEQUENCE: 77
agccgtgaat tcgaggcttt tactaaaaac a                              31

<210> SEQ ID NO 78
<211> LENGTH: 32
<212> TYPE: DNA
<213> ORGANISM: Artificial Sequence
<220> FEATURE:
<223> OTHER INFORMATION: oligonucleotide EcoRI-HMGS_R

<400> SEQUENCE: 78
aggcgtctag atgttcgtct ctacaaataa tt                             32

<210> SEQ ID NO 79
<211> LENGTH: 8116
<212> TYPE: DNA
<213> ORGANISM: Artificial Sequence
<220> FEATURE:
<223> OTHER INFORMATION: plasmid pMTL 82151-HMGS-Patp-HMGR

<400> SEQUENCE: 79
```

| | | |
|---|---|---|
| cctgcaggat aaaaaaattg tagataaatt ttataaaata gttttatcta caatttttt | 60 |
| atcaggaaac agctatgacc gcggccgctg tatccatatg accatgatta cgaattcgag | 120 |
| gcttttacta aaaacaataa aacaggagg aataatatg actataggaa ttgacaaaat | 180 |
| aaacttttac gtaccaaaat attatgtaga tatggcaaaa ttagcagaag caagacaagt | 240 |
| agacccaaat aaatttctta ttggaatagg acagactgaa atggcagtta gtccagtaaa | 300 |
| ccaagatata gtatcaatgg gtgctaatgc tgctaaagat ataataactg atgaagacaa | 360 |
| aaagaaaata ggaatggtaa tagtagcaac tgagtcagca gtagatgcag caaaggcagc | 420 |
| agcagtacag attcataatt tattaggtat tcaaccatt gcaagatgtt tcgaaatgaa | 480 |
| agaagcatgt tatgctgcta ctcctgcaat tcagttagct aaggattatt tagctacaag | 540 |
| accaaatgag aaagttttag ttatagctac agatacagct agatatggac ttaattcagg | 600 |
| tggtgaacct actcaaggtg ctggtgctgt tgctatggtt atagctcata atcctagtat | 660 |
| acttgcatta aatgaagacg ctgttgctta tacagaagat gtttatgatt tctggagacc | 720 |
| aacaggacat aagtatccat tagtagatgg tgctttatca aaagacgcat atattagatc | 780 |
| ttttcaacaa tcttggaatg aatatgctaa gagacaagga aagagtttag ctgattttgc | 840 |
| tagtctttgc tttcatgttc cttttactaa aatgggtaaa aaggctttag aatctataat | 900 |
| agataacgca gatgaaacaa ctcaagagag attaagatct ggatatgaag atgcagttga | 960 |
| ttacaataga tatgttggaa atatatacac aggaagtctt tatctttctc ttataagtct | 1020 |
| tcttgaaaat agagatttac aggctggtga actattgga ttattttcat acggatcagg | 1080 |
| ttctgttggt gaattttatt cagctacact tgtagaagga tataaagatc accttgatca | 1140 |
| ggcagcacac aaaagcacttt taaacaatag aactgaagta tcagtagatg catacgaaac | 1200 |
| attttttcaag agatttgatg atgtagaatt tgatgaagag caggatgcag ttcatgaaga | 1260 |

-continued

```
tagacatata ttctatcttt caaacataga gaataatgta agagaatatc atagacctga    1320
ataagagctc gttataattt tcaattttca ttcttttaa aggagattag catacatttt    1380
atcataatta tacagacaat atagtaatat atgatgttaa aatatcaata tatggttaaa    1440
aatctgtata ttttttccca ttttaattat ttgtactata atattacact gagtgtattg    1500
catatttaaa aaatatttgg tacaattagt tagttaaata aattctaaat tgtaaattat    1560
cagaatcctt attaaggaaa tacatagatt taaggagaaa tcataaaaag gtgtaatata    1620
aactggctaa aattgagcaa aaattgagca attaagactt tttgattgta tcttttata    1680 tatttaaggt atataatctt atttatattg ggggaaggta ccatgcaatc attagacaaa    1740
aatttcagac atttatcaag acaacaaaag ttacaacaat tagttgataa acagtggctt    1800
tcagaagatc agtttgatat tttacttaat catcctctta tagatgaaga agttgctaat    1860
agtcttatag aaaatgtaat tgcacagggt gcattaccag ttggacttct tcctaatata    1920
atagttgatg ataaggctta tgttgtacca atgatggttg aagaacctag tgttgttgca    1980
gctgcatctt atggtgctaa attagtaaat cagacaggtg gatttaaaac tgtatcatca    2040
gaaagaataa tgattggaca gatagtattt gatggtgtag atgacactga aaaattaagt    2100
gcagatatta aagcattaga aaaacaaata cataagattg cagatgaagc atatcctagt    2160
ataaaagcaa gaggtggtgg ttatcaaaga atagcaatag atacatttcc agagcaacaa    2220
cttttaagtc ttaaggtatt tgtagataca aaagatgcta tgggtgctaa tatgcttaat    2280
actatacttg aggcaataac tgcattcctt aaaaatgaat ctcctcaatc agatatatta    2340
atgtctatac tttcaaacca tgcaactgct agtgtagtaa aagtacaagg tgagatagat    2400
gtaaaagatc ttgctagagg tgaaagaaca ggtgaagaag tagctaagag aatggaaaga    2460
gcttctgtat tagctcaggt tgatattcat agagctgcaa cacataacaa aggtgttatg    2520
aatggaatac atgctgttgt tttagctaca ggaaatgata ctagaggtgc tgaagcatct    2580
gcacatgcat acgcatcaag agacggacaa tatagaggta tagcaacttg gagatatgat    2640
cagaagagac aaagacttat tggaactatt gaagttccaa tgacacttgc tatagtaggt    2700
ggtggtacta agtattacc aatagctaag gcatcattag agttattaaa tgttgattct    2760
gcacaagaac ttggacacgt agttgctgct gttggattag cacaaaactt tgctgcttgt    2820
agagcacttg tttctgaagg tattcaacaa ggacacatgt cattacaata taaaagttta    2880
gcaatagtag taggtgcaaa aggtgacgag atagcacaag tagcagaagc tcttaaacag    2940
gaaccaagag ctaatacaca ggttgctgaa agaattttac aggaaattag acagcaataa    3000
tctagagtcg acgtcacgcg tccatggaga tctcgaggcc tgcagacatg caagcttggc    3060
actggccgtc gttttacaac gtcgtgactg ggaaaaccct ggcgttaccc aacttaatcg    3120
ccttgcagca catcccccctt tcgccagctg gcgtaatagc gaagaggccc gcaccgatcg    3180
cccttcccaa cagttgcgca gcctgaatgg cgaatggcgc tagcataaaa ataagaagcc    3240
tgcatttgca ggcttcttat ttttatggcg cgccgttctg aatccttagc taatggttca    3300
acaggtaact atgacgaaga tagcaccctg gataagtctg taatggattc taaggcatt    3360 aatgaagacg tgtatataaa atgtgctaat gaaaagaaa atgcgttaaa agagcctaaa    3420
atgagttcaa atggttttga aattgattgg tagtttaatt taatatatt tttctattgg    3480 ctatctcgat acctatagaa tcttctgttc acttttgttt ttgaaatata aaagggggct    3540
ttttagcccc ttttttttaa aactccggag gagtttcttc attcttgata ctatacgtaa    3600
ctattttcga tttgacttca ttgtcaatta agctagtaaa atcaatggtt aaaaaacaaa    3660
```

```
aaacttgcat ttttctacct agtaatttat aattttaagt gtcgagttta aaagtataat    3720
ttaccaggaa aggagcaagt tttttaataa ggaaaaattt ttccttttaa aattctattt    3780
cgttatatga ctaattataa tcaaaaaaat gaaaataaac aagaggtaaa aactgcttta    3840
gagaaatgta ctgataaaaa aagaaaaaat cctagattta cgtcatacat agcaccttta    3900
actactaaga aaatattga aaggacttcc acttgtggag attatttgtt tatgttgagt     3960
gatgcagact tagaacattt taaattacat aaaggtaatt tttgcggtaa tagattttgt    4020
ccaatgtgta gttggcgact tgcttgtaag gatagtttag aaatatctat tcttatggag    4080
catttaagaa aagaagaaaa taagagtttt atatttttaa ctcttacaac tccaaatgta    4140
aaaagttatg atcttaatta ttctattaaa caatataata aatctttttaa aaaattaatg   4200 gagcgtaagg aagttaagga tataactaaa ggttatataa gaaaattaga agtaacttac    4260
caaaaggaaa aatacataac aaaggattta tggaaaataa aaaaagatta ttatcaaaaa    4320
aaaggacttg aaattggtga tttagaacct aattttgata cttataatcc tcattttcat    4380
gtagttattg cagttaataa aagttatttt acagataaaa attattatat aaatcgagaa    4440
agatggttgg aattatggaa gtttgctact aaggatgatt ctataactca agttgatgtt    4500
agaaaagcaa aaattaatga ttataaagag gttacgaac ttgcgaaata ttcagctaaa     4560
gacactgatt atttaatatc gaggccagta tttgaaattt tttataaagc attaaaaggc    4620
aagcaggtat tagttttag tggattttt aaagatgcac acaaattgta caagcaagga      4680
aaacttgatg tttataaaaa gaaagatgaa attaaatatg tctatatagt ttattataat    4740
tggtgcaaaa aacaatatga aaaaactaga ataagggaac ttacggaaga tgaaaaagaa    4800
gaattaaatc aagatttaat agatgaaata gaaatagatt aaagtgtaac tatacttat    4860 atatatga ttaaaaaaat aaaaaacaac agcctattag gttgttgttt tttattttct      4920
ttattaattt ttttaatttt tagttttttag ttcttttttta aaataagttt cagcctcttt  4980
ttcaatattt tttaaagaag gagtatttgc atgaattgcc tttttctaa cagacttagg     5040 aaatatttta acagtatctt cttgcgccgg tgattttgga acttcataac ttactaattt    5100
ataattatta ttttctttt taattgtaac agttgcaaaa gaagctgaac ctgttccttc     5160
aactagttta tcatcttcaa tataatattc ttgacctata tagtataaat atatttttat    5220
tatattttta ctttttttctg aatctattat tttataatca taaaaagttt taccaccaaa   5280
agaaggttgt actccttctg gtccaacata tttttttact atattatcta ataatttttt   5340
gggaactggt gttgtaattt gattaatcga acaaccagtt atacttaaag gaattataac    5400
tataaaaata tataggatta tcttttttaaa tttcattatt ggcctccttt ttattaaatt   5460
tatgttacca taaaaggac ataacgggaa tatgtagaat atttttaatg tagacaaaat     5520
tttacataaa tataagaaa ggaagtgttt gtttaaattt tatagcaaac tatcaaaaat     5580 taggggata aaaattttatg aaaaaaaggt tttcgatgtt attttttatgt ttaactttaa   5640 tagtttgtgg tttatttaca aattcggccg gccagtgggc aagttgaaaa attcacaaaa    5700
atgtggtata atatctttgt tcattagagc gataaacttg aatttgagag gaacttaga    5760 tggtatttga aaaaattgat aaaaatagtt ggaacagaaa agagtatttt gaccactact   5820
ttgcaagtgt accttgtacc tacagcatga ccgttaaagt ggatatcaca caaataaagg    5880
aaaagggaat gaaactatat cctgcaatgc tttattatat tgcaatgatt gtaaaccgcc    5940
attcagagtt taggacggca atcaatcaag atggtgaatt ggggatatat gatgagatga    6000
```

```
taccaagcta tacaatattt cacaatgata ctgaaacatt ttccagcctt tggactgagt    6060
gtaagtctga ctttaaatca ttttttagcag attatgaaag tgatacgcaa cggtatggaa   6120
acaatcatag aatggaagga aagccaaatg ctccggaaaa catttttaat gtatctatga    6180
taccgtggtc aaccttcgat ggctttaatc tgaatttgca gaaaggatat gattatttga    6240
ttcctatttt tactatgggg aaatattata aagaagataa caaaattata cttcctttgg    6300
caattcaagt tcatcacgca gtatgtgacg gatttcacat ttgccgtttt gtaaacgaat    6360
tgcaggaatt gataaatagt taacttcagg tttgtctgta actaaaaaca agtatttaag    6420
caaaaacatc gtagaaatac ggtgtttttt gttaccctaa gtttaaactc cttttttgata   6480 atctcatgac caaaatccct taacgtgagt tttcgttcca ctgagcgtca gaccccgtag    6540
aaaagatcaa aggatcttct tgagatcctt ttttctgcg cgtaatctgc tgcttgcaaa    6600
caaaaaaacc accgctacca gcggtggttt gtttgccgga tcaagagcta ccaactcttt   6660
ttccgaaggt aactggcttc agcagagcgc agataccaaa tactgttctt ctagtgtagc    6720
cgtagttagg ccaccacttc aagaactctg tagcaccgcc tacatacctc gctctgctaa    6780
tcctgttacc agtggctgct gccagtggcg ataagtcgtg tcttaccggg ttggactcaa    6840
gacgatagtt accggataag gcgcagcggt cgggctgaac ggggggttcg tgcacacagc    6900
ccagcttgga gcgaacgacc tacaccgaac tgagatacct acagcgtgag ctatgagaaa    6960
gcgccacgct tcccgaaggg agaaaggcgg acaggtatcc ggtaagcggc agggtcggaa    7020
caggagagcg cacgagggag cttccagggg gaaacgcctg gtatctttat agtcctgtcg    7080
ggtttcgcca cctctgactt gagcgtcgat ttttgtgatg ctcgtcaggg gggcggagcc    7140
tatggaaaaa cgccagcaac gcggcctttt tacggttcct ggccttttgc tggccttttg    7200
ctcacatgtt ctttcctgcg ttatcccctg attctgtgga taaccgtatt accgcctttg    7260
agtgagctga taccgctcgc cgcagccgaa cgaccgagcg cagcgagtca gtgagcgagg    7320
aagcggaaga gcgcccaata cgcagggccc cctgcttcgg ggtcattata gcgattttt    7380 cggtatatcc atccttttc gcacgatata caggattttg ccaaagggtt cgtgtagact    7440
ttccttggtg tatccaacgg cgtcagccgg gcaggatagg tgaagtaggc ccacccgcga    7500
gcgggtgttc cttcttcact gtcccttatt cgcacctggc ggtgctcaac gggaatcctg    7560
ctctgcgagg ctggccggct accgccggcg taacagatga gggcaagcgg atggctgatg    7620
aaaccaagcc aaccaggaag ggcagcccac ctatcaaggt gtactgcctt ccagacgaac    7680
gaagagcgat tgaggaaaag gcggcggcgg ccggcatgag cctgtcggcc tacctgctgg    7740
ccgtcggcca gggctacaaa atcacgggcg tcgtggacta tgagcacgtc cgcgagctgg    7800
cccgcatcaa tggcgacctg ggccgcctgg cggcctgct gaaactctgg ctcaccgacg    7860
acccgcgcac ggcgcggttc ggtgatgcca cgatcctcgc cctgctggcg aagatcgaag    7920
agaagcagga cgagcttggc aaggtcatga tgggcgtggt ccgcccgagg gcagagccat    7980
gactttttta gccgctaaaa cggccggggg gtgcgcgtga ttgccaagca cgtccccatg    8040
cgctccatca agaagagcga cttcgcggag ctggtgaagt acatcaccga cgagcaaggc    8100
aagaccgatc gggccc                                                   8116
```

<210> SEQ ID NO 80
<211> LENGTH: 55
<212> TYPE: DNA
<213> ORGANISM: Artificial Sequence
<220> FEATURE:
<223> OTHER INFORMATION: Oligonucleotide NotI-XbaI-Prnf-MK_F

<400> SEQUENCE: 80

```
atgcgcggcc gctaggtcta gaatatcgat acagataaaa aaatatataa tacag      55
```

<210> SEQ ID NO 81
<211> LENGTH: 27
<212> TYPE: DNA
<213> ORGANISM: Artificial Sequence
<220> FEATURE:
<223> OTHER INFORMATION: Oligonucleotide SalI-Prnf-MK_R

<400> SEQUENCE: 81

```
tggttctgta acagcgtatt cacctgc      27
```

<210> SEQ ID NO 82
<211> LENGTH: 4633
<212> TYPE: DNA
<213> ORGANISM: Artificial Sequence
<220> FEATURE:
<223> OTHER INFORMATION: plasmid pMTL8314-Prnf-MK

<400> SEQUENCE: 82

```
aaactccttt ttgataatct catgaccaaa atcccttaac gtgagttttc gttccactga      60
gcgtcagacc ccgtagaaaa gatcaaagga tcttcttgag atccttttttt tctgcgcgta    120
atctgctgct tgcaaacaaa aaaaccaccg ctaccagcgg tggtttgttt gccggatcaa    180
gagctaccaa ctcttttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat    600
ctttatagtc ctgtcgggtt tcgccacctc tgacttgagc gtcgattttt gtgatgctcg    660
tcaggggggc ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggccccctg caggataaaa    900
aaattgtaga taaattttat aaaatagttt tatctacaat tttttttatca ggaaacagct    960
atgaccgcgg ccgctaggtc tagaatatcg atacagataa aaaatatat aatacagaag    1020
aaaaaattat aaatttgtgg tataatataa agtatagtaa tttaagttta aacctcgtga    1080
aaacgctaac aaataatagg aggtcaattg atgatagctg ttccattaa cgctggaaaa    1140
ataaaagttt taattgaggc attagaatct ggaaattatt catcaataaa atcagatgta    1200
tatgacggaa tgttatatga tgcaccagat caccttaaat cattagtaaa cagatttgta    1260
gaacttaata atataactga gccattagca gtaactatac agacaaatct tcctccttca    1320
agaggtcttg gatctagtgc agctgttgct gttgcttttg taagagcaag ttatgatttc    1380
ttaggaaaaa gtttaactaa agaagagctt ataagaaaagg ctaattgggc tgaacaaata    1440
gctcatggaa agccatctgg aatagataca caaacaatag tatctggaaa gcctgtttgg    1500
tttcaaaagg gacatgcaga acacttaaaa actctttcac ttgatggata catggtagta    1560
```

```
attgatacag gtgttaaagg aagtacaaga caggctgtag aagatgttca taaactttgc    1620
gaagatcctc aatatatgag tcacgtaaaa cacataggaa aacttgtact tagagcatct    1680
gatgttattg aacatcataa ctttgaagca cttgctgata tattcaatga atgtcatgct    1740
gatttaaagg ctcttacagt aagtcatgac aaaatagaac agttaatgaa gataggaaaa    1800
gaaaatggtg ctatagctgg taaattaact ggtgctggta gaggtggttc aatgttatta    1860
cttgcaaaag acttaccaac tgcaaagaat atagttaaag cagtagagaa agctggtgca    1920
gcacatactt ggattgaaaa tttaggtggt taagtcgacg tcacgcgtcc atggagatct    1980
cgaggcctgc agacatgcaa gcttggcact ggccgtcgtt ttacaacgtc gtgactggga    2040
aaaccctggc gttacccaac ttaatcgcct tgcagcacat ccccctttcg ccagctggcg    2100
taatagcgaa gaggcccgca ccgatcgccc ttcccaacag ttgcgcagcc tgaatggcga    2160
atggcgctag cataaaaata gaagcctgca ttttgcaggc ttcttatttt tatggcgcgc    2220
cgccattatt tttttgaaca attgacaatt catttcttat tttttattaa gtgatagtca    2280
aaaggcataa cagtgctgaa tagaaagaaa tttacagaaa agaaaattat agaatttagt    2340
atgattaatt atactcattt atgaatgttt aattgaatac aaaaaaaaat acttgttatg    2400
tattcaatta cgggttaaaa tatagacaag ttgaaaaatt taataaaaaa ataagtcctc    2460
agctcttata tattaagcta ccaacttagt atataagcca aaacttaaat gtgctaccaa    2520
cacatcaagc cgttagagaa ctctatctat agcaatattt caaatgtacc gacatacaag    2580
agaaacatta actatatata ttcaatttat gagattatct taacagatat aaatgtaaat    2640
tgcaataagt aagatttaga agtttatagc ctttgtgtat tggaagcagt acgcaaaggc    2700
ttttttattt gataaaaatt agaagtatat ttatttttttc ataattaatt tatgaaaatg    2760 aaaggggtg agcaaagtga cagaggaaag cagtatctta tcaaataaca aggtattagc    2820
aatatcatta ttgactttag cagtaaacat tatgactttt atagtgcttg tagctaagta    2880
gtacgaaagg gggagcttta aaaagctcct tggaatacat agaattcata aattaattta    2940
tgaaaagaag ggcgtatatg aaaacttgta aaaattgcaa agagtttatt aaagatactg    3000
aaatatgcaa aatacattcg ttgatgattc atgataaaac agtagcaacc tattgcagta    3060
aatacaatga gtcaagatgt ttacataaag ggaaagtcca atgtattaat tgttcaaaga    3120
tgaaccgata tggatggtgt gccataaaaa tgagatgttt tacagaggaa gaacagaaaa    3180
aagaacgtac atgcattaaa tattatgcaa ggagctttaa aaaagctcat gtaaagaaga    3240 gtaaaagaa aaaataattt atttattaat ttaatattga gagtgccgac acagtatgca    3300
ctaaaaaata tatctgtggt gtagtgagcc gatacaaaag gatagtcact cgcattttca    3360
taatacatct tatgttatga ttatgtgtcg gtgggacttc acgacgaaaa cccacaataa    3420
aaaaagagtt cggggtaggg ttaagcatag ttgaggcaac taaacaatca agctaggata    3480
tgcagtagca gaccgtaagg tcgttgttta ggtgtgttgt aatacatacg ctattaagat    3540
gtaaaaatac ggataccaat gaagggaaaa gtataatttt tggatgtagt ttgtttgttc    3600
atctatgggc aaactacgtc caaagccgtt tccaaatctg ctaaaaagta tatcctttct    3660
aaaatcaaag tcaagtatga aatcataaat aaagtttaat tttgaagtta ttatgatatt    3720 atgttttttct attaaaataa attaagtata tagaatagtt taataatagt atatacttaa    3780
tgtgataagt gtctgacagt gtcacagaaa ggatgattgt tatggattat aagcggccgg    3840
ccagtgggca agttgaaaaa ttcacaaaaa tgtggtataa tatctttgtt cattagagcg    3900
ataaacttga atttgagagg gaacttagat ggtatttgaa aaaattgata aaaatagttg    3960
```

```
gaacagaaaa gagtattttg accactactt tgcaagtgta ccttgtacct acagcatgac    4020
cgttaaagtg gatatcacac aaataaagga aagggaatg aaactatatc ctgcaatgct     4080
ttattatatt gcaatgattg taaaccgcca ttcagagttt aggacggcaa tcaatcaaga    4140
tggtgaattg gggatatatg atgagatgat accaagctat acaatatttc acaatgatac    4200
tgaaacattt tccagccttt ggactgagtg taagtctgac tttaaatcat ttttagcaga    4260
ttatgaaagt gatacgcaac ggtatggaaa caatcataga atggaaggaa agccaaatgc    4320
tccggaaaac atttttaatg tatctatgat accgtggtca accttcgatg ctttaatct     4380 gaatttgcag aaaggatatg attatttgat tcctattttt actatgggga aatattataa    4440
agaagataac aaaattatac ttcctttggc aattcaagtt catcacgcag tatgtgacgg    4500
atttcacatt tgccgttttg taaacgaatt gcaggaattg ataaatagtt aacttcaggt    4560
ttgtctgtaa ctaaaaacaa gtatttaagc aaaaacatcg tagaaatacg gtgtttttg     4620 ttaccctaag ttt                                                       4633

<210> SEQ ID NO 83
<211> LENGTH: 6753
<212> TYPE: DNA
<213> ORGANISM: Artificial Sequence
<220> FEATURE:
<223> OTHER INFORMATION: plasmid pMTL 8314-Prnf-MK-PMK-PMD

<400> SEQUENCE: 83
aaactccttt ttgataatct catgaccaaa atcccttaac gtgagttttc gttccactga      60
gcgtcagacc ccgtagaaaa gatcaaagga tcttcttgag atcctttttt tctgcgcgta    120
atctgctgct tgcaaacaaa aaaaccaccg ctaccagcgg tggtttgttt gccggatcaa    180
gagctaccaa ctcttttcc gaaggtaact ggcttcagca gagcgcagat accaaatact     240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggaaa cgcctggtat    600 ctttatagtc ctgtcgggtt tcgccacctc tgacttgagc gtcgattttt gtgatgctcg    660 tcagggggg ggagcctatg gaaaaacgcc agcaacgcgg ccttttacg gttcctggcc     720 ttttgctggc cttttgctca catgttcttt cctgcgttat ccctgattc tgtggataac      780 cgtattaccg cctttgagtg agctgatacc gctcgccgca gccgaacgac cgagcgcagc    840
gagtcagtga gcgaggaagc ggaagagcgc ccaatacgca gggccccctg caggataaaa    900
aaattgtaga taaattttat aaaatagttt tatctacaat ttttttatca ggaaacagct    960
atgaccgcgg ccgctaggtc tagaatatcg atacagataa aaaatatat aatacagaag    1020 aaaaaattat aaatttgtgg tataatataa agtatagtaa tttaagttta aacctcgtga   1080
aaacgctaac aaataatagg aggtcaattg atgatagctg ttccatttaa cgctggaaaa    1140
ataaaagttt taattgaggc attagaatct ggaaattatt catcaataaa atcagatgta    1200
tatgacggaa tgttatatga tgcaccagat caccttaaat cattagtaaa cagatttgta    1260
gaacttaata atataactga gccattagca gtaactatac agacaaatct tcctcctcca    1320
```

-continued

```
agaggtcttg gatctagtgc agctgttgct gttgcttttg taagagcaag ttatgatttc    1380
ttaggaaaaa gtttaactaa agaagagctt atagaaaagg ctaattgggc tgaacaaata    1440
gctcatggaa agccatctgg aatagataca caaacaatag tatctggaaa gcctgtttgg    1500
tttcaaaagg gacatgcaga aacacttaaa actctttcac ttgatggata catggtagta    1560
attgatacag gtgttaaagg aagtacaaga caggctgtag aagatgttca taaactttgc    1620
gaagatcctc aatatatgag tcacgtaaaa cacataggaa aacttgtact tagagcatct    1680
gatgttattg aacatcataa ctttgaagca cttgctgata tattcaatga atgtcatgct    1740
gatttaaagg ctcttacagt aagtcatgac aaaatagaac agttaatgaa gataggaaaa    1800
gaaaatggtg ctatagctgg taaattaact ggtgctggta gaggtggttc aatgttatta    1860
cttgcaaaag acttaccaac tgcaaagaat atagttaaag cagtagagaa agctggtgca    1920
gcacatactt ggattgaaaa tttaggtggt taagtcgaca aagacactaa aaaattataa    1980
aagtaaagga ggacattaaa tgatacaagt aaaggcacca ggaaaattat atatagcagg    2040
tgaatacgct gttacagaac caggatataa atctgttctt atagctcttg atagatttgt    2100
tacagctact attgaggaag ctgatcaata caaaggaaca atacattcaa aggcattaca    2160
tcacaatcca gtaactttta gtagagatga agattctatt gttatatcag acccacacgc    2220
agcaaaacaa cttaattatg tagtaactgc tatagaaata tttgagcaat atgcaaaatc    2280
atgtgacata gcaatgaagc atttcatttt aactatagat tctaacttag atgatagtaa    2340
tggacataag tatggacttg atcttctgc tgctgtttta gtttcagtaa ttaaagtact    2400
taacgaattt tatgatatga aactttcaaa cctttatata tataagttag cagtaattgc    2460
taatatgaaa ttacagagtt tatcttcatg cggtgatata gcagtaagtg tttattcagg    2520
ttggttagct tattctacat ttgaccatga atgggtaaaa caccagatag aagatacaac    2580
agttgaagaa gtacttatta aaaattggcc tggattacac atagagccac ttcaagctcc    2640
tgaaaatatg gaagttctta taggttggac aggtagtcca gctagtagtc ctcattttgt    2700
ttctgaagtt aaaagactta agtcagatcc ttcattttac ggtgatttct tagaagattc    2760
acatagatgt gtagaaaaat taattcatgc attcaaaact aataatatta agggtgttca    2820
gaaaatggta agacagaata gaactattat acaaagaatg gataaggaag caacagttga    2880
tatagagact gagaagttaa aatatttatg tgatattgct gaaaaatatc atggtgcaag    2940
taaaacttca ggtgctggtg gtggtgattg cggaataact ataataaata aggatgtaga    3000
caaagagaaa atatatgatg aatggactaa acatggaata aagcctctta agtttaatat    3060
ttatcatgga caataaccat ggtcaataat cttacaataa ataaaagaaa ggaggcaaaa    3120
atatgataaa atctggaaaa gcaagagcac acactaatat agcacttata aaatattggg    3180
gtaagaaaga tgaggcatta ataataccaa tgaataactc aatatcagta actttagaaa    3240
agttttatac tgaaacaaaa gttacatttta acgatcagct tactcaagat caattttggc    3300
ttaatggtga aaaagtttct ggaaaagaat tagaaaagat ttcaaagtat atggatattg    3360
ttagaaatag agctggaata gattggtatg ctgagataga atctgataat tttgttccta    3420
cagctgctgg tcttgctagt tctgctagtg cttatgcagc attagctgct gcatgtaacc    3480
aagcacttga tttacagtta agtgataaag acttaagtag attagctaga attggatcag    3540
gatcagcatc aagatcaata tacggtggtt ttgcagaatg ggaaaaagga tataatgacg    3600
aaacttctta tgctgttcca ttagaaagta atcactttga agatgatctt gctatgattt    3660
ttgtagtaat aaaccaacat tctaaaaagg ttccttcaag atatggaatg tctcttacaa    3720
```

```
gaaatacaag tagattctat caatattggt tagaccatat tgatgaagat cttgcagaag    3780
caaaggcagc aatacaagat aaggatttta agagattagg tgaagttatt gaagagaatg    3840
gacttagaat gcatgctaca aatcttggat caactccacc ttttacttac ttagtacaag    3900
agtcatacga tgtaatggca ttagtacatg agtgtagaga agcaggatat ccatgctatt    3960
tcactatgga tgctggacct aatgtaaaaa tacttgtaga gaagaaaaac aaacaacaga    4020
taatagataa acttttaact cagttcgata ataatcagat aatagatagt gatattatag    4080
ctacaggtat tgaaattata gaataaacta gttccgctaa gcttggcact ggccgtcgtt    4140
ttacaacgtc gtgactggga aaaccctggc gttacccaac ttaatcgcct tgcagcacat    4200
ccccctttcg ccagctggcg taatagcgaa gaggcccgca ccgatcgccc ttcccaacag    4260
ttgcgcagcc tgaatggcga atggcgctag cataaaaata agaagcctgc atttgcaggc    4320
ttcttatttt tatggcgcgc cgccattatt tttttgaaca attgacaatt catttcttat    4380
tttttattaa gtgatagtca aaaggcataa cagtgctgaa tagaaagaaa tttacagaaa    4440
agaaaattat agaatttagt atgattaatt atactcattt atgaatgttt aattgaatac    4500
aaaaaaaaat acttgttatg tattcaatta cgggttaaaa tatagacaag ttgaaaaatt    4560
taataaaaaa ataagtcctc agctcttata tattaagcta ccaacttagt atataagcca    4620
aaacttaaat gtgctaccaa cacatcaagc cgttagagaa ctctatctat agcaatattt    4680
caaatgtacc gacatacaag agaaacatta actatatata ttcaatttat gagattatct    4740
taacagatat aaatgtaaat tgcaataagt aagatttaga agtttatagc ctttgtgtat    4800
tggaagcagt acgcaaaggc ttttttattt gataaaaatt agaagtatat ttatttttc    4860
ataattaatt tatgaaaatg aaaggggtg agcaaagtga cagaggaaag cagtatctta    4920
tcaaataaca aggtattagc aatatcatta ttgactttag cagtaaacat tatgactttt    4980
atagtgcttg tagctaagta gtacgaaagg gggagcttta aaaagctcct tggaatacat    5040
agaattcata aattaattta tgaaaagaag ggcgtatatg aaaacttgta aaaattgcaa    5100
agagtttatt aaagatactg aaatatgcaa aatacattcg ttgatgattc atgataaaac    5160
agtagcaacc tattgcagta aatacaatga gtcaagatgt ttacataaag ggaaagtcca    5220
atgtattaat tgttcaaaga tgaaccgata tggatggtgt gccataaaaa tgagatgttt    5280
tacagaggaa gaacagaaaa aagaacgtac atgcattaaa tattatgcaa ggagctttaa    5340
aaaagctcat gtaaagaaga gtaaaaagaa aaaataattt atttattaat ttaatattga    5400
gagtgccgac acagtatgca ctaaaaaata tatctgtggt gtagtgagcc gatacaaaag    5460
gatagtcact cgcattttca taatacatct tatgttatga ttatgtgtcg gtgggacttc    5520
acgacgaaaa cccacaataa aaaagagtt cggggtaggg ttaagcatag ttgaggcaac    5580
taaacaatca agctaggata tgcagtagca gaccgtaagg tcgttgttta ggtgtgttgt    5640
aatacatacg ctattaagat gtaaaaatac ggataccaat gaagggaaaa gtaaattttt    5700
tggatgtagt ttgtttgttc atctatgggc aaactacgtc caaagccgtt tccaaatctg    5760
ctaaaaagta tatcctttct aaaatcaaag tcaagtatga aatcataaat aaagtttaat    5820
tttgaagtta ttatgatatt atgttttct attaaaataa attaagtata tagaaatagtt    5880
taataatagt atatacttaa tgtgataagt gtctgacagt gtcacagaaa ggatgattgt    5940
tatggattat aagcggccgg ccagtgggca agttgaaaaa ttcacaaaaa tgtggtataa    6000
tatctttgtt cattagagcg ataaacttga atttgagagg gaacttagat ggtatttgaa    6060
```

| | |
|---|---:|
| aaaattgata aaaatagttg aacagaaaa gagtattttg accactactt tgcaagtgta | 6120 |
| ccttgtacct acagcatgac cgttaaagtg gatatcacac aaataaagga aagggaatg | 6180 |
| aaactatatc ctgcaatgct ttattatatt gcaatgattg taaaccgcca ttcagagttt | 6240 |
| aggacggcaa tcaatcaaga tggtgaattg gggatatatg atgagatgat accaagctat | 6300 |
| acaatatttc acaatgatac tgaaacattt tccagccttt ggactgagtg taagtctgac | 6360 |
| tttaaatcat ttttagcaga ttatgaaagt gatacgcaac ggtatggaaa caatcataga | 6420 |
| atggaaggaa agccaaatgc tccggaaaac atttttaatg tatctatgat accgtggtca | 6480 |
| accttcgatg gctttaatct gaatttgcag aaaggatatg attatttgat tcctattttt | 6540 |
| actatgggga aatattataa agaagataac aaaattatac ttcctttggc aattcaagtt | 6600 |
| catcacgcag tatgtgacgg atttcacatt tgccgttttg taaacgaatt gcaggaattg | 6660 |
| ataaatagtt aacttcaggt ttgtctgtaa ctaaaaacaa gtatttaagc aaaaacatcg | 6720 |
| tagaaatacg gtgttttttg ttaccctaag ttt | 6753 |

<210> SEQ ID NO 84
<211> LENGTH: 9198
<212> TYPE: DNA
<213> ORGANISM: Artificial Sequence
<220> FEATURE:
<223> OTHER INFORMATION: plasmid pMTL8314-Prnf-MK-PMK-PMD-Pfor-idi-ispS

<400> SEQUENCE: 84

| | |
|---|---:|
| aaactccttt ttgataatct catgaccaaa atcccttaac gtgagttttc gttccactga | 60 |
| gcgtcagacc ccgtagaaaa gatcaaagga tcttcttgag atcctttttt tctgcgcgta | 120 |
| atctgctgct tgcaaacaaa aaaaccaccg ctaccagcgg tggtttgttt gccggatcaa | 180 |
| gagctaccaa ctctttttcc gaaggtaact ggcttcagca gagcgcagat accaaatact | 240 |
| gttcttctag tgtagccgta gttaggccac cacttcaaga actctgtagc accgcctaca | 300 |
| tacctcgctc tgctaatcct gttaccagtg gctgctgcca gtggcgataa gtcgtgtctt | 360 |
| accgggttgg actcaagacg atagttaccg gataaggcgc agcggtcggg ctgaacgggg | 420 |
| ggttcgtgca cacagcccag cttggagcga acgacctaca ccgaactgag atacctacag | 480 |
| cgtgagctat gagaaagcgc cacgcttccc gaagggagaa aggcggacag gtatccggta | 540 |
| agcggcaggg tcggaacagg agagcgcacg agggagcttc cagggggaaa cgcctggtat | 600 |
| ctttatagtc ctgtcgggtt tcgccacctc tgacttgagc gtcgattttt gtgatgctcg | 660 |
| tcagggggc ggagcctatg gaaaaacgcc agcaacgcgg cctttttacg gttcctggcc | 720 |
| ttttgctggc cttttgctca catgttcttt cctgcgttat cccctgattc tgtggataac | 780 |
| cgtattaccg cctttgagtg agctgatacc gctcgccgca gccgaacgac cgagcgcagc | 840 |
| gagtcagtga gcgaggaagc ggaagagcgc ccaatacgca gggcccctg caggataaaa | 900 |
| aaattgtaga taaattttat aaaatagttt tatctacaat ttttttatca ggaaacagct | 960 |
| atgaccgcgg ccgctaggtc tagaatatcg atacagataa aaaatatat aatacagaag | 1020 |
| aaaaaattat aaatttgtgg tataatataa agtatagtaa tttaagttta aacctcgtga | 1080 |
| aaacgctaac aaataatagg aggtcaattg atgatagctg ttccatttaa cgctggaaaa | 1140 |
| ataaaagttt taattgaggc attagaatct ggaaattatt catcaataaa atcagatgta | 1200 |
| tatgacggaa tgttatatga tgcaccagat caccttaaat cattagtaaa cagatttgta | 1260 |
| gaacttaata atataactga gccattagca gtaactatac agacaaatct tcctccttca | 1320 |
| agaggtcttg gatctagtgc agctgttgct gttgcttttg taagagcaag ttatgatttc | 1380 |

```
ttaggaaaaa gtttaactaa agaagagctt atagaaaagg ctaattgggc tgaacaaata      1440
gctcatggaa agccatctgg aatagataca caaacaatag tatctggaaa gcctgtttgg      1500
tttcaaaagg gacatgcaga aacacttaaa actctttcac ttgatggata catggtagta      1560
attgatacag gtgttaaagg aagtacaaga caggctgtag aagatgttca taaactttgc      1620
gaagatcctc aatatatgag tcacgtaaaa cacataggaa aacttgtact tagagcatct      1680
gatgttattg aacatcataa ctttgaagca cttgctgata tattcaatga atgtcatgct      1740
gatttaaagg ctcttacagt aagtcatgac aaaatagaac agttaatgaa gataggaaaa      1800
gaaaatggtg ctatagctgg taaattaact ggtgctggta gaggtggttc aatgttatta      1860
cttgcaaaag acttaccaac tgcaaagaat atagttaaag cagtagagaa agctggtgca      1920
gcacatactt ggattgaaaa tttaggtggt taagtcgaca aagacactaa aaaattataa      1980
aagtaaagga ggacattaaa tgatacaagt aaaggcacca ggaaaattat atatagcagg      2040
tgaatacgct gttacagaac caggatataa atctgttctt atagctcttg atagatttgt      2100
tacagctact attgaggaag ctgatcaata caaaggaaca atacattcaa aggcattaca      2160
tcacaatcca gtaactttta gtagagatga agattctatt gttatatcag acccacacgc      2220
agcaaaacaa cttaattatg tagtaactgc tatagaaata tttgagcaat atgcaaaatc      2280
atgtgacata gcaatgaagc attttcattt aactatagat tctaacttag atgatagtaa      2340
tggacataag tatggacttg gatcttctgc tgctgtttta gtttcagtaa ttaaagtact      2400
taacgaattt tatgatatga aactttcaaa ccttttatata tataagttag cagtaattgc      2460
taatatgaaa ttacagagtt tatcttcatg cggtgatata gcagtaagtg tttattcagg      2520
ttggttagct tattctacat ttgaccatga atgggtaaaa caccagatag aagatacaac      2580
agttgaagaa gtacttatta aaaattggcc tggattacac atagagccac ttcaagctcc      2640
tgaaaatatg gaagttctta taggttggac aggtagtcca gctagtagtc ctcattttgt      2700
ttctgaagtt aaaagactta agtcagatcc ttcattttac ggtgatttct tagaagattc      2760
acatagatgt gtagaaaaat taattcatgc attcaaaact aatataatta agggtgttca      2820
gaaaatggta agacagaata gaactattat acaaagaatg gataaggaag caacagttga      2880
tatagagact gagaagttaa aatatttatg tgatattgct gaaaaatatc atggtgcaag      2940
taaaacttca ggtgctggtg gtggtgattg cggaataact ataataaata aggatgtaga      3000
caaagagaaa atatatgatg aatggactaa acatggaata aagcctctta agtttaatat      3060
ttatcatgga caataaccat ggtcaataat cttacaataa ataaagaaa ggaggcaaaa      3120 atatgataaa atctggaaaa gcaagagcac acactaatat agcacttata aaatatgggg    3180
gtaagaaaga tgaggcatta ataataccaa tgaataactc aatatcagta actttagaaa    3240
agttttatac tgaaacaaaa gttacattta acgatcagct tactcaagat caattttggc    3300
ttaatggtga aaaagtttct ggaaaagaat tagaaaagat ttcaaagtat atggatattg    3360
ttagaaatag agctggaata gattggtatg ctgagataga atctgataat tttgttccta    3420
cagctgctgg tcttgctagt tctgctagtg cttatgcagc attagctgct gcatgtaacc    3480
aagcacttga tttacagtta agtgataaag acttaagtag attagctaga attggatcag    3540
gatcagcatc aagatcaata tacggtggtt ttgcagaatg ggaaaaagga tataatgacg    3600
aaacttctta tgctgttcca ttagaaagta atcactttga agatgatctt gctatgattt    3660
ttgtagtaat aaaccaacat tctaaaaagg ttccttcaag atatggaatg tctcttacaa    3720
```

-continued

```
gaaatacaag tagattctat caatattggt tagaccatat tgatgaagat cttgcagaag    3780
caaaggcagc aatacaagat aaggatttta agagattagg tgaagttatt gaagagaatg    3840
gacttagaat gcatgctaca aatcttggat caactccacc ttttacttac ttagtacaag    3900
agtcatacga tgtaatggca ttagtacatg agtgtagaga agcaggatat ccatgctatt    3960
tcactatgga tgctggacct aatgtaaaaa tacttgtaga gaagaaaaac aaacaacaga    4020
taatagataa acttttaact cagttcgata taatcagat aatagatagt gatattatag     4080
ctacaggtat tgaaattata gaataaacta gttgtatatt aaaatagtag aatacataag    4140
atacttaatt taattaaaga tagttaagta cttttcaatg tgcttttta gatgtttaat     4200
acaaatcttt aattgtaaaa gaaatgctgt actatttact gttctagtga cgggattaaa    4260
ctgtattaat tataaataaa aaataagtac agttgtttaa aattatattt tgtattaaat    4320
ctaatagtac gatgtaagtt attttatact attgctagtt taataaaaag atttaattat    4380
atacttgaaa aggagaggaa ctcgagatgg cagagtatat aatagcagta gatgagttcg    4440
ataacgaaat aggatcaata gaaaagatgg aagctcatag aaaaggaaca cttcatagag    4500
cattcagtat tttagttttt aactcaaaga atcaacttt attacagaaa agaaatgtaa     4560
agaaatatca ctctccagga ttatggacaa acacttgttg tagtcaccca agatatggtg    4620
aatctcttca tgatgctata tacagaagat taaagaaga gatgggattt acttgcgaac     4680
ttgaagaagt attctcattc atatataagg taaaacttga agataattta tttgagaatg    4740
aatatgacca tgtatttatt ggtaaatatg atggtgagat aattgttaat aaagatgaag    4800
ttgatgattt taaatgggta gacattaatg aagttaaaaa ggacataata gaaagacctg    4860
aggcatatac ttactggttt aagtatcttg taaataaagc tgaaaataag atatttaaat    4920
aaaccggtgg gaggaaatga acatggcaac agaattatta tgtttacaca gacctatatc    4980
acttactcac aaactttta ggaatccatt acctaaagtt attcaagcta cacctttaac     5040
attaaaactt aggtgtagtg tttctacaga aaatgtatca tttagtgaga cagaaactga    5100
aacaagaaga tcagcaaatt atgaaccaaa ttcttgggat tatgattatc ttctttcttc    5160
tgatactgat gagtcaatag aagtacataa agataaggct aagaaattag aagctgaagt    5220
taggagagaa ataaataatg agaaggctga atttcttaca cttcttgaac ttattgataa    5280
tgtacaaaga cttggattag gatatagatt tgagtctgat ataagaagag cattagatag    5340
atttgtaagt agtggaggat ttgatggagt tactaaaact tcattacatg gaacagcatt    5400
atcatttagg ttattaaggc aacatggttt tgaagtatct caagaagctt ttagtggatt    5460
taaagatcag aatggaaact tcttgagaa tttaaaggaa gacataaaag caattctttc     5520
tctttatgaa gcatcatttt tagcattaga aggtgagaat atattagatg aggctaaagt    5580
atttgcaata tctcatctta agaacttag tgaagaaaag attggtaaag aattagctga     5640
acaagtttca catgctttag aattaccatt acatagaaga acacaaagat tagaagcagt    5700
ttggtcaata gaagcatata gaaagaaaga agacgcaaat caagtacttt tagaacttgc    5760
aatacttgac tacaatatga ttcaaagtgt atatcagagg gatttaagag aaacatcaag    5820
atggtggaga agagtaggat tagcaactaa attcattttt gctagagata ggcttattga    5880
aagtttttat tgggctgttg gagttgcttt tgaaccacaa tattctgatt gcagaaatag    5940
tgtagcaaag atgttttcat ttgttactat aattgacgat atttcgatg tatatggaac     6000
tttagatgaa cttgaacttt ttactgatgc agttgaaaga tgggatgtaa atgctattaa    6060
tgatcttcct gattatatga agttatgttt tcttgcactt tacaatacta ttaacgagat    6120
```

```
agcttacgat aacttaaaag ataaaggtga gaacatactt ccttatttaa caaaagcatg   6180
ggcagattta tgtaatgcat ttcttcaaga agctaagtgg ctttataata aatcaacacc   6240
tacatttgat gattattttg gaaatgcatg gaaaagttct agtggacctt tacagcttat   6300
ttttgcttat tttgctgtag tacagaacat taaaaaggaa gagattgaga atcttcagaa   6360
atatcatgac ataatatcaa gacctagtca cattttttagg ctttgtaatg atttagcatc   6420
tgcttcagca gaaatagcaa gaggtgaaac tgctaattct gtaagttgtt atatgagaac   6480
aaaaggtata tctgaagaat tagctactga aagtgttatg aatcttatag acgaaacttg   6540
gaagaaaatg aacaagaaa aacttggtgg atctttattt gcaaaacctt ttgttgagac    6600
tgctataaat ttagctagac agtctcattg cacatatcat aatggtgatg cacatactag   6660
tccagatgaa ttaactagga aaagagtact tagtgtaata actgaaccaa tattaccatt   6720
tgaaagataa gctagcataa aaataagaag cctgcatttg caggcttctt attttttatgg  6780 cgcgccgcca ttatttttttt gaacaattga caattcattt cttattttt attaagtgat   6840 agtcaaaagg cataacagtg ctgaatagaa agaaatttac agaaagaaa attatagaat    6900 ttagtatgat taattatact catttatgaa tgtttaattg aatacaaaaa aaaatacttg   6960
ttatgtattc aattacgggt taaaatatag acaagttgaa aaatttaata aaaaaataag   7020
tcctcagctc ttatatatta agctaccaac ttagtatata agccaaaact taaatgtgct   7080
accaacacat caagccgtta gagaactcta tctatagcaa tatttcaaat gtaccgacat   7140
acaagagaaa cattaactat atatattcaa tttatgagat tatcttaaca gatataaatg   7200
taaattgcaa taagtaagat ttagaagttt atagcctttg tgtattggaa gcagtacgca   7260
aaggcttttt tatttgataa aaattagaag tatatttatt ttttcataat taatttatga   7320
aaatgaaagg gggtgagcaa agtgacagag gaaagcagta tcttatcaaa taacaaggta   7380
ttagcaatat cattattgac tttagcagta aacattatga cttttatagt gcttgtagct   7440
aagtagtacg aaagggggag ctttaaaaag ctccttggaa tacatagaat tcataaatta   7500
atttatgaaa agaagggcgt atatgaaaac ttgtaaaaat tgcaaagagt ttattaaaga   7560
tactgaaata tgcaaaatac attcgttgat gattcatgat aaaacagtag caacctattg   7620
cagtaaatac aatgagtcaa gatgtttaca taaagggaaa gtccaatgta ttaattgttc   7680
aaagatgaac cgatatggat ggtgtgccat aaaaatgaga tgttttacag aggaagaaca   7740 gaaaaagaa cgtacatgca ttaaatatta tgcaaggagc tttaaaaaag ctcatgtaaa    7800
gaagagtaaa agaaaaaat aatttatta ttaatttaat attgagagtg ccgacacagt     7860
atgcactaaa aaatatatct gtggtgtagt gagccgatac aaaaggatag tcactcgcat   7920
tttcataata catcttatgt tatgattatg tgtcggtggg acttcacgac gaaaacccac   7980
aataaaaaaa gagttcgggg tagggttaag catagttgag gcaactaaac aatcaagcta   8040
ggatatgcag tagcagaccg taaggtcgtt gtttaggtgt gttgtaatac atacgctatt   8100
aagatgtaaa aatacggata ccaatgaagg gaaaagtata atttttggat gtagtttgtt   8160
tgttcatcta tgggcaaact acgtccaaag ccgtttccaa atctgctaaa aagtatatcc   8220
tttctaaaat caaagtcaag tatgaaatca taaataaagt ttaattttga agttattatg   8280
atattatgtt tttctattaa aataaattaa gtatatagaa tagtttaata atagtatata   8340
cttaatgtga taagtgtctg acagtgtcac agaaaggatg attgttatgg attataagcg   8400
gccggccagt gggcaagttg aaaaattcac aaaaatgtgg tataatatct tgttcatta    8460
```

```
gagcgataaa cttgaatttg agagggaact tagatggtat ttgaaaaaat tgataaaaat    8520
agttggaaca gaaagagta  ttttgaccac tactttgcaa gtgtaccttg tacctacagc    8580
atgaccgtta aagtggatat cacacaaata aaggaaaagg gaatgaaact atatcctgca    8640
atgctttatt atattgcaat gattgtaaac cgccattcag agtttaggac ggcaatcaat    8700
caagatggtg aattggggat atatgatgag atgataccaa gctatacaat atttcacaat    8760
gatactgaaa cattttccag cctttggact gagtgtaagt ctgactttaa atcattttta    8820
gcagattatg aaagtgatac gcaacggtat ggaaacaatc atagaatgga aggaaagcca    8880
aatgctccgg aaaacatttt taatgtatct atgataccgt ggtcaacctt cgatggcttt    8940
aatctgaatt tgcagaaagg atatgattat ttgattccta tttttactat ggggaaatat    9000
tataaagaag ataacaaaat tatacttcct ttggcaattc aagttcatca cgcagtatgt    9060
gacggatttc acatttgccg ttttgtaaac gaattgcagg aattgataaa tagttaactt    9120
caggtttgtc tgtaactaaa aacaagtatt taagcaaaaa catcgtagaa atacggtgtt    9180
ttttgttacc ctaagttt                                                  9198

<210> SEQ ID NO 85
<211> LENGTH: 6841
<212> TYPE: DNA
<213> ORGANISM: Artificial Sequence
<220> FEATURE:
<223> OTHER INFORMATION: plasmid pMTL83245-Pfor-FS-idi

<400> SEQUENCE: 85
aaactccttt ttgataatct catgaccaaa atcccttaac gtgagttttc gttccactga      60
gcgtcagacc ccgtagaaaa gatcaaagga tcttcttgag atcctttttt tctgcgcgta     120
atctgctgct tgcaaacaaa aaaaccaccg ctaccagcgg tggtttgttt gccggatcaa     180
gagctaccaa ctctttttcc gaaggtaact ggcttcagca gagcgcagat accaaatact     240
gttcttctag tgtagccgta gttaggccac cacttcaaga actctgtagc accgcctaca     300
tacctcgctc tgctaatcct gttaccagtg gctgctgcca gtggcgataa gtcgtgtctt     360
accgggttgg actcaagacg atagttaccg gataaggcgc agcggtcggg ctgaacgggg     420
ggttcgtgca cacagcccag cttggagcga acgacctaca ccgaactgag atacctacag     480
cgtgagctat gagaaagcgc cacgcttccc gaagggagaa aggcggacag gtatccggta     540
agcggcaggg tcggaacagg agagcgcacg agggagcttc caggggggaaa cgcctggtat     600 ctttatagtc ctgtcgggtt tcgccacctc tgacttgagc gtcgattttt gtgatgctcg     660 tcagggggc  ggagcctatg gaaaaacgcc agcaacgcgg cctttttacg gttcctggcc     720
ttttgctggc cttttgctca catgttcttt cctgcgttat cccctgattc tgtggataac     780
cgtattaccg cctttgagtg agctgatacc gctcgccgca gccgaacgac cgagcgcagc     840
gagtcagtga gcgaggaagc ggaagagcgc ccaatacgca gggccccctg caggataaaa     900
aaattgtaga taaattttat aaaatagttt tatctacaat ttttttatca ggaaacagct     960
atgaccgcgg ccgcaatatg atatttatgt ccattgtgaa agggattata ttcaactatt    1020
attccagtta cgttcataga aattttcctt tctaaaatat tttattccat gtcaagaact    1080
ctgtttattt cattaaagaa ctataagtac aaagtataag gcatttgaaa aaataggcta    1140
gtatattgat tgattattta ttttaaaatg cctaagtgaa atatatacat attataacaa    1200
taaaataagt attagtgtag gattttttaaa tagagtatct attttcagat taaatttttg    1260
attatttgat ttacattata taatattgag taaagtattg actagcaaaa ttttttgata    1320
```

```
ctttaatttg tgaaatttct tatcaaaagt tatattttg aataattttt attgaaaaat    1380
acaactaaaa aggattatag tataagtgtg tgtaattttg tgttaaattt aaagggagga    1440
aatgaacatg aaacatatgg tgaccatgat tacgaattcg agctcggtac ccggggatcc    1500
tctagttgta tattaaaata gtagaataca aagatactt aatttaatta aagatagtta    1560
agtacttttc aatgtgcttt tttagatgtt aatacaaat ctttaattgt aaaagaaatg    1620
ctgtactatt tactgttcta gtgacgggat taaactgtat taattataaa taaaaaataa    1680
gtacagttgt ttaaaattat attttgtatt aaatctaata gtacgatgta agttatttta    1740
tactattgct agtttaataa aaagatttaa ttatatactt gaaaaggaga ggaactcgag    1800
atggaattta gagtacattt acaggcagac aacgaacaga aaatatttca aaatcaaatg    1860
aaaccagagc cagaagcatc atatcttata aatcaaagaa gaagtgctaa ttataaacca    1920
aacatttgga aaaacgattt tcttgatcag tctttaatat caaatatga tggtgatgaa    1980 tatagaaaac tttcagaaaa gttaataaga gaagtaaaga tatacatatc agcagagact    2040
atggatttag ttgctaaatt agaacttata gattctgtta gaaacttggg acttgctaat    2100 cttttttgaga aagaaataaa ggaagcatta gacagtatag cagcaataga atcagataat    2160
ttaggaacta gagacgatct ttatggaaca gctcttcatt ttaagattct tagacagcat    2220
ggatataagg taagtcaaga tatatttggt agatttatgg atgagaaagg aacattagaa    2280
aatcatcact ttgcacactt aaaaggaatg ttagaattat ttgaggcaag taatcttgga    2340
tttgaaggtg aagacatatt agatgaagct aaagcatctc ttacacttgc tcttagagat    2400
tcaggacata tttgttatcc agactcaaac ttaagtagag atgtagttca tagtttagaa    2460
ttacctagtc atagaagagt tcaatggttc gatgtaaaat ggcagattaa tgcatacgaa    2520
aaagatattt gtagagtaaa tgcaacttta ttagagttag caaagttaaa ttttaatgtt    2580
gttcaagctc agcttcagaa gaatcttaga gaagctagta gatggtgggc taatcttggt    2640
ttcgcagata atttaaagtt tgctagagat agacttgtag agtgtttttc atgcgcagta    2700
ggtgtagcat ttgaaccaga gcattcatct tttagaatat gtttaactaa ggtaattaat    2760
cttgttctta ttatagatga tgtatacgat atatatggat ctgaagaaga gttaaaacat    2820
tttacaaatg ctgttgatag atgggacagt agagaaacag aacagcttcc tgaatgcatg    2880
aaaatgtgtt ttcaagtatt atataacact acttgcgaaa tagcaagaga gatagaagaa    2940
gaaaacggtt ggaatcaagt attacctcaa cttactaagg tttgggctga ttttttgtaag    3000 gctcttttag ttgaagcaga gtggtacaat aaatcacata ttccaacatt agaagaatat    3060
cttagaaacg gatgtatatc aagtagtgta tctgtacttt tagttcactc tttcttttca    3120
ataactcatg aaggtacaaa agaaatggct gatttcttac ataaaaatga agatctttta    3180
tacaacataa gtcttatagt aagattaaac aatgatttag gtacatcagc tgctgaacag    3240
gaaagaggtg attctccttc ttctatagtt tgctatatga gagaagttaa tgcttctgaa    3300
gagactgcaa gaaagaatat aaagggaatg attgataatg cttggaaaaa ggttaatgga    3360
aaatgtttca caactaacca agttccattt ctttcatcat tcatgaataa tgcaactaac    3420
atggcaagag tagcacactc attatataaa gacggtgatg gttttggtga tcaagaaaaa    3480
ggacctagaa cacatattct tagtttatta ttccaacctt tagtaaatta actgcagggt    3540
tcaaaacata gattaaaaaa ttaaaggagg ggaaaaaatg gcagagtata taatagcagt    3600
agatgagttc gataacgaaa taggatcaat agaaaagatg gaagctcata gaaaaggaac    3660
```

```
acttcataga gcattcagta ttttagtttt taactcaaag aatcaacttt tattacagaa      3720
aagaaatgta aagaaatatc actctccagg attatggaca aacacttgtt gtagtcaccc      3780
aagatatggt gaatctcttc atgatgctat atacagaaga ttaaaagaag agatgggatt      3840
tacttgcgaa cttgaagaag tattctcatt catatataag gtaaaacttg aagataattt      3900
atttgagaat gaatatgacc atgtatttat tggtaaatat gatggtgaga taattgttaa      3960
taaagatgaa gttgatgatt ttaaatgggt agacattaat gaagttaaaa aggacataat      4020
agaaagacct gaggcatata cttactggtt taagtatctt gtaaataaag ctgaaaataa      4080
gatatttaaa taaaagcttg gcactggccg tcgttttaca acgtcgtgac tgggaaaacc      4140
ctggcgttac ccaacttaat cgccttgcag cacatccccc tttcgccagc tggcgtaata      4200
gcgaagaggc ccgcaccgat cgcccttccc aacagttgcg cagcctgaat ggcgaatggc      4260
gctagcataa aaataagaag cctgcatttg caggcttctt atttttatgg cgcgccgcca      4320 ttatttttt gaacaattga caattcattt cttatttttt attaagtgat agtcaaaagg      4380
cataacagtg ctgaatagaa agaaatttac agaaaagaaa attatagaat ttagtatgat      4440
taattatact catttatgaa tgtttaattg aatacaaaaa aaaatacttg ttatgtattc      4500
aattacgggt taaaatatag acaagttgaa aaatttaata aaaaaataag tcctcagctc      4560
ttatatatta agctaccaac ttagtatata agccaaaact taaatgtgct accaacacat      4620
caagccgtta gagaactcta tctatagcaa tatttcaaat gtaccgacat acaagagaaa      4680
cattaactat atatattcaa tttatgagat tatcttaaca gatataaatg taaattgcaa      4740
taagtaagat ttagaagttt atagcctttg tgtattggaa gcagtacgca aaggcttttt      4800
tatttgataa aaattagaag tatatttatt ttttcataat taatttatga aaatgaaagg      4860
gggtgagcaa agtgacagag gaaagcagta tcttatcaaa taacaaggta ttagcaatat      4920
cattattgac tttagcagta acattatga cttttatagt gcttgtagct aagtagtacg      4980 aaaggggag cttaaaaag ctccttggaa tacatagaat tcataaatta atttatgaaa      5040
agaagggcgt atatgaaaac ttgtaaaaat tgcaagagt ttattaaaga tactgaaata      5100
tgcaaaatac attcgttgat gattcatgat aaaacagtag caacctattg cagtaaaatac      5160 aatgagtcaa gatgtttaca taaagggaaa gtccaatgta ttaattgttc aaagatgaac      5220
cgatatggat ggtgtgccat aaaaatgaga tgttttacag aggaagaaca gaaaaagaa      5280 cgtacatgca ttaaatatta tgcaaggagc tttaaaaaag ctcatgtaaa gaagagtaaa      5340 aagaaaaat aatttattta ttaatttaat attgagagtg ccgacacagt atgcactaaa      5400
aaatatatct gtggtgtagt gagccgatac aaaaggatag tcactcgcat tttcataata      5460
catcttatgt tatgattatg tgtcggtggg acttcacgac gaaaacccac aataaaaaaa      5520
gagttcgggg tagggttaag catagttgag gcaactaaac aatcaagcta ggatatgcag      5580
tagcagaccg taaggtcgtt gtttaggtgt gttgtaatac atacgctatt aagatgtaaa      5640
aatacggata ccaatgaagg gaaaagtata atttttggat gtagtttgtt tgttcatcta      5700
tgggcaaact acgtccaaag ccgtttccaa atctgctaaa aagtatatcc tttctaaaat      5760
caaagtcaag tatgaaatca taaataaagt ttaattttga agttattatg atattatgtt      5820

tttctattaa ataaatttaa gtatatagaa tagtttaata atagtatata cttaatgtga      5880
taagtgtctg acagtgtcac agaaaggatg attgttatgg attaaagcg gccggccgaa      5940 gcaaacttaa gagtgtgttg atagtgcagt atcttaaaat tttgtataat aggaattgaa      6000
gttaaattag atgctaaaaa tttgtaatta agaaggagtg attacatgaa caaaaatata      6060
```

```
aaatattctc aaaacttttt aacgagtgaa aaagtactca accaaataat aaaacaattg      6120
aatttaaaag aaaccgatac cgtttacgaa attggaacag gtaaagggca tttaacgacg      6180
aaactggcta aaataagtaa acaggtaacg tctattgaat tagacagtca tctattcaac      6240
ttatcgtcag aaaaattaaa actgaatact cgtgtcactt taattcacca agatattcta      6300
cagtttcaat tccctaacaa acagaggtat aaaattgttg ggagtattcc ttaccattta      6360
agcacacaaa ttattaaaaa agtggttttt gaaagccatg cgtctgacat ctatctgatt      6420
gttgaagaag gattctacaa gcgtaccttg gatattcacc gaacactagg gttgctcttg      6480
cacactcaag tctcgattca gcaattgctt aagctgccag cggaatgctt tcatcctaaa      6540
ccaaaagtaa acagtgtctt aataaaactt acccgccata ccacagatgt tccagataaa      6600
tattggaagc tatatacgta ctttgtttca aaatgggtca atcgagaata tcgtcaactg      6660
tttactaaaa atcagtttca tcaagcaatg aaacacgcca agtaaacaa tttaagtacc       6720 gttacttatg agcaagtatt gtctattttt aatagttatc tattatttaa cgggaggaaa      6780
taattctatg agtcgctttt gtaaatttgg aaagttacac gttactaaag ggaatgtgtt      6840
t                                                                     6841
```

<210> SEQ ID NO 86
<211> LENGTH: 36
<212> TYPE: DNA
<213> ORGANISM: Artificial Sequence
<220> FEATURE:
<223> OTHER INFORMATION: Oligonucleotide idi_F2

<400> SEQUENCE: 86

```
aggcactcga gatggcagag tatataaatag cagtag                                  36
```

<210> SEQ ID NO 87
<211> LENGTH: 47
<212> TYPE: DNA
<213> ORGANISM: Artificial Sequence
<220> FEATURE:
<223> OTHER INFORMATION: Oligonucleotide idi_R2

<400> SEQUENCE: 87

```
aggcgcaagc ttggcgcacc ggtttattta aatatcttat tttcagc                       47
```

<210> SEQ ID NO 88
<211> LENGTH: 5075
<212> TYPE: DNA
<213> ORGANISM: Artificial Sequence
<220> FEATURE:
<223> OTHER INFORMATION: plasmid pMTL83245-Pfor-idi

<400> SEQUENCE: 88

```
aaactccttt ttgataatct catgaccaaa atcccttaac gtgagttttc gttccactga       60
gcgtcagacc ccgtagaaaa gatcaaagga tcttcttgag atcctttttt tctgcgcgta     120
atctgctgct tgcaaacaaa aaaaccaccg ctaccagcgg tggtttgttt gccggatcaa     180
gagctaccaa ctcttttttcc gaaggtaact ggcttcagca gagcgcagat accaaatact     240
gttcttctag tgtagccgta gttaggccac cacttcaaga actctgtagc accgcctaca     300
tacctcgctc tgctaatcct gttaccagtg gctgctgcca gtggcgataa gtcgtgtctt     360
accgggttgg actcaagacg atagttaccg gataaggcgc agcggtcggg ctgaacgggg     420
ggttcgtgca cacagcccag cttggagcga acgacctaca ccgaactgag atacctacag     480
```

| | |
|---|---|
| cgtgagctat gagaaagcgc cacgcttccc gaagggagaa aggcggacag gtatccggta | 540 |
| agcggcaggg tcggaacagg agagcgcacg agggagcttc caggggggaaa cgcctggtat | 600 |
| ctttatagtc ctgtcgggtt tcgccacctc tgacttgagc gtcgattttt gtgatgctcg | 660 |
| tcagggggc ggagcctatg gaaaaacgcc agcaacgcgg cctttttacg gttcctggcc | 720 |
| ttttgctggc cttttgctca catgttcttt cctgcgttat ccctgattc tgtggataac | 780 |
| cgtattaccg cctttgagtg agctgatacc gctcgccgca gccgaacgac cgagcgcagc | 840 |
| gagtcagtga gcgaggaagc ggaagagcgc ccaatacgca gggcccctg caggataaaa | 900 |
| aaattgtaga taaatttat aaaatagttt tatctacaat tttttatca ggaaacagct | 960 |
| atgaccgcgg ccgcaatatg atatttatgt ccattgtgaa aggattata ttcaactatt | 1020 |
| attccagtta cgttcataga attttccctt tctaaaatat tttattccat gtcaagaact | 1080 |
| ctgtttatt cattaaagaa ctataagtac aaagtataag gcatttgaaa aaataggcta | 1140 |
| gtatattgat tgattattta ttttaaaatg cctaagtgaa atatatacat attataacaa | 1200 |
| taaaataagt attagtgtag gattttaaa tagagtatct attttcagat taaatttttg | 1260 |
| attatttgat ttacattata taatattgag taaagtattg actagcaaaa tttttgata | 1320 |
| ctttaatttg tgaaatttct tatcaaaagt tatattttg aataattttt attgaaaat | 1380 |
| acaactaaaa aggattatag tataagtgtg tgtaattttg tgttaaattt aaagggagga | 1440 |
| aatgaacatg aaacatatgg tgaccatgat tacgaattcg agctcggtac ccggggatcc | 1500 |
| tctagttgta tattaaaata gtagaataca aagatactt aatttaatta aagatagtta | 1560 |
| agtactttc aatgtgcttt tttagatgtt taatacaaat cttaattgt aaaagaaatg | 1620 |
| ctgtactatt tactgttcta gtgacgggat taaactgtat taattataaa taaaaaataa | 1680 |
| gtacagttgt ttaaattat attttgtatt aaatctaata gtacgatgta agttatttta | 1740 |
| tactattgct agtttaataa aaagatttaa ttatatactt gaaaaggaga ggaactcgag | 1800 |
| atggcagagt atataaatagc agtagatgag ttcgataacg aaataggatc aatagaaaag | 1860 |
| atggaagctc atagaaaagg aacacttcat agagcattca gtattttagt ttttaactca | 1920 |
| aagaatcaac ttttattaca gaaaagaaat gtaaagaaat atcactctcc aggattatgg | 1980 |
| acaaacactt gttgtagtca cccaagatat ggtgaatctc ttcatgatgc tatatacaga | 2040 |
| agattaaaag aagagatggg atttacttgc gaacttgaag aagtattctc attcatatat | 2100 |
| aaggtaaaac ttgaagataa tttatttgag aatgaatatg accatgtatt tattggtaaa | 2160 |
| tatgatggtg agataattgt taataaagat gaagttgatg attttaaatg ggtagacatt | 2220 |
| aatgaagtta aaaaggacat aatagaaaga cctgaggcat atacttactg gtttaagtat | 2280 |
| cttgtaaaata aagctgaaaa taagatattt aaataaaccg gtgcgccaag cttggcactg | 2340 |
| gccgtcgttt tacaacgtcg tgactgggaa acccctggcg ttacccaact taatcgcctt | 2400 |
| gcagcacatc ccccttttcgc cagctggcgt aatagcgaag aggcccgcac cgatcgccct | 2460 |
| tcccaacagt tgcgcagcct gaatggcgaa tggcgctagc ataaaataa gaagcctgca | 2520 |
| tttgcaggct tcttatttt atggcgcgcc gccattattt ttttgaacaa ttgacaattc | 2580 |
| atttcttat ttttattaag tgatagtcaa aaggcataac agtgctgaat agaaagaaat | 2640 |
| ttacagaaaa gaaaattata gaatttagta tgattaatta tactcattta tgaatgttta | 2700 |
| attgaataca aaaaaaaata cttgttatgt attcaattac gggttaaaat atagacaagt | 2760 |
| tgaaaaattt aataaaaaaa taagtcctca gctcttatat attaagctac caacttagta | 2820 |
| tataagccaa aacttaaatg tgctaccaac acatcaagcc gttagagaac tctatctata | 2880 |

```
gcaatatttc aaatgtaccg acatacaaga gaaacattaa ctatatatat tcaatttatg    2940
agattatctt aacagatata aatgtaaatt gcaataagta agatttagaa gtttatagcc    3000
tttgtgtatt ggaagcagta cgcaaaggct tttttatttg ataaaaatta gaagtatatt    3060
tattttttca taattaattt atgaaaatga aggggggtga gcaaagtgac agaggaaagc    3120
agtatcttat caaataacaa ggtattagca atatcattat tgactttagc agtaaacatt    3180
atgactttta tagtgcttgt agctaagtag tacgaaaggg ggagctttaa aaagctcctt    3240
ggaatacata gaattcataa attaattat gaaagaagg gcgtatatga aaacttgtaa    3300
aaattgcaaa gagtttatta aagatactga aatatgcaaa atacattcgt tgatgattca    3360
tgataaaaca gtagcaacct attgcagtaa atacaatgag tcaagatgtt tacataaagg    3420
gaaagtccaa tgtattaatt gttcaaagat gaaccgatat ggatggtgtg ccataaaaat    3480
gagatgtttt acagaggaag aacagaaaaa agaacgtaca tgcattaaat attatgcaag    3540
gagctttaaa aaagctcatg taagaagag taaaagaaa aataatttta tttattaatt    3600
taatattgag agtgccgaca cagtatgcac taaaaaatat atctgtggtg tagtgagccg    3660
atacaaaagg atagtcactc gcattttcat aatacatctt atgttatgat tatgtgtcgg    3720
tgggacttca cgacgaaaac ccacaataaa aaagagttc ggggtagggt taagcatagt    3780
tgaggcaact aaacaatcaa gctaggatat gcagtagcag accgtaaggt cgttgtttag    3840
gtgtgttgta atacatacgc tattaagatg taaaaatacg ataccaatg aagggaaaag    3900 tataattttt ggatgtagtt tgtttgttca tctatgggca aactacgtcc aaagccgttt    3960
ccaaatctgc taaaaagtat atcctttcta aaatcaaagt caagtatgaa atcataaata    4020
aagtttaatt ttgaagttat tatgatatta tgttttctcta ttaaaataaa ttaagtatat    4080
agaatagttt aataatagta tatacttaat gtgataagtg tctgacagtg tcacagaaag    4140
gatgattgtt atggattata agcggccggc cgaagcaaac ttaagagtgt gttgatagtg    4200
cagtatctta aaattttgta ataggaat tgaagttaaa ttagatgcta aaaatttgta    4260
attaagaagg agtgattaca tgaacaaaaa tataaaatat tctcaaaact ttttaacgag    4320
tgaaaaagta ctcaaccaaa taataaaaca attgaattta aaagaaaccg ataccgttta    4380
cgaaattgga acaggtaaag ggcattaac gacgaaactg gctaaaataa gtaaacaggt    4440
aacgtctatt gaattagaca gtcatctatt caacttatcg tcagaaaaat taaaactgaa    4500
tactcgtgtc actttaattc accaagatat tctacagttt caattccta acaaacagag    4560 gtataaaatt gttgggagta ttccttacca tttaagcaca caaattatta aaaagtggt    4620 ttttgaaagc catgcgtctg acatctatct gattgttgaa aaggattct acaagcgtac    4680 cttggatatt caccgaacac tagggttgct cttgcacact caagtctcga ttcagcaatt    4740
gcttaagctg ccagcggaat gctttcatcc taaaccaaaa gtaaacagtg tcttaataaa    4800
acttacccgc cataccacag atgttccaga taaatattgg aagctatata cgtactttgt    4860
ttcaaaatgg gtcaatcgag aatatcgtca actgtttact aaaatcagt ttcatcaagc    4920 aatgaaacac gccaaagtaa acaatttaag taccgttact tatgagcaag tattgtctat    4980
ttttaatagt tatctattat ttaacgggag gaaataattc tatgagtcgc ttttgtaaat    5040
ttggaaagtt acacgttact aaagggaatg tgttt                              5075
```

<210> SEQ ID NO 89
<211> LENGTH: 6662
<212> TYPE: DNA

<213> ORGANISM: Artificial Sequence
<220> FEATURE:
<223> OTHER INFORMATION: plasmid pMTL83245-Pfor-idi-FS

<400> SEQUENCE: 89

```
aaactccttt tgataatct catgaccaaa atcccttaac gtgagttttc gttccactga    60
gcgtcagacc ccgtagaaaa gatcaaagga tcttcttgag atcctttttt tctgcgcgta   120
atctgctgct tgcaaacaaa aaaccaccg ctaccagcgg tggtttgttt gccggatcaa    180
gagctaccaa ctcttttttcc gaaggtaact ggcttcagca gagcgcagat accaaatact   240
gttcttctag tgtagccgta gttaggccac cacttcaaga actctgtagc accgcctaca   300
tacctcgctc tgctaatcct gttaccagtg gctgctgcca gtggcgataa gtcgtgtctt   360
accgggttgg actcaagacg atagttaccg gataaggcgc agcggtcggg ctgaacgggg   420
ggttcgtgca cacagcccag cttggagcga acgacctaca ccgaactgag atacctacag   480
cgtgagctat gagaaagcgc cacgcttccc gaagggagaa aggcggacag gtatccggta   540
agcggcaggg tcggaacagg agagcgcacg agggagcttc caggggggaaa cgcctggtat   600
ctttatagtc ctgtcgggtt tcgccacctc tgacttgagc gtcgattttt gtgatgctcg   660
tcagggggc ggagcctatg gaaaaacgcc agcaacgcgg ccttttttacg gttcctggcc    720
ttttgctggc cttttgctca catgttctttc cctgcgttat cccctgattc tgtggataac   780
cgtattaccg cctttgagtg agctgatacc gctcgccgca gccgaacgac cgagcgcagc   840
gagtcagtga gcgaggaagc ggaagagcgc ccaatacgca gggcccctg caggataaaa    900
aaattgtaga taaattttat aaaatagttt tatctacaat ttttttatca ggaaacagct   960
atgaccgcgg ccgcaatatg atatttatgt ccattgtgaa agggattata ttcaactatt  1020
attccagtta cgttcataga aattttcctt tctaaaatat tttattccat gtcaagaact  1080
ctgtttattt cattaaagaa ctataagtac aaagtataag gcatttgaaa aaataggcta  1140
gtatattgat tgattattta ttttaaaatg cctaagtgaa atatatacat attataacaa  1200
taaaataagt attagtgtag gattttttaaa tagagtatct attttcagat taaattttttg  1260
attatttgat ttacattata taatattgag taaagtattg actagcaaaa ttttttgata  1320
ctttaatttg tgaaatttct tatcaaaagt tatatttttg aataattttt attgaaaaat  1380
acaactaaaa aggattatag tataagtgtg tgtaattttg tgttaaattt aaagggagga  1440
aatgaacatg aaacatatgg tgaccatgat tacgaattcg agctcggtac ccggggatcc  1500
tctagttgta tattaaaata gtaaatacaa aagatacttt aatttaatta agatagtta    1560
agtacttttc aatgtgcttt tttagatgtt taatacaaat ctttaattgt aaaagaaatg  1620
ctgtactatt tactgttcta gtgacgggat taaactgtat taattataaa taaaaaataa  1680
gtacagttgt ttaaaattat attttgtatt aaatctaata gtacgatgta agttatttta  1740
tactattgct agtttaataa aaagatttaa ttatatactt gaaaggaga ggaactcgag   1800
atggcagagt atataatagc agtagatgag ttcgataacg aaataggatc aatagaaaag  1860
atggaagctc atagaaaagg aacacttcat agagcattca gtatttttagt ttttaactca  1920
aagaatcaac ttttattaca gaaaagaaat gtaaagaaat atcactctcc aggattatgg  1980
acaaacactt gttgtagtca cccaagatat ggtgaatctc ttcatgatgc tatatacaga  2040
agattaaaag aagagatggg atttacttgc gaacttgaag aagtattctc attcatatat  2100
aaggtaaaac ttgaagataa tttatttgag aatgaatatg accatgtatt tattggtaaa  2160
tatgatggtg agataattgt taataaagat gaagttgatg attttaaatg ggtagacatt  2220
```

| | |
|---|---|
| aatgaagtta aaaaggacat aatagaaaga cctgaggcat atacttactg gtttaagtat | 2280 |
| cttgtaaata aagctgaaaa taagatattt aaataaaccg gtgcgccaag cttttaaagg | 2340 |
| agggaaaaaa atggaattta gagtacattt acaggcagac aacgaacaga aaatatttca | 2400 |
| aaatcaaatg aaaccagagc cagaagcatc atatcttata aatcaaagaa gaagtgctaa | 2460 |
| ttataaaccca aacatttgga aaacgattt tcttgatcag tctttaatat caaaatatga | 2520 |
| tggtgatgaa tatagaaaac tttcagaaaa gttaatagaa gaagtaaaga tatacatatc | 2580 |
| agcagagact atggatttag ttgctaaatt agaacttata gattctgtta gaaaacttgg | 2640 |
| acttgctaat cttttgaga aagaaataaa ggaagcatta gacagtatag cagcaataga | 2700 |
| atcagataat ttaggaacta gagacgatct ttatggaaca gctcttcatt ttaagattct | 2760 |
| tagacagcat ggataaagg taagtcaaga tatatttggt agatttatgg atgagaaagg | 2820 |
| aacattagaa aatcatcact ttgcacactt aaaaggaatg ttagaattat ttgaggcaag | 2880 |
| taatcttgga tttgaaggtg aagacatatt agatgaagct aaagcatctc ttacacttgc | 2940 |
| tcttagagat tcaggacata tttgttatcc agactcaaac ttaagtagag atgtagttca | 3000 |
| tagtttagaa ttacctagtc atagaagagt tcaatggttc gatgtaaaat ggcagattaa | 3060 |
| tgcatacgaa aaagatattt gtagagtaaa tgcaacttta ttagagttag caaagttaaa | 3120 |
| ttttaatgtt gttcaagctc agcttcagaa gaatcttaga gaagctagta gatggtgggc | 3180 |
| taatcttggt ttcgcagata atttaaagtt tgctagagat agacttgtag agtgtttttc | 3240 |
| atgcgcagta ggtgtagcat ttgaaccaga gcattcatct tttagaatat gtttaactaa | 3300 |
| ggtaattaat cttgttctta ttatagatga tgtatacgat atatatggat ctgaagaaga | 3360 |
| gttaaaacat tttacaaatg ctgttgatag atgggacagt agagaaacag aacagcttcc | 3420 |
| tgaatgcatg aaaatgtgtt ttcaagtatt atataacact acttgcgaaa tagcaagaga | 3480 |
| gatagaagaa gaaaacggtt ggaatcaagt attacctcaa cttactaagg tttgggctga | 3540 |
| ttttttgtaag gctctttag ttgaagcaga gtggtacaat aaatcacata ttccaacatt | 3600 |
| agaagaatat cttagaaacg gatgtatatc aagtagtgta tctgtacttt tagttcactc | 3660 |
| tttcttttca ataactcatg aaggtacaaa agaaatggct gatttcttac ataaaaatga | 3720 |
| agatctttta tacaacataa gtcttatagt aagattaaac aatgatttag gtacatcagc | 3780 |
| tgctgaacag gaaagaggtg attctccttc ttctatagtt tgctatatga gagaagttaa | 3840 |
| tgcttctgaa gagactgcaa gaaagaatat aaagggaatg attgataatg cttggaaaaa | 3900 |
| ggttaatgga aaatgtttca caactaacca agttccattt ctttcatcat tcatgaataa | 3960 |
| tgcaactaac atggcaagag tagcacactc attatataaa gacggtgatg gttttggtga | 4020 |
| tcaagaaaaa ggacctagaa cacatattct tagtttatta ttccaacctt tagtaaatta | 4080 |
| agctagcata aaaataagaa gcctgcattt gcaggcttct tattttttatg gcgcgccgcc | 4140 |
| attattttt tgaacaattg acaattcatt tcttatttt tattaagtga tagtcaaaag | 4200 |
| gcataacagt gctgaataga aagaaattta cagaaaagaa aattatagaa tttagtatga | 4260 |
| ttaattatac tcatttatga atgtttaatt gaatacaaaa aaaaatactt gttatgtatt | 4320 |
| caattacggg ttaaaatata gacaagttga aaaatttaat aaaaaaataa gtcctcagct | 4380 |
| cttatatatt aagctaccaa cttagtatat aagccaaaac ttaaatgtgc taccaacaca | 4440 |
| tcaagccgtt agagaactct atctatagca atatttcaaa tgtaccgaca tacaagagaa | 4500 |
| acattaacta tatatattca atttatgaga ttatcttaac agatataaat gtaaattgca | 4560 |

```
ataagtaaga tttagaagtt tatagccttt gtgtattgga agcagtacgc aaaggctttt    4620
ttatttgata aaaattagaa gtatatttat tttttcataa ttaatttatg aaaatgaaag    4680
ggggtgagca aagtgacaga ggaaagcagt atcttatcaa ataacaaggt attagcaata    4740
tcattattga ctttagcagt aaacattatg acttttatag tgcttgtagc taagtagtac    4800
gaaaggggga gctttaaaaa gctccttgga atacatagaa ttcataaatt aatttatgaa    4860
aagaagggcg tatatgaaaa cttgtaaaaa ttgcaaagag tttattaaag atactgaaat    4920
atgcaaaata cattcgttga tgattcatga taaaacagta gcaacctatt gcagtaaata    4980
caatgagtca agatgtttac ataaagggaa agtccaatgt attaattgtt caaagatgaa    5040
ccgatatgga tggtgtgcca taaaaatgag atgttttaca gaggaagaac agaaaaaaga    5100
acgtacatgc attaaatatt atgcaaggag ctttaaaaaa gctcatgtaa agaagagtaa    5160
aaagaaaaaa taatttattt attaatttaa tattgagagt gccgacacag tatgcactaa    5220
aaaatatatc tgtggtgtag tgagccgata caaaaggata gtcactcgca ttttcataat    5280
acatcttatg ttatgattat gtgtcggtgg gacttcacga cgaaacccca caataaaaaa    5340
agagttcggg gtagggttaa gcatagttga ggcaactaaa caatcaagct aggatatgca    5400
gtagcagacc gtaaggtcgt tgtttaggtg tgttgtaata catacgctat taagatgtaa    5460
aaatacggat accaatgaag ggaaaagtat aattttggga tgtagtttgt ttgttcatct    5520
atgggcaaac tacgtccaaa gccgtttcca aatctgctaa aaagtatatc ctttctaaaa    5580
tcaaagtcaa gtatgaaatc ataaataaag tttaattttg aagttattat gatattatgt    5640
ttttctatta aaataaatta agtatataga atagtttaat aatagtatat acttaatgtg    5700
ataagtgtct gacagtgtca cagaaaggat gattgttatg gattataagc ggccggccga    5760
agcaaactta agagtgtgtt gatagtgcag tatcttaaaa ttttgtataa taggaattga    5820
agttaaatta gatgctaaaa atttgtaatt aagaaggagt gattacatga acaaaaatat    5880
aaaatattct caaaactttt taacgagtga aaaagtactc aaccaaataa taaacaatt    5940 gaatttaaaa gaaaccgata ccgtttacga aattggaaca ggtaaagggc atttaacgac    6000
gaaactggct aaaataagta aacaggtaac gtctattgaa ttagacagtc atctattcaa    6060
cttatcgtca gaaaaattaa aactgaatac tcgtgtcact ttaattcacc aagatattct    6120
acagtttcaa ttccctaaca aacagaggta taaaattgtt gggagtattc cttaccattt    6180
aagcacacaa attattaaaa aagtggtttt tgaaagccat gcgtctgaca tctatctgat    6240
tgttgaagaa ggattctaca agcgtacctt ggatattcac cgaacactag ggttgctctt    6300
gcacactcaa gtctcgattc agcaattgct taagctgcca gcggaatgct ttcatcctaa    6360
accaaaagta aacagtgtct taataaaact tacccgccat accacagatg ttccagataa    6420
atattggaag ctatatacgt actttgtttc aaaatgggtc aatcgagaat atcgtcaact    6480
gtttactaaa aatcagtttc atcaagcaat gaaacacgcc aaagtaaaca atttaagtac    6540
cgttacttat gagcaagtat tgtctatttt taatagttat ctattattta acgggaggaa    6600
ataattctat gagtcgcttt tgtaaatttg gaaagttaca cgttactaaa gggaatgtgt    6660
tt                                                                    6662
```

<210> SEQ ID NO 90
<211> LENGTH: 7077
<212> TYPE: DNA
<213> ORGANISM: Artificial Sequence
<220> FEATURE:
<223> OTHER INFORMATION: plasmid pMTL83245-Pfor-idi-ispA-FS

<400> SEQUENCE: 90

```
aaactccttt ttgataatct catgaccaaa atcccttaac gtgagttttc gttccactga    60
gcgtcagacc ccgtagaaaa gatcaaagga tcttcttgag atccttttt tctgcgcgta    120
atctgctgct tgcaaacaaa aaaaccaccg ctaccagcgg tggtttgttt gccggatcaa    180
gagctaccaa ctcttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggaaa cgcctggtat    600
ctttatagtc ctgtcgggtt tcgccacctc tgacttgagc gtcgattttt gtgatgctcg    660
tcaggggggc ggagcctatg gaaaaacgcc agcaacgcgg ccttttacg gttcctggcc    720
ttttgctggc cttttgctca catgttcttt cctgcgttat ccctgattc tgtggataac    780
cgtattaccg cctttgagtg agctgatacc gctcgccgca gccgaacgac cgagcgcagc    840
gagtcagtga cgaggaagc ggaagagcgc ccaatacgca gggccccctg caggataaaa    900
aaattgtaga taaatttat aaaatagttt tatctacaat ttttttatca ggaaacagct    960
atgaccgcgg ccgcaccgag actagttgta tattaaaata gtagaataca taagatactt    1020
aatttaatta aagatagtta agtactttc aatgtgcttt tttagatgtt taatacaaat    1080
ctttaattgt aaaagaaatg ctgtactatt tactgttcta gtgacgggat taaactgtat    1140
taattataaa taaaaaataa gtacagttgt ttaaaattat attttgtatt aaatctaata    1200
gtacgatgta agttatttta tactattgct agtttaataa aaagatttaa ttatatactt    1260
gaaaaggaga ggaactcgag atggcagagt atataatagc agtagatgag ttcgataacg    1320
aaataggatc aatagaaaag atggaagctc atagaaaagg aacacttcat agagcattca    1380
gtattttagt ttttaactca aagaatcaac ttttattaca gaaaagaaat gtaaagaaat    1440
atcactctcc aggattatgg acaaacactt gttgtagtca cccaagatat ggtgaatctc    1500
ttcatgatgc tatatacaga agattaaaag aagagatggg atttacttgc gaacttgaag    1560
aagtattctc attcatatat aaggtaaaac ttgaagataa tttatttgag aatgaatatg    1620
accatgtatt tattggtaaa tatgatggtg agataattgt taataaagat gaagttgatg    1680
attttaaatg ggtagacatt aatgaagtta aaaaggacat aatagaaaga cctgaggcat    1740
atacttactg gtttaagtat cttgtaaata agctgaaaa taagatattt aaataaaccg    1800
gtcagtaacg aatagaatta gaaaaacaaa ggaggcaaga caatggattt cccacaacaa    1860
ttagaagcat gtgtaaaaca ggctaatcag gcacttagta gatttattgc tcctcttcct    1920
tttcaaaata caccagtagt agaaactatg caatacggtg cacttttagg tggtaaaaga    1980
ttaagaccat tcttagtata tgctacagga cacatgtttg gtgtatcaac taatacttta    2040
gacgctccag ctgctgctgt tgaatgtatt catgcttatc ttaatacat gatgacttaa    2100
ccagcaatgg atgacgatga tttaagaaga ggtttaccta catgtcatgt taaatttggt    2160
gaagctaatg caattttagc aggtgacgct ttacaaactt tagcttttc tatactttca    2220
gatgcagaca tgcctgaagt ttcagataga gatagaattt ctatgatatc agagcttgca    2280
```

```
tctgcatcag gaatagctgg aatgtgcggt ggtcaagcac ttgatttaga tgcagaaggt    2340
aaacacgtac cacttgatgc tttagagaga atacatagac ataaaacagg tgctcttata    2400
agagcagcag taagattagg tgctttaagt gctggtgaca agggtagaag agcacttcca    2460
gtacttgata agtatgcaga aagtatagga ttagcttttc aagttcaaga tgacatactt    2520
gacgttgttg gtgatactgc tactttagga aaaagacagg gtgcagatca gcaattagga    2580
aaatctacat accctgcttt acttggatta gaacaggcta gaaagaaagc aagagactta    2640
atagatgacg caagacaaag tcttaaacag ttagctgaac aatcacttga cacaagtgca    2700
cttgaagcac ttgcagatta tattatacag agaaacaagt aaaagctttt aaggaggggg    2760
aaaaaatgga atttagagta catttacagg cagacaacga acagaaaata tttcaaaatc    2820
aaatgaaacc agagccagaa gcatcatatc ttataaatca agaagaagt gctaattata    2880 aaccaaacat ttggaaaaac gattttcttg atcagtcttt aatatcaaaa tatgatggtg    2940
atgaatatag aaaactttca gaaaagttaa tagaagaagt aaagatatac atatcagcag    3000
agactatgga tttagttgct aaattagaac ttatagattc tgttagaaaa cttggacttg    3060
ctaatctttt tgagaaagaa ataaaggaag cattagacag tatagcagca atagaatcag    3120
ataatttagg aactagagac gatctttatg gaacagctct tcattttaag attcttagac    3180
agcatggata aaggtaagt caagatatat ttggtagatt tatggatgag aaaggaacat    3240
tagaaaatca tcactttgca cacttaaaag gaatgttaga attatttgag gcaagtaatc    3300
ttggatttga aggtgaagac atattagatg aagctaaagc atctcttaca cttgctctta    3360
gagattcagg acatatttgt tatccagact caaacttaag tagagatgta gttcatagtt    3420
tagaattacc tagtcataga agagttcaat ggttcgatgt aaaatggcag attaatgcat    3480
acgaaaaaga tatttgtaga gtaaatgcaa ctttattaga gttagcaaag ttaaatttta    3540
atgttgttca agctcagctt cagaagaatc ttagagaagc tagtagatgg tgggctaatc    3600
ttggtttcgc agataattta aagtttgcta gagatagact tgtagagtgt ttttcatgcg    3660
cagtaggtgt agcatttgaa ccagagcatt catcttttag aatatgttta actaaggtaa    3720
ttaatcttgt tcttattata gatgatgtat acgatatata tggatctgaa gaagagttaa    3780
aacattttac aaatgctgtt gatagatggg acagtagaga aacagaacag cttcctgaat    3840
gcatgaaaat gtgtttcaa gtattatata acactacttg cgaaatagca agagagatag    3900
aagaagaaaa cggttggaat caagtattac ctcaacttac taaggtttgg gctgattttt    3960
gtaaggctct tttagttgaa gcagagtggt acaataaatc acatattcca acattagaag    4020
aatatcttag aaacggatgt atatcaagta gtgtatctgt actttagtt cactctttct    4080 tttcaataac tcatgaaggt acaaaagaaa tggctgattt cttacataaa aatgaagatc    4140
ttttatacaa cataagtctt atagtaagat aaaacaatga tttaggtaca tcagctgctg    4200
aacaggaaag aggtgattct ccttcttcta tagtttgcta tatgagagaa gttaatgctt    4260
ctgaagagac tgcaagaaag aatataaagg gaatgattga taatgcttgg aaaaaggtta    4320
atggaaaatg tttcacaact aaccaagttc catttctttc atcattcatg aataatgcaa    4380
ctaacatggc aagagtagca cactcattat ataaagacgg tgatggtttt ggtgatcaag    4440
aaaaaggacc tagaacacat attcttagtt tattattcca acctttagta aattaagcta    4500
gcataaaaat aagaagcctg catttgcagg cttcttattt ttatggcgcg ccgccattat    4560
ttttttgaac aattgacaat tcatttctta ttttttatta agtgatagtc aaaaggcata    4620
acagtgctga atagaaagaa atttacagaa aagaaaatta tagaatttag tatgattaat    4680
```

```
tatactcatt tatgaatgtt taattgaata caaaaaaaaa tacttgttat gtattcaatt    4740
acgggttaaa atatagacaa gttgaaaaat ttaataaaaa aataagtcct cagctcttat    4800
atattaagct accaacttag tatataagcc aaaacttaaa tgtgctacca acacatcaag    4860
ccgttagaga actctatcta tagcaatatt tcaaatgtac cgacatacaa gagaaacatt    4920
aactatatat attcaattta tgagattatc ttaacagata taaatgtaaa ttgcaataag    4980
taagatttag aagtttatag cctttgtgta ttggaagcag tacgcaaagg cttttttatt    5040
tgataaaaat tagaagtata tttatttttt cataattaat ttatgaaaat gaaaggtggt    5100
gagcaaagtg acagaggaaa gcagtatctt atcaaataac aaggtattag caatatcatt    5160
attgacttta gcagtaaaca ttatgacttt tatagtgctt gtagctaagt agtacgaaag    5220
ggggagcttt aaaaagctcc ttggaataca tagaattcat aaattaattt atgaaaagaa    5280
gggcgtatat gaaaacttgt aaaaattgca aagagtttat taaagatact gaaatatgca    5340
aaatacattc gttgatgatt catgataaaa cagtagcaac ctattgcagt aaatacaatg    5400
agtcaagatg tttacataaa gggaaagtcc aatgtattaa ttgttcaaag atgaaccgat    5460
atggatggtg tgccataaaa atgagatgtt ttacagagga agaacagaaa aaagaacgta    5520
catgcattaa atattatgca aggagcttta aaaaagctca tgtaaagaag agtaaaaaga    5580
aaaaataatt tatttattaa tttaatattg agagtgccga cacagtatgc actaaaaaat    5640
atatctgtgg tgtagtgagc cgatacaaaa ggatagtcac tcgcattttc ataatacatc    5700
ttatgttatg attatgtgtc ggtgggactt cacgacgaaa acccacaata aaaaagagt    5760 tcggggtagg gttaagcata gttgaggcaa ctaaacaatc aagctaggat atgcagtagc    5820
agaccgtaag gtcgttgttt aggtgtgttg taatacatac gctattaaga tgtaaaaata    5880
cggataccaa tgaagggaaa agtataattt ttggatgtag tttgtttgtt catctatggg    5940
caaactacgt ccaaagccgt ttccaaatct gctaaaaagt atatcctttc taaaatcaaa    6000
gtcaagtatg aaatcataaa taaagtttaa ttttgaagtt attatgatat tatgttttc     6060 tattaaaata aattaagtat atagaatagt ttaataatag tatatactta atgtgataag    6120
tgtctgacag tgtcacagaa aggatgattg ttatggatta taagcggccg gccgaagcaa    6180
acttaagagt gtgttgatag tgcagtatct taaaattttg tataatagga attgaagtta    6240
aattagatgc taaaaatttg taattaagaa ggagtgatta catgaacaaa aatataaaat    6300
attctcaaaa cttttttaacg agtgaaaaag tactcaacca aataataaaa caattgaatt    6360
taaaagaaac cgataccgtt tacgaaattg aacaggtaa agggcattta acgacgaaac    6420
tggctaaaat aagtaaacag gtaacgtcta ttgaattaga cagtcatcta ttcaacttat    6480
cgtcagaaaa attaaaactg aatactcgtg tcactttaat tcaccaagat attctacagt    6540
ttcaattccc taacaaacag aggtataaaa ttgttgggag tattccttac catttaagca    6600
cacaaattat taaaaaagtg gtttttgaaa gccatgcgtc tgacatctat ctgattgttg    6660
aagaaggatt ctacaagcgt accttggata ttcaccgaac actagggttg ctcttgcaca    6720
ctcaagtctc gattcagcaa ttgcttaagc tgccagcgga atgctttcat cctaaaccaa    6780
aagtaaacag tgtcttaata aaacttaccc gccataccac agatgttcca gataaatatt    6840
ggaagctata tacgtacttt gtttcaaaat gggtcaatcg agaatatcgt caactgttta    6900
ctaaaaatca gttcatcaa gcaatgaaac acgccaaagt aaacaattta agtaccgtta    6960
cttatgagca agtattgtct attttaata gttatctatt atttaacggg aggaaataat    7020
```
tctatgagtc gcttttgtaa atttggaaag ttacacgtta ctaaagggaa tgtgttt    7077

<210> SEQ ID NO 91
<211> LENGTH: 10090
<212> TYPE: DNA
<213> ORGANISM: Artificial Sequence
<220> FEATURE:
<223> OTHER INFORMATION: plasmid pMTL 8314-Prnf-MK-PMK-PMD-Pfor-idi-
      ispA-FS

<400> SEQUENCE: 91

```
aaactccttt ttgataatct catgaccaaa atcccttaac gtgagttttc gttccactga      60
gcgtcagacc ccgtagaaaa gatcaaagga tcttcttgag atccttttt tctgcgcgta     120
atctgctgct tgcaaacaaa aaaccaccg ctaccagcgg tggtttgttt gccggatcaa     180
gagctaccaa ctcttttcc gaaggtaact ggcttcagca gagcgcagat accaaatact     240
gttcttctag tgtagccgta gttaggccac cacttcaaga actctgtagc accgcctaca     300
tacctcgctc tgctaatcct gttaccagtg ctgctgcca gtggcgataa gtcgtgtctt     360
accgggttgg actcaagacg atagttaccg gataaggcgc agcggtcggg ctgaacgggg     420
ggttcgtgca cacagcccag cttggagcga acgacctaca ccgaactgag atacctacag     480
cgtgagctat gagaaagcgc cacgcttccc gaagggagaa aggcggacag gtatccggta     540
agcggcaggg tcggaacagg agagcgcacg agggagcttc caggggggaaa cgcctggtat     600
ctttatagtc ctgtcgggtt tcgccacctc tgacttgagc gtcgatttt tgtgatgctcg     660
tcagggggc ggagcctatg gaaaaacgcc agcaacgcgg cctttttacg gttcctggcc     720
ttttgctggc cttttgctca catgttcttt cctgcgttat ccctgattc tgtggataac     780
cgtattaccg cctttgagtg agctgatacc gctcgccgca gccgaacgac cgagcgcagc     840
gagtcagtga gcgaggaagc ggaagagcgc ccaatacgca gggcccctg caggataaaa     900
aaattgtaga taaatttat aaaatagttt tatctacaat ttttttatca ggaaacagct     960
atgaccgcgg ccgctaggtc tagaatatcg atacagataa aaaatatat aatacagaag    1020
aaaaaattat aaatttgtgg tataatataa agtatagtaa tttaagttta aacctcgtga    1080
aaacgctaac aaataatagg aggtcaattg atgatagctg ttccatttaa cgctggaaaa    1140
ataaagttt taattgaggc attagaatct ggaaattatt catcaataaa atcagatgta    1200
tatgacggaa tgttatatga tgcaccagat caccttaaat cattagtaaa cagatttgta    1260
gaacttaata atataactga gccattagca gtaactatac agacaaatct tcctccttca    1320
agaggtcttg gatctagtgc agctgttgct gttgcttttg taagagcaag ttatgatttc    1380
ttaggaaaaa gtttaactaa agaagagctt ataagaaagg ctaattgggc tgaacaaata    1440
gctcatggaa agccatctgg aatagataca caaacaatag tatctggaaa gcctgttggg    1500
tttcaaaagg gacatgcaga aacacttaaa actctttcac ttgatggata catggtagta    1560
attgatacag gtgttaaagg aagtacaaga caggctgtag aagatgttca taaactttgc    1620
gaagatcctc aatatatgag tcacgtaaaa cacataggaa aacttgtact tagagcatct    1680
gatgttattg aacatcataa ctttgaagca cttgctgata tattcaatga atgtcatgct    1740
gatttaaagg ctcttacagt aagtcatgac aaaataagaac agttaatgaa gataggaaaa    1800
gaaaatggtg ctatagctgg taaattaact ggtgctggta gaggtggttc aatgttatta    1860
cttgcaaaag acttaccaac tgcaaagaat atagttaaag cagtagagaa agctggtgca    1920
gcacatactt ggattgaaaa tttaggtggt taagtcgaca aagacactaa aaaattataa    1980
```

```
aagtaaagga ggacattaaa tgatacaagt aaaggcacca ggaaaattat atatagcagg    2040
tgaatacgct gttacagaac caggatataa atctgttctt atagctcttg atagatttgt    2100
tacagctact attgaggaag ctgatcaata caaaggaaca atacattcaa aggcattaca    2160
tcacaatcca gtaactttta gtagagatga agattctatt gttatatcag acccacacgc    2220
agcaaaacaa cttaattatg tagtaactgc tatagaaata tttgagcaat atgcaaaatc    2280
atgtgacata gcaatgaagc attttcattt aactatagat tctaacttag atgatagtaa    2340
tggacataag tatggacttg gatcttctgc tgctgtttta gtttcagtaa ttaaagtact    2400
taacgaattt tatgatatga aactttcaaa cctttatata tataagttag cagtaattgc    2460
taatatgaaa ttacagagtt tatcttcatg cggtgatata gcagtaagtg tttattcagg    2520
ttggttagct tattctacat ttgaccatga atgggtaaaa caccagatag aagatacaac    2580
agttgaagaa gtacttatta aaaattggcc tggattacac atagagccac ttcaagctcc    2640
tgaaaatatg gaagttctta taggttggac aggtagtcca gctagtagtc ctcattttgt    2700
ttctgaagtt aaaagactta agtcagatcc ttcattttac ggtgatttct tagaagattc    2760
acatagatgt gtagaaaaat taattcatgc attcaaaact aataatatta agggtgttca    2820
gaaaatggta agacagaata gaactattat acaaagaatg gataaggaag caacagttga    2880
tatagagact gagaagttaa aatatttatg tgatattgct gaaaaatatc atggtgcaag    2940
taaaacttca ggtgctggtg gtggtgattg cggaataact ataataaata aggatgtaga    3000
caaagagaaa atatatgatg aatggactaa acatggaata aagcctctta agttaaatat    3060
ttatcatgga caataaccat ggtcaataat cttacaataa ataaagaaa ggaggcaaaa    3120 atatgataaa atctggaaaa gcaagagcac acactaatat agcacttata aaatattggg    3180
gtaagaaaga tgaggcatta ataataccaa tgataactc aatatcagta actttagaaa    3240
agttttatac tgaaacaaaa gttacattta acgatcagct tactcaagat caattttggc    3300
ttaatggtga aaaagtttct ggaaaagaat tagaaaagat ttcaaagtat atggatattg    3360
ttagaaatag agctggaata gattggtatg ctgagataga atctgataat tttgttccta    3420
cagctgctgg tcttgctagt tctgctagtg cttatgcagc attagctgct gcatgtaacc    3480
aagcacttga tttacagtta agtgataaag acttaagtag attagctaga attggatcag    3540
gatcagcatc aagatcaata tacggtggtt ttgcagaatg ggaaaaagga tataatgacg    3600
aaacttctta tgctgttcca ttagaaagta atcactttga agatgatctt gctatgattt    3660
ttgtagtaat aaaccaacat tctaaaaagg ttccttcaag atatggaatg tctcttacaa    3720
gaaatacaag tagattctat caatattggt tagaccatat tgatgaagat cttgcagaag    3780
caaaggcagc aatacaagat aaggatttta agagattagg tgaagttatt gaagagaatg    3840
gacttagaat gcatgctaca aatcttggat caactccacc ttttacttac ttagtacaag    3900
agtcatacga tgtaatggca ttagtacatg agtgtagaga agcaggatat ccatgctatt    3960
tcactatgga tgctggacct aatgtaaaaa tacttgtaga aagaaaaac aaacaacaga    4020 taatagataa acttttaact cagttcgata ataatcagat aatagatagt gatattatag    4080
ctacaggtat tgaaattata gaataaacta gttgtatatt aaaatagtag aatacataag    4140
atacttaatt taattaaaga tagttaagta cttttcaatg tgctttttta gatgtttaat    4200
acaaatcttt aattgtaaaa gaaatgctgt actatttact gttctagtga cgggattaaa    4260
ctgtattaat tataaataaa aaataagtac agttgtttaa aattatattt tgtattaaat    4320
ctaatagtac gatgtaagtt attttatact attgctagtt taataaaaag atttaattat    4380
```

```
atacttgaaa aggagaggaa ctcgagatgg cagagtatat aatagcagta gatgagttcg    4440
ataacgaaat aggatcaata gaaaagatgg aagctcatag aaaaggaaca cttcatagag    4500
cattcagtat tttagttttt aactcaaaga atcaacttt attacagaaa agaaatgtaa     4560
agaaatatca ctctccagga ttatggacaa acacttgttg tagtcaccca agatatggtg    4620
aatctcttca tgatgctata tacagaagat taaagaaga gatgggattt acttgcgaac    4680
ttgaagaagt attctcattc atatataagg taaaacttga agataattta tttgagaatg    4740
aatatgacca tgtatttatt ggtaaatatg atggtgagat aattgttaat aaagatgaag    4800
ttgatgattt taaatgggta gacattaatg aagttaaaaa ggacataata gaaagacctg    4860
aggcatatac ttactggttt aagtatcttg taaataaagc tgaaaataag atatttaaat    4920
aaaccggtca gtaacgaata gaattagaaa acaaaggag gcaagacaat ggatttccca     4980
caacaattag aagcatgtgt aaaacaggct aatcaggcac ttagtagatt tattgctcct    5040
cttccttttc aaaatacacc agtagtagaa actatgcaat acggtgcact ttaggtggt     5100 aaaagattaa gaccattctt agtatatgct acaggacaca tgtttggtgt atcaactaat    5160
actttagacg ctccagctgc tgctgttgaa tgtattcatg cttattcttt aatacatgat    5220
gacttaccag caatggatga cgatgattta agaagaggtt tacctacatg tcatgttaaa    5280
tttggtgaag ctaatgcaat tttagcaggt gacgctttac aaactttagc ttttctata    5340 cttcagatg cagacatgcc tgaagtttca gatagagata gaatttctat gatatcagag    5400
cttgcatctg catcaggaat agctggaatg tgcggtggtc aagcacttga tttagatgca    5460
gaaggtaaac acgtaccact tgatgcttta gagagaatac atagacataa aacaggtgct    5520
cttataagag cagcagtaag attaggtgct ttaagtgctg gtgacaaggg tagaagagca    5580
cttccagtac ttgataagta tgcagaaagt ataggattag ctttttcaagt tcaagatgac    5640 atacttgacg ttgttggtga tactgctact ttaggaaaaa gacagggtgc agatcagcaa    5700
ttaggaaaat ctacataccc tgctttactt ggattagaac aggctagaaa gaaagcaaga    5760
gacttaatag atgacgcaag acaaagtctt aaacagttag ctgaacaatc acttgacaca    5820
agtgcacttg aagcacttgc agattatatt atacagagaa acaagtaaaa gcttttaaag    5880
gaggggaaaa aatggaattt agagtacatt tacaggcaga caacgaacag aaaatatttc    5940
aaaatcaaat gaaccagag ccagaagcat catatcttat aaatcaaaga agaagtgcta    6000 attataaaacc aaacatttgg aaaaacgatt ttcttgatca gtctttaata tcaaaatatg    6060
atggtgatga atatagaaaa ctttcagaaa agttaataga agaagtaaag atatacatat    6120
cagcagagac tatggattta gttgctaaat tagaacttat agattctgtt agaaaacttg    6180
gacttgctaa tctttttgag aaagaaataa aggaagcatt agacagtata gcagcaatag    6240
aatcagataa tttaggaact agagacgatc tttatggaac agctcttcat tttaagattc    6300
ttagacagca tggatataag gtaagtcaag atatatttgg tagatttatg gatgagaaag    6360
gaacattaga aaatcatcac tttgcacact aaaaggaat gttagaatta tttgaggcaa    6420
gtaatcttgg atttgaaggt gaagacatat tagatgaagc taaagcatct cttacacttg    6480
ctcttagaga ttcaggacat atttgttatc cagactcaaa cttaagtaga gatgtagttc    6540
atagtttaga attacctagt catagaagag ttcaatggtt cgatgtaaaa tggcagatta    6600
atgcatacga aaaagatatt tgtagagtaa atgcaacttt attagagtta gcaaagttaa    6660
attttaatgt tgttcaagct cagcttcaga agaatcttag agaagctagt agatggtggg    6720
```

```
ctaatcttgg tttcgcagat aatttaaagt ttgctagaga tagacttgta gagtgttttt    6780
catgcgcagt aggtgtagca tttgaaccag agcattcatc ttttagaata tgtttaacta    6840
aggtaattaa tcttgttctt attatagatg atgtatacga tatatatgga tctgaagaag    6900
agttaaaaca ttttacaaat gctgttgata gatgggacag tagagaaaca gaacagcttc    6960
ctgaatgcat gaaaatgtgt tttcaagtat tatataacac tacttgcgaa atagcaagag    7020
agatagaaga agaaaacggt tggaatcaag tattacctca acttactaag gtttgggctg    7080
atttttgtaa ggctctttta gttgaagcag agtggtacaa taaatcacat attccaacat    7140
tagaagaata tcttagaaac ggatgtatat caagtagtgt atctgtactt ttagttcact    7200
cttttctttc aataactcat gaaggtacaa agaaatggc tgatttctta cataaaaatg      7260
aagatctttt atacaacata agtcttatag taagattaaa caatgattta ggtacatcag    7320
ctgctgaaca ggaaagaggt gattctcctt cttctatagt ttgctatatg agagaagtta    7380
atgcttctga agagactgca agaaagaata taaagggaat gattgataat gcttggaaaa    7440
aggttaatgg aaaatgtttc acaactaacc aagttccatt tctttcatca ttcatgaata    7500
atgcaactaa catggcaaga gtagcacact cattatataa agacggtgat ggttttggtg    7560
atcaagaaaa aggacctaga acacatattc ttagtttatt attccaacct ttagtaaatt    7620
aagctagcat aaaaataaga agcctgcatt tgcaggcttc ttatttttat ggcgcgccgc    7680
cattatttt ttgaacaatt gacaattcat ttcttatttt ttattaagtg atagtcaaaa      7740
ggcataacag tgctgaatag aaagaaattt acagaaaaga aaattataga atttagtatg    7800
attaattata ctcatttatg aatgtttaat tgaatacaaa aaaaaatact tgttatgtat    7860
tcaattacgg gttaaaatat agacaagttg aaaaatttaa taaaaaaata agtcctcagc    7920
tcttatatat taagctacca acttagtata taagccaaaa cttaaatgtg ctaccaacac    7980
atcaagccgt tagagaactc tatctatagc aatatttcaa atgtaccgac atacaagaga    8040
aacattaact atatatattc aatttatgag attatcttaa cagatataaa tgtaaattgc    8100
aataagtaag atttagaagt ttatagccctt tgtgtattgg aagcagtacg caaaggcttt    8160
tttatttgat aaaaattaga agtatatttta tttttttcata attaatttat gaaaatgaaa    8220
gggggtgagc aaagtgacag aggaaagcag tatcttatca aataacaagg tattagcaat    8280
atcattattg actttagcag taaacattat gactttttata gtgcttgtag ctaagtagta    8340
cgaaaggggg agctttaaaa agctccttgg aatacataga attcataaat taatttatga    8400
aaagaagggc gtatatgaaa acttgtaaaa attgcaaaga gttattaaaa gatactgaaa    8460
tatgcaaaat acattcgttg atgattcatg ataaaacagt agcaacctat tgcagtaaat    8520
acaatgagtc aagatgttta cataaaggga aagtccaatg tattaattgt tcaaagatga    8580
accgatatgg atggtgtgcc ataaaaatga gatgttttac agaggaagaa cagaaaaaag    8640
aacgtacatg cattaaatat tatgcaagga gctttaaaaa agctcatgta aagaagagta    8700
aaaagaaaaa ataatttatt tattaattta atattgagag tgccgacaca gtatgcacta    8760
aaaatatat ctgtggtgta gtgagccgat acaaaaggat agtcactcgc attttcataa      8820
tacatcttat gttatgatta tgtgtcggtg ggacttcacg acgaaaaccc acaataaaaa    8880
aagagttcgg ggtagggtta agcatagttg aggcaactaa acaatcaagc taggatatgc    8940
agtagcagac cgtaaggtcg ttgtttaggt gtgttgtaat acatacgcta ttaagatgta    9000
aaaatacgga taccaatgaa gggaaaagta aatttttgg atgtagttg tttgttcatc      9060
tatgggcaaa ctacgtccaa agccgtttcc aaatctgcta aaaagtatat cctttctaaa    9120
```

-continued

```
atcaaagtca agtatgaaat cataaataaa gtttaatttt gaagttatta tgatattatg    9180
tttttctatt aaaataaatt aagtatatag aatagtttaa taatagtata tacttaatgt    9240
gataagtgtc tgacagtgtc acagaaagga tgattgttat ggattataag cggccggcca    9300
gtgggcaagt tgaaaaattc acaaaaatgt ggtataatat ctttgttcat tagagcgata    9360
aacttgaatt tgagagggaa cttagatggt atttgaaaaa attgataaaa atagttggaa    9420
cagaaaagag tattttgacc actactttgc aagtgtacct tgtacctaca gcatgaccgt    9480
taaagtggat atcacacaaa taaaggaaaa gggaatgaaa ctatatcctg caatgcttta    9540
ttatattgca atgattgtaa accgccattc agagtttagg acggcaatca atcaagatgg    9600
tgaattgggg atatatgatg agatgatacc aagctataca atatttcaca atgatactga    9660
aacattttcc agcctttgga ctgagtgtaa gtctgacttt aaatcatttt tagcagatta    9720
tgaaagtgat acgcaacggt atggaaacaa tcatagaatg gaaggaaagc caaatgctcc    9780
ggaaaacatt tttaatgtat ctatgatacc gtggtcaacc ttcgatggct ttaatctgaa    9840
tttgcagaaa ggatatgatt atttgattcc tatttttact atggggaaat attataaaga    9900
agataacaaa attatacttc ctttggcaat tcaagttcat cacgcagtat gtgacggatt    9960
tcacatttgc cgttttgtaa acgaattgca ggaattgata aatagttaac ttcaggtttg   10020
tctgtaacta aaaacaagta tttaagcaaa aacatcgtag aaatacggtg ttttttgtta   10080
ccctaagttt                                                          10090
```

<210> SEQ ID NO 92
<211> LENGTH: 25
<212> TYPE: DNA
<213> ORGANISM: Artificial Sequence
<220> FEATURE:
<223> OTHER INFORMATION: oligonucleotide repHF

<400> SEQUENCE: 92
aagaagggcg tatatgaaaa cttgt                                             25

<210> SEQ ID NO 93
<211> LENGTH: 25
<212> TYPE: DNA
<213> ORGANISM: Artificial Sequence
<220> FEATURE:
<223> OTHER INFORMATION: oligonucleotide catR

<400> SEQUENCE: 93
ttcgtttaca aaacggcaaa tgtga                                             25

<210> SEQ ID NO 94
<211> LENGTH: 20
<212> TYPE: DNA
<213> ORGANISM: Artificial Sequence
<220> FEATURE:
<223> OTHER INFORMATION: oligonucleotide MK-RTPCR-F

<400> SEQUENCE: 94
gtgctggtag aggtggttca                                                   20

<210> SEQ ID NO 95
<211> LENGTH: 20
<212> TYPE: DNA
<213> ORGANISM: Artificial Sequence
<220> FEATURE:
<223> OTHER INFORMATION: oligonucleotide MK-RTPCR-R

```
<400> SEQUENCE: 95
ccaagtatgt gctgcaccag                                               20

<210> SEQ ID NO 96
<211> LENGTH: 20
<212> TYPE: DNA
<213> ORGANISM: Artificial Sequence
<220> FEATURE:
<223> OTHER INFORMATION: oligonucleotide PMK-RTPCR-F

<400> SEQUENCE: 96
atatcagacc cacacgcagc                                               20

<210> SEQ ID NO 97
<211> LENGTH: 24
<212> TYPE: DNA
<213> ORGANISM: Artificial Sequence
<220> FEATURE:
<223> OTHER INFORMATION: oligonucleotide PMK-RTPCR-R

<400> SEQUENCE: 97
aatgcttcat tgctatgtca catg                                          24

<210> SEQ ID NO 98
<211> LENGTH: 20
<212> TYPE: DNA
<213> ORGANISM: Artificial Sequence
<220> FEATURE:
<223> OTHER INFORMATION: oligonucleotide PMD-RTPCR-F

<400> SEQUENCE: 98
gcagaagcaa aggcagcaat                                               20

<210> SEQ ID NO 99
<211> LENGTH: 23
<212> TYPE: DNA
<213> ORGANISM: Artificial Sequence
<220> FEATURE:
<223> OTHER INFORMATION: oligonucleotide PMD-RTPCR-R

<400> SEQUENCE: 99
ttgatccaag atttgtagca tgc                                           23

<210> SEQ ID NO 100
<211> LENGTH: 24
<212> TYPE: DNA
<213> ORGANISM: Artificial Sequence
<220> FEATURE:
<223> OTHER INFORMATION: oligonucleotide idi-RTPCR-F

<400> SEQUENCE: 100
ggacaaacac ttgttgtagt cacc                                          24

<210> SEQ ID NO 101
<211> LENGTH: 22
<212> TYPE: DNA
<213> ORGANISM: Artificial Sequence
<220> FEATURE:
<223> OTHER INFORMATION: oligonucleotide idi-RTPCR-R

<400> SEQUENCE: 101
tcaagttcgc aagtaaatcc ca                                            22

<210> SEQ ID NO 102
<211> LENGTH: 20
```

```
<212> TYPE: DNA
<213> ORGANISM: Artificial Sequence
<220> FEATURE:
<223> OTHER INFORMATION: oligonucleotide ispA-RTPCR-F

<400> SEQUENCE: 102
accagcaatg gatgacgatg                                              20

<210> SEQ ID NO 103
<211> LENGTH: 21
<212> TYPE: DNA
<213> ORGANISM: Artificial Sequence
<220> FEATURE:
<223> OTHER INFORMATION: oligonucleotide ispA-RTPCR-R

<400> SEQUENCE: 103
agtttgtaaa gcgtcacctg c                                            21

<210> SEQ ID NO 104
<211> LENGTH: 20
<212> TYPE: DNA
<213> ORGANISM: Artificial Sequence
<220> FEATURE:
<223> OTHER INFORMATION: oligonucleotide FS-RTPCR-F

<400> SEQUENCE: 104
aagctagtag atggtgggct                                              20

<210> SEQ ID NO 105
<211> LENGTH: 20
<212> TYPE: DNA
<213> ORGANISM: Artificial Sequence
<220> FEATURE:
<223> OTHER INFORMATION: oligonucleotide FS-RTPCR-R

<400> SEQUENCE: 105
aatgctacac ctactgcgca                                              20

<210> SEQ ID NO 106
<211> LENGTH: 18
<212> TYPE: DNA
<213> ORGANISM: Artificial Sequence
<220> FEATURE:
<223> OTHER INFORMATION: oligonucleotide ermB-F

<400> SEQUENCE: 106
tttgtaatta agaaggag                                                18

<210> SEQ ID NO 107
<211> LENGTH: 18
<212> TYPE: DNA
<213> ORGANISM: Artificial Sequence
<220> FEATURE:
<223> OTHER INFORMATION: oligonucleotide ermB-R

<400> SEQUENCE: 107
gtagaatcct tcttcaac                                                18

<210> SEQ ID NO 108
<211> LENGTH: 20
<212> TYPE: DNA
<213> ORGANISM: Artificial Sequence
<220> FEATURE:
<223> OTHER INFORMATION: oligonucleotide GnK-F

<400> SEQUENCE: 108
```

```
tcaggacctt ctggaactgg                                               20

<210> SEQ ID NO 109
<211> LENGTH: 20
<212> TYPE: DNA
<213> ORGANISM: Artificial Sequence
<220> FEATURE:
<223> OTHER INFORMATION: oligonucleotide GnK-R

<400> SEQUENCE: 109
acctcccctt ttcttggaga                                               20

<210> SEQ ID NO 110
<211> LENGTH: 20
<212> TYPE: DNA
<213> ORGANISM: Artificial Sequence
<220> FEATURE:
<223> OTHER INFORMATION: oligonucleotide FoT4L-F

<400> SEQUENCE: 110
caggtttcgg tgctgaccta                                               20

<210> SEQ ID NO 111
<211> LENGTH: 20
<212> TYPE: DNA
<213> ORGANISM: Artificial Sequence
<220> FEATURE:
<223> OTHER INFORMATION: oligonucleotide FoT4L-F

<400> SEQUENCE: 111
aactccgccg ttgtatttca                                               20
```

MICROBIAL FERMENTATION FOR THE PRODUCTION OF TERPENES

CROSS REFERENCE TO RELATED APPLICATIONS

This application is a continuation of U.S. patent application Ser. No. 15/867,306 filed Jan. 10, 2018, which is a continuation of U.S. patent application Ser. No. 14/656,827 filed Mar. 13, 2015, which is a continuation of U.S. patent application Ser. No. 13/909,012 filed Jun. 3, 2013, which claims the benefit of U.S. Provisional Patent Application 61/654,412 filed Jun. 1, 2012, the entirety of which are incorporated herein by reference.

SEQUENCE LISTING

This application includes a nucleotide/amino acid sequence listing submitted concurrently herewith, the entirety of which is incorporated herein by reference.

FIELD OF THE INVENTION

The present invention relates to recombinant microorganisms and methods for the production of terpenes and/or precursors thereof by microbial fermentation of a substrate comprising CO.

BACKGROUND OF THE INVENTION

Terpenes are a diverse class of naturally occurring chemicals composed of five-carbon isoprene units. Terpene derivatives include terpenoids (also known as isoprenoids) which may be formed by oxidation or rearrangement of the carbon backbone or a number of functional group additions or rearrangements.

Examples of terpenes include: isoprene (C5 hemiterpene), farnesene (C15 Sesquiterpenes), artemisinin (C15 Sesquiterpenes), citral (C10 Monoterpenes), carotenoids (C40 Tetraterpenes), menthol (C10 Monoterpenes), Camphor (C10 Monoterpenes), and cannabinoids.

Terpenes are valuable commercial products used in a diverse number of industries. The highest tonnage uses of terpenes are as resins, solvents, fragrances and vitamins. For example, isoprene is used in the production of synthetic rubber (cis-1,4-polyisoprene) for example in the tyre industry; farnesene is used as an energy dense drop-in fuel used for transportation or as jet-fuel; artemisinin is used as a malaria drug; and citral, carotenoids, menthol, camphor, and cannabinoids are used in the manufacture of pharmaceuticals, butadiene, and as aromatic ingredients.

Terpenes may be produced from petrochemical sources and from terpene feed-stocks, such as turpentine. For example, isoprene is produced petrochemically as a by-product of naphtha or oil cracking in the production of ethylene. Many terpenes are also extracted in relatively small quantities from natural sources. However, these production methods are expensive, unsustainable and often cause environmental problems including contributing to climate change.

Due to the extremely flammable nature of isoprene, known methods of production require extensive safeguards to limit potential for fire and explosions.

It is an object of the invention to overcome one or more of the disadvantages of the prior art, or at least to provide the public with an alternative means for producing terpenes and other related products.

SUMMARY OF THE INVENTION

Microbial fermentation provides an alternative option for the production of terpenes. Terpenes are ubiquitous in nature, for example they are involved in bacterial cell wall biosynthesis, and they are produced by some trees (for example poplar) to protect leaves from UV light exposure. However, not all bacteria comprise the necessary cellular machinery to produce terpenes and/or their precursors as metabolic products. For example, carboxydotrophic acetogens, such as *C. autoethanogenum* or *C. ljungdahlii*, which are able to ferment substrates comprising carbon monoxide to produce products such as ethanol, are not known to produce and emit any terpenes and/or their precursors as metabolic products. In addition, most bacteria are not known to produce any terpenes which are of commercial value.

The invention generally provides, inter alia, methods for the production of one or more terpenes and/or precursors thereof by microbial fermentation of a substrate comprising CO, and recombinant microorganisms of use in such methods.

In a first aspect, the invention provides a carboxydotrophic acetogenic recombinant microorganism capable of producing one or more terpenes and/or precursors thereof and optionally one or more other products by fermentation of a substrate comprising CO.

In one particular embodiment, the microorganism is adapted to express one or more enzymes in the mevalonate (MVA) pathway not present in a parental microorganism from which the recombinant microorganism is derived (may be referred to herein as an exogenous enzyme). In another embodiment, the microorganism is adapted to over-express one or more enzymes in the mevalonate (MVA) pathway which are present in a parental microorganism from which the recombinant microorganism is derived (may be referred to herein as an endogenous enzyme).

In a further embodiment, the microorganism is adapted to:
a) express one or more exogenous enzymes in the mevalonate (MVA) pathway and/or overexpress one or more endogenous enzyme in the mevalonate (MVA) pathway; and
b) express one or more exogenous enzymes in the DXS pathway and/or overexpress one or more endogenous enzymes in the DXS pathway.

In one embodiment, the one or more enzymes from the mevalonate (MVA) pathway is selected from the group consisting of:
a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33), and
g) a functionally equivalent variant of any one thereof.

In a further embodiment, the one or more enzymes from the DXS pathway is selected from the group consisting of:
a) 1-deoxy-D-xylulose-5-phosphate synthase DXS (EC: 2.2.1.7),
b) 1-deoxy-D-xylulose 5-phosphate reductoisomerase DXR (EC:1.1.1.267),
c) 2-C-methyl-D-erythritol 4-phosphate cytidylyltransferase IspD (EC:2.7.7.60),
d) 4-diphosphocytidyl-2-C-methyl-D-erythritol kinase IspE (EC:2.7.1.148),
e) 2-C-methyl-D-erythritol 2,4-cyclodiphosphate synthase IspF (EC:4.6.1.12), f) 4-hydroxy-3-methylbut-2-en-1-yl diphosphate synthase IspG (EC:1.17.7.1),
g) 4-hydroxy-3-methylbut-2-enyl diphosphate reductase (EC:1.17.1.2), and
h) a functionally equivalent variant of any one thereof.

In a further embodiment, one or more further exogenous or endogenous enzymes are expressed or over-expressed to result in the production of a terpene compound or a precursor thereof wherein the exogenous enzyme that is expressed, or the endogenous enzyme that is overexpressed, is selected from the group consisting of:
a) geranyltranstransferase Fps (EC:2.5.1.10),
b) heptaprenyl diphosphate synthase (EC:2.5.1.10),
c) octaprenyl-diphosphate synthase (EC:2.5.1.90),
d) isoprene synthase (EC 4.2.3.27),
e) isopentenyl-diphosphate delta-isomerase (EC 5.3.3.2),
f) farnesene synthase (EC 4.2.3.46/EC 4.2.3.47), and
g) a functionally equivalent variant of any one thereof.

In one embodiment, the parental microorganism is capable of fermenting a substrate comprising CO to produce Acetyl CoA, but not of converting Acetyl CoA to mevalonic acid or isopentenyl pyrophosphate (IPP) and the recombinant microorganism is adapted to express one or more enzymes involved in the mevalonate pathway.

In one embodiment, the one or more terpene and/or precursor thereof is chosen from mevalonic acid, IPP, dimethylallyl pyrophosphate (DMAPP), isoprene, geranyl pyrophosphate (GPP), farnesyl pyrophosphate (FPP) and farnesene.

In one embodiment, the microorganism comprises one or more exogenous nucleic acids adapted to increase expression of one or more endogenous nucleic acids and which one or more endogenous nucleic acids encode one or more of the enzymes referred to herein before.

In one embodiment, the one or more exogenous nucleic acids adapted to increase expression is a regulatory element. In one embodiment, the regulatory element is a promoter. In one embodiment, the promoter is a constitutive promoter. In one embodiment, the promoter is selected from the group comprising Wood-Ljungdahl gene cluster or Phosphotransacetylase/Acetate kinase operon promoters.

In one embodiment, the microorganism comprises one or more exogenous nucleic acids encoding and adapted to express one or more of the enzymes referred to hereinbefore. In one embodiment, the microorganisms comprise one or more exogenous nucleic acids encoding and adapted to express at least two of the enzymes. In other embodiments, the microorganism comprises one or more exogenous nucleic acids encoding and adapted to express at least three, at least four, at least five, at least six, at least seven, at least eight, at least nine or more of the enzymes.

In one embodiment, the one or more exogenous nucleic acid is a nucleic acid construct or vector, in one particular embodiment a plasmid, encoding one or more of the enzymes referred to hereinbefore in any combination.

In one embodiment, the exogenous nucleic acid is an expression plasmid.

In one particular embodiment, the parental microorganism is selected from the group of carboxydotrophic acetogenic bacteria. In certain embodiments the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kivui.*

In one embodiment the parental microorganism is *Clostridium autoethanogenum* or *Clostridium ljungdahlii.* In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks one or more genes in the DXS pathway and/or the mevalonate (MVA) pathway. In one embodiment, the parental microorganism lacks one or more genes encoding an enzyme selected from the group consisting of:
a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33),
g) 1-deoxy-D-xylulose-5-phosphate synthase DXS (EC: 2.2.1.7),
h) 1-deoxy-D-xylulose 5-phosphate reductoisomerase DXR (EC:1.1.1.267),
i) 2-C-methyl-D-erythritol 4-phosphate cytidylyltransferase IspD (EC:2.7.7.60),
j) 4-diphosphocytidyl-2-C-methyl-D-erythritol kinase IspE (EC:2.7.1.148),
k) 2-C-methyl-D-erythritol 2,4-cyclodiphosphate synthase IspF (EC:4.6.1.12),
l) 4-hydroxy-3-methylbut-2-en-1-yl diphosphate synthase IspG (EC:1.17.7.1),
m) 4-hydroxy-3-methylbut-2-enyl diphosphate reductase (EC:1.17.1.2), and
n) a functionally equivalent variant of any one thereof.

In a second aspect, the invention provides a nucleic acid encoding one or more enzymes which when expressed in a microorganism allows the microorganism to produce one or more terpenes and/or precursors thereof by fermentation of a substrate comprising CO.

In one embodiment, the nucleic acid encodes two or more enzymes which when expressed in a microorganism allows the microorganism to produce one or more terpenes and/or precursors thereof by fermentation of a substrate comprising CO. In one embodiment, a nucleic acid of the invention encodes at least three, at least four, at least five, at least six, at least seven, at least eight, at least nine or more of such enzymes.

In one embodiment, the nucleic acid encodes one or more enzymes in the mevalonate (MVA) pathway. In one embodiment, the one or more enzymes is chosen from the group consisting of:
a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33), and
g) a functionally equivalent variant of any one thereof.

In a particular embodiment, the nucleic acid encodes thiolase (which may be an acetyl CoA c-acetyltransferase), HMG-CoA synthase and HMG-CoA reductase.

In a further embodiment, the nucleic acid encodes one or more enzymes in the mevalonate (MVA) pathway and one or more further nucleic acids in the DXS pathway. In one embodiment, the one or more enzymes from the DXS pathway is selected from the group consisting of:
a) 1-deoxy-D-xylulose-5-phosphate synthase DXS (EC: 2.2.1.7),
b) 1-deoxy-D-xylulose 5-phosphate reductoisomerase DXR (EC:1.1.1.267),
c) 2-C-methyl-D-erythritol 4-phosphate cytidylyltransferase IspD (EC:2.7.7.60),
d) 4-diphosphocytidyl-2-C-methyl-D-erythritol kinase IspE (EC:2.7.1.148),
e) 2-C-methyl-D-erythritol 2,4-cyclodiphosphate synthase IspF (EC:4.6.1.12),
4-hydroxy-3-methylbut-2-en-1-yl diphosphate synthase IspG (EC:1.17.7.1),
g) 4-hydroxy-3-methylbut-2-enyl diphosphate reductase (EC:1.17.1.2), and
h) a functionally equivalent variant of any one thereof.

In a further embodiment, the nucleic acid encodes one or more further exogenous or endogenous enzymes are expressed or over-expressed to result in the production of a terpene compound or a precursor thereof wherein the exogenous nucleic acid that is expressed, or the endogenous enzyme that is overexpressed, encodes and enzyme selected from the group consisting of:
a) geranyltranstransferase Fps (EC:2.5.1.10),
b) heptaprenyl diphosphate synthase (EC:2.5.1.10),
c) octaprenyl-diphosphate synthase (EC:2.5.1.90),
d) isoprene synthase (EC 4.2.3.27),
e) isopentenyl-diphosphate delta-isomerase (EC 5.3.3.2),
f) farnesene synthase (EC 4.2.3.46/EC 4.2.3.47), and
g) a functionally equivalent variant of any one thereof.

In one embodiment, the nucleic acid encoding thiolase (EC 2.3.1.9) has the sequence SEQ ID NO: 40 or is a functionally equivalent variant thereof.

In one embodiment, the nucleic acid encoding thiolase (EC 2.3.1.9) is acetyl CoA c-acetyl transferase that has the sequence SEQ ID NO: 41 or is a functionally equivalent variant thereof.

In one embodiment, the nucleic acid encoding HMG-CoA synthase (EC 2.3.3.10) has the sequence SEQ ID NO: 42 or is a functionally equivalent variant thereof.

In one embodiment, the nucleic acid encoding HMG-CoA reductase (EC 1.1.1.88) has the sequence SEQ ID NO: 43 or is a functionally equivalent variant thereof.

In one embodiment, the nucleic acid encoding Mevalonate kinase (EC 2.7.1.36) has the sequence SEQ ID NO: 51 or is a functionally equivalent variant thereof.

In one embodiment, the nucleic acid encoding Phosphomevalonate kinase (EC 2.7.4.2) has the sequence SEQ ID NO: 52 or is a functionally equivalent variant thereof.

In one embodiment, the nucleic acid encoding Mevalonate Diphosphate decarboxylase (EC 4.1.1.33) has the sequence SEQ ID NO: 53 or is a functionally equivalent variant thereof.

In one embodiment, the nucleic acid encoding 1-deoxy-D-xylulose-5-phosphate synthase DXS (EC:2.2.1.7) has the sequence SEQ ID NO: 1 or is a functionally equivalent variant thereof.

In one embodiment, the nucleic acid encoding 1-deoxy-D-xylulose 5-phosphate reductoisomerase DXR (EC:1.1.1.267) has the sequence SEQ ID NO: 3 or is a functionally equivalent variant thereof.

In one embodiment, the nucleic acid encoding 2-C-methyl-D-erythritol 4-phosphate cytidylyltransferase IspD (EC:2.7.7.60) has the sequence SEQ ID NO: 5 or is a functionally equivalent variant thereof.

In one embodiment, the nucleic acid encoding 4-diphosphocytidyl-2-C-methyl-D-erythritol kinase IspE (EC: 2.7.1.148) has the sequence SEQ ID NO: 7 or is a functionally equivalent variant thereof.

In one embodiment, the nucleic acid encoding 2-C-methyl-D-erythritol 2,4-cyclodiphosphate synthase IspF (EC:4.6.1.12) has the sequence SEQ ID NO: 9 or is a functionally equivalent variant thereof.

In one embodiment, the nucleic acid encoding 4-hydroxy-3-methylbut-2-en-1-yl diphosphate synthase IspG (EC: 1.17.7.1) has the sequence SEQ ID NO: 11 or is a functionally equivalent variant thereof.

In one embodiment, the nucleic acid encoding 4-hydroxy-3-methylbut-2-enyl diphosphate reductase (EC:1.17.1.2) has the sequence SEQ ID NO: 13 or is a functionally equivalent variant thereof.

In one embodiment, the nucleic acid encoding geranyltranstransferase Fps has the sequence SEQ ID NO: 15, or it is a functionally equivalent variant thereof.

In one embodiment, the nucleic acid encoding heptaprenyl diphosphate synthase has the sequence SEQ ID NO: 17, or it is a functionally equivalent variant thereof.

In one embodiment, the nucleic acid encoding octaprenyl-diphosphate synthase (EC:2.5.1.90) wherein the octaprenyl-diphosphate synthase is polyprenyl synthetase is encoded by sequence SEQ ID NO: 19, or it is a functionally equivalent variant thereof.

In one embodiment, the nucleic acid encoding isoprene synthase (ispS) has the sequence SEQ ID NO: 21, or it is a functionally equivalent variant thereof.

In one embodiment, the nucleic acid encoding Isopentenyl-diphosphate delta-isomerase (idi) has the sequence SEQ ID NO: 54, or it is a functionally equivalent variant thereof.

In one embodiment, the nucleic acid encoding farnesene synthase has the sequence SEQ ID NO: 57, or it is a functionally equivalent variant thereof.

In one embodiment, the nucleic acid encodes the following enzymes:
a) isoprene synthase;
b) Isopentenyl-diphosphate delta-isomerase (idi); and
c) 1-deoxy-D-xylulose-5-phosphate synthase DXS;
or functionally equivalent variants thereof.

In one embodiment, the nucleic acid encodes the following enzymes:
a) Thiolase;
b) HMG-CoA synthase;
c) HMG-CoA reductase;
d) Mevalonate kinase;
e) Phosphomevalonate kinase;
f) Mevalonate Diphosphate decarboxylase;
g) Isopentenyl-diphosphate delta-isomerase (idi); and
h) isoprene synthase;
or functionally equivalent variants thereof.

In one embodiment, the nucleic acid encodes the following enzymes:
a) geranyltranstransferase Fps; and
b) farnesene synthase
or functionally equivalent variants thereof.

In one embodiment, the nucleic acids of the invention further comprise a promoter. In one embodiment, the promoter allows for constitutive expression of the genes under its control. In a particular embodiment a Wood-Ljungdahl cluster promoter is used. In another particular embodiment, a Phosphotransacetylase/Acetate kinase operon promoter is used. In one particular embodiment, the promoter is from *C. autoethanogenum*.

In a third aspect, the invention provides a nucleic acid construct or vector comprising one or more nucleic acid of the second aspect.

In one particular embodiment, the nucleic acid construct or vector is an expression construct or vector. In one particular embodiment, the expression construct or vector is a plasmid.

In a fourth aspect, the invention provides host organisms comprising any one or more of the nucleic acids of the second aspect or vectors or constructs of the third aspect.

In a fifth aspect, the invention provides a composition comprising an expression construct or vector as referred to in the third aspect of the invention and a methylation construct or vector.

Preferably, the composition is able to produce a recombinant microorganism according to the first aspect of the invention.

In one particular embodiment, the expression construct/vector and/or the methylation construct/vector is a plasmid.

In a sixth aspect, the invention provides a method for the production of one or more terpenes and/or precursors thereof and optionally one or more other products by microbial fermentation comprising fermenting a substrate comprising CO using a recombinant microorganism of the first aspect of the invention.

In one embodiment the method comprises the steps of:
(a) providing a substrate comprising CO to a bioreactor containing a culture of one or more microorganisms of the first aspect of the invention; and
(b) anaerobically fermenting the culture in the bioreactor to produce at least one terpene and/or precursor thereof.

In one embodiment the method comprises the steps of:
(a) capturing CO-containing gas produced as a result of the industrial process;
(b) anaerobic fermentation of the CO-containing gas to produce at least one terpene and/or precursor thereof by a culture containing one or more microorganism of the first aspect of the invention.

In particular embodiments of the method aspects, the microorganism is maintained in an aqueous culture medium.

In particular embodiments of the method aspects, the fermentation of the substrate takes place in a bioreactor.

In one embodiment, the one or more terpene and/or precursor thereof is chosen from mevalonic acid, IPP, dimethylallyl pyrophosphate (DMAPP), isoprene, geranyl pyrophosphate (GPP), farnesyl pyrophosphate (FPP) and farnesene.

Preferably, the substrate comprising CO is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In certain embodiments the methods further comprise the step of recovering a terpene and/or precursor thereof and optionally one or more other products from the fermentation broth.

In a seventh aspect, the invention provides one or more terpene and/or precursor thereof when produced by the method of the sixth aspect. In one embodiment, the one or more terpene and/or precursor thereof is chosen from the group consisting of mevalonic acid, IPP, dimethylallyl pyrophosphate (DMAPP), isoprene, geranyl pyrophosphate (GPP), farnesyl pyrophosphate (FPP) and farnesene.

In another aspect, the invention provides a method for the production of a microorganism of the first aspect of the invention comprising transforming a carboxydotrophic acetogenic parental microorganism by introduction of one or more nucleic acids such that the microorganism is capable of producing, or increasing the production of, one or more terpenes and/or precursors thereof and optionally one or more other products by fermentation of a substrate comprising CO, wherein the parental microorganism is not capable of producing, or produces at a lower level, the one or more terpene and/or precursor thereof by fermentation of a substrate comprising CO.

In one particular embodiment, a parental microorganism is transformed by introducing one or more exogenous nucleic acids adapted to express one or more enzymes in the mevalonate (MVA) pathway and optionally the DXS pathway. In another embodiment, a parental microorganism is transformed with one or more nucleic acids adapted to over-express one or more enzymes in the mevalonate (MVA) pathway and optionally the DXS pathway which are naturally present in the parental microorganism.

In certain embodiments, the one or more enzymes are as herein before described.

In one embodiment an isolated, genetically engineered, carboxydotrophic, acetogenic bacteria are provided which comprise an exogenous nucleic acid encoding an enzyme in a mevalonate pathway or in a DXS pathway or in a terpene biosynthesis pathway, whereby the bacteria express the enzyme. The enzyme is selected from the group consisting of:
a) thiolase (EC 2.3.1.9);
b) HMG-CoA synthase (EC 2.3.3.10);
c) HMG-CoA reductase (EC 1.1.1.88);
d) Mevalonate kinase (EC 2.7.1.36);
e) Phosphomevalonate kinase (EC 2.7.4.2);
f) Mevalonate Diphosphate decarboxylase (EC 4.1.1.33); 1-deoxy-D-xylulose-5-phosphate synthase DXS (EC: 2.2.1.7);
g) 1-deoxy-D-xylulose 5-phosphate reductoisomerase DXR (EC:1.1.1.267);
h) 2-C-methyl-D-erythritol 4-phosphate cytidylyltransferase IspD (EC:2.7.7.60);
i) 4-diphosphocytidyl-2-C-methyl-D-erythritol kinase IspE (EC:2.7.1.148);
j) 2-C-methyl-D-erythritol 2;4-cyclodiphosphate synthase IspF (EC:4.6.1.12);
k) 4-hydroxy-3-methylbut-2-en-1-yl diphosphate synthase IspG (EC:1.17.7.1);
l) 4-hydroxy-3-methylbut-2-enyl diphosphate reductase (EC:1.17.1.2); geranyltranstransferase Fps (EC: 2.5.1.10);
m) heptaprenyl diphosphate synthase (EC:2.5.1.10);
n) octaprenyl-diphosphate synthase (EC:2.5.1.90);
o) isoprene synthase (EC 4.2.3.27);
p) isopentenyl-diphosphate delta-isomerase (EC 5.3.3.2); and
q) farnesene synthase (EC 4.2.3.46/EC 4.2.3.47).

In some aspects the bacteria do not express the enzyme in the absence of said nucleic acid. In some aspects the bacteria which express the enzyme under anaerobic conditions.

One embodiment provides a plasmid which can replicate in a carboxydotrophic, acetogenic bacteria. The plasmid comprises a nucleic acid encoding an enzyme in a mevalonate pathway or in a DXS pathway or in a terpene biosynthesis pathway, whereby when the plasmid is in the bacteria, the enzyme is expressed by said bacteria. The enzyme is selected from the group consisting of:
a) thiolase (EC 2.3.1.9);
b) HMG-CoA synthase (EC 2.3.3.10);
c) HMG-CoA reductase (EC 1.1.1.88);
d) Mevalonate kinase (EC 2.7.1.36);
e) Phosphomevalonate kinase (EC 2.7.4.2);
f) Mevalonate Diphosphate decarboxylase (EC 4.1.1.33); 1-deoxy-D-xylulose-5-phosphate synthase DXS (EC: 2.2.1.7);
g) 1-deoxy-D-xylulose 5-phosphate reductoisomerase DXR (EC:1.1.1.267);
h) 2-C-methyl-D-erythritol 4-phosphate cytidylyltransferase IspD (EC:2.7.7.60);
i) 4-diphosphocytidyl-2-C-methyl-D-erythritol kinase IspE (EC:2.7.1.148);
j) 2-C-methyl-D-erythritol 2;4-cyclodiphosphate synthase IspF (EC:4.6.1.12);
k) 4-hydroxy-3-methylbut-2-en-1-yl diphosphate synthase IspG (EC:1.17.7.1);
l) 4-hydroxy-3-methylbut-2-enyl diphosphate reductase (EC:1.17.1.2); geranyltranstransferase Fps (EC: 2.5.1.10);
m) heptaprenyl diphosphate synthase (EC:2.5.1.10);
n) octaprenyl-diphosphate synthase (EC:2.5.1.90);
o) isoprene synthase (EC 4.2.3.27);
p) isopentenyl-diphosphate delta-isomerase (EC 5.3.3.2); and
q) farnesene synthase (EC 4.2.3.46/EC 4.2.3.47).

A process is provided in another embodiment for converting CO and/or $CO_2$ into isoprene. The process comprises: passing a gaseous CO-containing and/or $CO_2$-containing substrate to a bioreactor containing a culture of carboxydotrophic, acetogenic bacteria in a culture medium such that the bacteria convert the CO and/or $CO_2$ to isoprene, and recovering the isoprene from the bioreactor. The carboxydotrophic acetogenic bacteria are genetically engineered to express an isoprene synthase.

Another embodiment provides an isolated, genetically engineered, carboxydotrophic, acetogenic bacteria which comprise a nucleic acid encoding an isoprene synthase. The bacteria express the isoprene synthase and the bacteria are able to convert dimethylallyldiphosphate to isoprene. In one aspect the isoprene synthase is a *Populus tremuloides* enzyme. In another aspect the nucleic acid is codon optimized. In still another aspect, expression of the isoprene synthase is under the transcriptional control of a promoter for a pyruvate: ferredoxin oxidoreductase gene from *Clostridium autoethanogenum*.

Another embodiment provides a process for converting CO and/or $CO_2$ into isopentyldiphosphate (IPP). The process comprises: passing a gaseous CO-containing and/or $CO_2$-containing substrate to a bioreactor containing a culture of carboxydotrophic, acetogenic bacteria in a culture medium such that the bacteria convert the CO and/or $CO_2$ to isopentyldiphosphate (IPP), and recovering the IPP from the bioreactor. The carboxydotrophic acetogenic bacteria are genetically engineered to express a isopentyldiphosphate delta isomerase.

Still another embodiment provides isolated, genetically engineered, carboxydotrophic, acetogenic bacteria which comprise a nucleic acid encoding an isopentyldiphosphate delta isomerase. The bacteria express the isopentyldiphosphate delta isomerase and the bacteria are able to convert dimethylallyldiphosphate to isopentyldiphosphate. In some aspects the nucleic acid encodes a *Clostridium beijerinckii* isopentyldiphosphate delta isomerase. In other aspects, the nucleic acid is under the transcriptional control of a promoter for a pyruvate: ferredoxin oxidoreductase gene from *Clostridium autoethanogenum*. In still other aspects, the nucleic acid is under the transcriptional control of a promoter for a pyruvate: ferredoxin oxidoreductase gene from *Clostridium autoethanogenum* and downstream of a second nucleic acid encoding an isoprene synthase.

Still another embodiment provides a process for converting CO and/or $CO_2$ into isopentyldiphosphate (IPP) and/or isoprene. The process comprises: passing a gaseous CO-containing and/or $CO_2$-containing substrate to a bioreactor containing a culture of carboxydotrophic, acetogenic bacteria in a culture medium such that the bacteria convert the CO and/or $CO_2$ to isopentyldiphosphate (IPP) and/or isoprene, and recovering the IPP and/or isoprene from the bioreactor. The carboxydotrophic acetogenic bacteria are genetically engineered to have an increased copy number of a nucleic acid encoding a deoxyxylulose 5-phosphate synthase (DXS) enzyme, wherein the increased copy number is greater than 1 per genome.

Yet another embodiment provides isolated, genetically engineered, carboxydotrophic, acetogenic bacteria which comprise a copy number of greater than 1 per genome of a nucleic acid encoding a deoxyxylulose 5-phosphate synthase (DXS) enzyme. In some aspects, the isolated, genetically engineered, carboxydotrophic, acetogenic bacteria may further comprise a nucleic acid encoding an isoprene synthase. In other aspects, the isolated, genetically engineered, carboxydotrophic, acetogenic bacteria of may further comprise a nucleic acid encoding an isopentyldiphosphate delta isomerase. In still other aspects the isolated, genetically engineered, carboxydotrophic, acetogenic bacteria may further comprise a nucleic acid encoding an isopentyldiphosphate delta isomerase and a nucleic acid encoding an isoprene synthase.

Another embodiment provides isolated, genetically engineered, carboxydotrophic, acetogenic bacteria which comprise a nucleic acid encoding a phosphomevalonate kinase (PMK). The bacteria express the encoded enzyme and the enzyme is not native to the bacteria. In some aspects the enzymes are *Staphylococcus aureus* enzymes. In some aspects the enzyme is expressed under the control of one or more *C. autoethanogenum* promoters. In some aspects the bacteria further comprise a nucleic acid encoding thiolase (thlA/vraB), a nucleic acid encoding an HMG-CoA synthase (HMGS), and a nucleic acid encoding an HMG-CoA reductase (HMGR). In some aspects the thiolase is *Clostridium acetobutylicum* thiolase. In some aspects the bacteria further comprise a nucleic acid encoding a mevalonate diphosphate decarboxylase (PMD).

Still another embodiment provides isolated, genetically engineered, carboxydotrophic, acetogenic bacteria which comprise an exogenous nucleic acid encoding alpha-farnesene synthase. In some aspects the nucleic acid is codon optimized for expression in *C. autoethanogenum*. In some aspects the alpha-farnesene synthase is a *Malus x domestica* alpha-farnesene synthase. In some aspects the bacteria further comprise a nucleic acid segment encoding geranyltranstransferase. In some aspects the geranyltranstransferase is an *E. coli* geranyltranstransferase.

Suitable isolated, genetically engineered, carboxydotrophic, acetogenic bacteria for any of the aspects or embodiments of the invention may be selected from the group consisting of *Clostridium autoethanogenum, Clostridium ljungdahlii, Clostridium ragsdalei, Clostridium carboxidivorans, Clostridium drakei, Clostridium scatologenes,*

*Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kivui.*

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures.

DETAILED DESCRIPTION OF THE INVENTION

Figure 1:
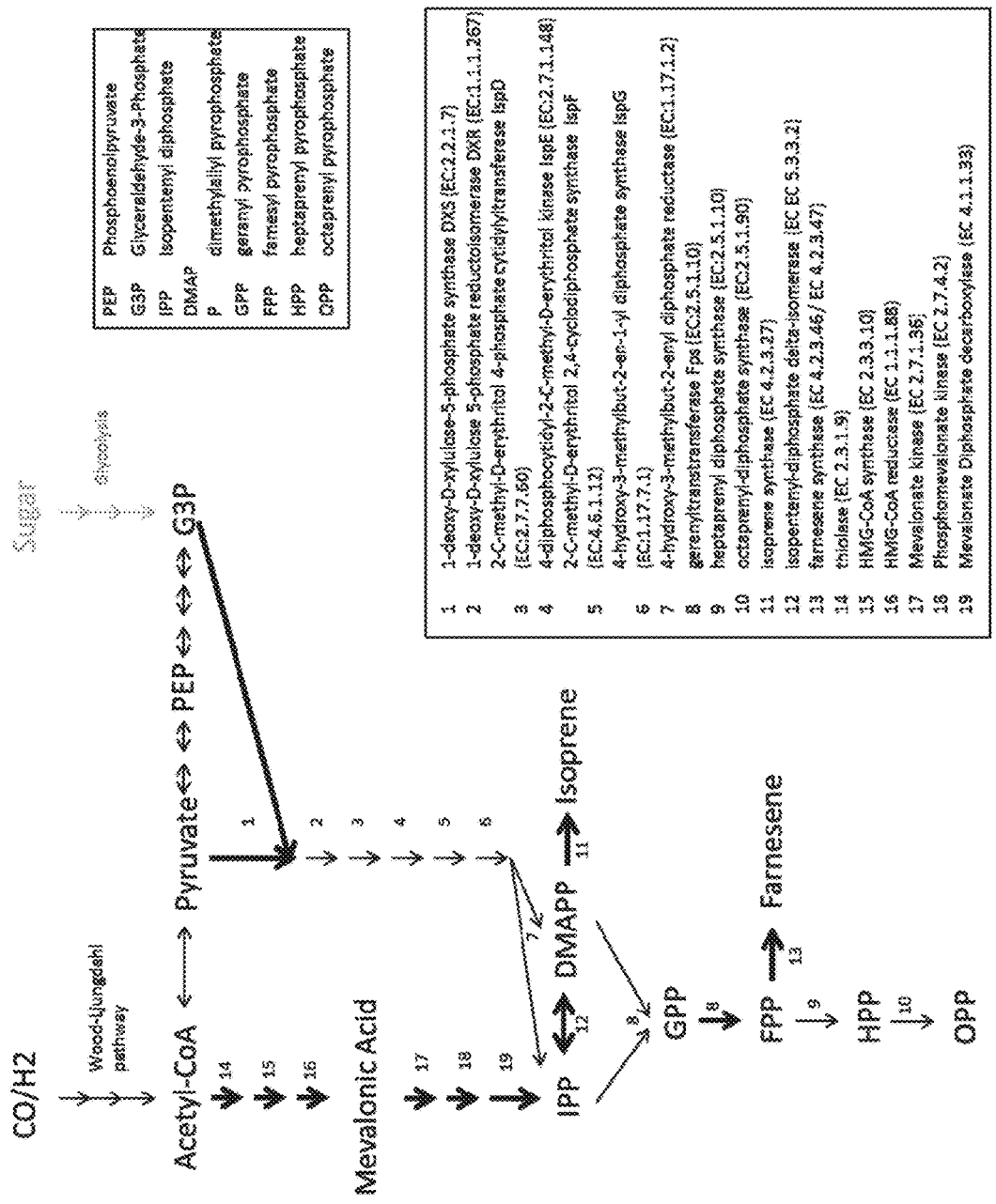
FIG. 1: Pathway diagram for production of terpenes, gene targets described in this application are highlighted with bold arrows.

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The inventors have surprisingly been able to engineer a carboxydotrophic acetogenic microorganism to produce terpene and precursors thereof including isoprene and farnesene by fermentation of a substrate comprising CO. This offers an alternative means for the production of these products which may have benefits over the current methods for their production. In addition, it offers a means of using carbon monoxide from industrial processes which would otherwise be released into the atmosphere and pollute the environment.

As referred to herein, a "fermentation broth" is a culture medium comprising at least a nutrient media and bacterial cells.

As referred to herein, a "shuttle microorganism" is a microorganism in which a methyltransferase enzyme is expressed and is distinct from the destination microorganism.

As referred to herein, a "destination microorganism" is a microorganism in which the genes included on an expression construct/vector are expressed and is distinct from the shuttle microorganism.

The term "main fermentation product" is intended to mean the one fermentation product which is produced in the highest concentration and/or yield.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx. 2:1, or 1:1, or 1:2 ratio of $H_2$:CO. In one embodiment the substrate comprises about 30% or less Hz by volume, 20% or less Hz by volume, about 15% or less Hz by volume or about 10% or less Hz by volume. In other embodiments, the substrate stream comprises low concentrations of Hz, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, the microorganism to which they are to be introduced (for example in a parental microorganism from which the recombinant microorganism is derived), strains or species of microorganisms which differ from the organism to which they are to be introduced, or they may be artificially or recombinantly created. In one embodiment, the exogenous nucleic acids represent nucleic acid sequences naturally present within the microorganism to which they are to be introduced, and they are introduced to increase expression of or over-express a particular gene (for example, by increasing the copy number of the sequence (for example a gene), or introducing a strong or constitutive promoter to increase expression). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state.

"Exogenous" may also be used to refer to proteins. This refers to a protein that is not present in the parental microorganism from which the recombinant microorganism is derived.

The term "endogenous" as used herein in relation to a recombinant microorganism and a nucleic acid or protein refers to any nucleic acid or protein that is present in a parental microorganism from which the recombinant microorganism is derived.

It should be appreciated that the invention may be practised using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants". By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein. These include homologous genes in species such as *Clostridium acetobutylicum, Clostridium beijerinckii, C. saccharobutylicum* and *C. saccharoperbutylacetonicum*, details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the invention may be practised using polypeptides whose sequence varies from the amino acid sequences specifically exemplified herein. These variants may be referred to herein as "functionally equivalent variants". A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using any number of known methods. However, by way of example, the methods described by Silver et al. (1991, *Plant Physiol.* 97: 1588-1591) or Zhao et al. (2011, *Appl Microbiol Biotechnol*, 90:1915-1922) for the isoprene synthase enzyme, by Green et al. (2007, *Phytochemistry;* 68:176-188) for the farnesene synthase enzyme, by Kuzuyama et al. (2000, *J Bacteriol.* 182, 891-897) for the 1-deoxy-D-xylulose 5-phosphate synthase Dxs, by Berndt and Schlegel (1975, *Arch. Microbiol.* 103, 21-30) or by Stim-Herndon et al. (1995, Gene 154: 81-85) for the thiolase, by Cabano et al. (1997, *Insect Biochem. Mol. Biol.* 27: 499-505) for the HMG-CoA synthase, by Ma et al. (2011, *Metab. Engin.,* 13:588-597) for the HMG-CoA reductase and mevalonate kinase enzyme, by Herdendorf and Miziorko (2007, *Biochemistry,* 46: 11780-8) for the phosphomevalonate kinase, and by Krepkiy et al. (2004, *Protein Sci.* 13: 1875-1881) for the mevalonate diphosphate decarboxylase. It is also possible to identify genes of DXS and mevalonate pathway using inhibitors like fosmidomycin or mevinoline as described by Trutko et al. (2005, Microbiology 74: 153-158).

"Over-express", "over expression" and like terms and phrases when used in relation to the invention should be taken broadly to include any increase in expression of one or more proteins (including expression of one or more nucleic acids encoding same) as compared to the expression level of the protein (including nucleic acids) of a parental microorganism under the same conditions. It should not be taken to mean that the protein (or nucleic acid) is expressed at any particular level.

A "parental microorganism" is a microorganism used to generate a recombinant microorganism of the invention. The parental microorganism may be one that occurs in nature (i.e. a wild type microorganism) or one that has been previously modified but which does not express or over-express one or more of the enzymes that are the subject of the present invention.

Accordingly, the recombinant microorganisms of the invention may have been modified to express or over-express one or more enzymes that were not expressed or over-expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

A "terpene" as referred to herein should be taken broadly to include any compound made up of $C_5$ isoprene units joined together including simple and complex terpenes and oxygen-containing terpene compounds such as alcohols, aldehydes and ketones. Simple terpenes are found in the essential oils and resins of plants such as conifers. More complex terpenes include the terpenoids and vitamin A, carotenoid pigments (such as lycopene), squalene, and rubber. Examples of monoterpenes include, but are not limited to isoprene, pinene, nerol, citral, camphor, menthol, limonene. Examples of sesquiterpenes include but are not limited to nerolidol, farnesol. Examples of diterpenes include but are not limited to phytol, vitamin Ai. Squalene is an example of a triterpene, and carotene (provitamin Ai) is a tetraterpene.

A "terpene precursor" is a compound or intermediate produced during the reaction to form a terpene starting from Acetyl CoA and optionally pyruvate. The term refers to a precursor compound or intermediate found in the mevalonate (MVA) pathway and optionally the DXS pathway as well as downstream precursors of longer chain terpenes, such as FPP and GPP. In particular embodiments, it includes but is not limited to mevalonic acid, IPP, dimethylallyl pyrophosphate (DMAPP), geranyl pyrophosphate (GPP) and farnesyl pyrophosphate (FPP).

The "DXS pathway" is the enzymatic pathway from pyruvate and D-glyceraldehyde-3-phosphate to DMAPP or IPP. It is also known as the deoxyxylulose 5-phosphate (DXP/DXPS/DOXP or DXS)/methylerythritol phosphate (MEP) pathway.

The "mevalonate (MVA) pathway" is the enzymatic pathway from acetyl-CoA to IPP.

Microorganisms

Two pathways for production of terpenes are known, the deoxyxylulose 5-phosphate (DXP/DXPS/DOXP or DXS)/methylerythritol phosphate (MEP) pathway (Hunter et al., 2007, *J. Biol. chem.* 282: 21573-77) starting from pyruvate and D-glyceraldehyde-3-phosphate (G3P), the two key intermediates in the glycolysis, and the mevalonate (MVA) pathway (Miziorko, 2011, *Arch Biochem Biophys*, 505: 131-143) starting from acetyl-CoA. Many different classes of microorganisms have been investigated for presence of either of these pathways (Lange et al., 2000, *PNAS*, 97: 13172-77; Trutko et al., 2005, *Microbiology*, 74: 153-158; Julsing et al., 2007, *Appl Microbiol Biotechnol*, 75: 1377-84), but not carboxydotrophic acetogens. The DXS pathway for example was found to be present in *E. coli*, *Bacillus*, or *Mycobacterium*, while the mevalonate pathway is present in yeast *Saccharomyces*, *Clorojlexus*, or *Myxococcus*.

Genomes of carboxydotrophic acetogens *C. autoethanogenum*, *C. ljungdahlii* were analysed by the inventors for presence of either of the two pathways. All genes of the DXS pathway were identified in *C. autoethanogenum* and *C. ljungdahlii* (Table 1), while the mevalonate pathway is absent. Additionally, carboxydotrophic acetogens such as *C. autoethanogenum* or *C. ljungdahlii* are not known to produce any terpenes as metabolic end products.

TABLE 1

Terpene biosynthesis genes of the DXS pathway identified in *C. autoethanogenum* and *C. ljungdahlii*:

| Gene/Enzyme | C. autoethanogenum | C. ljungdahlii |
|---|---|---|
| 1-deoxy-D-xylulose-5-synthase DXS (EC:2.2.1.7) | SEQ ID NO: 1-2 | YP_003779286.1; GI: 300854302, CLJU_c11160 |
| 1-deoxy-D-xylulose 5-phosphate reductoisomerase DXR (EC:1.1.1.267) | SEQ ID NO: 3-4 | YP_003779478.1; GI: 300854494, CLJU_c13080 |
| 2-C-methyl-D-erythritol 4-phosphate cytidylyltransferase IspD (EC:2.7.7.60) | SEQ ID NO: 5-6 | YP_003782252.1 GI: 300857268, CLJU_c41280 |
| 4-diphosphocytidyl-2-C-methyl-D-erythritol kinase IspE (EC:2.7.1.148) | SEQ ID NO: 7-8 | YP_003778403.1; GI: 300853419, CLJU_c02110 |
| 2-C-methyl-D-erythritol 2,4-cyclodiphosphate synthase IspF (EC:4.6.1.12) | SEQ ID NO: 9-10 | YP_003778349.1; GI: 300853365, CLJU_c01570 |
| 4-hydroxy-3-methylbut-2-en-1-yl diphosphate synthase IspG (EC:1.17.7.1) | SEQ ID NO: 11-12 | YP_003779480.1; GI: 300854496, CLJU_c13100 |
| 4-hydroxy-3-methylbut-2-enyl diphosphate reductase (EC:1.17.1.2) | SEQ ID NO: 13-14 | YP_003780294.1; GI: 300855310, CLJU_c21320 |

Genes for downstream synthesis of terpenes from isoprene units were also identified in both organisms (Table 2).

| Gene/Enzyme | C. autoethanogenum | C. ljungdahlii |
|---|---|---|
| geranyltranstransferase Fps (EC:2.5.1.10) | SEQ ID NO: 15-16 | YP_003779285.1; GI: 300854301, CLJU_c11150 |
| heptaprenyl diphosphate synthase (EC:2.5.1.10) | SEQ ID NO: 17-18 | YP_003779312.1; GI: 300854328, CLJU_c11420 |
| octaprenyl-diphosphate synthase [EC:2.5.1.90] | SEQ ID NO: 19-20 | YP_003782157.1; GI: 300857173, CLJU_c40310 |

Terpenes are energy dense compounds, and their synthesis requires the cell to invest energy in the form of nucleoside triposphates such as ATP. Using sugar as a substrate requires sufficient energy to be supplied from glycolysis to yield several molecules of ATP. The production of terpenes and/or their precursors via the DXS pathway using sugar as a substrate proceeds in a relatively straightforward manner due to the availability of pyruvate and D-glyceraldehyde-3-phosphate (G3P), G3P being derived from C5 pentose and C6 hexose sugars. These C5 and C6 molecules are thus relatively easily converted into C5 isoprene units from which terpenes are composed.

For anaerobic acetogens using a C1 substrate like CO or $CO_2$, it is more difficult to synthesise long molecules such as hemiterpenoids from C1 units. This is especially true for longer chain terpenes like C10 monoterpenes, C15 sesquiterpenes, or C40 tetraterpenes. To date the product with most carbon atoms reported in acetogens (both native and recombinant organisms) are C4 compounds butanol (Kopke et al., 2011, *Curr. Opin. Biotechnol.* 22: 320-325; Schiel-Bengelsdorf and Dune, 2012, *FEBS Letters:* 10.1016/j.febslet.2012.04.043; Kopke et al., 2011, *Proc. Nat. Sci. U.S.A.* 107: 13087-92; US patent 2011/0236941) and 2,3-butanediol (Kopke et al., 2011, *Appl. Environ. Microbiol.* 77:5467-75). The inventors have shown that it is surprisingly possible to anaerobically produce these longer chain terpene molecules using the C1 feedstock CO via the acetyl CoA intermediate.

Energetics of the Wood-Ljungdahl pathway of anaerobic acetogens are just emerging, but unlike under aerobic growth conditions or glycolysis of sugar fermenting organisms no ATP is gained in the Wood-Ljungdahl pathway by substrate level phosphorylation, in fact activation of $CO_2$ to formate actually requires one molecule of ATP and a membrane gradient is required. The inventors note that it is important that a pathway for product formation is energy efficient. The inventors note that in acetogens the substrate CO or $CO_2$ is channeled directly into acetyl-CoA, which represents the most direct route to terpenes and/or their precursors, especially when compared to sugar based systems, with only six reactions required (FIG. 1). Though less ATP is available in carboxydotrophic acetogens, the inventors believe that this more direct pathway may sustain a higher metabolic flux (owing to higher chemical motive force of intermediate reactions). A highly effective metabolic flux is important as several intermediates in the terpene biosynthesis pathway, such as key intermediates Mevalonate and FPP, are toxic to most bacteria when not turned over efficiently. Despite having a higher ATP availability, this problem of intermediate toxicity can be a bottleneck in production of terpenes from sugar.

Figure 6:
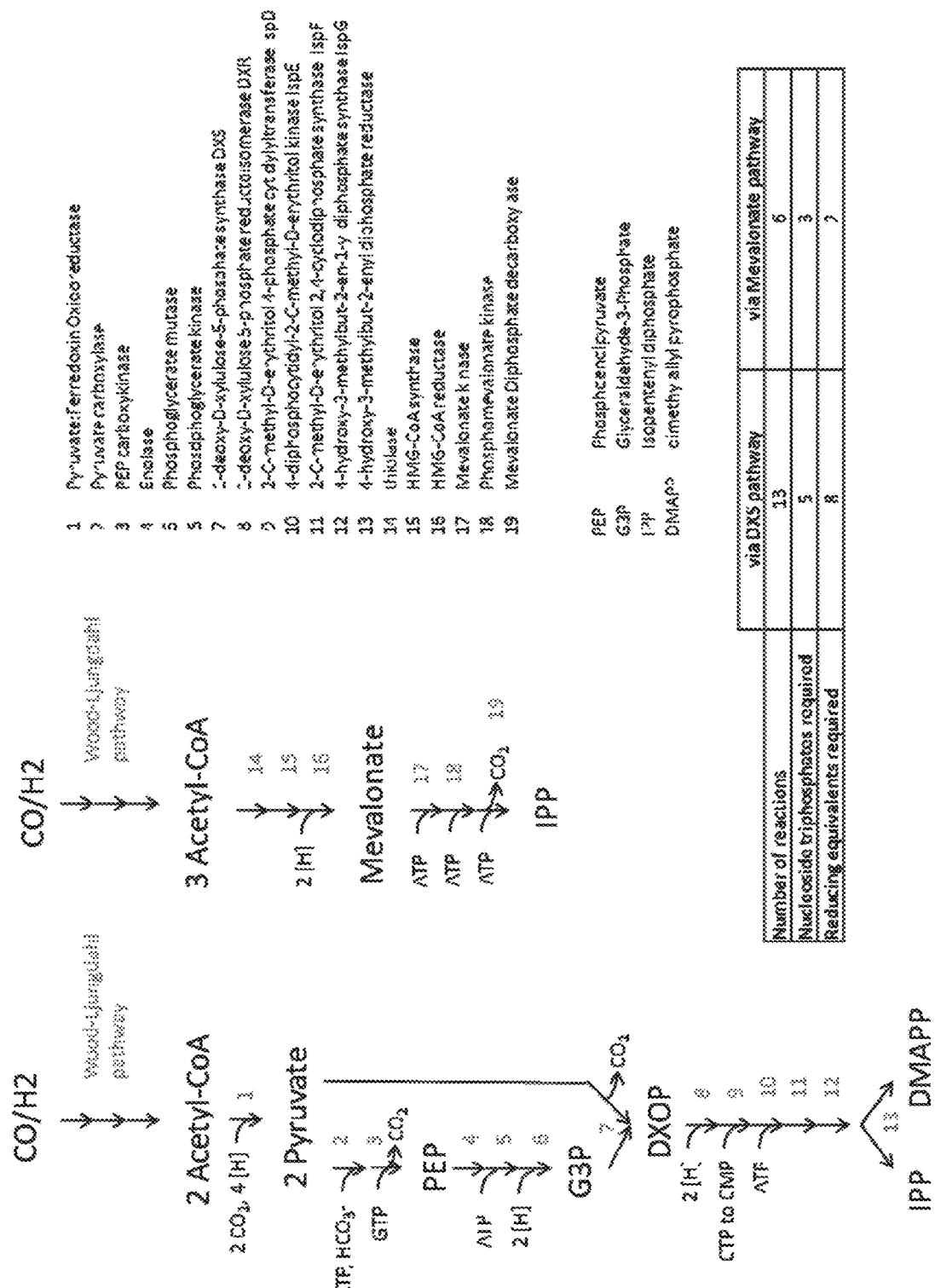
FIG. 6: Comparison of energetics for production of terpenes from CO via DXS and mevalonate pathway

When comparing the energetics of terpene precursor IPP and DMAPP production from CO (FIG. 6) via the mevalonate pathway versus the DXS pathway, the inventors noted that the mevalonate pathway requires less nucleoside tripospates as ATP, less reducing equivalents, and is also more direct when compared to the DXS pathway with only six necessary reaction steps from acetyl-CoA. This provides advantages in the speed of the reactions and metabolic fluxes and increases overall energy efficiency. Additionally, the lower number of enzymes required simplifies the recombination method required to produce a recombinant microorganism.

No acetogens with a mevalonate pathway have been identified, but the inventors have shown that it is possible to introduce the mevalonate pathway and optionally the DXS pathway into a carboxydotrophic acetogen such as *Clostridium autoethanogenum* or *C. ljungdahlii* to efficiently produce terpenes and/or precursors thereof from the C1 carbon substrate CO. They contemplate that this is applicable to all carboxydotrophic acetogenic microorganisms.

Additionally, the production of terpenes and/or precursors thereof has never been shown to be possible using recombinant microorganisms under anaerobic conditions. Anaerobic production of isoprene has the advantage of providing a safer operating environment because isoprene is extremely flammable in the presence of oxygen and has a lower flammable limit (LFL) of 1.5-2.0% and an upper flammable (UFL) limit of 2.0-12% at room temperature and atmospheric pressure. As flames cannot occur in the absence of oxygen, the inventors believe that an anaerobic fermentation process is desirable as it would be safer across all product concentrations, gas compositions, temperature and pressure ranges.

As discussed hereinbefore, the invention provides a recombinant microorganism capable of producing one or more terpenes and/or precursors thereof, and optionally one or more other products, by fermentation of a substrate comprising CO.

In a further embodiment, the microorganism is adapted to: express one or more exogenous enzymes from the mevalonate (MVA) pathway and/or overexpress one or more endogenous enzyme from the mevalonate (MVA) pathway; and a) express one or more exogenous enzymes from the DXS pathway and/or overexpress one or more endogenous enzymes from the DXS pathway.

In one embodiment, the parental microorganism from which the recombinant microorganism is derived is capable of fermenting a substrate comprising CO to produce Acetyl CoA, but not of converting Acetyl CoA to mevalonic acid or isopentenyl pyrophosphate (IPP) and the recombinant microorganism is adapted to express one or more enzymes involved in the mevalonate pathway.

The microorganism may be adapted to express or over-express the one or more enzymes by any number of recombinant methods including, for example, increasing expression of native genes within the microorganism (for example, by introducing a stronger or constitutive promoter to drive expression of a gene), increasing the copy number of a gene encoding a particular enzyme by introducing exogenous nucleic acids encoding and adapted to express the enzyme, introducing an exogenous nucleic acid encoding and adapted to express an enzyme not naturally present within the parental microorganism.

In one embodiment, the one or more enzymes are from the mevalonate (MVA) pathway and are selected from the group consisting of:
a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33), and
g) a functionally equivalent variant of any one thereof.

In a further embodiment, the optional one or more enzymes are from the DXS pathway is selected from the group consisting of:
a) 1-deoxy-D-xylulose-5-phosphate synthase DXS (EC: 2.2.1.7),
b) 1-deoxy-D-xylulose 5-phosphate reductoisomerase DXR (EC:1.1.1.267),
c) 2-C-methyl-D-erythritol 4-phosphate cytidylyltransferase IspD (EC:2.7.7.60),
d) 4-diphosphocytidyl-2-C-methyl-D-erythritol kinase IspE (EC:2.7.1.148),
e) 2-C-methyl-D-erythritol 2,4-cyclodiphosphate synthase IspF (EC:4.6.1.12),
f) 4-hydroxy-3-methylbut-2-en-1-yl diphosphate synthase IspG (EC:1.17.7.1),
g) 4-hydroxy-3-methylbut-2-enyl diphosphate reductase (EC:1.17.1.2), and
h) a functionally equivalent variant of any one thereof.

In a further embodiment, one or more exogenous or endogenous further enzymes are expressed or over-expressed to result in the production of a terpene compound and/or precursor thereof wherein the exogenous enzyme that is expressed, or the endogenous enzyme that is overexpressed is selected from the group consisting of:
a) geranyltranstransferase Fps (EC:2.5.1.10),
b) heptaprenyl diphosphate synthase (EC:2.5.1.10),
c) octaprenyl-diphosphate synthase (EC:2.5.1.90),
d) isoprene synthase (EC 4.2.3.27),
e) isopentenyl-diphosphate delta-isomerase (EC 5.3.3.2),
f) farnesene synthase (EC 4.2.3.46/EC 4.2.3.47), and
g) a functionally equivalent variant of any one thereof.

By way of example only, sequence information for each of the enzymes is listed in the figures herein.

The enzymes of use in the microorganisms of the invention may be derived from any appropriate source, including different genera and species of bacteria, or other organisms. However, in one embodiment, the enzymes are derived from *Staphylococcus aureus*.

In one embodiment, the enzyme isoprene synthase (ispS) is derived from *Poplar tremuloides*. In a further embodiment, it has the nucleic acid sequence exemplified in SEQ ID NO: 21 hereinafter, or it is a functionally equivalent variant thereof.

In one embodiment, the enzyme deoxyxylulose 5-phosphate synthase is derived from *C. autoethanogenum*, encoded by the nucleic acid sequence exemplified in SEQ ID NO: 1 and/or with the amino acid sequence exemplified in SEQ ID NO: 2 hereinafter, or it is a functionally equivalent variant thereof.

In one embodiment, the enzyme 1-deoxy-D-xylulose 5-phosphate reductoisomerase DXR is derived from *C. autoethanogenum* and is encoded by the nucleic acid sequence exemplified in SEQ ID NO: 3 or is a functionally equivalent variant thereof.

In one embodiment, the enzyme 2-C-methyl-D-erythritol 4-phosphate cytidylyltransferase IspD is derived from *C. autoethanogenum* and is encoded by the nucleic acid sequence exemplified in SEQ ID NO: 5 or is a functionally equivalent variant thereof.

In one embodiment, the enzyme 4-diphosphocytidyl-2-C-methyl-D-erythritol kinase IspE is derived from *C. autoethanogenum* and is encoded by the nucleic acid sequence exemplified in SEQ ID NO: 7 or is a functionally equivalent variant thereof.

In one embodiment, the enzyme 2-C-methyl-D-erythritol 2,4-cyclodiphosphate synthase IspF is derived from *C. autoethanogenum* and is encoded by the nucleic acid sequence exemplified in SEQ ID NO: 9 or is a functionally equivalent variant thereof.

In one embodiment, the enzyme 4-hydroxy-3-methylbut-2-en-1-yl diphosphate synthase IspG is derived from *C. autoethanogenum* and is encoded by the nucleic acid sequence exemplified in SEQ ID NO: 11 or is a functionally equivalent variant thereof.

In one embodiment, the enzyme 4-hydroxy-3-methylbut-2-enyl diphosphate reductase is derived from *C. autoethanogenum* and is encoded by the nucleic acid sequence exemplified in SEQ ID NO: 13 or is a functionally equivalent variant thereof.

In one embodiment, the enzyme mevalonate kinase (MK) is derived from *Staphylococcus aureus* subsp. *aureus* Mu50 and is encoded by the nucleic acid sequence exemplified in SEQ ID NO: 51 hereinafter, or it is a functionally equivalent variant thereof.

In one embodiment, the enzyme phosphomevalonate kinase (PMK) is derived from *Staphylococcus aureus* subsp. *aureus* Mu50 and is encoded by the nucleic acid sequence exemplified in SEQ ID NO: 52 hereinafter, or it is a functionally equivalent variant thereof.

In one embodiment, the enzyme mevalonate diphosphate decarboxylase (PMD) is derived from *Staphylococcus aureus* subsp. *aureus* Mu50 and is encoded by the nucleic acid sequence exemplified in SEQ ID NO: 53 hereinafter, or it is a functionally equivalent variant thereof.

In one embodiment, the enzyme Isopentenyl-diphosphate delta-isomerase (idi) is derived from *Clostridium beijerinckii* and is encoded by the nucleic acid sequence exemplified in SEQ ID NO: 54 hereinafter, or it is a functionally equivalent variant thereof.

In one embodiment, the enzyme thiolase (thlA) is derived from *Clostridium acetobutylicum* ATCC824 and is encoded by the nucleic acid sequence exemplified in SEQ ID NO: 40 hereinafter, or it is a functionally equivalent variant thereof.

In one embodiment, the enzyme is a thiolase enzyme, and is an acetyl-CoA c-acetyltransferase (vraB) derived from *Staphylococcus aureus* subsp. *aureus* Mu50 and is encoded by the nucleic acid sequence exemplified in SEQ ID NO: 41 hereinafter, or it is a functionally equivalent variant thereof.

In one embodiment, the enzyme 3-hydroxy-3-methylglutaryl-CoA synthase (HMGS) is derived from *Staphylococcus aureus* subsp. *aureus* Mu50 and is encoded by the nucleic acid sequence exemplified in SEQ ID NO: 42 hereinafter, or it is a functionally equivalent variant thereof.

In one embodiment, the enzyme Hydroxymethylglutaryl-CoA reductase (HMGR) is derived from *Staphylococcus aureus* subsp. *aureus* Mu50 and is encoded by the nucleic acid sequence exemplified in SEQ ID NO: 43 hereinafter, or it is a functionally equivalent variant thereof.

In one embodiment, the enzyme Geranyltranstransferase (ispA) is derived from *Escherichia coli* str. K-12 substr. MG1655 is encoded by the nucleic acid sequence exemplified in SEQ ID NO: 56 hereinafter, or it is a functionally equivalent variant thereof.

In one embodiment, the enzyme heptaprenyl diphosphate synthase is derived from *C. autoethanogenum* and is encoded by the nucleic acid sequence exemplified in SEQ ID NO: 17 or is a functionally equivalent variant thereof.

In one embodiment, the enzyme polyprenyl synthetase is derived from *C. autoethanogenum* and is encoded by the nucleic acid sequence exemplified in SEQ ID NO: 19 or is a functionally equivalent variant thereof.

In one embodiment, the enzyme Alpha-farnesene synthase (FS) is derived from *Malus x domestica* and is encoded by the nucleic acid sequence exemplified in SEQ ID NO: 57 hereinafter, or it is a functionally equivalent variant thereof.

The enzymes and functional variants of use in the microorganisms may be identified by assays known to one of skill in the art. In particular embodiments, the enzyme isoprene synthase may be identified by the method outlined Silver et al. (1991, *Plant Physiol.* 97: 1588-1591) or Zhao et al. (2011, *Appl Microbiol Biotechnol*, 90:1915-1922). In a further particular embodiment, the enzyme farnesene synthase may be identified by the method outlined in Green et al., 2007, *Phytochemistry;* 68:176-188. In further particular embodiments, enzymes from the mevalonate pathway may be identified by the method outlined in Cabano et al. (1997, *Insect Biochem. Mol. Biol.* 27: 499-505) for the HMG-CoA synthase, Ma et al. (2011, *Metab. Engin.*, 13:588-597) for the HMG-CoA reductase and mevalonate kinase enzyme, Herdendorf and Miziorko (2007, *Biochemistry*, 46: 11780-8) for the phosphomevalonate kinase, and Krepkiy et al. (2004, *Protein Sci.* 13: 1875-1881) for the mevalonate diphosphate decarboxylase. Ma et al., 2011, *Metab. Engin.*, 13:588-597. The 1-deoxy-D-xylulose 5-phosphate synthase of the DXS pathway can be assayed using the method outlined in Kuzuyama et al. (2000, *J. Bacteriol.* 182, 891-897). It is also possible to identify genes of DXS and mevalonate pathway using inhibitors like fosmidomycin or mevinoline as described by Trutko et al. (2005, *Microbiology* 74: 153-158).

In one embodiment, the microorganism comprises one or more exogenous nucleic acids adapted to increase expression of one or more endogenous nucleic acids and which one or more endogenous nucleic acids encode one or more of the enzymes referred to herein before. In one embodiment, the one or more exogenous nucleic acid adapted to increase expression is a regulatory element. In one embodiment, the regulatory element is a promoter. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster or Phosphotransacetylase/Acetate kinase operon promoters. It will be appreciated by those of skill in the art that other promoters which can direct expression, preferably a high level of expression under appropriate fermentation conditions, would be effective as alternatives to the exemplified embodiments.

In one embodiment, the microorganism comprises one or more exogenous nucleic acids encoding and adapted to express one or more of the enzymes referred to herein before. In one embodiment, the microorganisms comprise one or more exogenous nucleic acid encoding and adapted to express at least two, at least of the enzymes. In other embodiments, the microorganism comprises one or more exogenous nucleic acid encoding and adapted to express at least three, at least four, at least five, at least six, at least seven, at least eight, at least nine or more of the enzymes.

In one particular embodiment, the microorganism comprises one or more exogenous nucleic acid encoding an enzyme of the invention or a functionally equivalent variant thereof.

The microorganism may comprise one or more exogenous nucleic acids. Where it is desirable to transform the parental microorganism with two or more genetic elements (such as genes or regulatory elements (for example a promoter)) they may be contained on one or more exogenous nucleic acids.

In one embodiment, the one or more exogenous nucleic acid is a nucleic acid construct or vector, in one particular embodiment a plasmid, encoding one or more of the enzymes referred to hereinbefore in any combination.

The exogenous nucleic acids may remain extra-chromosomal upon transformation of the parental microorganism or may integrate into the genome of the parental microorganism. Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences).

In one embodiment, the exogenous nucleic acids encoding one or enzymes as mentioned herein before will further comprise a promoter adapted to promote expression of the one or more enzymes encoded by the exogenous nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster and Phosphotransacetylase/Acetate kinase promoters. It will be appreciated by those of skill in the art that other promoters which can direct expression, preferably a high level of expression under appropriate fermentation conditions, would be effective as alternatives to the exemplified embodiments.

In one embodiment, the exogenous nucleic acid is an expression plasmid.

In one particular embodiment, the parental microorganism is selected from the group of carboxydotrophic acetogenic bacteria. In certain embodiments the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kivui.*

In one particular embodiment, the parental microorganism is selected from the cluster of ethanologenic, acetogenic Clostridia comprising the species *C. autoethanogenum, C. ljungdahlii,* and *C. ragsdalei* and related isolates. These include but are not limited to strains *C. autoethanogenum* JAI-1T (DSM10061) [Abrini J, Naveau H, Nyns E-J: *Clostridium autoethanogenum*, sp. nov., an anaerobic bacterium that produces ethanol from carbon monoxide. *Arch Microbiol* 1994, 4: 345-351], *C. autoethanogenum* LBS1560 (DSM19630) [Simpson S D, Forster R L, Tran P T, Rowe M J, Warner I L: Novel bacteria and methods thereof. International patent 2009, WO/2009/064200], *C. autoethanogenum* LBS1561 (DSM23693), *C. ljungdahlii* PETC$^T$ (DSM13528=ATCC 55383) [Tanner R S, Miller L M, Yang D: *Clostridium ljungdahlii* sp. nov., an Acetogenic Species in Clostridial rRNA Homology Group I. *Int J Syst Bacteriol* 1993, 43: 232-236], *C. ljungdahlii* ERI-2 (ATCC 55380) [Gaddy J L: *Clostridium* stain which produces acetic acid from waste gases. US patent 1997, U.S. Pat. No. 5,593,886], *C. ljungdahlii* C-01 (ATCC 55988) [Gaddy J L, Clausen E C, Ko C-W: Microbial process for the preparation of acetic acid as well as solvent for its extraction from the fermentation broth. US patent, 2002, U.S. Pat. No. 6,368,819], *C. ljungdahlii* O-52 (ATCC 55989) [Gaddy J L, Clausen E C, Ko C-W: Microbial process for the preparation of acetic acid as well as solvent for its extraction from the fermentation broth. US patent, 2002, U.S. Pat. No. 6,368,819], *C. ragsdalei* PU$^T$ (ATCC BAA-622) [Huhnke R L, Lewis R S, Tanner R S: Isolation and Characterization of novel Clostridial Species. International patent 2008, WO 2008/028055], related isolates such as "*C. coskatii*" [Zahn et al—Novel ethanologenic species *Clostridium coskatii* (US Patent Application number U520110229947)] and "*Clostridium* sp." (Tyurin et al., 2012, 1 *Biotech Res.* 4: 1-12), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a sub-cluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species [Huhnke R L, Lewis R S, Tanner R S: Isolation and Characterization of novel Clostridial Species. International patent 2008, WO 2008/028055].

All species of this cluster have a similar morphology and size (logarithmic growing cells are between 0.5-0.7×3-5 μm), are mesophilic (optimal growth temperature between 30-37° C.) and strictly anaerobe [Tanner R S, Miller L M, Yang D: *Clostridium ljungdahlii* sp. nov., an Acetogenic Species in Clostridial rRNA Homology Group I. *Int J Syst Bacteriol* 1993, 43: 232-236; Abrini J, Naveau H, Nyns E-J: *Clostridium autoethanogenum*, sp. nov., an anaerobic bacterium that produces ethanol from carbon monoxide. *Arch Microbiol* 1994, 4: 345-351; Huhnke R L, Lewis R S, Tanner R S: Isolation and Characterization of novel Clostridial Species. International patent 2008, WO 2008/028055]. Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions. [Tanner R S, Miller L M, Yang D: *Clostridium ljungdahlii* sp. nov., an Acetogenic Species in Clostridial rRNA Homology Group I. *Int J Syst Bacteriol* 1993, 43: 232-236; Abrini J, Naveau H, Nyns E-J: *Clostridium autoethanogenum*, sp. nov., an anaerobic bacterium that produces ethanol from carbon monoxide. *Arch Microbiol* 1994, 4: 345-351; Huhnke R L, Lewis R S, Tanner R S: Isolation and Characterization of novel Clostridial Species. International patent 2008, WO 2008/028055]. Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover, some of the species were found to be auxotroph to certain vitamins (e.g. thiamine, biotin) while others were not.

In one embodiment, the parental carboxydotrophic acetogenic microorganism is selected from the group consisting of *Clostridium autoethanogenum, Clostridium ljungdahlii, Clostridium ragsdalei, Clostridium carboxidivorans, Clostridium drakei, Clostridium scatologenes, Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter pfennigii*, and *Thermoanaerobacter kivui*.

In one particular embodiment of the first or second aspects, the parental microorganism is selected from the group of carboxydotrophic Clostridia comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum*.

In a one embodiment, the microorganism is selected from a cluster of carboxydotrophic Clostridia comprising the species *C. autoethanogenum, C. ljungdahlii*, and "*C. ragsdalei*" and related isolates. These include but are not limited to strains *C. autoethanogenum* JAI-1$^T$ (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, & Yang, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* 0-52 (ATCC 55989) (U.S. Pat. No. 6,368,819), or "*C. ragsdalei* P11$^T$" (ATCC BAA-622) (WO 2008/028055), and related isolates such as "*C. coskatii*" (US patent 2011/0229947), "*Clostridium* sp. MT351" (Michael Tyurin & Kiriukhin, 2012) and mutant strains thereof such as *C. ljungdahlii* OTA-1 (Tirado-Acevedo O. Production of Bioethanol from Synthesis Gas Using *Clostridium ljungdahlii*. PhD thesis, North Carolina State University, 2010).

These strains form a subcluster within the Clostridial rRNA cluster I (Collins et al., 1994), having at least 99% identity on 16S rRNA gene level, although being distinct species as determined by DNA-DNA reassociation and DNA fingerprinting experiments (WO 2008/028055, US patent 2011/0229947).

The strains of this cluster are defined by common characteristics, having both a similar genotype and phenotype, and they all share the same mode of energy conservation and fermentative metabolism. The strains of this cluster lack cytochromes and conserve energy via an Rnf complex.

All strains of this cluster have a genome size of around 4.2 MBp (Kopke et al., 2010) and a GC composition of around 32% mol (Abrini et al., 1994; Kopke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde:ferredoxin oxidoreductase (Kopke et al., 2010, 2011). The organization and number of Wood-Ljungdahl pathway genes, responsible for gas uptake, has been found to be the same in all species, despite differences in nucleic and amino acid sequences (Kopke et al., 2011).

The strains all have a similar morphology and size (logarithmic growing cells are between 0.5-0.7×3-5 pin), are mesophilic (optimal growth temperature between 30-37° C.) and strictly anaerobe (Abrini et al., 1994; Tanner et al., 1993)(WO 2008/028055). Moreover, they all share the same major phylogenetic traits, such as same pH range (pH 4-7.5, with an optimal initial pH of 5.5-6), strong autotrophic growth on CO containing gases with similar growth rates, and a metabolic profile with ethanol and acetic acid as main fermentation end product, with small amounts of 2,3-butanediol and lactic acid formed under certain conditions (Abrini et al., 1994; Kopke et al., 2011; Tanner et al., 1993) However, the species differentiate in substrate utilization of various sugars (e.g. rhamnose, arabinose), acids (e.g. gluconate, citrate), amino acids (e.g. arginine, histidine), or other substrates (e.g. betaine, butanol). Some of the species were found to be auxotroph to certain vitamins (e.g. thiamine, biotin) while others were not. Reduction of carboxylic acids into their corresponding alcohols has been shown in a range of these organisms (Perez, Richter, Loftus, & Angenent, 2012).

The traits described are therefore not specific to one organism like *C. autoethanogenum* or *C. ljungdahlii*, but rather general traits for carboxydotrophic, ethanol-synthesizing Clostridia. Thus, the invention can be anticipated to work across these strains, although there may be differences in performance.

The recombinant carboxydotrophic acetogenic microorganisms of the invention may be prepared from a parental carboxydotrophic acetogenic microorganism and one or more exogenous nucleic acids using any number of techniques known in the art for producing recombinant microorganisms. By way of example only, transformation (including transduction or transfection) may be achieved by electroporation, electrofusion, ultrasonication, polyethylene glycol-mediated transformation, conjugation, or chemical and natural competence. Suitable transformation techniques are described for example in Sambrook J, Fritsch E F, Maniatis T: Molecular Cloning: A laboratory Manual, Cold Spring Harbour Laboratory Press, Cold Spring Harbour, 1989.

Electroporation has been described for several carboxydotrophic acetogens as *C. ljungdahlii* (Kopke et al., 2010; Leang, Ueki, Nevin, & Lovley, 2012) (PCT/NZ2011/000203; WO2012/053905), *C. autoethanogenum* (PCT/NZ2011/000203; WO2012/053905), *Acetobacterium woodii* (Stratz, Sauer, Kuhn, & Dune, 1994) or *Moorella thermoacetica* (Kita et al., 2012) and is a standard method used in many Clostridia such as *C. acetobutylicum* (Mermelstein, Welker, Bennett, & Papoutsakis, 1992), *C. cellulolyticum* (Jennert, Tardif, Young, & Young, 2000) or *C. thermocellum* (MV Tyurin, Desai, & Lynd, 2004).

Electrofusion has been described for acetogenic *Clostridium* sp. MT351 (Tyurin and Kiriukhin, 2012).

Prophage induction has been described for carboxydotrophic acetogen as well in case of *C. scatologenes* (Prasanna Tamarapu Parthasarathy, 2010, Development of a Genetic Modification System in *Clostridium scatologenes* ATCC 25775 for Generation of Mutants, Masters Project Western Kentucky University).

Conjugation has been described as method of choice for acetogen *Clostridium difficile* (Herbert, O'Keeffe, Purdy, Elmore, & Minton, 2003) and many other Clostridia including *C. acetobutylicum* (Williams, Young, & Young, 1990).

In one embodiment, the parental strain uses CO as its sole carbon and energy source.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

Nucleic Acids

The invention also provides one or more nucleic acids or nucleic acid constructs of use in generating a recombinant microorganism of the invention.

In one embodiment, the nucleic acid comprises sequences encoding one or more of the enzymes in the mevalonate (MVA) pathway and optionally the DXS pathway which when expressed in a microorganism allows the microorganism to produce one or more terpenes and/or precursors thereof by fermentation of a substrate comprising CO. In one particular embodiment, the invention provides a nucleic acid encoding two or more enzymes which when expressed in a microorganism allows the microorganism to produce one or more terpene and/or precursor thereof by fermentation of substrate comprising CO. In one embodiment, a nucleic acid of the invention encodes three, four, five or more of such enzymes.

In one embodiment, the one or more enzymes encoded by the nucleic acid are from the mevalonate (MVA) pathway and are selected from the group consisting of:
a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33), and
g) a functionally equivalent variant of any one thereof.

In a further embodiment, the one or more optional enzymes encoded by the nucleic acid are from the DXS pathway are selected from the group consisting of:
a) 1-deoxy-D-xylulose-5-phosphate synthase DXS (EC: 2.2.1.7),
b) 1-deoxy-D-xylulose 5-phosphate reductoisomerase DXR (EC:1.1.1.267),
c) 2-C-methyl-D-erythritol 4-phosphate cytidylyltransferase IspD (EC:2.7.7.60),
d) 4-diphosphocytidyl-2-C-methyl-D-erythritol kinase IspE (EC:2.7.1.148),
e) 2-C-methyl-D-erythritol 2,4-cyclodiphosphate synthase IspF (EC:4.6.1.12),
f) 4-hydroxy-3-methylbut-2-en-1-yl diphosphate synthase IspG (EC:1.17.7.1),
g) 4-hydroxy-3-methylbut-2-enyl diphosphate reductase (EC:1.17.1.2), and
h) a functionally equivalent variant of any one thereof.

In a further embodiment, the nucleic acid encodes one or more further enzymes that are expressed or over-expressed to result in the production of a terpene compound and/or precursor thereof wherein the exogenous enzyme that is expressed, or the endogenous enzyme that is overexpressed is selected from the group consisting of:
a) geranyltranstransferase Fps (EC:2.5.1.10),
b) heptaprenyl diphosphate synthase (EC:2.5.1.10),
c) octaprenyl-diphosphate synthase (EC:2.5.1.90),
d) isoprene synthase (EC 4.2.3.27),
e) isopentenyl-diphosphate delta-isomerase (EC 5.3.3.2),
f) farnesene synthase (EC 4.2.3.46/EC 4.2.3.47), and
g) a functionally equivalent variant of any one thereof.

Exemplary amino acid sequences and nucleic acid sequences encoding each of the above enzymes are provided herein or can be obtained from GenBank as mentioned hereinbefore. However, skilled persons will readily appreciate alternative nucleic acid sequences encoding the enzymes or functionally equivalent variants thereof, having regard to the information contained herein, in GenBank and other databases, and the genetic code.

In a further embodiment, the nucleic acid encoding thiolase (thlA) derived from *Clostridium acetobutylicum* ATCC824 is encoded by the nucleic acid sequence exemplified in SEQ ID NO: 40 hereinafter, or it is a functionally equivalent variant thereof.

In a further embodiment, the nucleic acid encoding thiolase wherein the thiolase is acetyl-CoA c-acetyltransferase (vraB) derived from *Staphylococcus aureus* subsp. *aureus* Mu50 is encoded by the nucleic acid sequence exemplified in SEQ ID NO: 41 hereinafter, or it is a functionally equivalent variant thereof.

In a further embodiment, the nucleic acid encoding 3-hydroxy-3-methylglutaryl-CoA synthase (HMGS) derived from *Staphylococcus aureus* subsp. *aureus* Mu50 is encoded by the nucleic acid sequence exemplified in SEQ ID NO: 42 hereinafter, or it is a functionally equivalent variant thereof.

In a further embodiment, the nucleic acid encoding Hydroxymethylglutaryl-CoA reductase (HMGR) derived from *Staphylococcus aureus* subsp. *aureus* Mu50 is encoded by the nucleic acid sequence exemplified in SEQ ID NO: 43 hereinafter, or it is a functionally equivalent variant thereof.

In a further embodiment, the nucleic acid encoding mevalonate kinase (MK) derived from *Staphylococcus aureus* subsp. *aureus* Mu50 is encoded by the nucleic acid sequence exemplified in SEQ ID NO: 51 hereinafter, or it is a functionally equivalent variant thereof.

In a further embodiment, the nucleic acid encoding phosphomevalonate kinase (PMK) derived from *Staphylococcus aureus* subsp. *aureus* Mu50 is encoded by the nucleic acid sequence exemplified in SEQ ID NO: 52 hereinafter, or it is a functionally equivalent variant thereof.

In a further embodiment, the nucleic acid encoding mevalonate diphosphate decarboxylase (PMD) derived from *Staphylococcus aureus* subsp. *aureus* Mu50 is encoded by the nucleic acid sequence exemplified in SEQ ID NO: 53 hereinafter, or it is a functionally equivalent variant thereof.

In a further embodiment, the nucleic acid encoding deoxyxylulose 5-phosphate synthase derived from *C. autoethanogenum*, is encoded by the nucleic acid sequence exemplified in SEQ ID NO: 1 and/or with the amino acid sequence exemplified in SEQ ID NO: 2 hereinafter, or it is a functionally equivalent variant thereof.

In one embodiment, the nucleic acid encoding 1-deoxy-D-xylulose 5-phosphate reductoisomerase DXR (EC: 1.1.1.267) has the sequence SEQ ID NO: 3 or is a functionally equivalent variant thereof.

In one embodiment, the nucleic acid encoding 2-C-methyl-D-erythritol 4-phosphate cytidylyltransferase IspD (EC:2.7.7.60) has the sequence SEQ ID NO: 5 or is a functionally equivalent variant thereof.

In one embodiment, the nucleic acid encoding 4-diphosphocytidyl-2-C-methyl-D-erythritol kinase IspE (EC: 2.7.1.148) has the sequence SEQ ID NO: 7 or is a functionally equivalent variant thereof.

In one embodiment, the nucleic acid encoding 2-C-methyl-D-erythritol 2,4-cyclodiphosphate synthase IspF (EC:4.6.1.12) has the sequence SEQ ID NO: 9 or is a functionally equivalent variant thereof.

In one embodiment, the nucleic acid encoding 4-hydroxy-3-methylbut-2-en-1-yl diphosphate synthase IspG (EC: 1.17.7.1) has the sequence SEQ ID NO: 11 or is a functionally equivalent variant thereof.

In one embodiment, the nucleic acid encoding 4-hydroxy-3-methylbut-2-enyl diphosphate reductase (EC:1.17.1.2) has the sequence SEQ ID NO: 13 or is a functionally equivalent variant thereof.

In a further embodiment, the nucleic acid encoding Geranyltranstransferase (ispA) derived from *Escherichia coli* str. K-12 substr. MG1655 is encoded by the nucleic acid sequence exemplified in SEQ ID NO: 56 hereinafter, or it is a functionally equivalent variant thereof.

In one embodiment, the nucleic acid encoding heptaprenyl diphosphate synthase has the sequence SEQ ID NO: 17, or it is a functionally equivalent variant thereof.

In one embodiment, the nucleic acid encoding octaprenyl-diphosphate synthase (EC:2.5.1.90) wherein the octaprenyl-diphosphate synthase is polyprenyl synthetase is encoded by sequence SEQ ID NO: 19, or it is a functionally equivalent variant thereof.

In one embodiment, the nucleic acid encoding isoprene synthase (ispS) derived from *Poplar tremuloides* is exemplified in SEQ ID NO: 21 hereinafter, or it is a functionally equivalent variant thereof.

In a further embodiment, the nucleic acid encoding Isopentenyl-diphosphate delta-isomerase (idi) derived from *Clostridium beijerinckii* is encoded by the nucleic acid sequence exemplified in SEQ ID NO: 54 hereinafter, or it is a functionally equivalent variant thereof.

In a further embodiment, the nucleic acid encoding Alpha-farnesene synthase (FS) derived from *Malus x domestica* is encoded by the nucleic acid sequence exemplified in SEQ ID NO: 57 hereinafter, or it is a functionally equivalent variant thereof.

In one embodiment, the nucleic acids of the invention will further comprise a promoter. In one embodiment, the promoter allows for constitutive expression of the genes under its control. However, inducible promoters may also be employed. Persons of skill in the art will readily appreciate promoters of use in the invention. Preferably, the promoter can direct a high level of expression under appropriate fermentation conditions. In a particular embodiment a Wood-Ljungdahl cluster promoter is used. In another embodiment, a Phosphotransacetylase/Acetate kinase promoter is used. In another embodiment a pyruvate:ferredoxin oxidoreductase promoter, an Rnf complex operon promoter or an ATP synthase operon promoter. In one particular embodiment, the promoter is from *C. autoethanogenum*.

The nucleic acids of the invention may remain extra-chromosomal upon transformation of a parental microorganism or may be adapted for integration into the genome of the microorganism. Accordingly, nucleic acids of the invention may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In one embodiment, the nucleic acid is nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

Methods of Producing Organisms

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) Microbial. *Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps:

b) introduction into a shuttle microorganism of (i) of an expression construct/vector as described herein and (ii) a methylation construct/vector comprising a methyltransferase gene;

c) expression of the methyltransferase gene;

d) isolation of one or more constructs/vectors from the shuttle microorganism; and, e) introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism, that facilitates the methylation of the nucleic acid sequences that make up the expression construct/vector. In a particular embodiment, the shuttle microorganism is a restriction negative *E. coli*, *Bacillus subtilis*, or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thio-galactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and the methyltransferase described in the Examples herein after may be used. In one embodiment, the methyltransferase has the amino acid sequence of SEQ ID NO: 60 or is a functionally equivalent variant thereof. Nucleic acids encoding suitable methyltransferases will be readily appreciated having regard to the sequence of the desired methyltransferase and the genetic code. In one embodiment, the nucleic acid encoding a methyltransferase is as described in the Examples herein after (for example the nucleic acid of SEQ ID NO: 63, or it is a functionally equivalent variant thereof).

Any number of constructs/vectors adapted to allow expression of a methyltransferase gene may be used to generate the methylation construct/vector. However, by way of example, the plasmid described in the Examples section hereinafter may be used.

Methods of Production

The invention provides a method for the production of one or more terpenes and/or precursors thereof, and optionally one or more other products, by microbial fermentation comprising fermenting a substrate comprising CO using a recombinant microorganism of the invention. Preferably, the one or more terpene and/or precursor thereof is the main fermentation product. The methods of the invention may be used to reduce the total atmospheric carbon emissions from an industrial process.

Preferably, the fermentation comprises the steps of anaerobically fermenting a substrate in a bioreactor to produce at least one or more terpenes and/or a precursor thereof using a recombinant microorganism of the invention.

In one embodiment, the one or more terpene and/or precursor thereof is chosen from mevalonic acid, IPP, dimethylallyl pyrophosphate (DMAPP), isoprene, geranyl pyrophosphate (GPP), farnesyl pyrophosphate (FPP) and farnesene.

Instead of producing isoprene directly from terpenoid key intermediates IPP and DMAPP then using this to synthesise longer chain terpenes, it is also possible to synthesise longer chain terpenes, such as C10 Monoterpenoids or C15 Sesquiterpenoids, directly via a geranyltransferase (see Table 6). From C15 Sesquiterpenoid building block farnesyl-PP it is possible to produce farnesene, which, similarly to ethanol, can be used as a transportation fuel.

In one embodiment the method comprises the steps of:
(a) providing a substrate comprising CO to a bioreactor containing a culture of one or more microorganism of the invention; and
(b) anaerobically fermenting the culture in the bioreactor to produce at least one or more terpene and/or precursor thereof.

In one embodiment the method comprises the steps of:
a) capturing CO-containing gas produced as a result of the industrial process;
b) anaerobic fermentation of the CO-containing gas to produce the at least one or more terpene and/or precursor thereof by a culture containing one or more microorganism of the invention.

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing a terpene for use as a biofuel. Depending on the composition of the gaseous CO—containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and CO-to-at least one or more terpene and/or precursor thereof to occur, in addition to the CO-containing substrate gas, a suitable liquid nutrient medium will need to be fed to the bioreactor. The substrate and media may be fed to the bioreactor in a continuous, batch or batch fed fashion. A nutrient medium will contain vitamins and minerals sufficient to permit growth of the micro-organism used. Anaerobic media suitable for fermentation to produce a terpene and/or a precursor thereof using CO are known in the art. For example, suitable media are described Biebel (2001). In one embodiment of the invention the media is as described in the Examples section herein after.

The fermentation should desirably be carried out under appropriate conditions for the CO-to-the at least one or more terpene and/or precursor thereof fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of at least one or more terpene and/or precursor thereof. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO-to-at least one or more terpene and/or precursor thereof conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that one or more product is consumed by the culture.

The composition of gas streams used to feed a fermentation reaction can have a significant impact on the efficiency and/or costs of that reaction. For example, 02 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

Terpenes and/or precursors thereof, or a mixed stream containing one or more terpenes, precursors thereof and/or one or more other products, may be recovered from the fermentation broth by methods known in the art, such as fractional distillation or evaporation, pervaporation, gas stripping and extractive fermentation, including for example, liquid-liquid extraction.

In certain preferred embodiments of the invention, the one or more terpene and/or precursor thereof and one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

EXAMPLES

The invention will now be described in more detail with reference to the following non-limiting examples.

Example 1—Expression of Isoprene Synthase in *C. autoethanogenum* for Production of Isoprene from CO The inventors have identified terpene biosynthesis genes in carboxydotrophic acetogens such as *C. autoethanogenum* and *C. ljungdahlii*. A recombinant organism was engineered to produce isoprene. Isoprene is naturally emitted by some plant such as poplar to protect its leave from UV radiation. Isoprene synthase (EC 4.2.3.27) gene of *Poplar* was codon optimized and introduced into a carboxydotrophic acetogen *C. autoethanogenum* to produce isoprene from CO. The enzyme takes key intermediate DMAPP (Dimethylallyl diphosphate) of terpenoid biosynthesis to isoprene in an irreversible reaction (FIG. 1).

Strains and Growth Conditions:

All subcloning steps were performed in *E. coli* using standard strains and growth conditions as described earlier (Sambrook et al, Molecular Cloning: A laboratory Manual, Cold Spring Harbour Laboratory Press, Cold Spring Harbour, 1989; Ausubel et al, Current protocols in molecular biology, John Wiley & Sons, Ltd., Hoboken, 1987).

*C. autoethanogenum* DSM10061 and DSM23693 (a derivative of DSM10061) were obtained from DSMZ (The German Collection of Microorganisms and Cell Cultures, InhoffenstraBe 7 B, 38124 Braunschweig, Germany). Growth was carried out at 37° C. using strictly anaerobic conditions and techniques (Hungate, 1969, Methods in Microbiology, vol. 3B. Academic Press, New York: 117-132; Wolfe, 1971, *Adv. Microb. Physiol.*, 6: 107-146). Chemically defined PETC media without yeast extract (Table 1) and 30 psi carbon monoxide containing steel mill waste gas (collected from New Zealand Steel site in Glenbrook, NZ; composition: 44% CO, 32% $N_2$, 22% $CO_2$, 2% $H_2$) as sole carbon and energy source was used.

TABLE 1

| Media component | Concentration per 1.0 L of media |
|---|---|
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution | 10 ml |
| Resazurin (2 g/L stock) | 0.5 ml |
| $NaHCO_3$ | 2 g |
| Reducing agent | 0.006-0.008 % (v/v) |
| Distilled water | Up to 1 L, pH 5.5 (adjusted with HCl) |
| Wolfe's vitamin solution | per L of Stock |
| Biotin | 2 mg |
| Folic acid | 2 mg |
| Pyridoxine hydrochloride | 10 mg |
| Riboflavin | 5 mg |
| Nicotinic acid | 5 mg |
| Calcium D-(+)-pantothenate | 5 mg |
| Vitamin $B_{12}$ | 0.1 mg |
| p-Aminobenzoic acid | 5 mg |
| Lipoic acid | 5 mg |
| Thiamine | 5 mg |
| Distilled water | To 1 L |
| Trace metal solution | per L of stock |
| Nitrilotriacetic Acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |
| Distilled water | To 1 L |
| Reducing agent stock | per 100 mL of stock |
| NaOH | 0.9 g |
| Cystein•HCl | 4 g |
| $Na_2S$ | 4 g |
| Distilled water | To 100 mL |

Construction of expression plasmid:

Standard Recombinant DNA and molecular cloning techniques were used in this invention (Sambrook J, Fritsch E F, Maniatis T: Molecular Cloning: A laboratory Manual, Cold Spring Harbour Laboratory Press, Cold Spring Harbour, 1989; Ausubel F M, Brent R, Kingston R E, Moore D D, Seidman J G, Smith J A, Struhl K: Current protocols in molecular biology. John Wiley & Sons, Ltd., Hoboken, 1987). The isoprene synthase of *Poplar tremuloides* (AAQ16588.1; GI:33358229) was codon-optimized (SEQ ID NO: 21) and synthesized. A promoter region of the Pyruvate:ferredoxin oxidoreductase of *C. autoethanogenum* (SEQ ID NO: 22) was used to express the gene.

Genomic DNA from *Clostridium autoethanogenum* DSM23693 was isolated using a modified method by Bertram and Dune (1989). A 100-ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 300 µl lysozyme (~100,000 U) was added and the mixture was incubated at 37° C. for 30 min, followed by addition of 280 µl of a 10% (w/v) SDS solution and another incubation for 10 min. RNA was digested at room temperature by addition of 240 µl of an EDTA solution (0.5 M, pH 8), 20 µl Tris-HCl (1 M, pH 7.5), and 10 µl RNase A (Fermentas Life Sciences). Then, 100 µl Proteinase K (0.5

U) was added and proteolysis took place for 1-3 h at 37° C. Finally, 600 µl of sodium perchlorate (5 M) was added, followed by a phenol-chloroform extraction and an isopropanol precipitation. DNA quantity and quality was inspected spectrophotometrically. The Pyruvate:ferredoxin oxidoreductase promoter sequence was amplified by PCR using oligonucleotides Ppfor-NotI-F (SEQ ID NO: 23: AAGCGGCCGCAAAATAGTTGATAATAATGC) and Ppfor-NdeI-R (SEQ ID NO: 24: TACGCATATGAAT-TCCTCTCCTTTTCAAGC) using iProof High Fidelity DNA Polymerase (Bio-Rad Laboratories) and the following program: initial denaturation at 98° C. for 30 seconds, followed by 32 cycles of denaturation (98° C. for 10 seconds), annealing (50-62° C. for 30-120 seconds) and elongation (72° C. for 30-90 seconds), before a final extension step (72° C. for 10 minutes).

Figure 2:
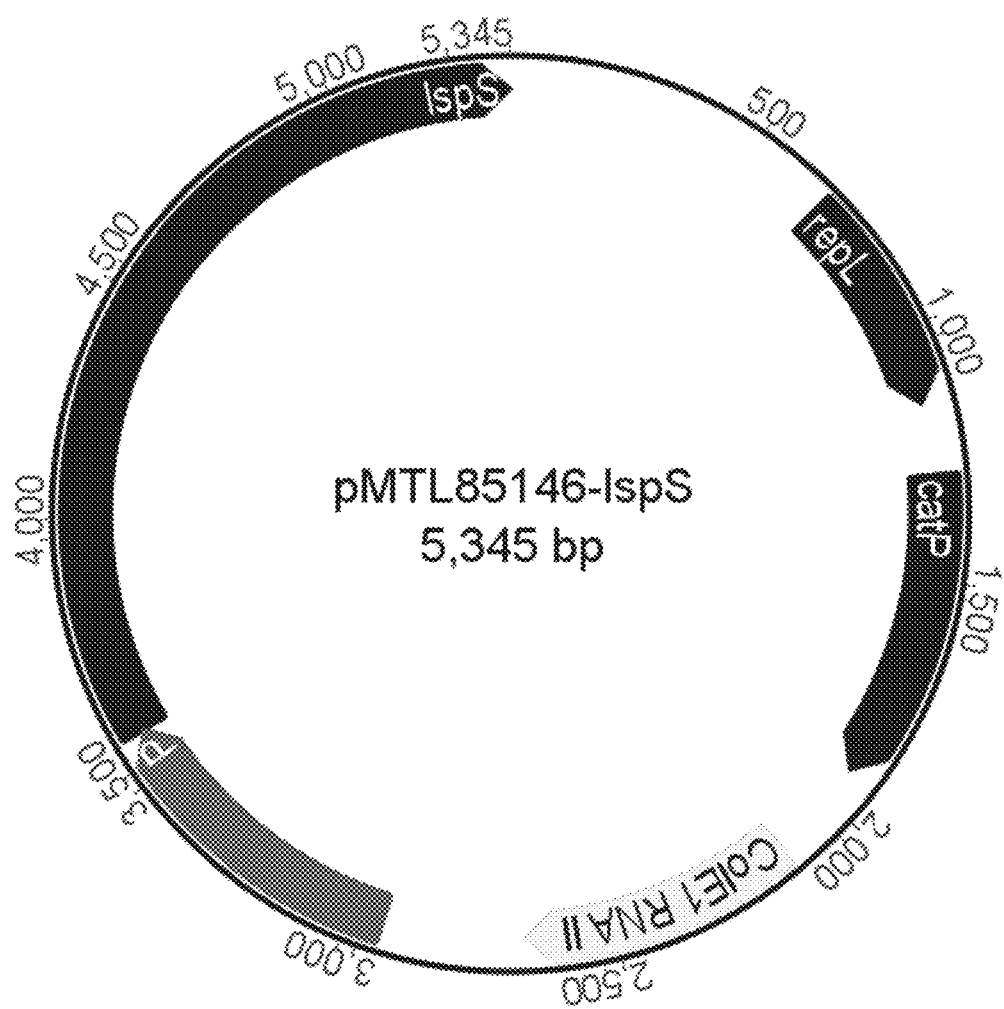
FIG. 2: Genetic map of plasmid pMTL 85146-ispS

Construction of isoprene synthase expression plasmid:

Construction of an expression plasmid was performed in *E. coli* DH5α-T1$^R$ (Invitrogen) and XL1-Blue MRF' Kan (Stratagene). In a first step, the amplified $P_{pfor}$ promoter region was cloned into the *E. coli-Clostridium* shuttle vector pMTL85141 (FJ797651.1; Nigel Minton, University of Nottingham; Heap et al., 2009) using NotI and NdeI restriction sites, generating plasmid pMTL85146. As a second step, ispS was cloned into pMTL85146 using restriction sites NdeI and EcoRI, resulting in plasmid pMTL 85146-ispS (FIG. 2, SEQ ID NO: 25).

Transformation and expression in *C. autoethanogenum*

Prior to transformation, DNA was methylated in vivo in *E. coli* using a synthesized hybrid Type II methyltransferase (SEQ ID NO: 63) co-expressed on a methylation plasmid (SEQ ID NO: 64) designed from methyltransferase genes from *C. autoethanogenum, C. ragsdalei* and *C. ljungdahlii* as described in US patent 2011/0236941.

Both expression plasmid and methylation plasmid were transformed into same cells of restriction negative *E. coli* XL1-Blue MRF' Kan (Stratagene), which is possible due to their compatible Gram-(−) origins of replication (high copy ColE1 in expression plasmid and low copy p15A in methylation plasmid). In vivo methylation was induced by addition of 1 mM IPTG, and methylated plasmids were isolated using QIAGEN Plasmid Midi Kit (QIAGEN). The resulting mixture was used for transformation experiments with *C. autoethanogenum* DSM23693, but only the abundant (high-copy) expression plasmid has a Gram-(+) replication origin (repL) allowing it to replicate in Clostridia.

Transformation into *C. autoethanogenum*:

During the complete transformation experiment, *C. autoethanogenum* DSM23693 was grown in PETC media (Table 1) supplemented with 1 g/L yeast extract and 10 g/l fructose as well as 30 psi steel mill waste gas (collected from New Zealand Steel site in Glenbrook, NZ; composition: 44% CO, 32% $N_2$, 22% $CO_2$, 2% $H_2$) as carbon source.

To make competent cells, a 50 ml culture of *C. autoethanogenum* DSM23693 was subcultured to fresh media for 3 consecutive days. These cells were used to inoculate 50 ml PETC media containing 40 mM DL-threonine at an $OD_{600\ nm}$ of 0.05. When the culture reached an $OD_{600\ nm}$ of 0.4, the cells were transferred into an anaerobic chamber and harvested at 4,700×g and 4° C. The culture was twice washed with ice-cold electroporation buffer (270 mM sucrose, 1 mM MgCl2, 7 mM sodium phosphate, pH 7.4) and finally suspended in a volume of 600 µl fresh electroporation buffer. This mixture was transferred into a pre-cooled electroporation cuvette with a 0.4 cm electrode gap containing 1 µg of the methylated plasmid mixture and immediately pulsed using the Gene pulser Xcell electroporation system (Bio-Rad) with the following settings: 2.5 kV, 600Ω, and 25 µf. Time constants of 3.7-4.0 ms were achieved. The culture was transferred into 5 ml fresh media. Regeneration of the cells was monitored at a wavelength of 600 nm using a Spectronic Helios Epsilon Spectrophotometer (Thermo) equipped with a tube holder. After an initial drop in biomass, the cells started growing again. Once the biomass has doubled from that point, the cells were harvested, suspended in 200 µl fresh media and plated on selective PETC plates (containing 1.2% Bacto™ Agar (BD)) with appropriate antibiotics 4 µg/ml Clarithromycin or 15 µg/ml thiamphenicol. After 4-5 days of inoculation with 30 psi steel mill gas at 37° C., colonies were visible.

The colonies were used to inoculate 2 ml PETC media with antibiotics. When growth occurred, the culture was scaled up into a volume of 5 ml and later 50 ml with 30 psi steel mill gas as sole carbon source.

Confirmation of the successful transformation:

To verify the DNA transfer, a plasmid mini prep was performed from 10 ml culture volume using Zyppy plasmid miniprep kit (Zymo). Since the quality of the isolated plasmid was not sufficient for a restriction digest due to Clostridial exonuclease activity [Burchhardt and Mine, 1990], a PCR was performed with the isolated plasmid with oligonucleotide pairs colE1-F (SEQ ID NO: 65: CGTCA-GACCCCGTAGAAA) plus colE1-R (SEQ ID NO: 66: CTCTCCTGTTCCGACCCT). PCR was carried out using iNtRON Maximise Premix PCR kit (Intron Bio Technologies) with the following conditions: initial denaturation at 94° C. for 2 minutes, followed by 35 cycles of denaturation (94° C. for 20 seconds), annealing (55° C. for 20 seconds) and elongation (72° C. for 60 seconds), before a final extension step (72° C. for 5 minutes).

To confirm the identity of the clones, genomic DNA was isolated (see above) from 50 ml cultures of *C. autoethanogenum* DSM23693. A PCR was performed against the 16s rRNA gene using oligonucleotides fD1 (SEQ ID NO: 67: CCGAATTCGTCGACAACAGAGTTT-GATCCTGGCTCAG) and rP2 (SEQ ID NO: 68: CCCGG-GATCCAAGCTTACGGCTACCTTGTTACGACTT) [Weisberg et al., 1991] and iNtRON Maximise Premix PCR kit (Intron Bio Technologies) with the following conditions: initial denaturation at 94° C. for 2 minutes, followed by 35 cycles of denaturation (94° C. for 20 seconds), annealing (55° C. for 20 seconds) and elongation (72° C. for 60 seconds), before a final extension step (72° C. for 5 minutes). Sequencing results were at least 99.9% identity against the 16s rRNA gene (rrsA) of *C. autoethanogenum* (Y18178, GI:7271109).

Expression of Isoprene Synthase Gene qRT-PCR experiments were performed to confirm successful expression of introduced isoprene synthase gene in *C. autoethanogenum*.

A culture harboring isoprene synthase plasmid pMTL 85146-ispS and a control culture without plasmid was grown in 50 mL serum bottles and PETC media (Table 1) with 30 psi steel mill waste gas (collected from New Zealand Steel site in Glenbrook, NZ; composition: 44% CO, 32% $N_2$, 22% $CO_2$, 2% $H_2$) as sole energy and carbon source. 0.8 mL samples were taken during logarithmic growth phase at an $OD_{600\ nm}$ of around 0.5 and mixed with 1.6 mL RNA protect reagent (Qiagen). The mixture was centrifuged (6,000×g, 5 min, 4° C.), and the cell sediment snap frozen in liquid nitrogen and stored at −80° C. until RNA extraction. Total RNA was isolated using RNeasy Mini Kit (Qiagen) according to protocol 5 of the manual. Disruption of the cells was carried out by passing the mixture through a syringe 10 times and eluted in 50 μL of RNase/DNase-free water. After DNase I treatment using DNA-free™ Kit (Ambion), the reverse transcription step was then carried out using Super-Script III Reverse Transcriptase Kit (Invitrogen, Carlsbad, Calif., USA). RNA was checked using an Agilent Bioanalyzer 2100 (Agilent Technologies, Santa Clara, Calif., USA), Qubit Fluorometer (Invitrogen, Carlsbad, Calif., USA) and by gel electrophoresis. A non-RT control was performed for every oligonucleotide pair. All qRT-PCR reactions were performed in duplicate using a MyiQ™ Single Colour Detection System (Bio-Rad Laboratories, Carlsbad, Calif., USA) in a total reaction volume of 15 μL with 25 ng of cDNA template, 67 nM of each oligonucleotide (Table 2), and 1× iQ™ SYBR® Green Supermix (Bio-Rad Laboratories, Carlsbad, Calif., USA). The reaction conditions were 95° C. for 3 min, followed by 40 cycles of 95° C. for 15 s, 55° C. for 15 s and 72° C. for 30 s. For detection of oligonucleotide dimerisation or other artifacts of amplification, a melting-curve analysis was performed immediately after completion of the qPCR (38 cycles of 58° C. to 95° C. at 1° C./s). Two housekeeping genes (guanylate kinase and formate tetrahydrofolate ligase) were included for each cDNA sample for normalization. Determination of relative gene expression was conducted using Relative Expression Software Tool (REST©) 2008 V2.0.7 (38). Dilution series of cDNA spanning 4 log units were used to generate standard curves and the resulting amplification efficiencies to calculate concentration of mRNA.

Figure 3:
FIG. 3: Genetic map of plasmid pMTL 85246-ispS-idi

Construction of Isopentenyl-Diphosphate Delta-Isomerase Expression Plasmid:

An Isopentenyl-diphosphate delta-isomerase gene idi from *C. beijerinckii* (Gene ID:5294264), encoding an Isopentenyl-diphosphate delta-isomerase (YP 001310174.1), was cloned downstream of ispS. The gene was amplified using oligonucleotide Idi-Cbei-SacI-F (SEQ ID NO: 26: GTGAGCTCGAAAGGGGAAAT-TAAATG) and Idi-Cbei-KpnI-R (SEQ ID NO: 27: ATGGTACCCCAAATCTTTATTTAGACG) from genomic DNA of *C. beijerinckii* NCIMB8052, obtained using the same method as described above for *C. autoethanogenum*. The PCR product was cloned into vector pMTL 85146-ispS using SacI and KpnI restriction sites to yield plasmid pMTL85146-ispS-idi (SEQ ID NO: 28). The antibiotic resistance marker was exchanged from catP to ermB (released from vector pMTL82254 (FJ797646.1; Nigel Minton, University of Nottingham; Heap et al., 2009) using restriction enzymes PmeI and FseI to form plasmid pMTL85246-ispS-idi (FIG. 3).

Transformation and expression in *C. autoethanogenum* was carried out as described for plasmid pMTL 85146-ispS. After successful transformation, growth experiment was carried out in 50 mL 50 mL serum bottles and PETC media (Table 1) with 30 psi steel mill waste gas (collected from New Zealand Steel site in Glenbrook, NZ; composition: 44% CO, 32% $N_2$, 22% $CO_2$, 2% $H_2$) as sole energy and carbon source. To confirm that the plasmid has been suc-

TABLE 2

Oligonucleotides for qRT-PCR

| Target | Oligonucleotide Name | DNA Sequence (5' to 3') | SEQ ID NO: |
|---|---|---|---|
| Guanylate kinase (gnk) | GnK-F | TCAGGACCTTCTGGAACTGG | 108 |
| | GnK-R | ACCTCCCCTTTTCTTGGAGA | 109 |
| Formate tetrahydrofolate ligase (FoT4L) | FoT4L-F | CAGGTTTCGGTGCTGACCTA | 110 |
| | FoT4L-F | AACTCCGCCGTTGTATTTCA | 111 |
| Isoprene Synthase | ispS-F | AGG CTG AAT TTC TTA CAC TTC TTG A | 69 |
| | ispS-R | GTA ACT CCA TCA AAT CCT CCA CTA C | 70 |

While no amplification was observed with the wild-type strain using oligonucleotide pair ispS, a signal with the ispS oligonucleotide pair was measured for the strain carrying plasmid pMTL 85146-ispS, confirming successful expression of the ispS gene.

Example 2—Expression of Isopentenyl-Diphosphate Delta-Isomerase to Convert Between Key Terpene Precursors DMAPP (Dimethylallyl Diphosphate) and IPP (Isopentenyl Diphosphate)

Figure 8:
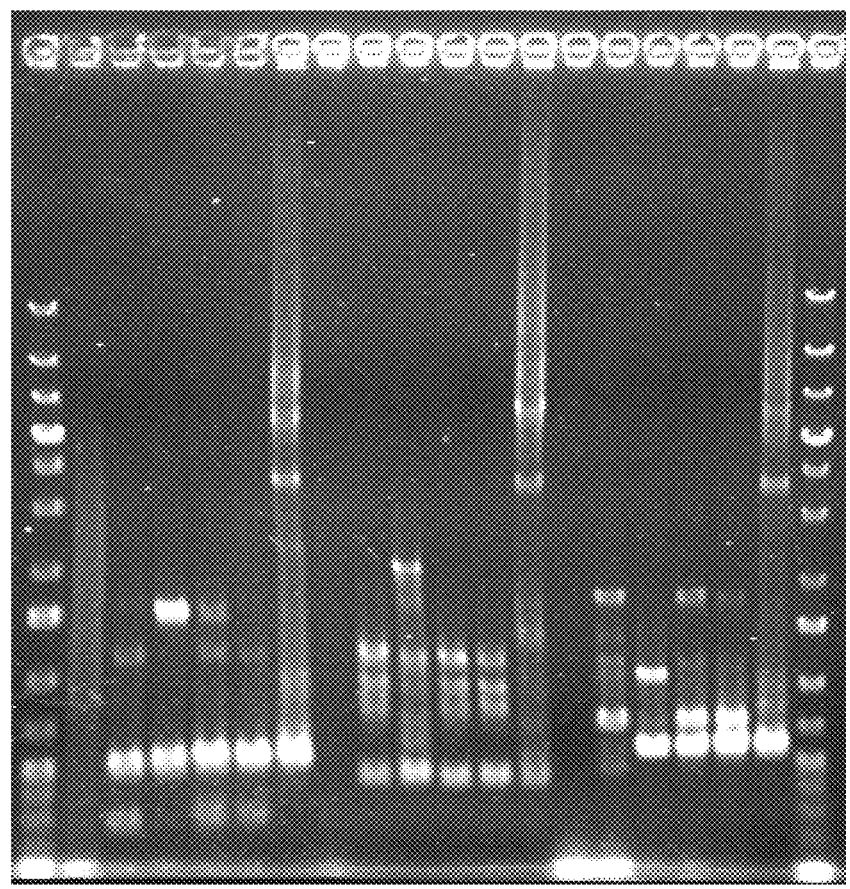
FIG. 8: Agarose gel electrophoresis image confirming presence of isoprene expression plasmid pMTL 85246-ispS-idi in *C. autoethanogenum* transformants. Lanes 1, and 20 show 100 bp Plus DNA Ladder. Lane 3-6, 9-12, 15-18 show PCR with isolated plasmids from 4 different clones as template, each in the following order: colE1, ermB, and idi. Lanes 2, 8, and 14 show PCR without template as negative control, each in the following order: colE1, ermB, and idi. Lanes 7, 13, and 19 show PCR with pMTL 85246-ispS-idi from *E. coli* as positive control, each in the following order: colE1, ermB, and idi.
Figure 9:
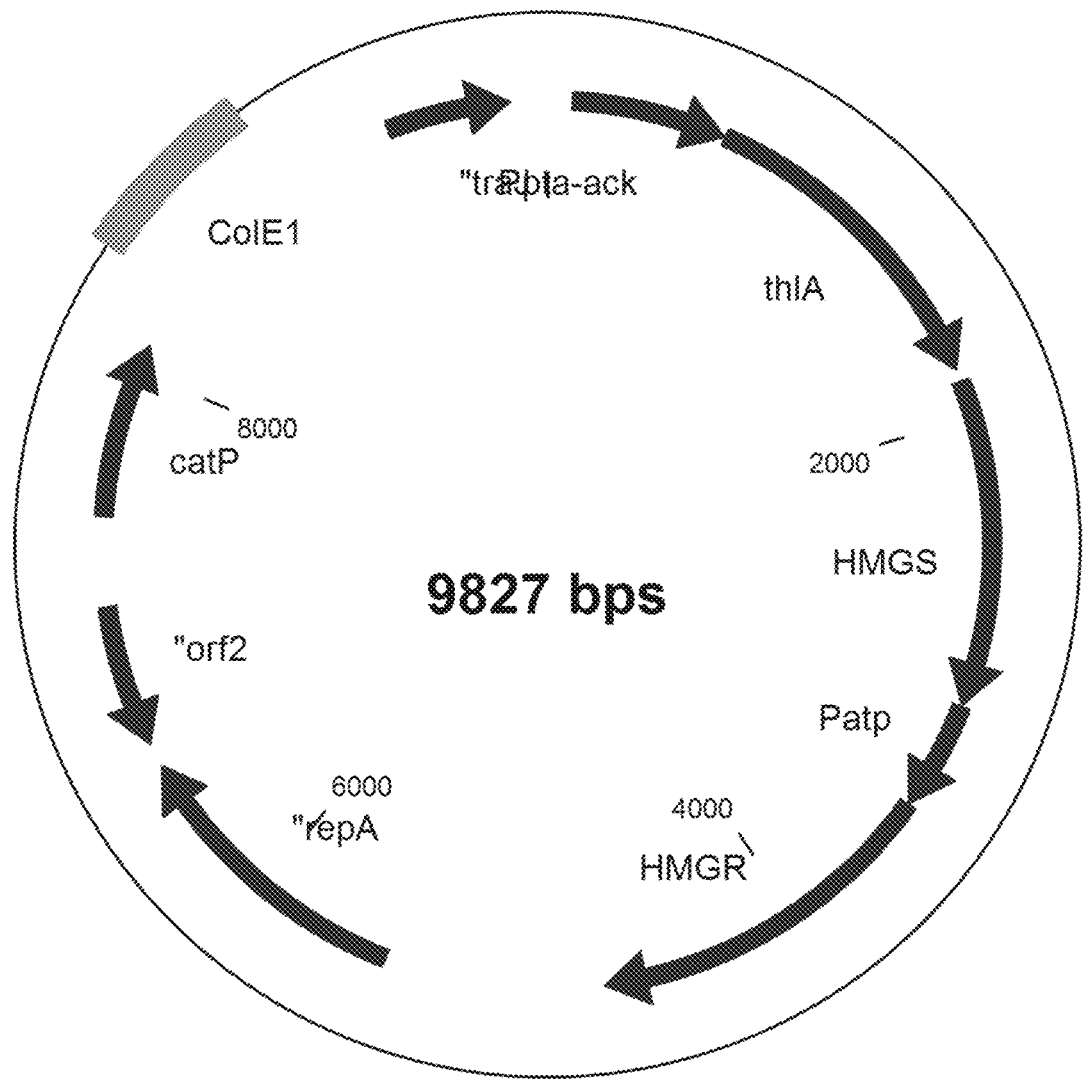
FIG. 9—Mevalonate expression plasmid pMTL8215-Pptaack-thlA-HMGS-Patp-HMGR

Availability and balance of precursors DMAPP (Dimethylallyl diphosphate) and IPP (Isopentenyl diphosphate) is crucial for production of terpenes. While the DXS pathway synthesizes both IPP and DMAPP equally, in the mevalonate pathway the only product is IPP. Production of isoprene requires only the precursor DMAPP to be present in conjunction with an isoprene synthase, while for production of higher terpenes and terpenoids, it is required to have equal amounts of IPP and DMAPP available to produce Geranyl-PP by a geranyltransferase.

cessfully introduced, plasmid mini prep DNA was carried out from transformants as described previously. PCR against the isolated plasmid using oligonucleotide pairs that target colE1 (colE1-F: SEQ ID NO: 65: CGTCA-GACCCCGTAGAAA and colE1-R: SEQ ID NO: 66: CTCTCCTGTTCCGACCCT), ermB (ermB-F: SEQ ID NO: 106: TTTGTAATTAAGAAGGAG and ermB-R: SEQ ID NO: 107:

GTAGAATCCTTCTTCAAC) and idi (Idi-Cbei-SacI-F: SEQ ID NO: 26: GTGAGCTCGAAAGGGGAAAT-TAAATG and Idi-Cbei-KpnI-R (SEQ ID NO: 27: ATGGTACCCCAAATCTTTATTTAGACG) confirmed transformation success (FIG. 8). Similarly, genomic DNA from these transformants were extracted, and the resulting 16s rRNA amplicon using oligonucleotides fD1 and rP2 (see above) confirmed 99.9% identity against the 16S rRNA gene of *C. autoethanogenum* (Y18178, GI:7271109).

Figure 14:
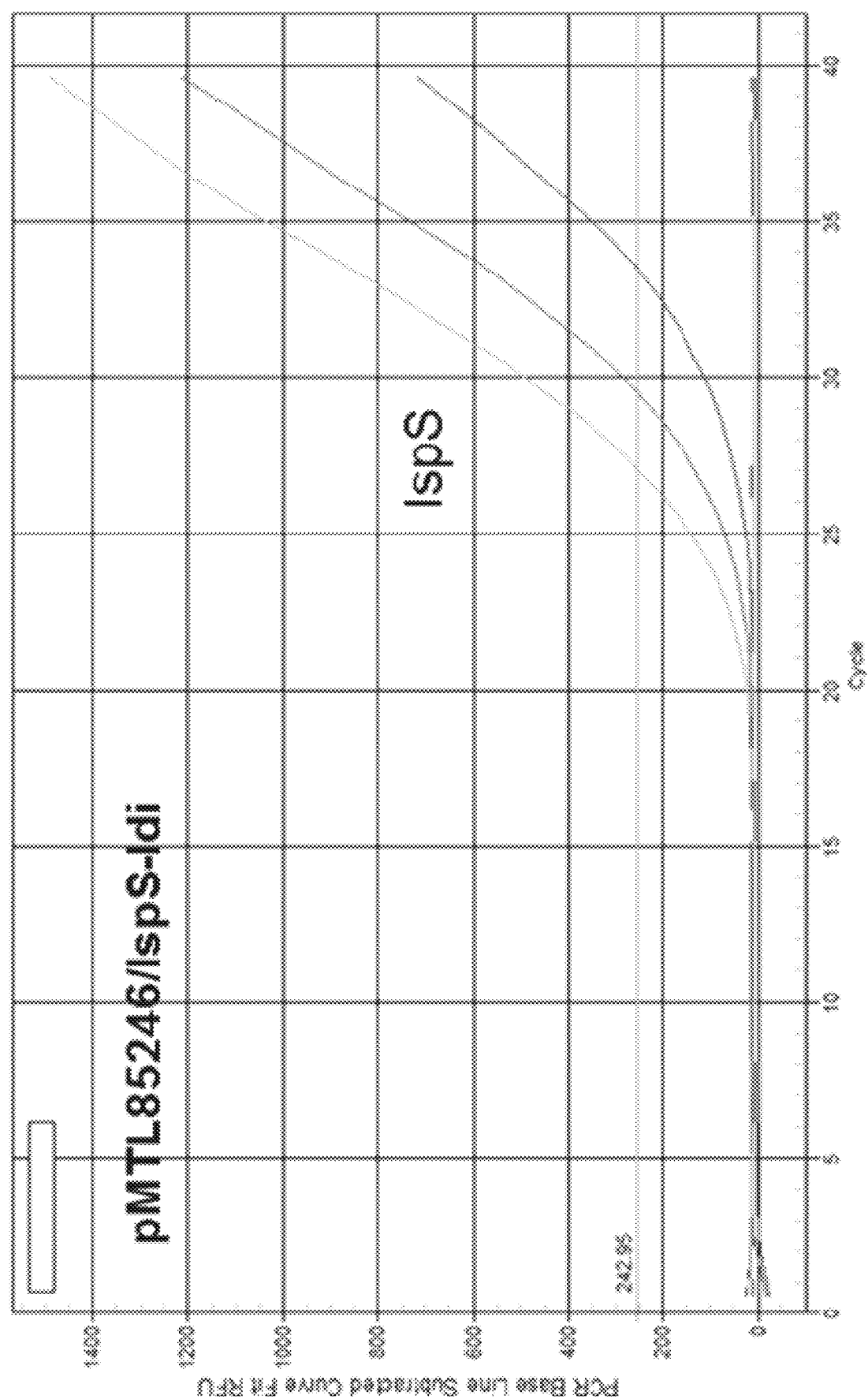

Successful confirmation of gene expression was carried out as described above using a oligonucleotide pair against Isopentenyl-diphosphate delta-isomerase gene idi (idi-F, SEQ ID NO: 71: ATA CGT GCT GTA GTC ATC CAA GAT A and idiR, SEQ ID NO: 72: TCT TCA AGT TCA CAT GTA AAA CCC A) and a sample from a serum bottle growth experiment with *C. autoethanogenum* carrying plasmid pMTL 85146-ispS-idi. A signal for the isoprene synthase gene ispS was also observed (FIG. 14).

Example 3—Overexpression of DXS Pathway

To improve flow through the DXS pathway, genes of the pathway were overexpressed. The initial step of the pathway, converting pyruvate and D-glyceraldehyde-3-phosphate (G3P) into deoxyxylulose 5-phosphate (DXP/DXPS/DOXP), is catalyzed by an deoxyxylulose 5-phosphate synthase (DXS).

Figure 4:
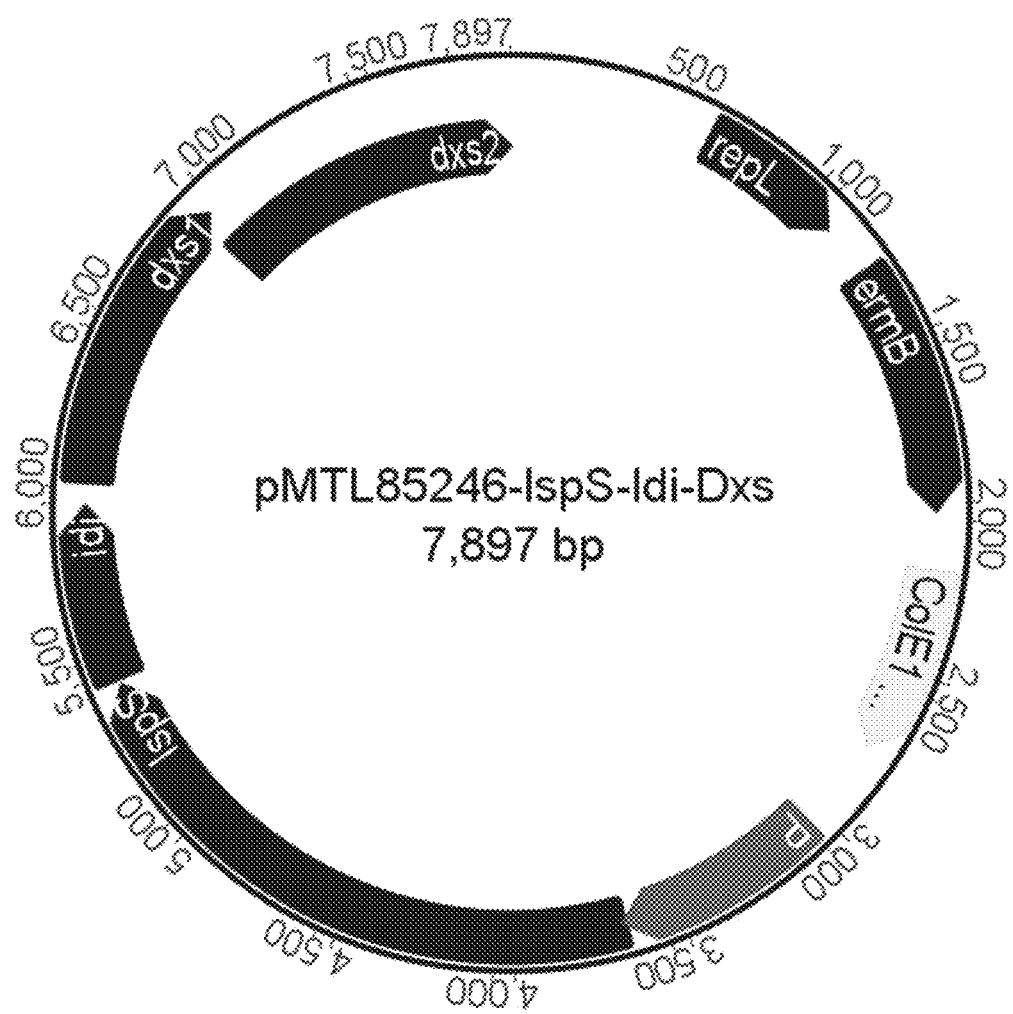
FIG. 4: Genetic map of plasmid pMTL 85246-ispS-idi-dxs
Figure 5:
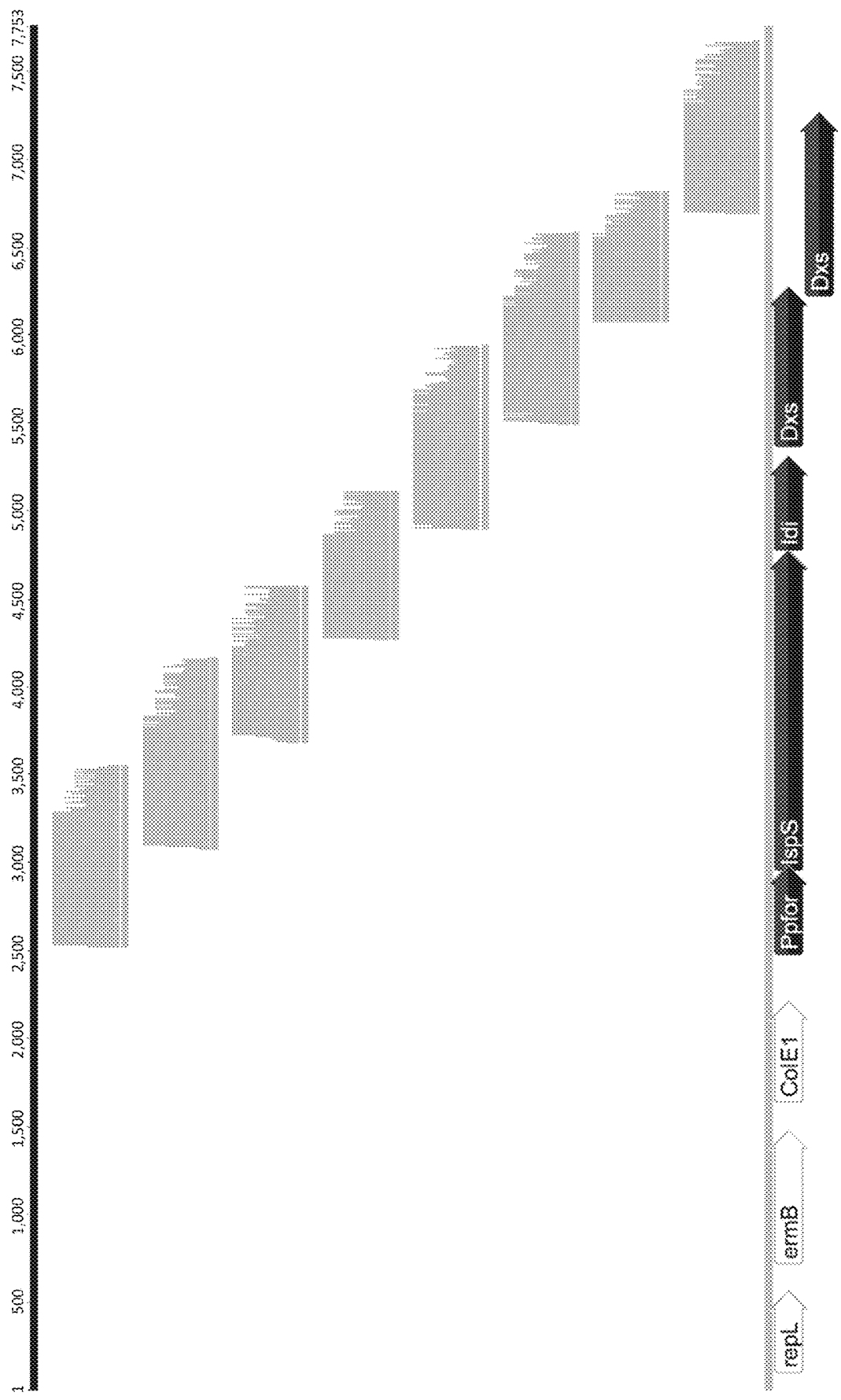
FIG. 5: Sequencing results for plasmid pMTL 85246-ispS-idi-dxs

Construction of DXS Overexpression Expression Plasmid:

The dxs gene of *C. autoethanogenum* was amplified from genomic DNA with oligonucleotides Dxs-SalI-F (SEQ ID NO: 29: GCAGTCGACTTTATTAAAGGGATAGATAA) and Dxs-XhoI-R (SEQ ID NO: 30: TGCTCGAGT-TAAAATATATGACTTACCTCTG) as described for other genes above. The amplified gene was then cloned into plasmid pMTL85246-ispS-idi with SalI and XhoI to produce plasmid pMTL85246-ispS-idi-dxs (SEQ ID NO: 31 and FIG. 4). DNA sequencing using oligonucleotides given in Table 3 confirmed successful cloning of ispS, idi, and dxs without mutations (FIG. 5). The ispS and idi genes are as described in example 1 and 2 respectively.

TABLE 3

Oligonucleotides for sequencing

| Oligonucleotide Name | DNA Sequence (5' to 3') | SEQ ID NO: |
|---|---|---|
| M13R | CAGGAAACAGCTATGAC | 32 |
| Isoprene-seq1 | GTTATTCAAGCTACACCTTT | 33 |
| Isoprene-seq2 | GATTGGTAAAGAATTAGCTG | 34 |
| Isoprene-seq3 | TCAAGAAGCTAAGTGGCT | 35 |
| Isoprene-seq4 | CTCACCGTAAAGGAACA | 36 |
| Isoprene-seq5 | GCTAGCTAGAGAAATTAGAA | 37 |
| Isoprene-seq6 | GGAATGGCAAAATATCTTGA | 38 |
| Isoprene-seq7 | GAAACACATCAGGGAATATT | 39 |

Transformation and expression in *C. autoethanogenum*

Figure 15:
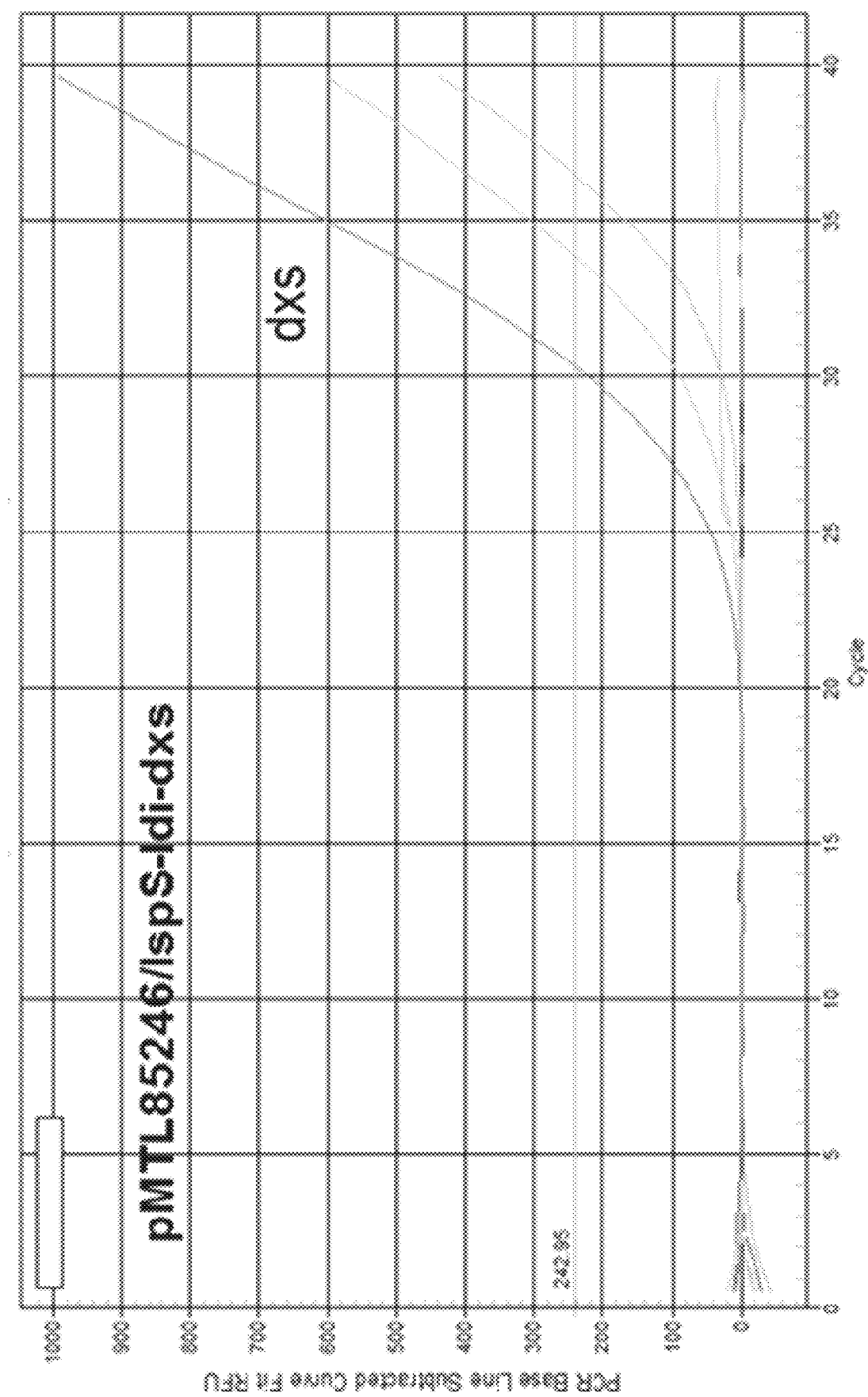

Transformation and expression in *C. autoethanogenum* was carried out as described for plasmid pMTL 85146-ispS. After successful transformation, a growth experiment was carried out in 50 mL 50 mL serum bottles and PETC media (Table 1) with 30 psi steel mill waste gas (collected from New Zealand Steel site in Glenbrook, NZ; composition: 44% CO, 32% N2, 22% $CO_2$, 2% $H_2$) as sole energy and carbon source. Confirmation of gene expression was carried out as described above from a sample collected at $OD_{600\,nm}$=0.75. Oligonucleotide pair dxs-F (SEQ ID NO: 73: ACAAAGTATCTAAGACAGGAGGTCA) and dxs-R (SEQ ID NO: 74: GATGTCCCACATCCCATATAAGTTT) was used to measure expression of gene dxs in both wild-type strain and strain carrying plasmid pMTL 85146-ispS-idi-dxs. mRNA levels in the strain carrying the plasmid were found to be over 3 times increased compared to the wild-type (FIG. 15). Biomass was normalized before RNA extraction.

Example 4—Introduction and Expression of Mevalonate Pathway

Figure 7:
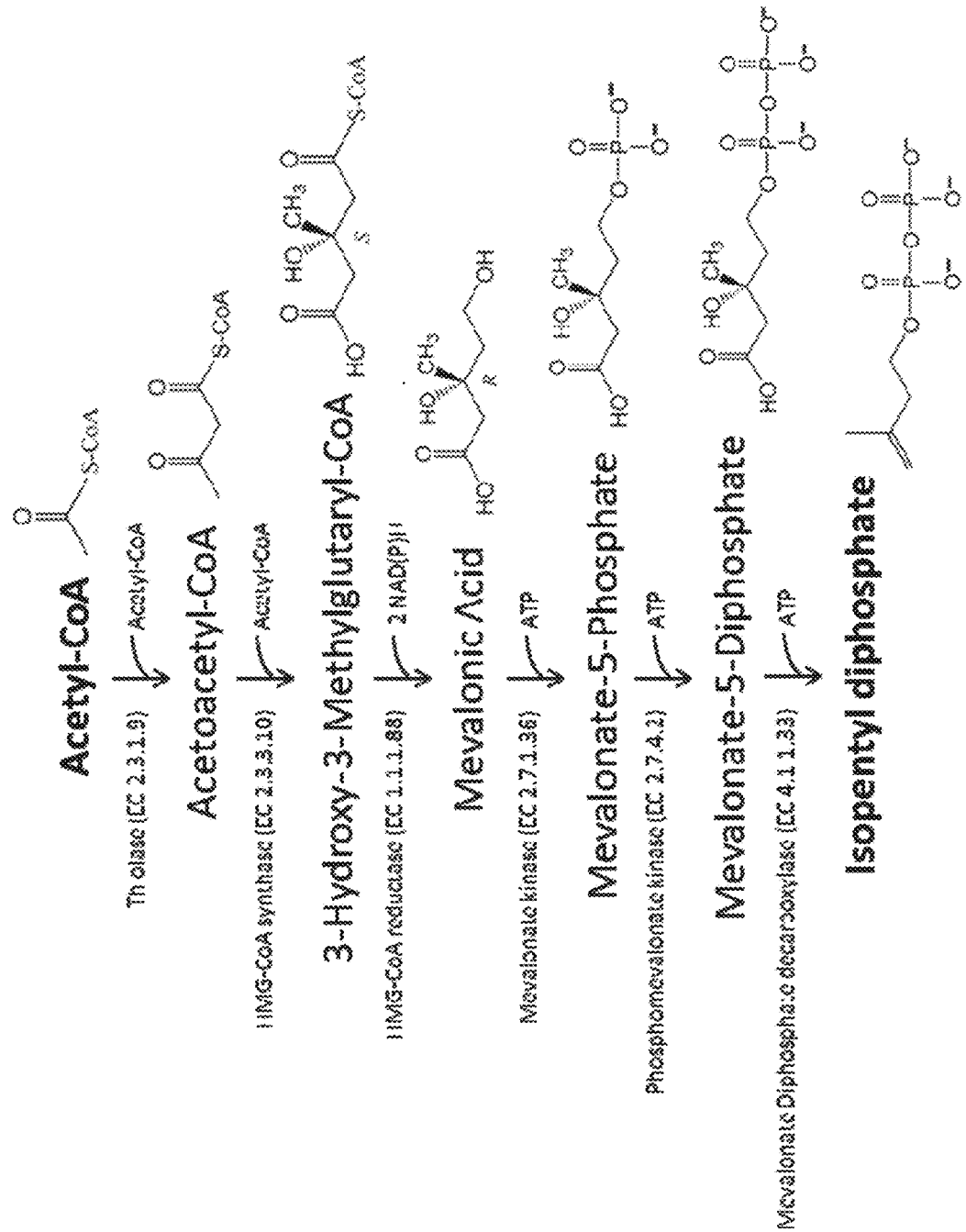
FIG. 7: Mevalonate pathway

The first step of the mevalonate pathway (FIG. 7) is catalyzed by a thiolase that converts two molecules of acetyl-CoA into acetoacetyl-CoA (and HS-CoA). This enzyme has been successfully expressed in carboxydotrophic acetogens *Clostridium autoethanogenum* and *C. ljungdahlii* by the same inventors (US patent 2011/0236941). Constructs for the remaining genes of the mevalonate pathway have been designed.

Construction of Mevalonate Expression Plasmid:

Standard recombinant DNA and molecular cloning techniques were used (Sambrook, J., and Russell, D., Molecular cloning: *A Laboratory Manual* 3rd Ed., Cold Spring Harbour Lab Press, Cold Spring Harbour, N Y, 2001). The three genes required for mevalonate synthesis via the upper part of the mevalonate pathway, i.e., thiolase (thlA/vraB), HMG-CoA synthase (HMGS) and HMG-CoA reductase (HMGR), were codon-optimised as an operon ($P_{ptaack}$-thlA/vraB-HMGS-$P_{atp}$-HMGR).

The Phosphotransacetylase/Acetate kinase operon promoter ($P_{pta-ack}$) of *C. autoethanogenum* (SEQ ID NO: 61) was used for expression of the thiolase and HMG-CoA synthase while a promoter region of the ATP synthase ($P_{atp}$) of *C. autoethanogenum* was used for expression of the HMG-CoA reductase. Two variants of thiolase, thlA from *Clostridium acetobutylicum* and vraB from *Staphylococcus aureus*, were synthesised and flanked by NdeI and EcoRI restriction sites for further sub-cloning. Both HMG-CoA synthase (HMGS) and HMG-CoA reductase (HMGR) were synthesised from *Staphylococcus aureus* and flanked by EcoRI-SacI and KpnI-XbaI restriction sites respectively for further sub-cloning. All optimized DNA sequences used are given in Table 4.

TABLE 4

Sequences of mevalonate expression plasmid

| Description | Source | SEQ ID NO: |
|---|---|---|
| Thiolase (thlA) | *Clostridium acetobutylicum* ATCC 824; NC_003030.1; GI: 1119056 | 40 |
| Acetyl-CoA c-acetyltransferase (vraB) | *Staphylococcus aureus* subsp. *aureus* Mu50; NC_002758.2; region: 652965 . . . 654104; including GI: 15923566 | 41 |
| 3-hydroxy-3-methylglutaryl-CoA synthase (HMGS) | *Staphylococcus aureus* subsp. *aureus* Mu50; NC_002758.2; region: 2689180 . . . 2690346; including GI: 15925536 | 42 |
| Hydroxy methyl-glutaryl-CoA reductase (HMGR) | *Staphylococcus aureus* subsp. *aureus* Mu50; NC_002758.2; region: complement(2687648 . . . 2688925); including GI: 15925535 | 43 |
| Phosphotrans-acetylase-acetate kinase operon ($P_{pta-ack}$) | *Clostridium autoethanogenum* DSM10061 | 44 |
| ATP synthase promoter ($P_{atp}$) | *Clostridium autoethanogenum* DSM10061 | 45 |

The ATP synthase promoter ($P_{atp}$) together with the hydroxymethylglutaryl-CoA reductase (HMGR) was amplified using oligonucleotides pUC57-F (SEQ ID NO: 46: AGCAGATTGTACTGAGAGTGC) and pUC57-R (SEQ ID NO: 47: ACAGCTATGACCATGATTACG) and pUC57-Patp-HMGR as a template. The 2033 bp amplified fragment was digested with SacI and XbaI and ligated into the *E. coli-Clostridium* shuttle vector pMTL 82151 (FJ7976; Nigel Minton, University of Nottingham, UK; Heap et al., 2009, *J Microbiol Methods*. 78: 79-85) resulting in plasmid pMTL 82151-Patp-HMGR (SEQ ID NO: 76).

3-hydroxy-3-methylglutaryl-CoA synthase (HMGS) was amplified from the codon-synthesised plasmid pGH-seq3.2 using oligonucleotides EcoRI-HMGS F (SEQ ID NO: 77: AGCCGTGAATTCGAGGCTTTTACTAAAAACA) and EcoRI-HMGS R (SEQ ID NO: 78: AGGCGTCTAGATGTTCGTCTCTACAAATAATT). The 1391 bp amplified fragment was digested with SacI and EcoRI and ligated into the previously created plasmid pMTL 82151-Patp-HMGR to give pMTL 82151-HMGS-Patp-HMGR (SEQ ID NO: 79). The created plasmid pMTL 82151-HMGS-Patp-HMGR (SEQ ID NO: 79) and the 1768 bp codon-optimised operon of $P_{ptaack}$-th1A/vraB were both cut with NotI and EcoRI. A ligation was performed and subsequently transformed into *E. coli* XL1-Blue MRF' Kan resulting in plasmid pMTL8215-Pptaack-thlA/vraB-HMGS-Patp-HMGR (SEQ ID NO: 50).

The five genes required for synthesis of terpenoid key intermediates from mevalonate via the bottom part of the mevalonate pathway, i.e., mevalonate kinase (MK), phosphomevalonate kinase (PMK), mevalonate diphosphate decarboxylase (PMD), isopentenyl-diphosphate delta-isomerase (idi) and isoprene synthase (ispS) were codon-optimised by ATG:Biosynthetics GmbH (Merzhausen, Germany). Mevalonate kinase (MK), phosphomevalonate kinase (PMK) and mevalonate diphosphate decarboxylase (PMD) were obtained from *Staphylococcus aureus*.

The promoter region of the RNF Complex (Prof) of *C. autoethanogenum* (SEQ ID NO: 62) was used for expression of mevalonate kinase (MK), phosphomevalonate kinase (PMK) and mevalonate diphosphate decarboxylase (PMD), while the promoter region of the Pyruvate:ferredoxin oxidoreductase (Pfor) of *C. autoethanogenum* (SEQ ID NO: 22) was used for expression of isopentenyl-diphosphate delta-isomerase (idi) and isoprene synthase (ispS). All DNA sequences used are given in Table 5. The codon-optimised Prnf-MK was amplified from the synthesised plasmid pGH-Prnf-MK-PMK-PMD with oligonucleotides NotI-XbaI-Prnf-MK F (SEQ ID NO: 80: ATGCGCGGCCGCTAGGTCTAGAATATCGATACAGA-TAAAAAAATATATAATACA G) and SalI-Prnf-MK R (SEQ ID NO: 81: TGGTTCTGTAACAGCGTATT-CACCTGC). The amplified gene was then cloned into plasmid pMTL83145 (SEQ ID NO: 49) with NotI and SalI to produce plasmid pMTL8314-Prnf-MK (SEQ ID NO: 82). This resulting plasmid and the 2165 bp codon optimised fragment PMK-PMD was subsequently digested with SalI and HindIII. A ligation was performed resulting in plasmid pMTL 8314-Prnf-MK-PMK-PMD (SEQ ID NO: 83).

Figure 10:
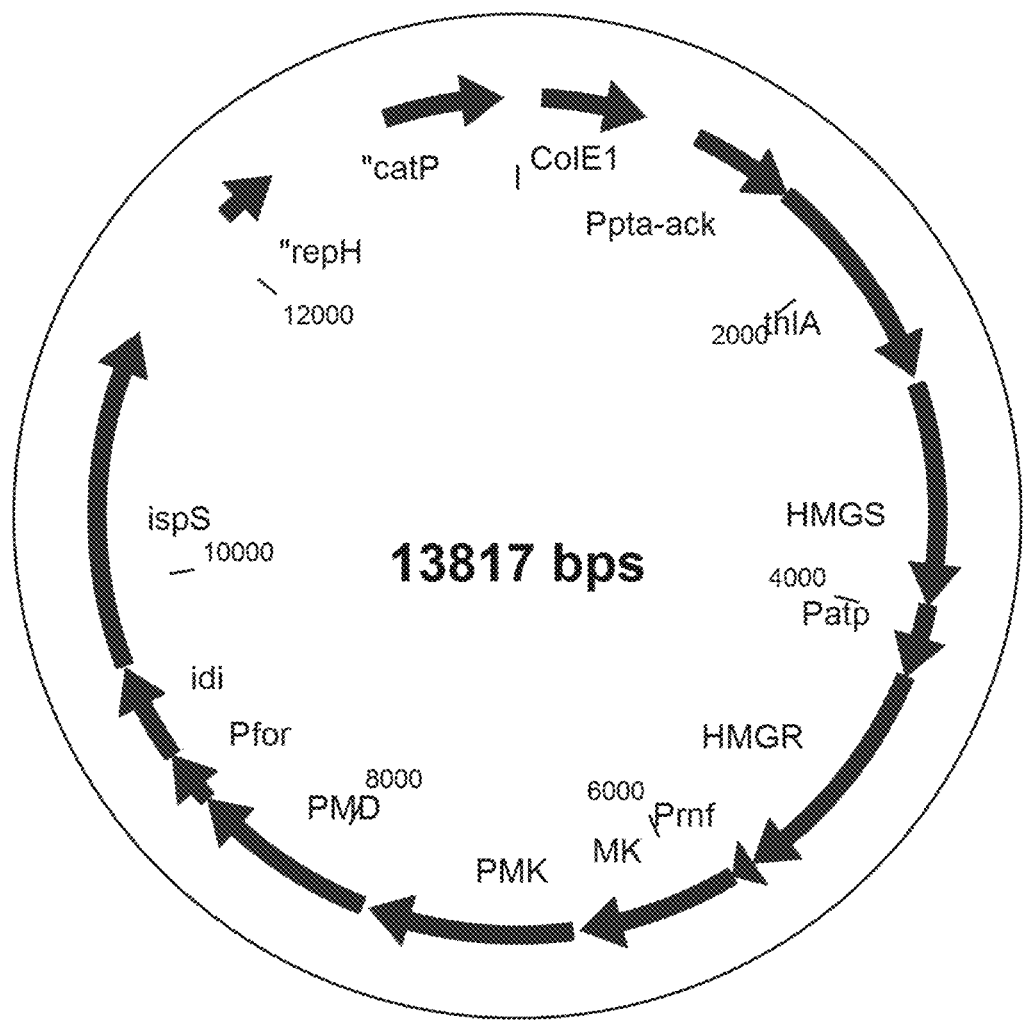
FIG. 10—Isoprene expression plasmid pMTL 8314-Pptaack-th1A-HMGS-Patp-HMGR-Prnf-MK-PMK-PMD-Pfor-idi-ispS FIG. 11—Farnesene expression plasmid pMTL8314-Pptaack-th1A-HMGS-Patp-HMGR-Prnf-MK-PMK-PMD-Pfor-idi-ispA-FS FIG. 12—Genetic map of plasmid pMTL 85246-ispS-idi-dxs FIG. 13—Amplification chart for gene expression experiment with *C. autoethanogenum* carrying plasmid pMTL 85146-ispS FIG. 14—Amplification chart for gene expression experiment with *C. autoethanogenum* carrying plasmid pMTL 85246-ispS-idi FIG. 15—Amplification chart for gene expression experiment with *C. autoethanogenum* carrying plasmid pMTL 85246-ispS-idi-dxs FIG. 16—PCR check for the presence of the plasmid pMTL8314Prnf-MK-PMK-PMD-Pfor-idi-ispA-FS. Expected band size 1584 bp. The DNA marker Fermentas 1 kb DNA ladder.
Figure 11:
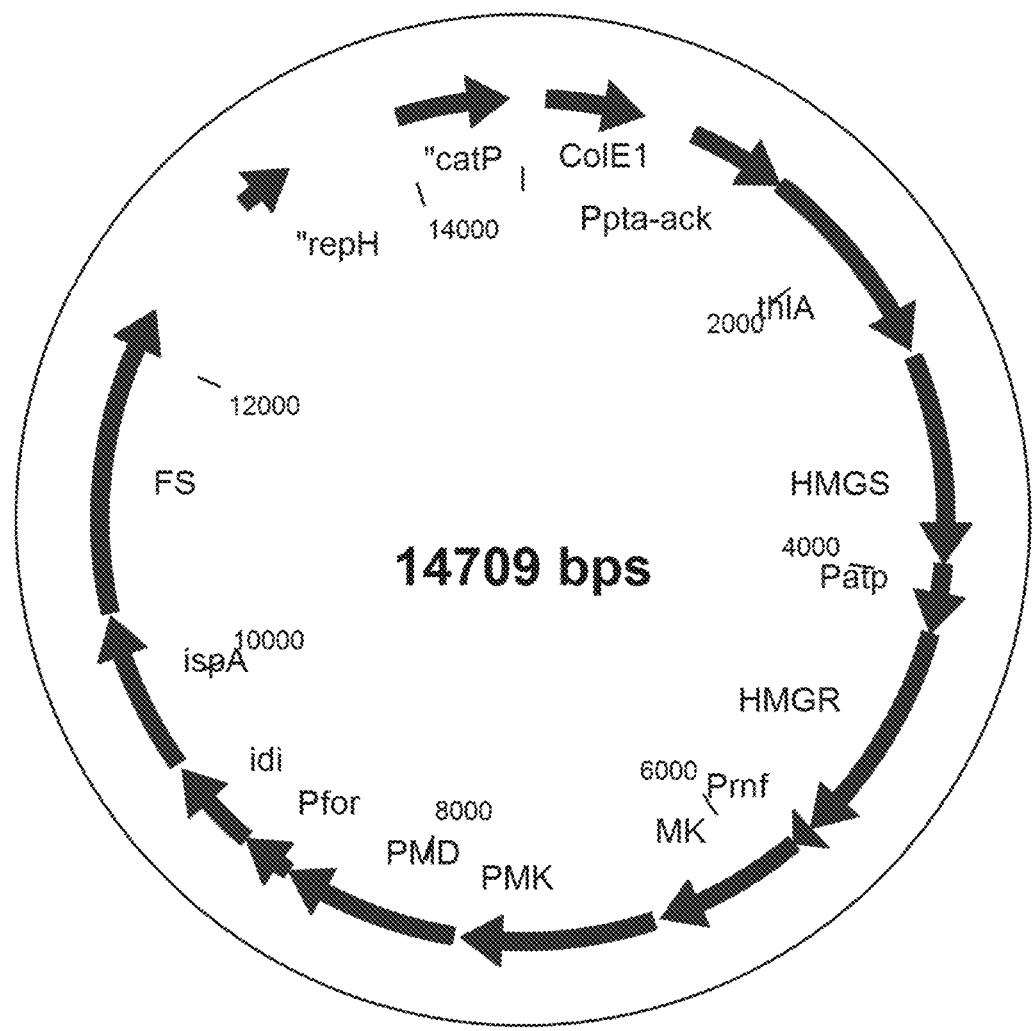
Figure 12:
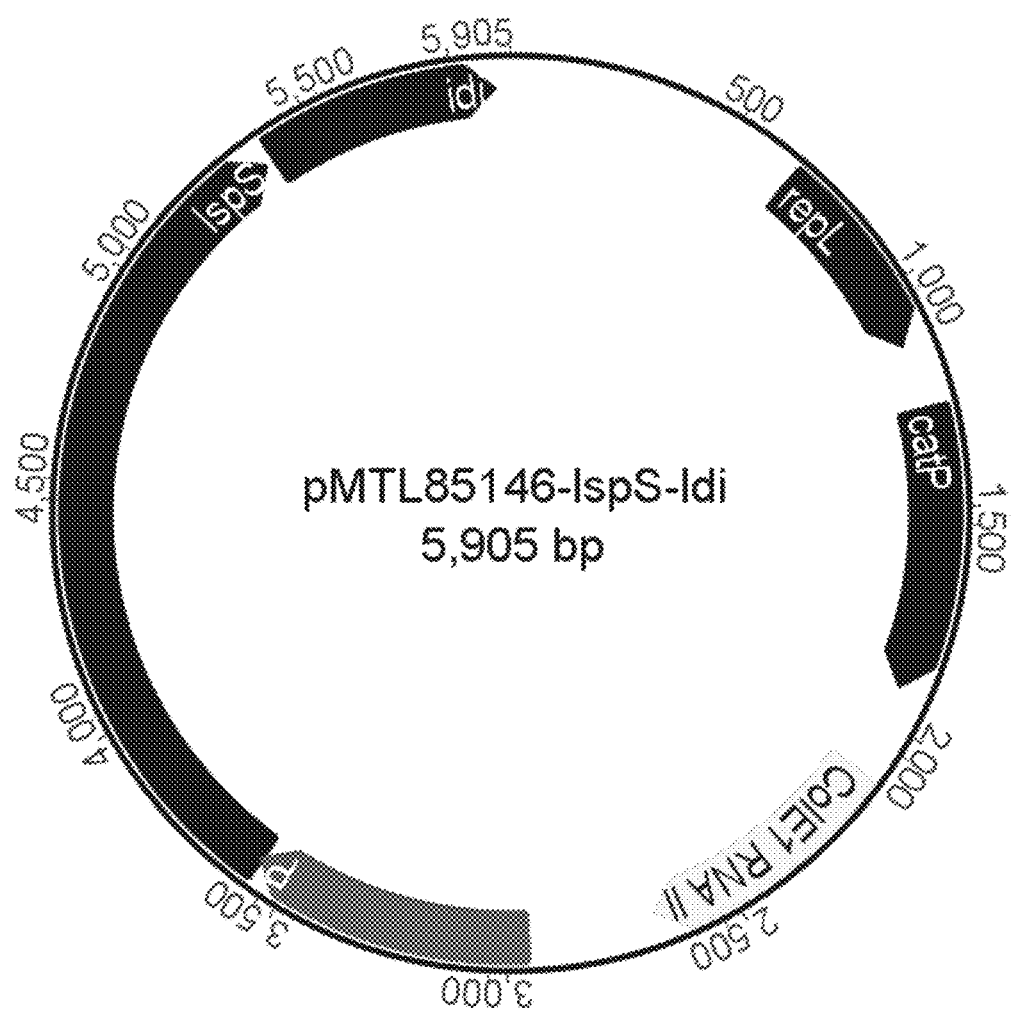
Figure 13:
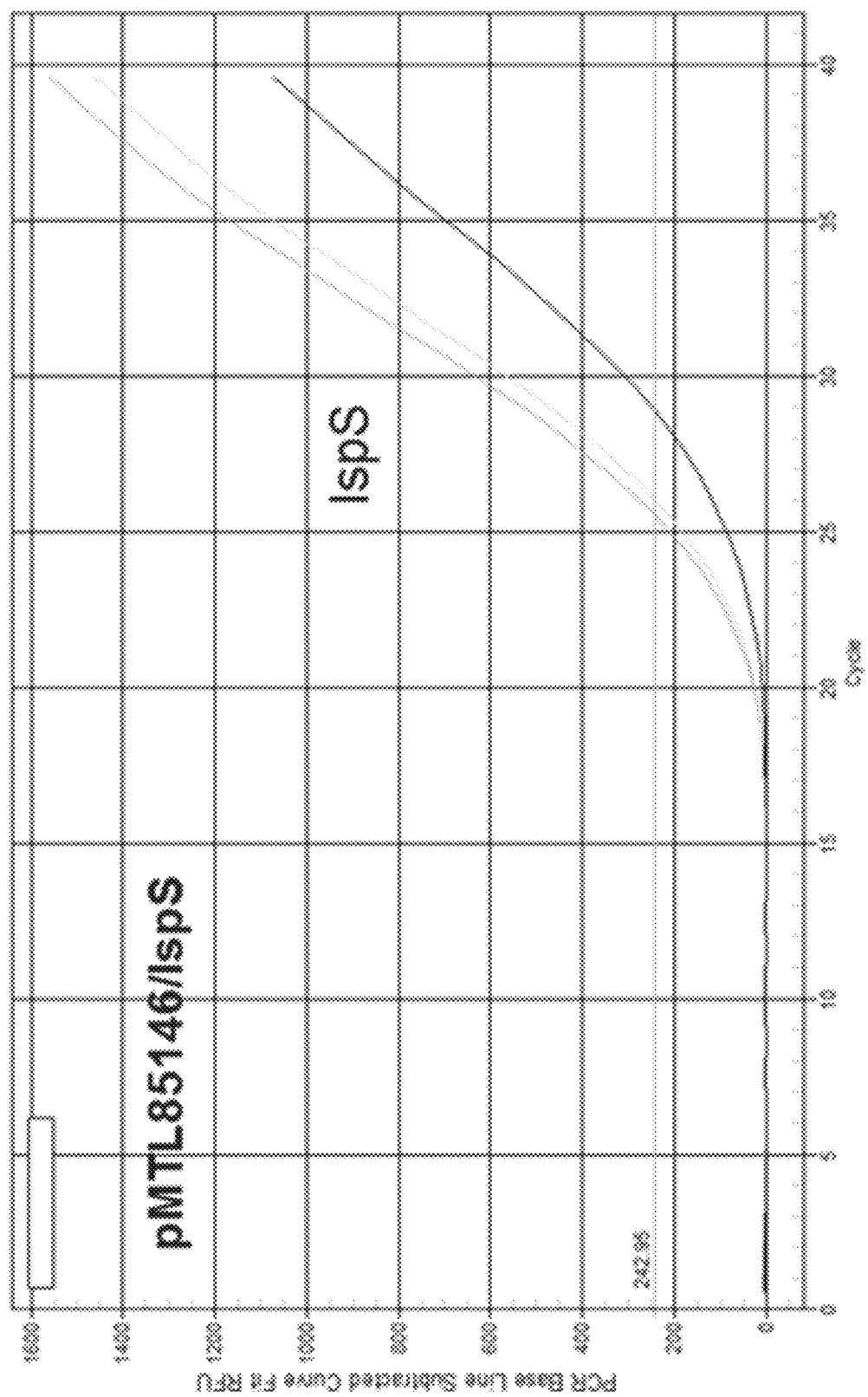

The isoprene expression plasmid without the mevalonate pathway was created by ligating the isoprene synthase (ispS) flanked by restriction sites AgeI and NheI to the previously created farnesene plasmid, pMTL 8314-Prnf-MK-PMK-PMD-Pfor-idi-ispA-FS (SEQ ID NO:91) to result in plasmid pMTL8314-Prnf-MK-PMK-PMD-Pfor-idi-ispS (SEQ ID NO:84). The final isoprene expression plasmid, pMTL 8314-Pptaack-th1A-HMGS-Patp-HMGR-Prnf-MK-PMK-PMD-Pfor-idi-ispS (SEQ ID NO: 58, FIG. 10) is created by ligating the 4630 bp fragment of Pptaack-thlA-HMGS-Patp-HMGR from pMTL 8215-Pptaack-thlA-HMGS-Patp-HMGR (SEQ ID NO: 50) with pMTL 8314-Prnf-MK-PMK-PMD-Pfor-idi-ispS (SEQ ID NO: 84) using restriction sites NotI and XbaI.

TABLE 5

Sequences of isoprene expression plasmid from mevalonate pathway

| Description | Source | SEQ ID NO: |
|---|---|---|
| Mevalonate kinase (MK) | *Staphylococcus aureus* subsp. *aureus* Mu50; NC_002758.2; region: 665080 . . . 665919; including GI: 15923580 | 51 |
| Phosphomevalonate kinase (PMK) | *Staphylococcus aureus* subsp. *aureus* Mu50; NC_002758.2; region: 666920 . . . 667996; including GI: 15923582 | 52 |
| Mevalonate diphosphate decarboxylase (PMD) | *Staphylococcus aureus* subsp. *aureus* Mu50; NC_002758.2; region: 665924 . . . 666907; including GI: 15923581 | 53 |
| Isoprene synthase (isIS) | isoprene synthase of *Poplar tremuloides* (AAQ16588.1; GI: 33358229) | 21 |
| Isopentenyl-diphosphate delta-isomerase (idi) | *Clostridium beijerinckii* NCIMB 8052; YP_001310174.1; region: complement(3597793 . . . 3598308); including GI: 150017920 | 54 |
| RNF Complex promoter ($P_{rnf}$) | *Clostridium autoethanogenum* DSM10061 | 55 |

Example 5—Introduction of Farnesene Synthase in *C. autoethanogenum* for Production of Farnesene from CO Via the Mevalonate Pathway Instead of producing isoprene directly from terpenoid key intermediates IPP and DMAPP then using this to synthesise longer chain terpenes, it is also possible to synthesise longer chain terpenes, such as C10 Monoterpenoids or C15 Sesquiterpenoids, directly via a geranyltransferase (see Table 6). From C15 Sesquiterpenoid building block farnesyl-PP it is possible to produce farnesene, which, similarly to ethanol, can be used as a transportation fuel.

Construction of Farnesene Expression Plasmid

The two genes required for farnesene synthesis from IPP and DMAPP via the mevalonate pathway, i.e., geranyltranstransferase (ispA) and alpha-farnesene synthase (FS) were codon-optimised. Geranyltranstransferase (ispA) was obtained from *Escherichia coli* str. K-12 substr. MG1655 and alpha-farnesene synthase (FS) was obtained from *Malus x domestica*. All DNA sequences used are given in Table 6. The codon-optimised idi was amplified from the synthesised plasmid pMTL83245-Pfor-FS-idi (SEQ ID NO: 85) with via the mevalonate pathways idi_F (SEQ ID NO: 86: AGGCACTCGAGATGGCAGAGTATATAATAGCAGTAG) and idi R2 (SEQ ID NO:87: AGGCGCAAGCTTGGCGCACCGGTTTATT-TAAATATCTTATTTTCAGC). The amplified gene was then cloned into plasmid pMTL83245-Pfor with XhoI and HindIII to produce plasmid pMTL83245-Pfor-idi (SEQ ID NO: 88). This resulting plasmid and the 1754 bp codon optimised fragment of farnesene synthase (FS) was subsequently digested with HindIII and NheI. A ligation was performed resulting in plasmid pMTL83245-Pfor-idi-FS (SEQ ID NO: 89). The 946 bp fragment of ispA and pMTL83245-Pfor-idi-FS was subsequently digested with AgeI and HindIII and ligated to create the resulting plasmid pMTL83245-Pfor-idi-ispA-FS (SEQ ID NO: 90). The farnesene expression plasmid without the upper mevalonate pathway was created by ligating the 2516 bp fragment of Pfor-idi-ispA-FS from pMTL83245-Pfor-idi-ispA-FS to pMTL 8314-Prnf-MK-PMK-PMD to result in plasmid pMTL 8314-Prnf-MK-PMK-PMD-Pfor-idi-ispA-FS (SEQ ID NO: 91). The final farnesene expression plasmid pMTL83145-th1A-HMGS-Patp-HMGR-Prnf-MK-PMK- PMD-Pfor-idi-ispA-FS (SEQ ID NO: 59 and FIG. 18) is created by ligating the 4630 bp fragment of Pptaack-thlA-HMGS-Patp-HMGR from pMTL8215-Pptaack-thlA-HMGS-Patp-HMGR (SEQ ID NO: 50) with pMTL 8314-Prnf-MK-PMK-PMD-Pfor-idi-ispA-FS (SEQ ID NO: 91) using restriction sites NotI and XbaI.

TABLE 6

Sequences of farnesene expression plasmid from mevalonate pathway

| Description | Source | SEQ ID NO: |
|---|---|---|
| Geranyltransferase (ispA) | *Escherichia coli* str. K-12 substr. MG1655; NC_000913.2; region: complement(439426..440325); including GI: 16128406 | 56 |
| Alpha-farnesene synthase (FS) | *Malus x domestica*; AY787633.1; GI: 60418690 | 57 |

Transformation into *C. autoethanogenum*

Transformation and expression in *C. autoethanogenum* was carried out as described in example 1.

Confirmation of Successful Transformation

Figure 16:
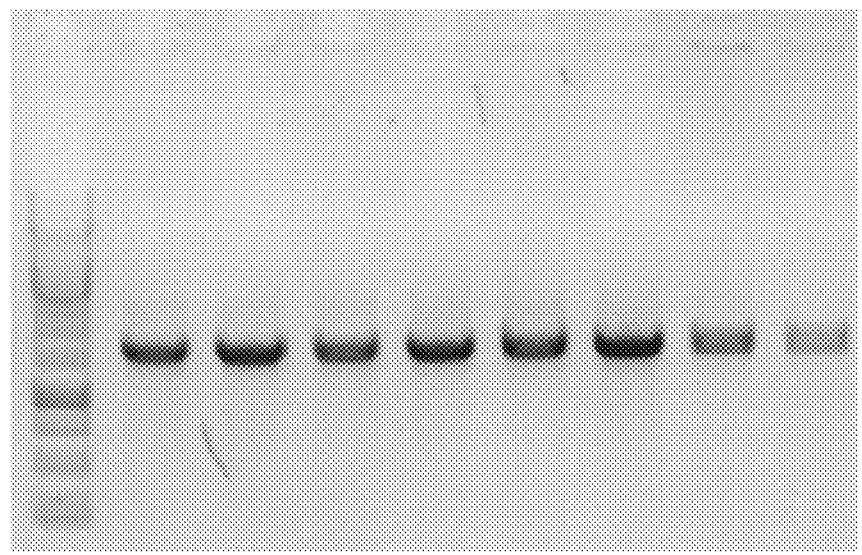

The presence of pMTL8314-Prnf-MK-PMK-PMD-Pfor-idi-ispA-FS (SEQ ID NO: 59) was confirmed by colony PCR using oligonucleotides repHF (SEQ ID NO: 92:AAGAAGGGCGTATATGAAAACTTGT) and catR (SEQ ID NO: 93: TTCGTTTA-CAAAACGGCAAATGTGA) which selectively amplifies a portion of the garm +ve perplicon and most of the cat gene on the pMTL83 lxxx series plasmids. Yielding a band of 1584 bp (FIG. 16).

Expression of lower mevalonate pathway in *C. autoethanogenum*

Confirmation of expression of the lower mevalonate pathway genes Mevalonate kinase (MK SEQ ID NO: 51), Phosphomevalonate Kinase (PMK SEQ ID NO: 52), Mevalonate Diphosphate Decarboxylase (PMD SEQ ID NO: 53), Isopentyl-diphosphate Delta-isomerase (idi; SEQ ID NO: 54), Geranyltransferase (ispA; SEQ ID NO: 56) and Farnesene synthase (FS SEQ ID NO: 57) was done as described above in example 1. Using oligonucleotides listed in table 7.

TABLE 7

List of oligonucleotides used for the detection of expression of the genes in the lower mevalonate pathway carried on plasmid pMTL8314Pmf-MK-PMK-PMD-Pfor-idi-ispA-FS (SEQ ID NO: 91)

| Target | Oligonucleotide Name | DNA Sequence (5' to 3') | SEQ ID NO: |
|---|---|---|---|
| Mevalonate kinase | MK-RTPCR-F | GTGCTGGTAGAGGTGGTTCA | 94 |
|  | MK-RTPCR-R | CCAAGTATGTGCTGCACCAG | 95 |
| Phosphomevalonate Kinase | PMK-RTPCR-F | ATATCAGACCCACACGCAGC | 96 |
|  | PMK-RTPCR-R | AATGCTTCATTGCTATGTCACATG | 97 |
| Mevalonate Diphosphate Decarboxylase | PMD-RTPCR-F | GCAGAAGCAAAGGCAGCAAT | 98 |
|  | PMD-RTPCR-R | TTGATCCAAGATTTGTAGCATGC | 99 |
| Isopentyl-diphosphate Delta-isomerase | idi-RTPCR-F | GGACAAACACTTGTTGTAGTCACC | 100 |
|  | idi-RTPCR-R | TCAAGTTCGCAAGTAAATCCCA | 101 |
| Geranyltranstransferase | ispA-RTPCR-F | ACCAGCAATGGATGACGATG | 102 |
|  | ispA-RTPCR-R | AGTTTGTAAAGCGTCACCTGC | 103 |
| Farnesene synthase | FS-RTPCR-F | AAGCTAGTAGATGGTGGGCT | 104 |
|  | FS-RTPCR-R | AATGCTACACCTACTGCGCA | 105 |

Figure 18:
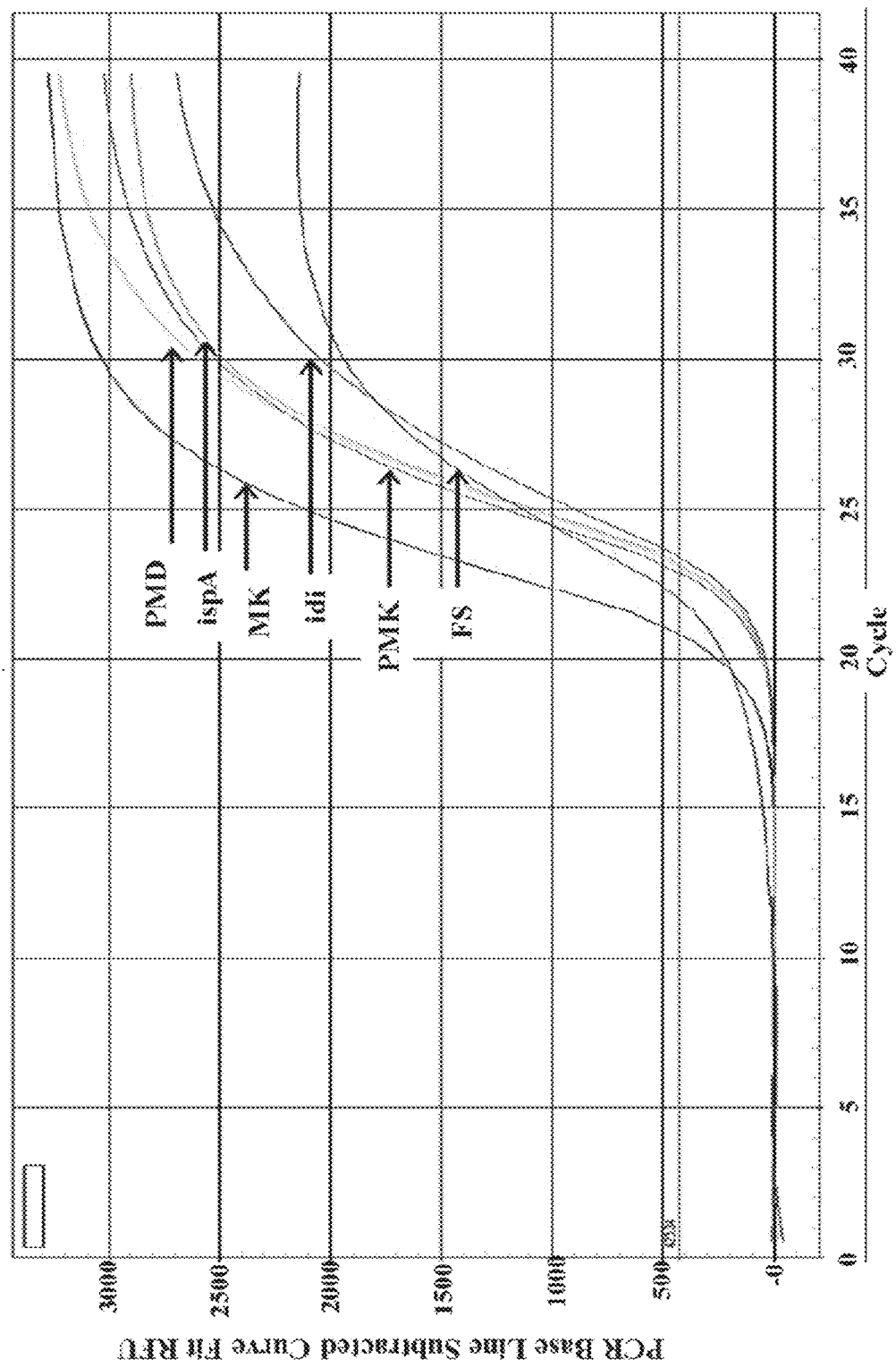
FIG. 18—RT-PRC data showing the expression of the genes Mevalonate kinase (MK SEQ ID NO: 51), Phosphomevalonate Kinase (PMK SEQ ID NO: 52), Mevalonate Diphosphate Decarboxylase (PMD SEQ ID NO: 53), Isopentyl-diphosphate Delta-isomerase (idi SEQ ID NO: 54), Geranyltranstransferase (ispA SEQ ID NO: 56) and Farnesene synthase (FS SEQ ID NO: 57).

Rt-PCR data confirming expression of all genes in the lower mevalonate pathway is shown in FIG. 18, this data is also summarised in Table 8.

TABLE 8

Average CT values for the genes genes Mevalonate kinase (MK SEQ ID NO: 51), Phosphomevalonate Kinase (PMK SEQ ID NO: 52), Mevalonate Diphosphate Decarboxylase (PMD SEQ ID NO: 53), Isopentyl-diphosphate Delta-isomerase (idi SEQ ID NO: 54), Geranyltranstransferase (ispA SEQ ID NO: 56) and Farnesene synthase (FS SEQ ID NO: 57). for two independent samples taken from the two starter cultures for the mevalonate feeding experiment (see below).

| Gene | Sample 1 (Ct Mean) | Sample 2 (Ct Mean) |
|---|---|---|
| MK | 21.9 | 20.82 |
| PMK | 23.64 | 22.81 |
| PMD | 24 | 22.83 |
| Idi | 24.23 | 27.54 |
| ispA | 23.92 | 23.22 |
| FS | 21.28 (single Ct) | 21.95 (single Ct) |
| HK (rho) | 31.5 | 28.88 |

Production of Alpha-Farnesene from Mevalonate

Figure 17:
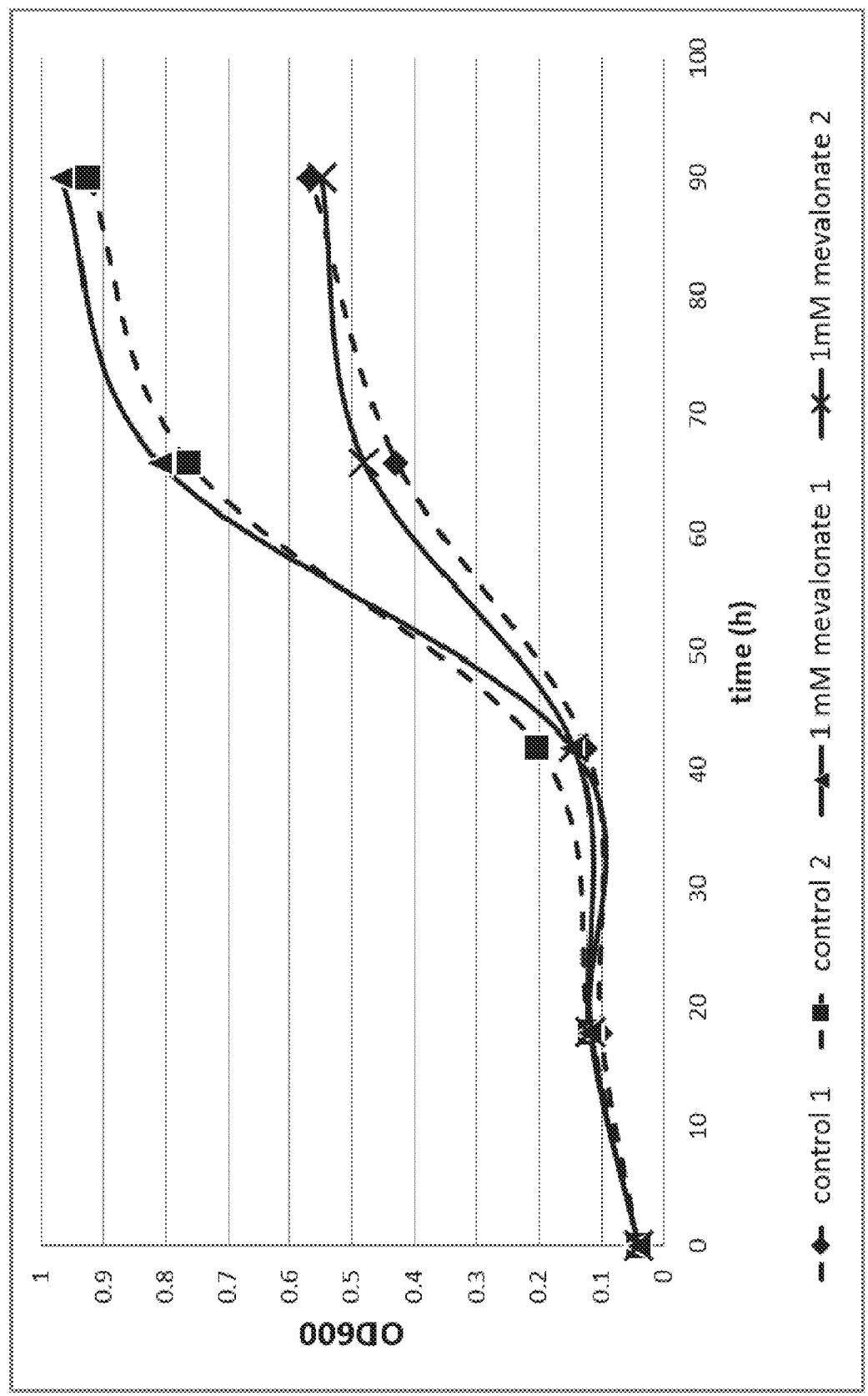
FIG. 17—Growth curve for transformed *C. autoethanogenum* carrying plasmid pMTL8314Prnf-MK-PMK-PMD-Pfor-idi-ispA-FS.
Figure 19:
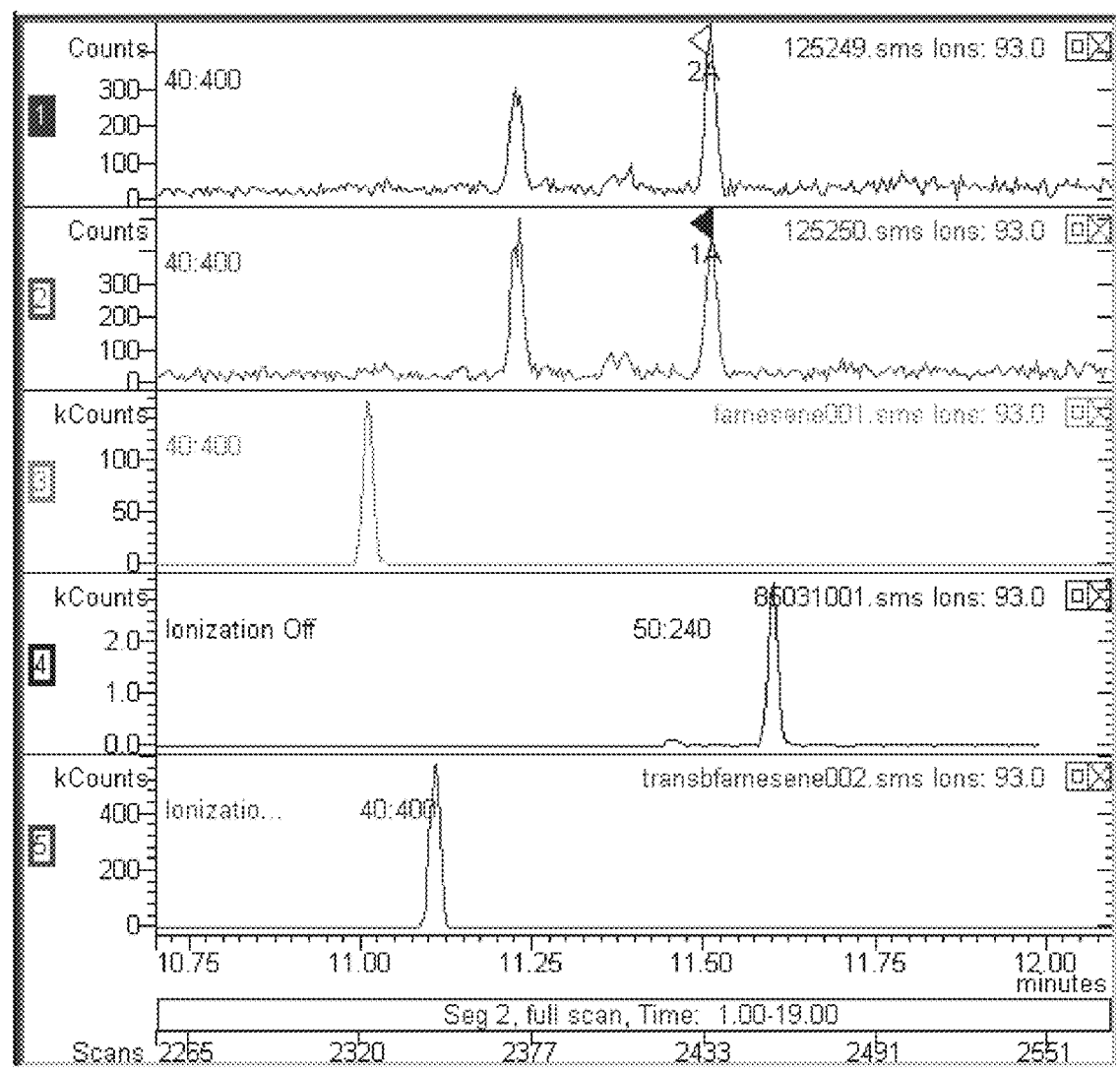
FIG. 19—GC-MS detection and conformation of the presence of farnesene in 1 mM mevalonate spiked cultures carrying pMTL8314Prnf-MK-PMK-PMD-Pfor-idi-ispA-FS. GC-MS chromatogram scanned for peaks containing ions with a mass of 93. Chromatogram 1 and 2 are transformed *C. autoethanogenum,* 3 is beta-farnesene standard run at the same time as the *C. autoethanogenum* samples. 4 is *E. coli* carrying the plasmids pMTL8314Prnf-MK-PMK-PMD-Pfor-idi-ispA-FS grown on M9 Glucose showing alpha-farnesene production and 5 is beta-farnesene standard run at the time of the *E. coli* samples. The difference in retention time between the *E. coli* and the *C. autoethanogenum* samples are due to minor changes to the instrument. However, the difference in retention time between the beta-farnesene standard and the produced alpha-farnesene are the exact same in both cases, which together with the match in mass spectra's confirm the production of alpha-farnesene in *C. autoethanogenum.*
Figure 20:
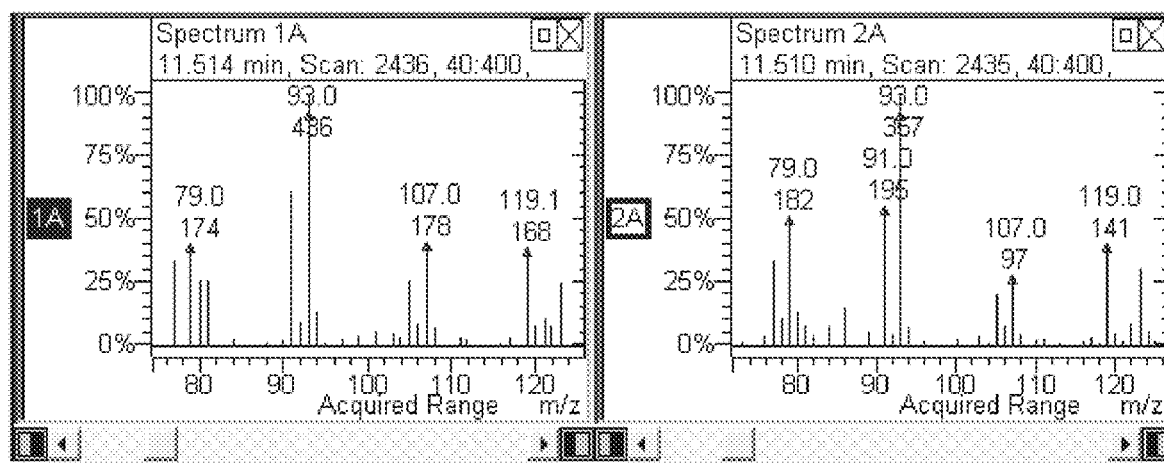
FIG. 20—MS spectrums for peaks labeled 1A and 2A in FIG. 19. The MS spectra's matches up with the NIST database spectra (FIG. 21) confirming the peak is alpha-farnesene.
Figure 21:
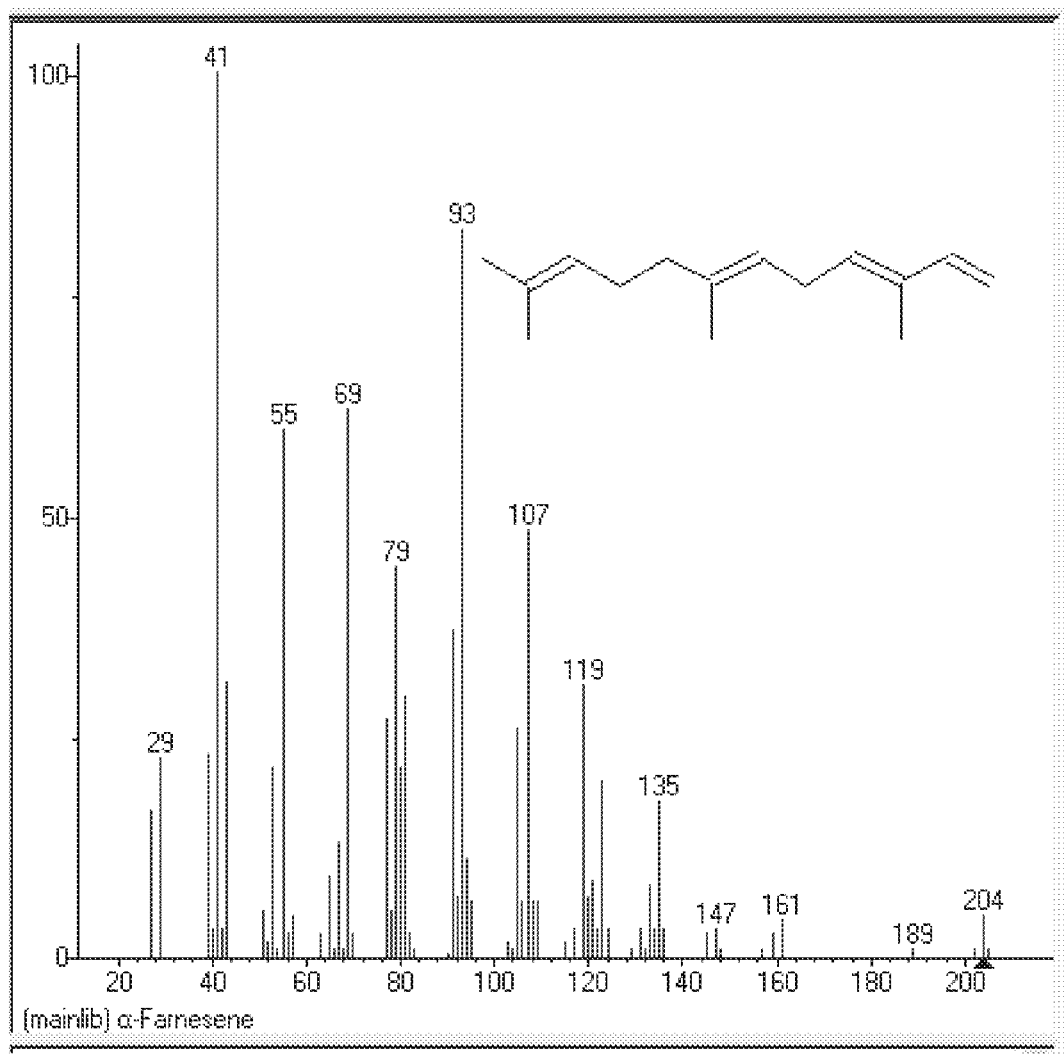
FIG. 21—MS spectrum for alpha-farnesene from the NIST Mass Spectral Database.

After conformation of successfully transformed of the plasmid pMTL8314-Prnf-MK-PMK-PMD-Pfor-idi-ispA-FS, a growth experiment was carried out in 50 ml PETC media (Table 1) in 250 ml serum bottles with 30 psi Real Mill Gas (collected from New Zealand Steel site in Glenbrook, NZ; composition: 44% CO, 32% $N_2$, 22% $CO_2$, 2% $H_2$) as sole energy and carbon source. All cultures were incubated at 37° C. on an orbital shaker adapted to hold serum bottles. Transformants were first grown up to an OD600 of ~0.4 before being subcultured into fresh media supplemented with 1 mM mevalonic acid. Controls without mevalonic acid were set up at the same time from the same culture. Samples for GC-MS (Gas Chromatography—Mass Spectroscopy) were taken at each time point. FIG. 17 shows a representative growth curve for 2 control cultures and two cultures fed 1 mM mevalonate. Farnesene was detected in the samples taken at 66 h and 90 h after start of experiment (FIG. 19-21). Detection of Alpha-Farnesene by Gas Chromatography—Mass Spectroscopy For GC-MS detection of alpha-farnesene hexane extraction was performed on 5 ml of culture by adding 2 ml hexane and shaking vigorously to mix in a sealed glass balch tube. The tubes were then incubated in a sonicating water bath for 5 min to encourage phase separation. 400 µl hexane extract were transferred to a GC vail and loaded on to the auto loader. The samples was analysed on a VARIAN GC3800 MS4000 iontrap GC/MS (Varian Inc, CA, USA. Now Agilent Technologies) with a EC-1000 column 0.25 µm film thickness (Grace Davidson, OR, USA) Varian MS workstation (Varian Inc, Ca. Now Agilent Technologies, CA, USA) and NIST MS Search 2.0 (Agilent Technologies, CA, USA). Injection volume of 1 µl with Helium carrier gas flow rate of 1 ml per min.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to."

The invention claimed is:

1. A recombinant C1-fixing microorganism capable of producing mevalonic acid, or a terpene precursor, from a carbon source comprising a nucleic acid encoding a group of exogenous enzymes comprising thiolase, 3-hydroxy-3-methylglutaryl coenzyme A (HMG-CoA) synthase, and HMG-CoA reductase, wherein the microorganism is from *Clostridium* or *Moorella*.

2. The microorganism according to claim 1, further comprising a nucleic acid encoding a group of enzymes comprising mevalonate kinase, phosphomevalonate kinase, and mevalonate diphosphate decarboxylase.

3. The microorganism according to claim 2, wherein the terpene precursor is isopentenyl diphosphate.

4. The microorganism according to claim 2, further comprising a nucleic acid encoding an exogenous enzyme selected from the group consisting of isopentenyl diphosphate isomerase and geranyltranstransferase.

5. The microorganism according to claim 4, wherein the terpene precursor is dimethylallyl pyrophosphate or geranyl pyrophosphate.

6. The microorganism according to claim 4, further comprising a nucleic acid encoding an exogenous enzyme comprising isoprene synthase.

7. The microorganism according to claim 6, wherein the nucleic acid encoding isoprene synthase comprises SEQ ID NO: 21.

8. The microorganism according to claim 4, wherein the terpene precursor is farnesyl pyrophosphate.

9. The microorganism according to claim 4, further comprising a nucleic acid encoding an exogenous enzyme comprising farnesene synthase.

10. The microorganism according to claim 9, wherein the nucleic acid encoding farnesene synthase comprises SEQ ID NO: 57.

11. The microorganism according to claim 2, further comprising a nucleic acid encoding both an exogenous enzyme isopentenyl diphosphate isomerase and an exogenous enzyme geranyltranstransferase.

12. The microorganism according to claim 1, wherein the microorganism is selected from the group consisting of *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*, *Moorella thermoacetica*, and *Moorella thermautotrophica*.

13. The microorganism according to claim 1, wherein the carbon source is at least one C1 compound selected from the group consisting of carbon monoxide and carbon dioxide as the carbon source.

14. The microorganism according to claim 1, wherein the mevalonic acid, or the terpene precursor, is converted to a terpene selected from the group consisting of terpenoids, isoprene, pinene, limonene, farnesene, and any combination thereof.

15. The microorganism according to claim 1, having carbon monoxide dehydrogenase.

16. The microorganism according to claim 1, further comprising a nucleic acid encoding at least one enzyme acting in a 1-deoxy-D-xylulose-5-phosphate synthase (DXS) pathway.

17. The microorganism according to claim 16, wherein the DXS pathway is that of a different organism than the microorganism.

18. The microorganism according to claim 1, wherein the exogenous enzymes are derived from a plant.

19. The microorganism according to claim 1, wherein the nucleic acid encoding the exogenous enzymes is codon optimized.

20. The microorganism according to claim 1, wherein the nucleic acid encoding the exogenous enzymes is integrated into the genome of the microorganism.

21. The microorganism according to claim 1, wherein the nucleic acid encoding the exogenous enzymes is incorporated in a plasmid.

22. The microorganism according to claim 1, wherein the nucleic acid encoding the exogenous enzymes is regulated by one or more constitutive promoters.

23. A method for producing mevalonic acid, or a terpene precursor, by culturing the recombinant C1-fixing microorganism according to claim 1 using at least one C1 compound selected from the group consisting of carbon monoxide and carbon dioxide as a carbon source, to allow the recombinant C1-fixing microorganism to produce mevalonic acid, or a terpene precursor.

24. The method according to claim 23, wherein the microorganism is provided with a gas comprising hydrogen.

25. The method according to claim 23, wherein the mevalonic acid, or terpene precursor, is recovered.

26. The method of claim 23, wherein the C1 compound is derived from an industrial process selected from the group consisting of ferrous metal products manufacturing, non-ferrous products manufacturing, petroleum refining, coal gasification, electric power production, carbon black production, ammonia production, methanol production, and coke manufacturing.

27. The method of claim 23, wherein the C1 compound is syngas. 26. The bacteria according to claim 7, wherein the nucleic acid encoding isoprene synthase comprises SEQ ID NO: 21.

28. A method for producing a terpene precursor by providing at least one C1 compound selected from the group consisting of carbon monoxide and carbon dioxide into contact with the recombinant C1-fixing microorganism according to claim 1, to allow the microorganism to produce a terpene precursor from the C1 compound.

29. The method according to claim 28, wherein the microorganism is provided with a gas comprising hydrogen.

30. The method according to claim 28, wherein the terpene precursor is recovered.

* * * * *